United States Patent
Dominguez et al.

(10) Patent No.: US 10,065,948 B2
(45) Date of Patent: Sep. 4, 2018

(54) HISTONE DEACETYLASE INHIBITORS AND COMPOSITIONS AND METHODS OF USE THEREOF

(71) Applicant: CHDI Foundation, Inc., New York, NY (US)

(72) Inventors: Celia Dominguez, Los Angeles, CA (US); Ignacio Muñoz-Sanjuán, Los Angeles, CA (US); Roland W. Bürli, Saffron Walden (GB); Christopher A. Luckhurst, Saffron Walden (GB); Daniel R. Allen, Saffron Walden (GB); Gilles Raphy, Saffron Walden (GB); Perla Breccia, Saffron Walden (GB); Alan F. Haughan, Saffron Walden (GB); Grant Wishart, Saffron Walden (GB); Samantha J. Hughes, Saffron Walden (GB); Rebecca E. Jarvis, Saffron Walden (GB); Huw D. Vater, Saffron Walden (GB); Stephen D. Penrose, Saffron Walden (GB); Michael Wall, Saffron Walden (GB); Andrew J. Stott, Saffron Walden (GB); Elizabeth A. Saville-Stones, Saffron Walden (GB)

(73) Assignee: CHDI Foundation, Inc., New York, NY (US)

( * ) Notice: Subject to any disclaimer, the term of this patent is extended or adjusted under 35 U.S.C. 154(b) by 0 days.

(21) Appl. No.: 15/315,713

(22) PCT Filed: Jun. 1, 2015

(86) PCT No.: PCT/US2015/033511
§ 371 (c)(1),
(2) Date: Dec. 1, 2016

(87) PCT Pub. No.: WO2015/187542
PCT Pub. Date: Dec. 10, 2015

(65) Prior Publication Data
US 2017/0101402 A1   Apr. 13, 2017

Related U.S. Application Data

(60) Provisional application No. 62/006,534, filed on Jun. 2, 2014.

(51) Int. Cl.
| C07D 417/04 | (2006.01) |
| C07D 231/54 | (2006.01) |
| C07D 401/04 | (2006.01) |
| C07D 403/04 | (2006.01) |
| C07D 231/56 | (2006.01) |
| C07D 239/88 | (2006.01) |
| C07D 277/60 | (2006.01) |
| C07D 239/70 | (2006.01) |
| C07C 259/08 | (2006.01) |

(52) U.S. Cl.
CPC .......... *C07D 417/04* (2013.01); *C07C 259/08* (2013.01); *C07D 231/54* (2013.01); *C07D 231/56* (2013.01); *C07D 239/70* (2013.01); *C07D 239/88* (2013.01); *C07D 277/60* (2013.01); *C07D 401/04* (2013.01); *C07D 403/04* (2013.01)

(58) Field of Classification Search
CPC ............................ C07D 417/04; C07D 231/54
See application file for complete search history.

(56) References Cited

U.S. PATENT DOCUMENTS

| 4,003,859 A | 1/1977 | Reymore, Jr. et al. |
| 4,760,174 A | 7/1988 | Frickel et al. |
| 5,384,331 A | 1/1995 | Kogan et al. |
| 6,384,072 B1 | 5/2002 | Hattori et al. |

(Continued)

FOREIGN PATENT DOCUMENTS

| EP | 1446155 | 2/2008 |
| WO | WO 2008/122115 | 10/2008 |
| WO | WO 2012/103008 | 8/2012 |

OTHER PUBLICATIONS

International Search Report and Written Opinion of PCT/US2015/33511 dated Nov. 4, 2015 (10 pages).

(Continued)

*Primary Examiner* — Golam M Shameem
(74) *Attorney, Agent, or Firm* — Sheppard Mullin Richter & Hampton LLP

(57) ABSTRACT

Provided are certain histone deacetylase (HDAC) inhibitors of Formula I, or pharmaceutically acceptable salts thereof, compositions thereof, and methods of their use. The condition or disorder mediated by HDAC comprises a neurodegenerative pathology. Accordingly, also provided is a method of treating a neurodegenerative pathology mediated by HDAC in a subject in need of such a treatment, comprising administering to the subject a therapeutically effective amount of at least one compound, or pharmaceutically acceptable salt thereof, described herein.

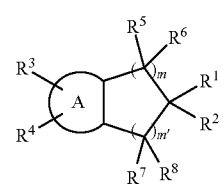

(I)

51 Claims, No Drawings

(56) References Cited

U.S. PATENT DOCUMENTS

| | | |
|---|---|---|
| 9,505,736 B2 | 11/2016 | Dominguez et al. |
| 9,562,021 B2 | 2/2017 | Dominguez et al. |
| 9,617,259 B2 | 4/2017 | Dominguez et al. |
| 2006/0019944 A1 | 1/2006 | Wu et al. |
| 2007/0111967 A1 | 5/2007 | Miller |
| 2008/0269294 A1 | 10/2008 | Andrews et al. |
| 2009/0181943 A1 | 7/2009 | Tessier et al. |
| 2011/0046139 A1 | 2/2011 | Schoentjes et al. |
| 2011/0319420 A1 | 12/2011 | Yang et al. |
| 2012/0121502 A1 | 5/2012 | Van Duzer et al. |
| 2014/0163009 A1 | 6/2014 | Luckhurst et al. |
| 2015/0203468 A1 | 7/2015 | Dominguez et al. |
| 2016/0024019 A1 | 1/2016 | Dominguez et al. |
| 2016/0031863 A1 | 2/2016 | Dominguez et al. |
| 2016/0031876 A1 | 2/2016 | Dominguez et al. |
| 2016/0039745 A1 | 2/2016 | Dominguez et al. |
| 2017/0042892 A1 | 2/2017 | Dominguez et al. |
| 2017/0224684 A1 | 8/2017 | Dominguez et al. |

OTHER PUBLICATIONS

U.S. Appl. No. 15/482,327, filed Apr. 7, 2017, Dominguez et al.
Database CAPLUS in STN, Acct. No. 1991:631727, Dang et al., Journal of the Chemical Society, Perkin Transactions 2: Physical Organic Chemistry (1972-1999)(1991), 5, pp. 721-734 (abstract).
Database CAPLUS; Accession No. 1984: 185792, Tihanyi et al., HU 27601, 1980.
Extended European Search Report dated Aug. 26, 2016 for EP 14775535.9. (7 pages).
Extended European Search Report dated Jul. 6, 2016 for EP 14775793.4. (9 pages).
Heinemann, B. Prophage Induction in Lysogenic *Escherichia coil* with Simple Hydroxylamine and Hydrazine Compounds. Applied Microbiology, vol. 21, No. 4, Apr. 1971, pp. 726-731.
International Search Report and Written Opinion dated Aug. 4, 2014 for PCT Application No. PCT/US2014/022550 (8 pages).
International Search Report and Written Opinion dated Jul. 1, 2014 for PCT/US2014/022597. (8 pages).
International Search Report and Written Opinion dated Jul. 21, 2014 for PCT Application No. PCT/US2014/022567 (13 pages).
Pubchem CID 21702499, Dec. 5, 2007, pp. 1-10 [online], [retrieved on Jun. 16, 2016]. Retrieved from the Internet <URL: https://pubchem.ncbi.nlm.nih.gov/summary/summary.cgi?cid=21702499>; p. 1, formula.
Pubchem CID 331910, Mar. 26, 2005, pp. 1-14 [online], [retrieved on Jun. 16, 2016]. Retrieved from the Internet <URL: https://pubchem.ncbi.nlm.nih.gov/summary/summary.cgi?cid=331910>; p. 1, formula.
Pubchem CID 57779614, Aug. 19, 2012, pp. 1-4 [online], [retrieved on Jun. 16, 2014]. Retrieved from the Internet <URL: https://pubchem.ncbi.nlm.nih.gov/summary/summary.cgi?cid=57779614&loc=ec_rcs>; p. 1, formula.
Pubchem CID 59191078, Aug. 20, 2012, pp. 1-4 [online], [retrieved on Jun. 16, 2014]. Retrieved from the Internet <URL:https://pubchem.ncbi.nlm.nih.gov/summary/summary.cgi?cid=59191078&loc=ec_rcs >; p. 1, formula.
Wu Z, et al., A High-Affinity Fluorenone-Based Beta2-Adrenergic Receptor Antagonist with a Photoactivatable Pharmacophore, Biochemistry, Vo.I. 39, No. 42, 2000, pp. 13044-13052.

HISTONE DEACETYLASE INHIBITORS AND COMPOSITIONS AND METHODS OF USE THEREOF

CROSS REFERENCE TO RELATED APPLICATIONS

This application is a U.S. National Stage Application under 35 U.S.C. § 371 of PCT Application No. PCT/US2015/033511, filed Jun. 1, 2015, which claims the benefit of priority of U.S. Application No. 62/006,534, filed Jun. 2, 2014, which is incorporated by reference herein for all purposes.

Provided herein are certain histone deacetylase (HDAC) inhibitors, compositions thereof, and methods of their use.

Histone deacetylases (HDACs) are zinc-containing enzymes which catalyse the removal of acetyl groups from the ε-amino termini of lysine residues clustered near the amino terminus of nucleosomal histones. There are 11 known metal-dependent human histone deacetylases, grouped into four classes based on the structure of their accessory domains. Class I includes HDAC1, HDAC2, HDAC3, and HDAC8 and have homology to yeast RPD3. HDAC4, HDAC5, HDAC7, and HDAC9 belong to Class IIa and have homology to yeast HDAC1. HDAC6 and HDAC10 contain two catalytic sites and are classified as Class IIb, whereas HDAC11 has conserved residues in its catalytic center that are shared by both Class I and Class II deacetylases and is sometimes placed in Class IV.

Provided is a compound of Formula I, or a pharmaceutically acceptable salt thereof,

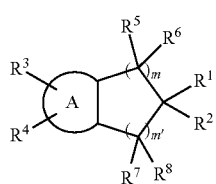

Formula I wherein:
$R^1$ is chosen from —C(O)NH(OH) and —N(OH)C(O)$R^9$;
$R^2$ is chosen from aryl, heteroaryl, and heterocycloalkyl, each of which is optionally substituted with 1 to 3 substituents independently chosen from halo, alkyl, cycloalkyl, haloalkyl, hydroxyl, alkoxy, and nitrile;
A is chosen from aryl and heteroaryl;
$R^3$ and $R^4$ are independently chosen from hydrogen, alkyl, halo, NHSO$_2$R$^{10}$, C(O)NR$^{11}$R$^{12}$, NR$^{11}$R$^{12}$, nitrile, cycloalkyl, heterocycloalkyl, aryl, heteroaryl, aralkyl, and heteroaralkyl, each of which is optionally substituted with 1 to 3 substituents independently chosen from halo, alkyl, cycloalkyl, haloalkyl, hydroxyl, alkoxy, aryl, heteroaryl, and nitrile, wherein alkyl and alkoxy are optionally substituted with amino, (alkyl)amino or di(alkyl)amino;
for each occurrence, $R^5$, $R^6$, $R^7$, and $R^8$ are independently chosen from hydrogen and lower alkyl;
$R^9$ is chosen from hydrogen and lower alkyl;
$R^{10}$ is chosen from lower alkyl, cycloalkyl, heterocycloalkyl, aryl, and heteroaryl;
$R^{11}$ and $R^{12}$ are independently chosen from hydrogen, lower alkyl, alkoxy, lower haloalkyl and cycloalkyl wherein alkyl and alkoxy are optionally substituted with amino, (alkyl)amino or di(alkyl)amino, and m and m' are independently chosen from 0, 1, 2, 3 and 4, provided that 2≤(m+m')≤4.

Also provided is a pharmaceutical composition comprising a compound, or a pharmaceutically acceptable salt thereof, described herein and at least one pharmaceutically acceptable excipient.

Also provided is a method of treating a condition or disorder mediated by at least one histone deacetylase in a subject in need of such a treatment which method comprises administering to the subject a therapeutically effective amount of a compound, or a pharmaceutically acceptable salt thereof, described herein.

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —CONH$_2$ is attached through the carbon atom.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

"Alkyl" encompasses straight chain and branched chain having, for example, the indicated number of carbon atoms, usually from 1 to 20 carbon atoms, for example 1 to 8 carbon atoms, such as 1 to 6 carbon atoms. For example $C_1$-$C_6$ alkyl encompasses both straight and branched chain alkyl of from 1 to 6 carbon atoms. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. Alkylene is another subset of alkyl, referring to the same residues as alkyl, but having two points of attachment. Alkylene groups will usually have from 2 to 20 carbon atoms, for example 2 to 8 carbon atoms, such as from 2 to 6 carbon atoms. For example, $C_0$ alkylene indicates a covalent bond and $C_1$ alkylene is a methylene group. When an alkyl residue having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl.

"Cycloalkyl" indicates a non-aromatic, fully saturated carbocyclic ring having, for example, the indicated number of carbon atoms, for example, 3 to 10, or 3 to 8, or 3 to 6 ring carbon atoms. Cycloalkyl groups may be monocyclic or polycyclic (e.g., bicyclic, tricyclic). Examples of cycloalkyl groups include cyclopropyl, cyclobutyl, cyclopentyl, cyclopentenyl and cyclohexyl, as well as bridged and caged ring groups (e.g., norbornane, bicyclo[2.2.2]octane). In addition, one ring of a polycyclic cycloalkyl group may be aromatic, provided the polycyclic cycloalkyl group is bound to the parent structure via a non-aromatic carbon. For example, a 1,2,3,4-tetrahydronaphthalen-1-yl group (wherein the moiety is bound to the parent structure via a non-aromatic carbon atom) is a cycloalkyl group, while 1,2,3,4-tetrahydronaphthalen-5-yl (wherein the moiety is bound to the parent structure via an aromatic carbon atom) is not considered a cycloalkyl group.

"Cycloalkenyl" indicates a non-aromatic ring having 3 to 10, or 3 to 8, or 3 to 6 ring carbon atoms, and at least one double bond derived by the removal of one molecule of hydrogen from two adjacent carbon atoms of the corresponding cycloalkyl.

By "alkoxy" is meant an alkyl group, for example, of the indicated number of carbon atoms attached through an oxygen bridge such as, for example, methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. Alkoxy groups will usually have from 1 to 6 carbon atoms attached through the oxygen bridge.

"Aryl" indicates an aromatic carbon ring having, for example, the indicated number of carbon atoms, for example, 6 to 12 or 6 to 10 carbon atoms. Aryl groups may be monocyclic or polycyclic (e.g., bicyclic, tricyclic). In some instances, both rings of a polycyclic aryl group are aromatic (e.g., naphthyl). In other instances, polycyclic aryl groups may include a non-aromatic ring (e.g., cycloalkyl, cycloalkenyl, heterocycloalkyl, heterocycloalkenyl) fused to an aromatic ring, provided the polycyclic aryl group is bound to the parent structure via an atom in the aromatic ring. Thus, a 1,2,3,4-tetrahydronaphthalen-5-yl group (wherein the moiety is bound to the parent structure via an aromatic carbon atom) is considered an aryl group, while 1,2,3,4-tetrahydronaphthalen-1-yl (wherein the moiety is bound to the parent structure via a non-aromatic carbon atom) is not considered an aryl group. Similarly, a 1,2,3,4-tetrahydroquinolin-8-yl group (wherein the moiety is bound to the parent structure via an aromatic carbon atom) is considered an aryl group, while 1,2,3,4-tetrahydroquinolin-1-yl group (wherein the moiety is bound to the parent structure via a non-aromatic nitrogen atom) is not considered an aryl group. However, the term "aryl" does not encompass or overlap with "heteroaryl", as defined herein, regardless of the point of attachment (e.g., both quinolin-5-yl and quinolin-2-yl are heteroaryl groups). In some instances, aryl is phenyl or naphthyl. In certain instances, aryl is phenyl.

Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene.

The term "halo" includes fluoro, chloro, bromo, and iodo, and the term "halogen" includes fluorine, chlorine, bromine, and iodine.

"Heteroaryl" indicates an aromatic ring containing, for example, the indicated number of atoms (e.g., 5 to 12, or 5 to 10 membered heteroaryl) made up of one or more heteroatoms (e.g., 1, 2, 3 or 4 heteroatoms) selected from N, O and S and with the remaining ring atoms being carbon. Heteroaryl groups do not contain adjacent S and O atoms. In some embodiments, the total number of S and O atoms in the heteroaryl group is not more than 2. In some embodiments, the total number of S and O atoms in the heteroaryl group is not more than 1. Unless otherwise indicated, heteroaryl groups may be bound to the parent structure by a carbon or nitrogen atom, as valency permits. For example, "pyridyl" includes 2-pyridyl, 3-pyridyl and 4-pyridyl groups, and "pyrrolyl" includes 1-pyrrolyl, 2-pyrrolyl and 3-pyrrolyl groups. When nitrogen is present in a heteroaryl ring, it may, where the nature of the adjacent atoms and groups permits, exist in an oxidized state (i.e., $N^+—O^-$). Additionally, when sulfur is present in a heteroaryl ring, it may, where the nature of the adjacent atoms and groups permits, exist in an oxidized state (i.e., $S^+—O^-$ or $SO_2$). Heteroaryl groups may be monocyclic or polycyclic (e.g., bicyclic, tricyclic).

In some instances, a heteroaryl group is monocyclic. Examples include pyrrole, pyrazole, imidazole, triazole (e.g., 1,2,3-triazole, 1,2,4-triazole, 1,3,4-triazole), tetrazole, furan, isoxazole, oxazole, oxadiazole (e.g., 1,2,3-oxadiazole, 1,2,4-oxadiazole, 1,3,4-oxadiazole), thiophene, isothiazole, thiazole, thiadiazole (e.g., 1,2,3-thiadiazole, 1,2,4-thiadiazole, 1,3,4-thiadiazole), pyridine, pyridazine, pyrimidine, pyrazine, triazine (e.g., 1,2,4-triazine, 1,3,5-triazine) and tetrazine.

In some instances, both rings of a polycyclic heteroaryl group are aromatic. Examples include indole, isoindole, indazole, benzoimidazole, benzotriazole, benzofuran, benzoxazole, benzoisoxazole, benzoxadiazole, benzothiophene, benzothiazole, benzoisothiazole, benzothiadiazole, 1H-pyrrolo[2,3-b]pyridine, 1H-pyrazolo[3,4-b]pyridine, 3H-imidazo[4,5-b]pyridine, 3H-[1,2,3]triazolo[4,5-b]pyridine, 1H-pyrrolo[3,2-b]pyridine, 1H pyrazolo[4,3-b]pyridine, 1H-imidazo[4,5-b]pyridine, 1H-[1,2,3]triazolo[4,5-b]pyridine, 1H-pyrrolo[2,3-c]pyridine, 1H-pyrazolo[3,4-c]pyridine, 3H-imidazo[4,5-c]pyridine, 3H-[1,2,3]triazolo[4,5-c]pyridine, 1H-pyrrolo[3,2-c]pyridine, 1H-pyrazolo[4,3-c]pyridine, 1H-imidazo[4,5-c]pyridine, 1H-[1,2,3]triazolo[4,5-c]pyridine, furo[2,3-b]pyridine, oxazolo[5,4-b]pyridine, isoxazolo[5,4-b]pyridine, [1,2,3]oxadiazolo[5,4-b]pyridine, furo[3,2-b]pyridine, oxazolo[4,5-b]pyridine, isoxazolo[4,5-b]pyridine, [1,2,3]oxadiazolo[4,5-b]pyridine, furo[2,3-c]pyridine, oxazolo[5,4-c]pyridine, isoxazolo[5,4-c]pyridine, [1,2,3]oxadiazolo[5,4-c]pyridine, furo[3,2-c]pyridine, oxazolo[4,5-c]pyridine, isoxazolo[4,5-c]pyridine, [1,2,3]oxadiazolo[4,5-c]pyridine, thieno[2,3-b]pyridine, thiazolo[5,4-b]pyridine, isothiazolo[5,4-b]pyridine, [1,2,3]thiadiazolo[5,4-b]pyridine, thieno[3,2-b]pyridine, thiazolo[4,5-b]pyridine, isothiazolo[4,5-b]pyridine, [1,2,3]thiadiazolo[4,5-b]pyridine, thieno[2,3-c]pyridine, thiazolo[5,4-c]pyridine, isothiazolo[5,4-c]pyridine, [1,2,3]thiadiazolo[5,4-c]pyridine, thieno[3,2-c]pyridine, thiazolo[4,5-c]pyridine, isothiazolo[4,5-c]pyridine, [1,2,3]thiadiazolo[4,5-c]pyridine, quinoline, isoquinoline, cinnoline, quinazoline, quinoxaline, phthalazine, naphthyridine (e.g., 1,8-naphthyridine, 1,7-naphthyridine, 1,6-naphthyridine, 1,5-naphthyridine, 2,7-naphthyridine, 2,6-naphthyridine), imidazo[1,2-a]pyridine, 1H-pyrazolo[3,4-d]thiazole, 1H-pyrazolo[4,3-d]thiazole and imidazo[2,1-b]thiazole.

In other instances, polycyclic heteroaryl groups may include a non-aromatic ring (e.g., cycloalkyl, cycloalkenyl, heterocycloalkyl, heterocycloalkenyl) fused to a heteroaryl ring, provided the polycyclic heteroaryl group is bound to the parent structure via an atom in the aromatic ring. For example, a 4,5,6,7-tetrahydrobenzo[d]thiazol-2-yl group (wherein the moiety is bound to the parent structure via an aromatic carbon atom) is considered a heteroaryl group, while 4,5,6,7-tetrahydrobenzo[d]thiazol-5-yl (wherein the moiety is bound to the parent structure via a non-aromatic carbon atom) is not considered a heteroaryl group.

"Heterocycloalkyl" indicates a non-aromatic, fully saturated ring having, for example, the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon. Heterocycloalkyl groups may be monocyclic or polycyclic (e.g., bicyclic, tricyclic).

Examples of monocyclic heterocycloalkyl groups include oxiranyl, aziridinyl, azetidinyl, pyrrolidinyl, imidazolidinyl, pyrazolidinyl, piperidinyl, piperazinyl, morpholinyl and thiomorpholinyl.

When nitrogen is present in a heterocycloalkyl ring, it may, where the nature of the adjacent atoms and groups permits, exist in an oxidized state (i.e., $N^+$—$O^-$). Examples include piperidinyl N-oxide and morpholinyl-N-oxide. Additionally, when sulfur is present in a heterocycloalkyl ring, it may, where the nature of the adjacent atoms and groups permits, exist in an oxidized state (i.e., $S^+$—$O^-$ or —$SO_2$—). Examples include thiomorpholine S-oxide and thiomorpholine S,S-dioxide.

In addition, one ring of a polycyclic heterocycloalkyl group may be aromatic (e.g., aryl or heteroaryl), provided the polycyclic heterocycloalkyl group is bound to the parent structure via a non-aromatic carbon or nitrogen atom. For example, a 1,2,3,4-tetrahydroquinolin-1-yl group (wherein the moiety is bound to the parent structure via a non-aromatic nitrogen atom) is considered a heterocycloalkyl group, while 1,2,3,4-tetrahydroquinolin-8-yl group (wherein the moiety is bound to the parent structure via an aromatic carbon atom) is not considered a heterocycloalkyl group.

"Heterocycloalkenyl" indicates a non-aromatic ring having, for example, the indicated number of atoms (e.g., 3 to 10, or 3 to 7, membered heterocycloalkenyl) made up of one or more heteroatoms (e.g., 1, 2, 3 or 4 heteroatoms) selected from N, O and S and with the remaining ring atoms being carbon, and at least one double bond derived by the removal of one molecule of hydrogen from adjacent carbon atoms, adjacent nitrogen atoms, or adjacent carbon and nitrogen atoms of the corresponding heterocycloalkyl. Heterocycloalkenyl groups may be monocyclic or polycyclic (e.g., bicyclic, tricyclic). When nitrogen is present in a heterocycloalkenyl ring, it may, where the nature of the adjacent atoms and groups permits, exist in an oxidized state (i.e., $N^+$—$O^-$). Additionally, when sulfur is present in a heterocycloalkenyl ring, it may, where the nature of the adjacent atoms and groups permits, exist in an oxidized state (i.e., $S^+$—$O^-$ or —$SO_2$—). Examples of heterocycloalkenyl groups include dihydrofuranyl (e.g., 2,3-dihydrofuranyl, 2,5-dihydrofuranyl), dihydrothiophenyl (e.g., 2,3-dihydrothiophenyl, 2,5-dihydrothiophenyl), dihydropyrrolyl (e.g., 2,3-dihydro-1H-pyrrolyl, 2,5-dihydro-1H-pyrrolyl), dihydroimidazolyl (e.g., 2,3-dihydro-1H-imidazolyl, 4,5-dihydro-1H-imidazolyl), pyranyl, dihydropyranyl (e.g., 3,4-dihydro-2H-pyranyl, 3,6-dihydro-2H-pyranyl), tetrahydropyridinyl (e.g., 1,2,3,4-tetrahydropyridinyl, 1,2,3, 6-tetrahydropyridinyl) and dihydropyridine (e.g., 1,2-dihydropyridine, 1,4-dihydropyridine). In addition, one ring of a polycyclic heterocycloalkenyl group may be aromatic (e.g., aryl or heteroaryl), provided the polycyclic heterocycloalkenyl group is bound to the parent structure via a non-aromatic carbon or nitrogen atom. For example, a 1,2-dihydroquinolin-1-yl group (wherein the moiety is bound to the parent structure via a non-aromatic nitrogen atom) is considered a heterocycloalkenyl group, while 1,2-dihydroquinolin-8-yl group (wherein the moiety is bound to the parent structure via an aromatic carbon atom) is not considered a heterocycloalkenyl group.

The term "substituted", as used herein, means that any one or more hydrogens on the designated atom or group is replaced with a selection from the indicated group, provided that the designated atom's normal valence is not exceeded. When a substituent is oxo (i.e., =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

The terms "substituted" alkyl (including without limitation $C_1$-$C_4$ alkyl), cycloalkyl, aryl, heterocycloalkyl, and heteroaryl, unless otherwise expressly defined, refer respectively to alkyl, cycloalkyl, aryl, heterocycloalkyl, and heteroaryl wherein one or more (such as up to 5, for example, up to 3) hydrogen atoms are replaced by a substituent independently chosen from
—$R^a$, —$OR^b$, —$O(C_1$-$C_2$ alkyl)O— (e.g., methylenedioxy-), —$SR^b$, guanidine (—NHC(=NH)$NH_2$), guanidine wherein one or more of the guanidine hydrogens are replaced with a $C_1$-$C_4$ alkyl group, —$NR^bR^c$, halo, cyano, oxo (as a substituent for heterocycloalkyl), nitro, —$COR^b$, —$CO_2R^b$, —$CONR^bR^c$, —$OCOR^b$, —$OCO_2R^a$, —$OCONR^bR^c$, —$NR^cCOR^b$, —$NR^cCO_2R^a$, —$NR^cCO$-$NR^bR^c$, —$SOR^a$, —$SO_2R^a$, —$SO_2NR^bR^c$, and —$NR^cSO_2R^a$, where $R^a$ is chosen from $C_1$-$C_6$ alkyl, cycloalkyl, aryl, heterocycloalkyl, and heteroaryl;

$R^b$ is chosen from H, $C_1$-$C_6$ alkyl, aryl, and heteroaryl; and $R^c$ is chosen from hydrogen and $C_1$-$C_4$ alkyl; or $R^b$ and $R^c$, and the nitrogen to which they are attached, form a heterocycloalkyl group; and where each $C_1$-$C_6$ alkyl, cycloalkyl, aryl, heterocycloalkyl, and heteroaryl is optionally substituted with one or more, such as one, two, or three, substituents independently selected from $C_1$-$C_4$ alkyl, $C_3$-$C_6$ cycloalkyl, aryl, heteroaryl, aryl-$C_1$-$C_4$ alkyl-, heteroaryl-$C_1$-$C_4$ alkyl-, $C_1$-$C_4$ haloalkyl-, —$OC_1$-$C_4$ alkyl, —$OC_1$-$C_4$ alkylphenyl, —$C_1$-$C_4$ alkyl-OH, —$C_1$-$C_4$ alkyl-O—$C_1$-$C_4$ alkyl, —$OC_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for heteroaryl), —$CO_2H$, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH(phenyl), —$NHSO_2$($C_1$-$C_4$ alkyl), —$NHSO_2$(phenyl), and —$NHSO_2$($C_1$-$C_4$ haloalkyl).

Compounds described herein include, but are not limited to, their optical isomers, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column.

Where the absolute configuration of a single enantiomer is not known the configuration has been denoted as E1 (enantiomer 1) and E2 (enantiomer 2) and the chiral center labeled with an asterisk. For example E1-(abs)-5-(3-fluoro-2-methylphenyl)-N-hydroxy-1-phenyl-4,5,6,7-tetrahydro- 1H-indazole-5-carboxamide and E2-(abs)-5-(3-fluoro-2-methylphenyl)-N-hydroxy-1-phenyl-4,5,6,7-tetrahydro-1H-indazole-5-carboxamide are single enantiomers for which the configuration at the chiral center is not known absolutely.

In addition, such compounds include Z- and E-forms (or cis- and trans-forms) of compounds with carbon-carbon double bonds. Where compounds described herein exist in various tautomeric forms, the term "compound" is intended to include all tautomeric forms of the compound. Such compounds also include crystal forms including polymorphs and clathrates. Similarly, the term "salt" is intended to include all tautomeric forms and crystal forms of the compound.

"Pharmaceutically acceptable salts" include, but are not limited to salts with inorganic acids, such as hydrochloride, phosphate, diphosphate, hydrobromide, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, HOOC—$(CH_2)_n$—COOH where n is 0-4, and like salts. Similarly, pharmaceutically acceptable cations include, but are not limited to sodium, potassium, calcium, aluminum, lithium, and ammonium.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

As used herein the terms "group", "radical" or "fragment" are synonymous and are intended to indicate functional groups or fragments of molecules attachable to a bond or other fragments of molecules.

The term "active agent" is used to indicate a compound or a pharmaceutically acceptable salt thereof which has biological activity. In some embodiments, an "active agent" is a compound or pharmaceutically acceptable salt thereof having pharmaceutical utility. For example an active agent may be an anti-neurodegenerative therapeutic.

The term "therapeutically effective amount" means an amount effective, when administered to a human or non-human patient, to provide a therapeutic benefit such as amelioration of symptoms, slowing of disease progression, or prevention of disease e.g., a therapeutically effective amount may be an amount sufficient to decrease the symptoms of a disease responsive to inhibition of HDAC activity.

As used herein, the terms "histone deacetylase" and "HDAC" are intended to refer to any one of a family of enzymes that remove $N^\varepsilon$-acetyl groups from the ε-amino groups of lysine residues of a protein (for example, a histone, or tubulin). Unless otherwise indicated by context, the term "histone" is meant to refer to any histone protein, including H1, H2A, H2B, H3, H4, and H5, from any species. In some embodiments, the histone deacetylase is a human HDAC, including, but not limited to, HDAC4, HDAC5, HDAC6, HDAC7, HDAC9, and HDAC10. In some embodiments, the at least one histone deacetylase is selected from HDAC4, HDAC5, HDAC7, and HDAC9. In some embodiments, the histone deacetylase is a class IIa HDAC. In some embodiments, the histone deacetylase is HDAC4. In some embodiments, the histone deacetylase is HDAC5. In some embodiments, the histone deacetylase is derived from a protozoal or fungal source.

The terms "histone deacetylase inhibitor" and "inhibitor of histone deacetylase" are intended to mean a compound, or a pharmaceutically acceptable salt thereof, described herein which is capable of interacting with a histone deacetylase and inhibiting its enzymatic activity.

The term "a condition or disorder mediated by HDAC" or "a condition or disorder mediated by histone deacetylase" as used herein refers to a condition or disorder in which HDAC and/or the action of HDAC is important or necessary, e.g., for the onset, progress, expression, etc. of that condition, or a condition which is known to be treated by HDAC inhibitors (such as, e.g., trichostatin A).

The term "effect" describes a change or an absence of a change in cell phenotype or cell proliferation. "Effect" can also describe a change or an absence of a change in the catalytic activity of HDAC. "Effect" can also describe a change or an absence of a change in an interaction between HDAC and a natural binding partner.

The term "inhibiting histone deacetylase enzymatic activity" is intended to mean reducing the ability of a histone deacetylase to remove an acetyl group from a protein, such as but not limited to a histone or tubulin. The concentration of inhibitor which reduces the activity of a histone deacetylase to 50% of that of the uninhibited enzyme is determined as the $IC_{50}$ value. In some embodiments, such reduction of histone deacetylase activity is at least 50%, such as at least about 75%, for example, at least about 90%. In some embodiments, histone deacetylase activity is reduced by at least 95%, such as by at least 99%. In some embodiments, the compounds and pharmaceutical acceptable salts thereof described herein have an $IC_{50}$ value less than 100 nanomolar. In some embodiments, the compounds and pharmaceutical acceptable salts thereof described herein have an $IC_{50}$ value from 100 nanomolar to 1 micromolar. In some embodiments, the compounds and pharmaceutical acceptable salts thereof described herein have an $IC_{50}$ value from 1 to 25 micromolar.

In some embodiments, such inhibition is specific, i.e., the histone deacetylase inhibitor reduces the ability of a histone deacetylase to remove an acetyl group from a protein at a concentration that is lower than the concentration of the inhibitor that is required to produce another, unrelated biological effect. In some embodiments, the concentration of the inhibitor required for histone deacetylase inhibitory activity is at least 2-fold lower, such as at least 5-fold lower, for example, at least 10-fold lower, such as at least 20-fold lower than the concentration required to produce an unrelated biological effect.

"Treatment" or "treating" means any treatment of a disease state in a patient, including
 a) preventing the disease, that is, causing the clinical symptoms of the disease not to develop;
 b) inhibiting the disease;
 c) slowing or arresting the development of clinical symptoms; and/or
 d) relieving the disease, that is, causing the regression of clinical symptoms.

"Subject" or "patient' refers to an animal, such as a mammal, that has been or will be the object of treatment, observation or experiment. The methods described herein may be useful in both human therapy and veterinary applications. In some embodiments, the subject is a mammal; and in some embodiments the subject is human.

Provided is a compound of Formula I, or a pharmaceutically acceptable salt thereof,

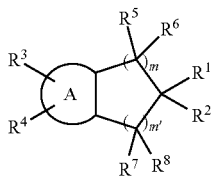

Formula I wherein:
R¹ is chosen from —C(O)NH(OH) and —N(OH)C(O)R⁹;
R² is chosen from aryl, heteroaryl, and heterocycloalkyl, each of which is optionally substituted with 1 to 3 substituents independently chosen from halo, alkyl, cycloalkyl, haloalkyl, hydroxyl, alkoxy, and nitrile;
A is chosen from aryl and heteroaryl;
R³ and R⁴ are independently chosen from hydrogen, alkyl, halo, NHSO₂R¹⁰, C(O)NR¹¹R¹², NR¹¹R¹², nitrile, cycloalkyl, heterocycloalkyl, aryl, heteroaryl, aralkyl, and heteroaralkyl, each of which is optionally substituted with 1 to 3 substituents independently chosen from halo, alkyl, cycloalkyl, haloalkyl, hydroxyl, alkoxy, aryl, heteroaryl, and nitrile, wherein alkyl and alkoxy are optionally substituted with amino, (alkyl)amino or di(alkyl)amino;
for each occurrence, R⁵, R⁶, R⁷, and R⁸ are independently chosen from hydrogen and lower alkyl;
R⁹ is chosen from hydrogen and lower alkyl;
R¹⁰ is chosen from lower alkyl, cycloalkyl, heterocycloalkyl, aryl, and heteroaryl;
R¹¹ and R¹² are independently chosen from hydrogen, lower alkyl, alkoxy, lower haloalkyl and cycloalkyl wherein alkyl and alkoxy are optionally substituted with amino, (alkyl)amino or di(alkyl)amino, and
m and m' are independently chosen from 0, 1, 2, 3 and 4, provided that 2 (m+m') 4.

In some embodiments, the compound of Formula I, or a pharmaceutically acceptable salt thereof, is chosen from compounds of Formula II, or a pharmaceutically acceptable salt thereof:

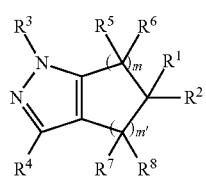

Formula II

In some embodiments of compounds of Formula II, or a pharmaceutically acceptable salt thereof, R³ is chosen from phenyl optionally substituted with one or two substituents independently chosen from lower alkyl, lower haloalkyl, lower alkoxy, lower haloalkoxy, and halo.

In some embodiments of compounds of Formula II, or a pharmaceutically acceptable salt thereof, R³ is chosen from phenyl, 2-methylphenyl, 3-methylphenyl, 4-methylphenyl, 2-fluorophenyl, 3-fluorophenyl, 4-fluorophenyl, 2-chlorophenyl, 3-chlorophenyl, 4-chlorophenyl, 3-chloro-2-fluorophenyl, 2,6-difluorophenyl, 2,5-dimethylphenyl, 2,6-dimethylphenyl, 2-chloro-6-fluorophenyl, 2-fluoro-6-methylphenyl, 2,4-difluorophenyl, 4-(difluoromethoxy)phenyl, and 3-fluoro-2-methylphenyl.

In some embodiments of compounds of Formula II, or a pharmaceutically acceptable salt thereof, R³ is chosen from pyridin-2-yl, pyridin-4-yl, and pyrazin-2-yl, each of which is optionally substituted with one or two substituents independently chosen from lower alkyl and halo.

In some embodiments of compounds of Formula II, or a pharmaceutically acceptable salt thereof, R³ is chosen from 5-fluoropyridin-2-yl, pyrazin-2-yl, and 3-methylpyridin-4-yl.

In some embodiments of compounds of Formula II, or a pharmaceutically acceptable salt thereof, R³ is chosen from cyclopropyl and cyclopentyl, each of which is optionally substituted with one or two substituents independently chosen from lower alkyl and halo.

In some embodiments of compounds of Formula II, or a pharmaceutically acceptable salt thereof, R³ is chosen from cyclopropyl and cyclopentyl.

In some embodiments of compounds of Formula II, or a pharmaceutically acceptable salt thereof, R³ is chosen from isopropyl.

In some embodiments of compounds of Formula II, or a pharmaceutically acceptable salt thereof, R⁴ is hydrogen.

In some embodiments, the compound of Formula I, or a pharmaceutically acceptable salt thereof, is chosen from compounds of Formula III, or a pharmaceutically acceptable salt thereof:

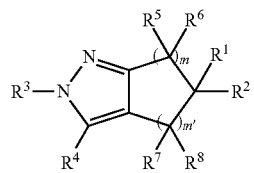

Formula III

In some embodiments of compounds of Formula III, or a pharmaceutically acceptable salt thereof, R³ is chosen from lower alkyl, lower haloalkyl, and aralkyl optionally substituted with halo.

In some embodiments of compounds of Formula III, or a pharmaceutically acceptable salt thereof, R³ is chosen form methyl, 2,2,2,-trifluoroethyl, and 4-fluorobenzyl.

In some embodiments of compounds of Formula III, or a pharmaceutically acceptable salt thereof, R³ is chosen from phenyl optionally substituted with one or two substituents independently chosen from lower alkyl, lower haloalkyl, lower alkoxy, lower haloalkoxy, and halo.

In some embodiments of compounds of Formula III, or a pharmaceutically acceptable salt thereof, R³ is chosen from 2-fluorophenyl, 4-(difluoromethoxy)phenyl, 4-fluoro-2-methylphenyl, and 3-methylphenyl.

In some embodiments of compounds of Formula III, or a pharmaceutically acceptable salt thereof, R³ is chosen from pyridin-2-yl and pyridin-4-yl, each of which is optionally substituted with one or two substituents independently chosen from lower alkyl and halo.

In some embodiments of compounds of Formula III, or a pharmaceutically acceptable salt thereof, R³ is chosen from 3-methylpyridin-4-yl, 3-chloropyridin-2-yl, and 3-fluoropyridin-2-yl.

In some embodiments of compounds of Formula III, or a pharmaceutically acceptable salt thereof, R⁴ is chosen from hydrogen, cyclopropyl, and phenyl optionally substituted with halo.

In some embodiments of compounds of Formula III, or a pharmaceutically acceptable salt thereof, $R^4$ is hydrogen.

In some embodiments, the compound of Formula I, or a pharmaceutically acceptable salt thereof, is chosen from compounds of Formula IV, or a pharmaceutically acceptable salt thereof:

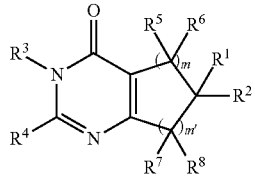

Formula IV

In some embodiments of compounds of Formula IV, or a pharmaceutically acceptable salt thereof, $R^3$ is hydrogen.

In some embodiments of compounds of Formula IV, or a pharmaceutically acceptable salt thereof, $R^4$ is cyclopropyl.

In some embodiments, the compound of Formula I, or a pharmaceutically acceptable salt thereof, is chosen from compounds of Formula V, or a pharmaceutically acceptable salt thereof:

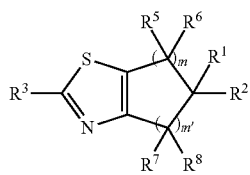

Formula V

In some embodiments of compounds of Formula V, or a pharmaceutically acceptable salt thereof, $R^3$ is chosen from
hydrogen,
cycloalkyl optionally substituted with one or two groups independently chosen from halo, lower alkyl, lower haloalkyl, and lower alkoxy,
heteroaryl optionally substituted with one or two groups independently chosen from halo, lower alkyl, lower haloalkyl, and lower alkoxy,
phenyl optionally substituted with one or two groups independently chosen from halo, lower alkyl, lower haloalkyl, and lower alkoxy,
benzyl optionally substituted on the aromatic portion with one or two groups independently chosen from halo, lower alkyl, lower haloalkyl, and lower alkoxy, and
—NHS(O)$_2$R$^{10}$ where R$^{10}$ is chosen from phenyl.

In some embodiments of compounds of Formula V, or a pharmaceutically acceptable salt thereof, $R^3$ is chosen from hydrogen, cyclopropyl, phenyl optionally substituted with one or two groups independently chosen from fluoro and methyl, pyrimidin-5-yl, 1H-pyrazol-5-yl optionally substituted with methyl, 1H-pyrazol-4-yl optionally substituted with methyl, pyridin-2-yl optionally substituted with methoxy, benzyl optionally substituted on the aromatic portion with trifluoromethyl, and —NHS(O)$_2$R$^{10}$ where R$^{10}$ is chosen from phenyl.

In some embodiments, the compound of Formula I, or a pharmaceutically acceptable salt thereof, is chosen from compounds of Formula VI, or a pharmaceutically acceptable salt thereof:

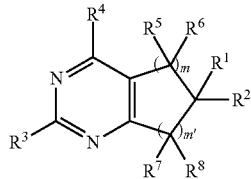

Formula VI

In some embodiments of compounds of Formula VI, or a pharmaceutically acceptable salt thereof, $R^3$ is chosen from hydrogen, lower alkyl, lower haloalkyl, cycloalkyl, phenyl optionally substituted with halo, and heteroaryl.

In some embodiments of compounds of Formula VI, or a pharmaceutically acceptable salt thereof, $R^3$ is chosen from hydrogen, trifluoromethyl, cyclopropyl, phenyl optionally substituted with halo, and pyridin-3-yl.

In some embodiments of compounds of Formula VI, or a pharmaceutically acceptable salt thereof, $R^4$ is hydrogen.

In some embodiments, the compound of Formula I, or a pharmaceutically acceptable salt thereof, is chosen from compounds of Formula VII, or a pharmaceutically acceptable salt thereof:

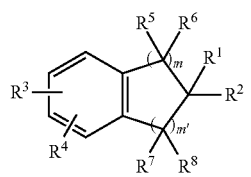

Formula VII

In some embodiments of compounds of Formula VII, or a pharmaceutically acceptable salt thereof, $R^3$ is hydrogen.

In some embodiments of compounds of Formula VII, or a pharmaceutically acceptable salt thereof, $R^4$ is hydrogen.

In some embodiments, the compound of Formula I, or a pharmaceutically acceptable salt thereof, is chosen from compounds of Formula VIII, or a pharmaceutically acceptable salt thereof:

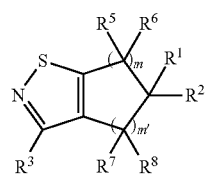

Formula VIII

In some embodiments of compounds of Formula VIII, or a pharmaceutically acceptable salt thereof, $R^3$ is phenyl optionally substituted with 1 to 3 substituents independently chosen from halo, alkyl, cycloalkyl, haloalkyl, hydroxyl, and alkoxy.

In some embodiments of compounds of Formula VIII, or a pharmaceutically acceptable salt thereof, $R^3$ is phenyl.

In some embodiments of compounds of Formula I-VIII, or a pharmaceutically acceptable salt thereof, $R^2$ is chosen from aryl optionally substituted with 1 to 3 substituents independently chosen from halo, alkyl, cycloalkyl, haloalkyl, hydroxyl, alkoxy, and nitrile.

In some embodiments of compounds of Formula I-VIII, or a pharmaceutically acceptable salt thereof, $R^2$ is chosen from phenyl optionally substituted with 1 to 3 substituents independently chosen from halo, alkyl, cycloalkyl, haloalkyl, hydroxyl, alkoxy, and nitrile.

In some embodiments of compounds of Formula I-VIII, or a pharmaceutically acceptable salt thereof, $R^2$ is chosen from phenyl optionally substituted with 1 to 3 substituent independently chosen from halo and alkyl.

In some embodiments of compounds of Formula I-VIII, or a pharmaceutically acceptable salt thereof, $R^2$ is chosen from phenyl and 3-fluoro-2-methylphenyl.

In some embodiments of compounds of Formula I-VIII, or a pharmaceutically acceptable salt thereof, $R^2$ is 3-fluoro-2-methylphenyl.

In some embodiments of compounds of Formula I-VIII, or a pharmaceutically acceptable salt thereof, m is 1 and m' is 1.

In some embodiments of compounds of Formula I-VIII, or a pharmaceutically acceptable salt thereof, m is 1 and m' is 2.

In some embodiments of compounds of Formula I-VIII, or a pharmaceutically acceptable salt thereof, m is 0 and m' is 2.

In some embodiments of compounds of Formula I-VIII, or a pharmaceutically acceptable salt thereof, m is 2 and m' is 2.

In some embodiments of compounds of Formula I-VIII, or a pharmaceutically acceptable salt thereof, $R^1$ is —N(OH)C(O)$R^9$. In some embodiments, $R^9$ is lower alkyl.

In some embodiments of compounds of Formula I-VIII, or a pharmaceutically acceptable salt thereof, $R^1$ is chosen from —C(O)NH(OH).

In some embodiments of compounds of Formula I-VIII, or a pharmaceutically acceptable salt thereof, for each occurrence, $R^5$, $R^6$, $R^7$, and $R^8$ are hydrogen.

Also provided is a compound of Formula I chosen from
(S)-5-(3-Fluoro-2-methylphenyl)-N-hydroxy-1-phenyl-1,4,5,6-tetrahydrocyclopenta[c]pyrazole-5-carboxamide;
(S)-5-(3-Fluoro-2-methylphenyl)-N-hydroxy-1-(o-tolyl)-1,4,5,6-tetrahydrocyclopenta[c]pyrazole-5-carboxamide;
(S)-5-(3-Fluoro-2-methylphenyl)-1-(2-fluorophenyl)-N-hydroxy-1,4,5,6-tetrahydrocyclopenta[c]pyrazole-5-carboxamide;
(S)-1-(3-Chlorophenyl)-5-(3-fluoro-2-methylphenyl)-N-hydroxy-1,4,5,6-tetrahydrocyclopenta[c]pyrazole-5-carboxamide;
(S)-5-(3-Fluoro-2-methylphenyl)-1-(4-fluorophenyl)-N-hydroxy-1,4,5,6-tetrahydrocyclopenta[c]pyrazole-5-carboxamide;
(S)-5-(3-Fluoro-2-methylphenyl)-1-(3-fluorophenyl)-N-hydroxy-1,4,5,6-tetrahydrocyclopenta[c]pyrazole-5-carboxamide;
(S)-1-(2-Chlorophenyl)-5-(3-fluoro-2-methylphenyl)-N-hydroxy-1,4,5,6-tetrahydrocyclopenta[c]pyrazole-5-carboxamide;
(S)-1-(4-Chlorophenyl)-5-(3-fluoro-2-methylphenyl)-N-hydroxy-1,4,5,6-tetrahydrocyclopenta[c]pyrazole-5-carboxamide;
(S)-5-(3-Fluoro-2-methylphenyl)-N-hydroxy-1-(p-tolyl)-1,4,5,6-tetrahydrocyclopenta[c]pyrazole-5-carboxamide;
(S)-1-(3-Chloro-2-fluorophenyl)-5-(3-fluoro-2-methylphenyl)-N-hydroxy-1,4,5,6-tetrahydrocyclopenta[c]pyrazole-5-carboxamide;
(S)-1-(2,6-Difluorophenyl)-5-(3-fluoro-2-methylphenyl)-N-hydroxy-1,4,5,6-tetrahydrocyclopenta[c]pyrazole-5-carboxamide;
(S)-1-(2,5-Dimethylphenyl)-5-(3-fluoro-2-methylphenyl)-N-hydroxy-1,4,5,6-tetrahydrocyclopenta[c]pyrazole-5-carboxamide;
(S)-1-(2,6-Dimethylphenyl)-5-(3-fluoro-2-methylphenyl)-N-hydroxy-1,4,5,6-tetrahydrocyclopenta[c]pyrazole-5-carboxamide;
(S)-1-(2-Chloro-6-fluorophenyl)-5-(3-fluoro-2-methylphenyl)-N-hydroxy-1,4,5,6-tetrahydrocyclopenta[c]pyrazole-5-carboxamide;
(S)-5-(3-Fluoro-2-methylphenyl)-1-(2-fluoro-6-methylphenyl)-N-hydroxy-1,4,5,6-tetrahydrocyclopenta[c]pyrazole-5-carboxamide;
(S)-5-(3-Fluoro-2-methylphenyl)-1-(5-fluoropyridin-2-yl)-N-hydroxy-1,4,5,6-tetrahydrocyclopenta[c]pyrazole-5-carboxamide;
(S)-1-(2,4-Difluorophenyl)-5-(3-fluoro-2-methylphenyl)-N-hydroxy-1,4,5,6-tetrahydrocyclopenta[c]pyrazole-5-carboxamide;
(S)-1-Cyclopentyl-5-(3-fluoro-2-methylphenyl)-N-hydroxy-1,4,5,6-tetrahydrocyclopenta[c]pyrazole-5-carboxamide;
(S)-5-(3-Fluoro-2-methylphenyl)-N-hydroxy-1-(pyrazin-2-yl)-1,4,5,6-tetrahydrocyclopenta[c]pyrazole-5-carboxamide;
(S)-1-(4-(Difluoromethoxy)phenyl)-5-(3-fluoro-2-methylphenyl)-N-hydroxy-1,4,5,6-tetrahydrocyclopenta[c]pyrazole-5-carboxamide;
(S)-2-(4-(Difluoromethoxy)phenyl)-5-(3-fluoro-2-methylphenyl)-N-hydroxy-2,4,5,6-tetrahydrocyclopenta[c]pyrazole-5-carboxamide;
(S)-5-(3-Fluoro-2-methylphenyl)-1-(4-fluoro-2-methylphenyl)-N-hydroxy-1,4,5,6-tetrahydrocyclopenta[c]pyrazole-5-carboxamide;
(S)-5-(3-Fluoro-2-methylphenyl)-2-(4-fluoro-2-methylphenyl)-N-hydroxy-2,4,5,6-tetrahydrocyclopenta[c]pyrazole-5-carboxamide;
(S)-5-(3-Fluoro-2-methylphenyl)-N-hydroxy-1-(m-tolyl)-1,4,5,6-tetrahydrocyclopenta[c]pyrazole-5-carboxamide;
(S)-5-(3-Fluoro-2-methylphenyl)-N-hydroxy-2-(m-tolyl)-2,4,5,6-tetrahydrocyclopenta[c]pyrazole-5-carboxamide;
(S)-5-(3-Fluoro-2-methylphenyl)-N-hydroxy-1-(3-methylpyridin-4-yl)-1,4,5,6-tetrahydrocyclopenta[c]pyrazole-5-carboxamide;
(S)-5-(3-Fluoro-2-methylphenyl)-N-hydroxy-2-(3-methylpyridin-4-yl)-2,4,5,6-tetrahydrocyclopenta[c]pyrazole-5-carboxamide;
(S)-2-(3-Chloropyridin-2-yl)-5-(3-fluoro-2-methylphenyl)-N-hydroxy-2,4,5,6-tetrahydrocyclopenta[c]pyrazole-5-carboxamide;
(S)-5-(3-Fluoro-2-methylphenyl)-2-(3-fluoropyridin-2-yl)-N-hydroxy-2,4,5,6-tetrahydrocyclopenta[c]pyrazole-5-carboxamide;
(R)-5-(3-Fluoro-2-methylphenyl)-N-hydroxy-1-phenyl-1,4,5,6-tetrahydrocyclopenta[c]pyrazole-5-carboxamide;
E1-(abs)-5-(3-Fluoro-2-methylphenyl)-N-hydroxy-1-phenyl-4,5,6,7-tetrahydro-1H-indazole-5-carboxamide;
E2-(abs)-5-(3-Fluoro-2-methylphenyl)-N-hydroxy-1-phenyl-4,5,6,7-tetrahydro-1H-indazole-5-carboxamide;
E1-(abs)-5-(3-Fluoro-2-methylphenyl)-2-(2-fluorophenyl)-N-hydroxy-4,5,6,7-tetrahydro-2H-indazole-5-carboxamide;
E2-(abs)-5-(3-Fluoro-2-methylphenyl)-2-(2-fluorophenyl)-N-hydroxy-4,5,6,7-tetrahydro-2H-indazole-5-carboxamide;
5-(3-Fluoro-2-methylphenyl)-N-hydroxy-1-(2,2,2-trifluoroethyl)-4,5,6,7-tetrahydro-1H-indazole-5-carboxamide and 5-(3-fluoro-2-methylphenyl)-N-hydroxy-2-(2,2,2-trifluoroethyl)-4,5,6,7-tetrahydro-2H-indazole-5-carboxamide;

5-(3-Fluoro-2-methylphenyl)-1-(4-fluorobenzyl)-N-hydroxy-4,5,6,7-tetrahydro-1H-indazole-5-carboxamide and 5-(3-fluoro-2-methylphenyl)-2-(4-fluorobenzyl)-N-hydroxy-4,5,6,7-tetrahydro-2H-indazole-5-carboxamide;

E1-(abs)-5-(3-Fluoro-2-methylphenyl)-N-hydroxy-1-(o-tolyl)-4,5,6,7-tetrahydro-1H-indazole-5-carboxamide;

E2-(abs)-5-(3-Fluoro-2-methylphenyl)-N-hydroxy-1-(o-tolyl)-4,5,6,7-tetrahydro-1H-indazole-5-carboxamide;

3-Cyclopropyl-5-(3-fluoro-2-methylphenyl)-N-hydroxy-2-(2,2,2-trifluoroethyl)-4,5,6,7-tetrahydro-2H-indazole-5-carboxamide;

2-Cyclopropyl-6-(3-fluoro-2-methylphenyl)-N-hydroxy-4-oxo-3,4,5,6,7,8-hexahydroquinazoline-6-carboxamide;

6-(3-Fluoro-2-methylphenyl)-N-hydroxy-2-(phenylsulfonamido)-4,5,6,7-tetrahydrobenzo[d]thiazole-6-carboxamide;

2-Cyclopropyl-6-(3-fluoro-2-methylphenyl)-N-hydroxy-4,5,6,7-tetrahydrobenzo[d]thiazole-6-carboxamide;

6-(3-Fluoro-2-methylphenyl)-N-hydroxy-2-(pyrimidin-5-yl)-4,5,6,7-tetrahydrobenzo[d]thiazole-6-carboxamide;

6-(3-Fluoro-2-methylphenyl)-N-hydroxy-4,5,6,7-tetrahydrobenzo[d]thiazole-6-carboxamide;

6-(3-Fluoro-2-methylphenyl)-N-hydroxy-5,6,7,8-tetrahydroquinazoline-6-carboxamide;

2-Cyclopropyl-6-(3-fluoro-2-methylphenyl)-N-hydroxy-5,6,7,8-tetrahydroquinazoline-6-carboxamide;

6-(3-Fluoro-2-methylphenyl)-N-hydroxy-2-phenyl-5,6,7,8-tetrahydroquinazoline-6-carboxamide;

(S)-2-(2-Chlorophenyl)-6-(3-fluoro-2-methylphenyl)-N-hydroxy-6,7-dihydro-5H-cyclopenta[d]pyrimidine-6-carboxamide;

(R)-2-(2-Chlorophenyl)-5-(3-fluoro-2-methylphenyl)-N-hydroxy-6,7-dihydro-5H-cyclopenta[d]pyrimidine-5-carboxamide;

(R)-2-Cyclopropyl-6-(3-fluoro-2-methylphenyl)-N-hydroxy-6,7-dihydro-5H-cyclopenta[d]pyrimidine-6-carboxamide;

(S)-2-Cyclopropyl-6-(3-fluoro-2-methylphenyl)-N-hydroxy-6,7-dihydro-5H-cyclopenta[d]pyrimidine-6-carboxamide;

(S)-2-Cyclopropyl-5-(3-fluoro-2-methylphenyl)-N-hydroxy-6,7-dihydro-5H-cyclopenta[d]pyrimidine-5-carboxamide;

(S)-5-(3-Fluoro-2-methylphenyl)-N-hydroxy-1-isopropyl-1,4,5,6-tetrahydrocyclopenta[c]pyrazole-5-carboxamide;

(R)-4-(3-Fluoro-2-methyl-phenyl)-1-phenyl-5,6-dihydrocyclopenta[c]pyrazole-4-carbohydroxamic acid;

(S)-6-(3-Fluoro-2-methyl-phenyl)-2-(4-fluorophenyl)-5,7-dihydrocyclopenta[d]pyrimidine-6-carbohydroxamic acid;

(S)-6-(3-Fluoro-2-methylphenyl)-N-hydroxy-2-(trifluoromethyl)-6,7-dihydro-5H-cyclopenta[d]pyrimidine-6-carboxamide;

(R)-2-Cyclopropyl-5-(3-fluoro-2-methylphenyl)-N-hydroxy-6,7-dihydro-5H-cyclopenta[d]pyrimidine-5-carboxamide;

(S)-1-Cyclopropyl-5-(3-fluoro-2-methylphenyl)-N-hydroxy-1,4,5,6-tetrahydrocyclopenta[c]pyrazole-5-carboxamide;

(R)-1-Cyclopropyl-4-(3-fluoro-2-methylphenyl)-N-hydroxy-1,4,5,6-tetrahydrocyclopenta[c]pyrazole-4-carboxamide;

(S)-6-(3-Fluoro-2-methylphenyl)-N-hydroxy-2-(pyridin-3-yl)-6,7-dihydro-5H-cyclopenta[d]pyrimidine-6-carboxamide;

E1-(abs)-5-(3-Fluoro-2-methylphenyl)-2-(2-fluorophenyl)-N-hydroxy-5,6-dihydro-4H-cyclopenta[d]thiazole-5-carboxamide;

E2-(abs)-5-(3-Fluoro-2-methylphenyl)-2-(2-fluorophenyl)-N-hydroxy-5,6-dihydro-4H-cyclopenta[d]thiazole-5-carboxamide;

5-(3-Fluoro-2-methylphenyl)-N-hydroxy-2-(3-(trifluoromethyl)benzyl)-5,6-dihydro-4H-cyclopenta[d]thiazole-5-carboxamide;

E1-(abs)-5-(3-Fluoro-2-methylphenyl)-2-(3-fluorophenyl)-N-hydroxy-5,6-dihydro-4H-cyclopenta[d]thiazole-5-carboxamide;

E2-(abs)-5-(3-Fluoro-2-methylphenyl)-2-(3-fluorophenyl)-N-hydroxy-5,6-dihydro-4H-cyclopenta[d]thiazole-5-carboxamide;

(R)-5-(3-Fluoro-2-methylphenyl)-2-(4-fluorophenyl)-N-hydroxy-5,6-dihydro-4H-cyclopenta[d]thiazole-5-carboxamide;

(S)-5-(3-Fluoro-2-methylphenyl)-2-(4-fluorophenyl)-N-hydroxy-5,6-dihydro-4H-cyclopenta[d]thiazole-5-carboxamide;

(S)-5-(3-Fluoro-2-methylphenyl)-N-hydroxy-2-(1-methyl-1H-pyrazol-5-yl)-5,6-dihydro-4H-cyclopenta[d]thiazole-5-carboxamide;

(R)-5-(3-Fluoro-2-methylphenyl)-N-hydroxy-2-(1-methyl-1H-pyrazol-5-yl)-5,6-dihydro-4H-cyclopenta[d]thiazole-5-carboxamide;

(R)-2-(1,3-Dimethyl-1H-pyrazol-5-yl)-5-(3-fluoro-2-methylphenyl)-N-hydroxy-5,6-dihydro-4H-cyclopenta[d]thiazole-5-carboxamide;

(R)-5-(3-Fluoro-2-methylphenyl)-N-hydroxy-2-(5-methoxypyridin-2-yl)-5,6-dihydro-4H-cyclopenta[d]thiazole-5-carboxamide;

(S)-2-Cyclopropyl-6-(3-fluoro-2-methylphenyl)-N-hydroxy-5,6-dihydro-4H-cyclopenta[d]thiazole-6-carboxamide;

(S)-6-(3-Fluoro-2-methylphenyl)-N-hydroxy-2-(o-tolyl)-5,6-dihydro-4H-cyclopenta[d]thiazole-6-carboxamide;

E1-(abs)-5-(3-Fluoro-2-methylphenyl)-2-(4-fluoro-2-methylphenyl)-N-hydroxy-5,6-dihydro-4H-cyclopenta[d]thiazole-5-carboxamide;

E2-(abs)-5-(3-Fluoro-2-methylphenyl)-2-(4-fluoro-2-methylphenyl)-N-hydroxy-5,6-dihydro-4H-cyclopenta[d]thiazole-5-carboxamide;

E1-(abs)-2-(1,5-Dimethyl-1H-pyrazol-4-yl)-5-(3-fluoro-2-methylphenyl)-N-hydroxy-5,6-dihydro-4H-cyclopenta[d]thiazole-5-carboxamide;

E2-(abs)-2-(1,5-dimethyl-1H-pyrazol-4-yl)-5-(3-fluoro-2-methylphenyl)-N-hydroxy-5,6-dihydro-4H-cyclopenta[d]thiazole-5-carboxamide;

(S)-6-(3-Fluoro-2-methylphenyl)-2-(4-fluorophenyl)-N-hydroxy-5,6-dihydro-4H-cyclopenta[d]thiazole-6-carboxamide;

(R)-5-(3-Fluoro-2-methylphenyl)-3-(4-fluorophenyl)-N-hydroxy-2-methyl-2,4,5,6-tetrahydrocyclopenta[c]pyrazole-5-carboxamide;

E1-(abs)-5-(3-fluoro-2-methylphenyl)-N-hydroxy-3-phenyl-5,6-dihydro-4H-cyclopenta[d]isothiazole-5-carboxamide;

E2-(abs)-5-(3-fluoro-2-methylphenyl)-N-hydroxy-3-phenyl-5,6-dihydro-4H-cyclopenta[d]isothiazole-5-carboxamide;

2-(3-Fluoro-2-methylphenyl)-N-hydroxy-2,3-dihydro-1H-indene-2-carboxamide;

2-Cyclopropyl-7-(3-fluoro-2-methylphenyl)-N-hydroxy-6,7,8,9-tetrahydro-5H-cyclohepta[d]pyrimidine-7-carboxamide;
E1-(abs)-6-(3-Fluoro-2-methylphenyl)-N-hydroxy-2-(2,2,2-trifluoroethyl)-2,4,5,6,7,8-hexahydrocyclohepta[c]pyrazole-6-carboxamide;
E2-(abs)-6-(3-Fluoro-2-methylphenyl)-N-hydroxy-2-(2,2,2-trifluoroethyl)-2,4,5,6,7,8-hexahydrocyclohepta[c]pyrazole-6-carboxamide;
N-Hydroxy-6-phenyl-2-(2,2,2-trifluoroethyl)-2,4,5,6,7,8-hexahydrocyclohepta[c]pyrazole-6-carboxamide;
E1-(abs)-N-Hydroxy-1-phenyl-2,3-dihydro-1H-indene-1-carboxamide;
E2-(abs)-N-hydroxy-1-phenyl-2,3-dihydro-1H-indene-1-carboxamide;
N-Hydroxy-2-phenyl-2,3-dihydro-1H-indene-2-carboxamide;
(R)-4-(3-Fluoro-2-methylphenyl)-2-(2-fluorobenzyl)-N-hydroxy-2,4,5,tetrahydrocyclopenta[c]pyrazole-4-carboxamide;
(S)-1-(2-Chloro-4-fluorophenyl)-5-(3-fluoro-2-methylphenyl)-N-hydroxy-1,4,5,6-tetrahydrocyclopenta[c]pyrazole-5-carboxamide;
(S)-2-(4,6-Dimethylpyrimidin-2-yl)-5-(3-fluoro-2-methylphenyl)-N-hydroxy-2,4,5,6-tetrahydrocyclopenta[c]pyrazole-5-carboxamide;
(S)-1-Benzyl-5-(3-fluoro-2-methylphenyl)-N-hydroxy-1,4,5,6-tetrahydrocyclopenta[c]pyrazole-5-carboxamide;
(R)-1-Benzyl-4-(3-fluoro-2-methylphenyl)-N-hydroxy-1,4,5,6-tetrahydrocyclopenta[c]pyrazole-4-carboxamide;
(R)-2-Benzyl-4-(3-fluoro-2-methylphenyl)-N-hydroxy-2,4,5,6-tetrahydrocyclopenta[c]pyrazole-4-carboxamide; and
(R)-2-Benzyl-4-(3-fluoro-2-methylphenyl)-N-hydroxy-2,4,5,6-tetrahydrocyclopenta[c]pyrazole-4-carboxamide,
or a pharmaceutically acceptable salt thereof.

Methods for obtaining the compounds, or pharmaceutically acceptable salts thereof, described herein will be apparent to those of ordinary skill in the art, suitable procedures being described, for example, in examples below, and in the references cited herein.

Also provided is a method for inhibiting at least one histone deacetylase. In some embodiments, at least one histone deacetylase is a class IIa HDAC. In some embodiments, at least one histone deacetylase is selected from HDAC4, HDAC5, HDAC7, and HDAC5. In some embodiments, the inhibition is in a cell. In some embodiments, the compound, or pharmaceutically acceptable salt thereof, described herein is selective for inhibiting at least one class II histone deacetylase. In some embodiments, the compound, or pharmaceutically acceptable salt thereof, described herein is a selective inhibitor of HDAC4 and/or HDAC5.

Also provided is a method of treating a condition or disorder mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a neurodegenerative pathology. Accordingly, also provided is a method of treating a neurodegenerative pathology mediated by HDAC in a subject in need of such a treatment, comprising administering to the subject a therapeutically effective amount of at least one compound, or pharmaceutically acceptable salt thereof, described herein.

In some embodiments, the neurodegenerative pathology is chosen from Alzheimer's disease, Parkinson's disease, neuronal intranuclear inclusion disease (NIID), Dentatorubral pallidolusyian atrophy (DRPLA), Friedreich's ataxia, Rubenstein-Taubi Syndrome, and polyglutamine diseases such as Huntington's disease; spinocerebellar ataxia 1 (SCA 1), spinocerebellar ataxia 7 (SCA 7), seizures, striatonigral degeneration, progressive supranuclear palsy, torsion dystonia, spasmodic torticollis, dyskinesis, familial tremor, Gilles de la Tourette syndrome, diffuse Lewy body disease, progressive supranuclear palsy, Pick's disease, primary lateral sclerosis, progressive neural muscular atrophy, spinal muscular atrophy, hypertrophic interstitial polyneuropathy, retinitis pigmentosa, hereditary optic atrophy, hereditary spastic paraplegia, Shy-Drager syndrome, Kennedy's disease, protein-aggregation-related neurodegeneration, Machado-Joseph's disease, spongiform encephalopathy, prion-related disease, multiple sclerosis (MS), progressive supranuclear palsy (Steel-Richardson-Olszewski disease), Hallervorden-Spatz disease, progressive familial myoclonic epilepsy, cerebellar degeneration, motor neuron disease, Werdnig-Hoffman disease, Wohlfart-Kugelberg-Welander disease, Charcot-Marie-Tooth disease, Dejerine-Sottas disease, retinitis pigmentosa, Leber's disease, progressive systemic sclerosis, dermatomyositis, and mixed connective tissue disease.

In some embodiments, the neurodegenerative pathology is an acute or chronic degenerative disease of the eye. Acute or chronic degenerative diseases of the eye include glaucoma, dry age-related macular degeneration, retinitis pigmentosa and other forms of heredodegenerative retinal disease, retinal detachment, macular pucker, ischemia affecting the outer retina, cellular damage associated with diabetic retinopathy and retinal ischemia, damage associated with laser therapy, ocular neovascular, diabetic retinopathy, rubeosis iritis, uveitis, Fuch's heterochromatic iridocyclitis, neovascular glaucoma, corneal neovascularization, retinal ischemia, choroidal vascular insufficiency, choroidal thrombosis, carotid artery ischemia, contusive ocular injury, retinopathy of permaturity, retinal vein occlusion, proliferative vitreoretinopathy, corneal angiogenesis, retinal microvasculopathy, and retinal eduema.

In some embodiments, the condition or disorder mediated by HDAC comprises a fibrotic disease such as liver fibrosis, cystic fibrosis, cirrhosis, and fibrotic skin diseases, e.g., hypertrophic scars, keloid, and Dupuytren's contracture. Accordingly, also provided is a method of treating a fibrotic disease mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a psychological disorder, such as depression, bipolar disease and dementia. In some embodiments, the condition or disorder mediated by HDAC comprises depression. Accordingly, also provided is a method of treating a psychological disorder, such as depression, mediated by HDAC in a subject in need of such a treatment, comprising administering to the subject a therapeutically effective amount of at least one compound, or pharmaceutically acceptable salt thereof, described herein. In some embodiments, the depression is chosen from major depressive disorder, and bipolar disorder.

In some embodiments, the condition or disorder mediated by HDAC comprises anxiety. Accordingly, also provided is a method of treating an anxiety mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises schizophrenia. Accordingly, also provided is a method of treating a schizophrenia mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a motor neuron disease, muscle atrophy/muscle wasting disorders, or amyotrophic lateral sclerosis (ALS). Accordingly, also provided is a method of treating a motor neuron disease, muscle atrophy/muscle wasting disorders, or amyotrophic lateral sclerosis (ALS) mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a cardiovascular condition. Accordingly, also provided is a method of treating a cardiovascular condition mediated by HDAC in a subject in need of such a treatment, comprising administering to the subject a therapeutically effective amount of at least one compound, or pharmaceutically acceptable salt thereof, described herein. In some embodiments, the cardiovascular condition is chosen from cardiomyopathy, cardiac hypertrophy, myocardial ischemia, heart failure, cardiac restenosis, and arteriosclerosis.

In some embodiments, the condition or disorder mediated by HDAC comprises cancer. Accordingly, also provided is a method of treating cancer mediated by HDAC in a subject in need of such a treatment, comprising administering to the subject a therapeutically effective amount of at least one compound, or pharmaceutically acceptable salt thereof, described herein. In some embodiments, the cancer is chosen from lymphoma, pancreatic cancer, colorectal cancer, hepatocellular carcinoma, Waldenstrom macroglobulinemia, hormone refractory cancer of the prostate, and leukaemia, breast cancer, lung cancer, ovarian cancer, prostate cancer, head and neck cancer, renal cancer, gastric cancer, brain cancer, B-cell lymphoma, peripheral T-cell lymphoma, and cutaneous T-cell lymphoma. In some further embodiments, the cancer is chosen from the following cancer types. Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma, cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma; and the sensitization of tumors to radiotherapy by administering the compound according to the invention before, during or after irradiation of the tumor for treating cancer.

In some embodiments, the condition or disorder mediated by HDAC comprises a condition or disorder treatable by immune modulation. Accordingly, also provided is a method of treating a condition or disorder treatable by immune modulation mediated by HDAC in a subject in need of such a treatment, comprising administering to the subject a therapeutically effective amount of at least one compound, or pharmaceutically acceptable salt thereof, described herein. In some embodiments, the condition or disorder treatable by immune modulation is chosen from asthma, irritable bowel syndrome, Crohn's disease, ulcerative colitis, bowel motility disorders, hypertension, rheumatoid arthritis, osteoarthritis, juvenile chronic arthritis, graft versus host disease, psoriasis, spondyloarthropathy, inflammatory bowel disease, alcoholic hepatitis, Sjogren's syndrome, ankylosing spondylitis, membranous glomerulopathy, discogenic pain, systemic lupus erythematosus, allergic bowel disease, coeliac disease, bronchitis, cystic fibrosis, rheumatoid spondylitis, osteoarthritis, uveitis, intis, and conjunctivitis, ischemic bowel disease, psoriasis, eczema, dermatitis, septic arthritis, gout, pseudogout, juvenile arthritis, Still's disease, Henoch-Schonlein purpura, psoriatic arthritis, myalgia, reactive arthritis (Reiter's syndrome), hemochromatosis, Wegener's granulomatosis, familial Mediterranean fever (FMF), HBDS (hyperimmunoglobulinemia D and periodic fever syndrome), TRAPS (TNF-alpha receptor associated periodic fever syndrome), chronic obstructive pulmonary disease, neonatal-onset multisystem inflammatory disease (NOMID), cryopyrin-associated periodic syndrome (CAPS), and familial cold autoinflammatory syndrome (FCAS).

In some embodiments, the condition or disorder mediated by HDAC comprises an allergic disease. Accordingly, also provided is a method of treating an allergic disease, mediated by HDAC in a subject in need of such a treatment, comprising administering to the subject a therapeutically effective amount of at least one compound, or pharmaceutically acceptable salt thereof, described herein. Allergic diseases include, but are not limited to, respiratory allergic diseases such as allergic rhinitis, hypersensitivity lung diseases, hypersensitivity pneumonitis, eosinophilic pneumonias, Loeffler's syndrome, chronic eosinophilic pneumonia, delayed-type hypersensitivity, interstitial lung diseases (ILD), idiopathic pulmonary fibrosis, polymyositis, dermatomyositis, systemic anaphylaxis, drug allergies (e.g., to penicillin or cephalosporins), and insect sting allergies.

In some embodiments, the condition or disorder mediated by HDAC comprises an infectious disease such as a fungal infection, bacterial infection, viral infection, and protozoal infection, e.g., malaria, giardiasis, leishmaniasis, Chaga's disease, dysentery, toxoplasmosis, and coccidiosis. In some embodiments, the condition or disorder mediated by HDAC comprises malaria. Accordingly, also provided is a method of treating an infectious disease, such as malaria, mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises autism or Rett syndrome. Accordingly, also provided is a method of treating autism or Rett syndrome mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a hematological disorder such as thalassemia, anemia, and sickle cell anemia. Accordingly, also provided is a method of treating a hematological disorder mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a metabolic disease such as prediabetes or diabetes (type I or II). Accordingly, also provided is a method of treating a metabolic disease, such as prediabetes or diabetes (type I or II), mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a disorder that may also be treated by progenitor/stem cell based therapies such as: disorders related to diabetes (organ failure, cerrosis, and hepatitis); central nervous system (CNS) disorders associated with dysregulation of progenitor cells in the brain (e.g., post-traumatic stress disorder (PTSD); tumors (e.g., retinoblastomas); disorders affecting oligodendrycoyte progenitor cells (e.g., astrocytomas and ependimal cell tumors); multiple sclerosis; demyelinating disorders such as the leukodystrophies; neuropathies associated with white matter loss; and cerebellar disorders such as ataxia; and olfactory progenitor disorders (e.g., anosmic conditions). Accordingly, also provided is a method of treating a disorder that is mediated by HDAC in a subject in need of such a treatment, comprising administering to the subject a therapeutically effective amount of at least one compound, or pharmaceutically acceptable salt thereof, described herein, either before, during, or after a treatment with progenitor/stem cell based therapies.

In some embodiments, the condition or disorder mediated by HDAC comprises a disorder related to the proliferation of epithelial and mesenchymal cells (e.g., tumors, wound healing, and surgeries). Accordingly, also provided is a method of treating a disorder related to the proliferation of epithelial and mesenchymal cells that is mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a disorder related to the proliferation of bone progenitors (e.g., osteoblasts and osteoclasts), disorders related to hair and epidermal progenitors (e.g., hair loss, cutaneous tumors, skin regeneration, burns, and cosmetic surgery); and disorders related to bone loss during menopause. Accordingly, also provided is a method of treating disorders related to the proliferation of bone progenitors, disorders related to hair and epidermal progenitors, or disorders related to bone loss that are mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC is a viral disorder for which blood cells become sensitized to other treatments after HDAC inhibition, following administering to the subject a therapeutically effective amount of at least one compound, or pharmaceutically acceptable salt thereof, as described herein.

In some embodiments, the condition or disorder mediated by HDAC is an immune disorder that may be co-treated with TNFα or other immune modulators, upon administering to the subject a therapeutically effective amount of at least one compound, or pharmaceutically acceptable salt thereof, as described herein.

In some embodiments, the condition or disorder mediated by HDAC comprises a graft rejection or transplant rejection. Accordingly, also provided is a method of treating a disorder related to a graft rejection or a transplant rejection that is mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a blood pressure disorder related to nitric oxide (NO) regulation (e.g., hypertension, erectile dysfunction, asthma; and ocular disorders as glaucoma). Accordingly, also provided is a method of treating a blood pressure disorder related to nitric oxide (NO) regulation that is mediated by HDAC in a subject in need of such a treatment, comprising administering to the subject a therapeutically effective amount of at least one compound, or pharmaceutically acceptable salt thereof, described herein. In some embodiments, the condition or disorder is a cardiac hypertrophic disorder. Accordingly, also provided is a method of treating a cardiac hypertrophic disorder that is mediated by HDAC in a subject in need of such a treatment, comprising administering to the subject a therapeutically effective amount of at least one compound, or pharmaceutically acceptable salt thereof, described herein.

Also provided are methods of treatment in which at least one compound, or pharmaceutically acceptable salt thereof, described herein is the only active agent given to the subject and also includes methods of treatment in which at least one compound, or pharmaceutically acceptable salt thereof, described herein is given to the subject in combination with one or more additional active agents.

In general, the compounds, or pharmaceutically acceptable salts thereof, described herein will be administered in a therapeutically effective amount by any of the accepted modes of administration for agents that serve similar utilities. The actual amount of the compound, i.e., the active ingredient, will depend upon numerous factors such as the severity of the disease to be treated, the age and relative health of the subject, the potency of the compound used, the route and form of administration, and other factors well known to the skilled artisan. The drug can be administered at least once a day, such as once or twice a day.

In some embodiments, the compounds, or pharmaceutically acceptable salts thereof, described herein are administered as a pharmaceutical composition. Accordingly, provided are pharmaceutical compositions comprising at least one compound, or pharmaceutically acceptable salt thereof, described herein, together with at least one pharmaceutically acceptable vehicle chosen from carriers, adjuvants, and excipients.

Pharmaceutically acceptable vehicles must be of sufficiently high purity and sufficiently low toxicity to render them suitable for administration to the animal being treated. The vehicle can be inert or it can possess pharmaceutical benefits. The amount of vehicle employed in conjunction with the compound, or pharmaceutically acceptable salt thereof, is sufficient to provide a practical quantity of material for administration per unit dose of the compound, or pharmaceutically acceptable salt thereof.

Exemplary pharmaceutically acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; synthetic oils; vegetable oils, such as peanut oil, cottonseed oil, sesame oil, olive oil, and corn oil; polyols such as propylene glycol, glycerine, sorbitol, mannitol, and polyethylene glycol; alginic acid; phosphate buffer solutions; emulsifiers, such as the TWEENS; wetting agents, such sodium lauryl sulfate; coloring agents; flavoring agents; tableting agents; stabilizers; antioxidants; preservatives; pyrogen-free water; isotonic saline; and phosphate buffer solutions.

Optional active agents may be included in a pharmaceutical composition, which do not substantially interfere with the activity of the compound, or pharmaceutically acceptable salt thereof, described herein.

Effective concentrations of at least one compound, or pharmaceutically acceptable salt thereof, described herein are mixed with a suitable pharmaceutically acceptable vehicle. In instances in which the compound, or pharmaceutically acceptable salt thereof, exhibits insufficient solubility, methods for solubilizing compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate.

Upon mixing or addition of a compound, or pharmaceutically acceptable salt thereof, described herein, the resulting mixture may be a solution, suspension, emulsion or the like. The form of the resulting mixture depends upon a number of factors, including the intended mode of administration and the solubility of the compound, or pharmaceutically acceptable salt thereof, in the chosen vehicle. The effective concentration sufficient for ameliorating the symptoms of the disease treated may be empirically determined The compounds, or pharmaceutically acceptable salts thereof, described herein may be administered orally, topically, parenterally, intravenously, by intramuscular injection, by inhalation or spray, sublingually, transdermally, via buccal administration, rectally, as an ophthalmic solution, or by other means, in dosage unit formulations.

Pharmaceutical compositions may be formulated for oral use, such as for example, tablets, troches, lozenges, aqueous or oily suspensions, dispersible powders or granules, emulsions, hard or soft capsules, or syrups or elixirs. Pharmaceutical compositions intended for oral use may be prepared according to any method known to the art for the manufacture of pharmaceutical compositions and such compositions may contain one or more agents, such as sweetening agents, flavoring agents, coloring agents and preserving agents, in order to provide pharmaceutically elegant and palatable preparations. In some embodiments, oral pharmaceutical compositions contain from 0.1 to 99% of at least one compound, or pharmaceutically acceptable salt thereof, described herein. In some embodiments, oral pharmaceutical compositions contain at least 5% (weight %) of at least one compound, or pharmaceutically acceptable salt thereof, described herein. Some embodiments contain from 25% to 50% or from 5% to 75% of at least one compound, or pharmaceutically acceptable salt thereof, described herein.

Orally administered pharmaceutical compositions also include liquid solutions, emulsions, suspensions, powders, granules, elixirs, tinctures, syrups, and the like. The pharmaceutically acceptable carriers suitable for preparation of such compositions are well known in the art. Oral pharmaceutical compositions may contain preservatives, flavoring agents, sweetening agents, such as sucrose or saccharin, taste-masking agents, and coloring agents.

Typical components of carriers for syrups, elixirs, emulsions and suspensions include ethanol, glycerol, propylene glycol, polyethylene glycol, liquid sucrose, sorbitol and water. Syrups and elixirs may be formulated with sweetening agents, for example glycerol, propylene glycol, sorbitol or sucrose. Such pharmaceutical compositions may also contain a demulcent.

The compound, or pharmaceutically acceptable salt thereof, described herein can be incorporated into oral liquid preparations such as aqueous or oily suspensions, solutions, emulsions, syrups, or elixirs, for example. Moreover, pharmaceutical compositions containing these at least one compound, or pharmaceutically acceptable salt thereof, can be presented as a dry product for constitution with water or other suitable vehicle before use. Such liquid preparations can contain conventional additives, such as suspending agents (e.g., sorbitol syrup, methyl cellulose, glucose/sugar, syrup, gelatin, hydroxyethyl cellulose, carboxymethyl cellulose, aluminum stearate gel, and hydrogenated edible fats), emulsifying agents (e.g., lecithin, sorbitan monsoleate, or acacia), non-aqueous vehicles, which can include edible oils (e.g., almond oil, fractionated coconut oil, silyl esters, propylene glycol and ethyl alcohol), and preservatives (e.g., methyl or propyl p-hydroxybenzoate and sorbic acid).

For a suspension, typical suspending agents include methylcellulose, sodium carboxymethyl cellulose, AVICEL RC-591, tragacanth and sodium alginate; typical wetting agents include lecithin and polysorbate 80; and typical preservatives include methyl paraben and sodium benzoate.

Aqueous suspensions contain the active material(s) in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents; may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol substitute, or condensation products of ethylene oxide with partial esters derived from fatty acids and hexitol anhydrides, for example polyethylene sorbitan substitute. The aqueous suspensions may also contain one or more preservatives, for example ethyl, or n-propyl p-hydroxybenzoate.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These pharmaceutical compositions may be preserved by the addition of an anti-oxidant such as ascorbic acid.

Pharmaceutical compositions may also be in the form of oil-in-water emulsions. The oily phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Tablets typically comprise conventional pharmaceutically acceptable adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, can be useful adjuvants for chewable tablets. Capsules (including time release and sustained release formulations) typically comprise one or more solid diluents disclosed above. The selection of carrier components often depends on secondary considerations like taste, cost, and shelf stability.

Such pharmaceutical compositions may also be coated by conventional methods, typically with pH or time-dependent coatings, such that the compound, or pharmaceutically acceptable salt thereof, is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methylcellulose phthalate, ethyl cellulose, Eudragit coatings, waxes and shellac.

Pharmaceutical compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable vehicle, for example as a solution in 1,3-butanediol. Among the acceptable vehicles that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid can be useful in the preparation of injectables.

The compound, or pharmaceutically acceptable salt thereof, described herein may be administered parenterally in a sterile medium. Parenteral administration includes subcutaneous injections, intravenous, intramuscular, intrathecal injection or infusion techniques. The compound, or pharmaceutically acceptable salt thereof, described herein, depending on the vehicle and concentration used, can either be suspended or dissolved in the vehicle. Advantageously, adjuvants such as local anesthetics, preservatives and buffering agents can be dissolved in the vehicle. In many pharmaceutical compositions for parenteral administration the carrier comprises at least 90% by weight of the total composition. In some embodiments, the carrier for parenteral administration is chosen from propylene glycol, ethyl oleate, pyrrolidone, ethanol, and sesame oil.

The compound, or pharmaceutically acceptable salt thereof, described herein may also be administered in the form of suppositories for rectal administration of the drug. These pharmaceutical compositions can be prepared by mixing the drug with a suitable non-irritating excipient that is solid at ordinary temperatures but liquid at rectal temperature and will therefore melt in the rectum to release the drug. Such materials include cocoa butter and polyethylene glycols.

The compound, or pharmaceutically acceptable salt thereof, described herein may be formulated for local or topical application, such as for topical application to the skin and mucous membranes, such as in the eye, in the form of gels, creams, and lotions and for application to the eye. Topical pharmaceutical compositions may be in any form including, for example, solutions, creams, ointments, gels, lotions, milks, cleansers, moisturizers, sprays, skin patches, and the like.

Such solutions may be formulated as 0.01%-10% isotonic solutions, pH 5-7, with appropriate salts. The compound, or pharmaceutically acceptable salt thereof, described herein may also be formulated for transdermal administration as a transdermal patch.

Topical pharmaceutical compositions comprising at least one compound, or pharmaceutically acceptable salt thereof, described herein can be admixed with a variety of carrier materials well known in the art, such as, for example, water, alcohols, aloe vera gel, allantoin, glycerine, vitamin A and E oils, mineral oil, propylene glycol, PPG-2 myristyl propionate, and the like.

Other materials suitable for use in topical carriers include, for example, emollients, solvents, humectants, thickeners and powders. Examples of each of these types of materials, which can be used singly or as mixtures of one or more materials, are as follows.

Representative emollients include stearyl alcohol, glyceryl monoricinoleate, glyceryl monostearate, propane-1,2-diol, butane-1,3-diol, mink oil, cetyl alcohol, iso-propyl isostearate, stearic acid, iso-butyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, iso-propyl myristate, iso-propyl palmitate, iso-propyl stearate, butyl stearate, polyethylene glycol, triethylene glycol, lanolin, sesame oil, coconut oil, *arachis* oil, castor oil, acetylated lanolin alcohols, petroleum, mineral oil, butyl myristate, isostearic acid, palmitic acid, isopropyl linoleate, lauryl lactate, myristyl lactate, decyl oleate, and myristyl myristate; propellants, such as propane, butane, iso-butane, dimethyl ether, carbon dioxide, and nitrous oxide; solvents, such as ethyl alcohol, methylene chloride, iso-propanol, castor oil, ethylene glycol monoethyl ether, diethylene glycol monobutyl ether, diethylene glycol monoethyl ether, dimethyl sulphoxide, dimethyl formamide, tetrahydrofuran; humectants, such as glycerin, sorbitol, sodium 2-pyrrolidone-5-carboxylate, soluble collagen, dibutyl phthalate, and gelatin; and powders, such as chalk, talc, fullers earth, kaolin, starch, gums, colloidal silicon dioxide, sodium polyacrylate, tetra alkyl ammonium smectites, trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, and ethylene glycol monostearate.

The compound, or pharmaceutically acceptable salt thereof, described herein may also be topically administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Other pharmaceutical compositions useful for attaining systemic delivery of the compound, or pharmaceutically acceptable salt thereof, include sublingual, buccal and nasal dosage forms. Such pharmaceutical compositions typically comprise one or more of soluble filler substances such as sucrose, sorbitol and mannitol, and binders such as acacia, microcrystalline cellulose, carboxymethyl cellulose, and hydroxypropyl methylcellulose. Glidants, lubricants, sweeteners, colorants, antioxidants and flavoring agents disclosed above may also be included.

Pharmaceutical compositions for inhalation typically can be provided in the form of a solution, suspension or emulsion that can be administered as a dry powder or in the form of an aerosol using a conventional propellant (e.g., dichlorodifluoromethane or trichlorofluoromethane).

The pharmaceutical compositions may also optionally comprise an activity enhancer. The activity enhancer can be chosen from a wide variety of molecules that function in different ways to enhance or be independent of therapeutic effects of the compound, or pharmaceutically acceptable salt thereof, described herein. Particular classes of activity enhancers include skin penetration enhancers and absorption enhancers.

Pharmaceutical compositions may also contain additional active agents that can be chosen from a wide variety of molecules, which can function in different ways to enhance the therapeutic effects of at least one compound, or pharmaceutically acceptable salt thereof, described herein. These optional other active agents, when present, are typically employed in the pharmaceutical compositions at a level ranging from 0.01% to 15%. Some embodiments contain from 0.1% to 10% by weight of the composition. Other embodiments contain from 0.5% to 5% by weight of the composition.

Also provided are packaged pharmaceutical compositions. Such packaged compositions include a pharmaceutical composition comprising at least one compound, or pharmaceutically acceptable salt thereof, described herein, and instructions for using the composition to treat a subject (typically a human patient). In some embodiments, the instructions are for using the pharmaceutical composition to treat a subject suffering a condition or disorder mediated by HDAC. The packaged pharmaceutical composition can include providing prescribing information; for example, to a patient or health care provider, or as a label in a packaged pharmaceutical composition. Prescribing information may include for example efficacy, dosage and administration, contraindication and adverse reaction information pertaining to the pharmaceutical composition.

In all of the foregoing the compound, or pharmaceutically acceptable salt thereof, can be administered alone, as mixtures, or in combination with other active agents.

The methods described herein include methods for treating Huntington's disease, including treating memory and/or cognitive impairment associated with Huntington's disease, comprising administering to a subject, simultaneously or sequentially, at least one compound, or pharmaceutically acceptable salt thereof, described herein and one or more additional agents used in the treatment of Huntington's disease such as, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone. In methods using simultaneous administration, the agents can be present in a combined composition or can be administered separately. As a result, also provided are pharmaceutical compositions comprising at least one compound, or pharmaceutically acceptable salt thereof, described herein and one or more additional pharmaceutical agents used in the treatment of Huntington's disease such as, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone. Similarly, also provided are packaged pharmaceutical compositions containing a pharmaceutical composition comprising at least one compound, or pharmaceutically acceptable salt thereof, described herein, and another composition comprising one or more additional pharmaceutical agents used in the treatment of Huntington's disease such as, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone.

Also provided are methods for Alzheimer's disease, including treating memory and/or cognitive impairment associated with Alzheimer's disease, comprising administering to a subject, simultaneously or sequentially, at least one compound, or pharmaceutically acceptable salt thereof, described herein and one or more additional agents used in the treatment of Alzheimer's disease such as, but not limited to, Reminyl, Cognex, Aricept, Exelon, Akatinol, Neotropin, Eldepryl, Estrogen and Clioquinol. In methods using simultaneous administration, the agents can be present in a combined composition or can be administered separately. Also provided are pharmaceutical compositions comprising at least one compound, or pharmaceutically acceptable salt thereof, described herein, and one or more additional pharmaceutical agents used in the treatment of Alzheimer's disease such as, but not limited to, Reminyl, Cognex, Aricept, Exelon, Akatinol, Neotropin, Eldepryl, Estrogen and Clioquinol. Similarly, also provided are packaged pharmaceutical compositions containing a pharmaceutical composition comprising at least one compound, or pharmaceutically acceptable salt thereof, described herein, and another composition comprising one or more additional pharmaceutical agents used in the treatment of Alzheimer's disease such as, but not limited to Reminyl, Cognex, Aricept, Exelon, Akatinol, Neotropin, Eldepryl, Estrogen and Clioquinol.

Also provided are methods for treating cancer comprising administering to a subject, simultaneously or sequentially, at least one compound, or pharmaceutically acceptable salt thereof, described herein and one or more additional agents used in the treatment of cancer such as, but not limited to, the following categories of anti-tumor agents (i) other cell cycle inhibitory agents that work by the same or different mechanisms from those defined hereinbefore, for example cyclin dependent kinase (CDK) inhibitors, in particular CDK2 inhibitors;

(ii) cytostatic agents such as antioestrogens (for example tamoxifen, toremifene, raloxifene, droloxifene, iodoxyfene), progestogens (for example megestrol acetate), aromatase inhibitors (for example anastrozole, letrazole, vorazole, exemestane), antiprogestogens, antiandrogens (for example flutamide, nilutamide, bicalutamide, cyproterone acetate), LHRH agonists and antagonists (for example goserelin acetate, luprolide), inhibitors of testosterone 5.alpha.-dihydroreductase (for example finasteride), anti-invasion agents (for example metalloproteinase inhibitors like marimastat and inhibitors of urokinase plasminogen activator receptor function) and inhibitors of growth factor function, (such growth factors include for example vascular endothelial growth factor, epithelial growth factor, platelet derived growth factor and hepatocyte growth factor such inhibitors include growth factor antibodies, growth factor receptor antibodies, tyrosine kinase inhibitors and serine/threonine kinase inhibitors);

(iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example *vinca* alkaloids like vincrisitine and taxoids like taxol, taxotere); topoisomerase inhibitors (for example epipodophyllotoxins like etoposide and teniposide, amsacrine, topotecan);

(iv) antiangiogenic agents that work by different mechanisms from those defined hereinbefore (for example receptor tyrosine kinases like Tie-2, inhibitors of integrin .alpha.v-.beta.3 function, angiostatin, razoxin, thalidomide), and including vascular targeting agents; and (v) differentiation agents (for example retinoic acid and vitamin D).

In methods using simultaneous administration, the agents can be present in a combined composition or can be administered separately. Also provided are pharmaceutical compositions comprising at least one compound, or pharmaceutically acceptable salt thereof, described herein, and one or more anti-tumor agent as described herein. Similarly, also provided are packaged pharmaceutical compositions containing a pharmaceutical composition comprising at least one compound, or pharmaceutically acceptable salt thereof, described herein, and another composition comprising one or more one or more anti-tumor agent as described herein. When used in combination with one or more additional pharmaceutical agent or agents, the described herein may be administered prior to, concurrently with, or following administration of the additional pharmaceutical agent or agents.

In some embodiments, the compounds, or pharmaceutically acceptable salts thereof, described herein, are administered in conjunction with surgery or radiotherapy, optionally in combination with one or more additional agents used in the treatment of cancer.

The dosages of the compounds described herein depend upon a variety of factors including the particular syndrome to be treated, the severity of the symptoms, the route of administration, the frequency of the dosage interval, the particular compound utilized, the efficacy, toxicology profile, pharmacokinetic profile of the compound, and the presence of any deleterious side-effects, among other considerations.

The compound, or pharmaceutically acceptable salt thereof, described herein is typically administered at dosage levels and in a manner customary for HDAC inhibitors. For example, the compound, or pharmaceutically acceptable salt thereof, can be administered, in single or multiple doses, by oral administration at a dosage level of generally 0.001-100 mg/kg/day, for example, 0.01-100 mg/kg/day, such as 0.1-70 mg/kg/day, for example, 0.5-10 mg/kg/day. Unit dosage forms can contain generally 0.01-1000 mg of at least one compound, or pharmaceutically acceptable salt thereof, described herein, for example, 0.1-50 mg of at least one compound, or pharmaceutically acceptable salt thereof, described herein. For intravenous administration, the compounds can be administered, in single or multiple dosages, at a dosage level of, for example, 0.001-50 mg/kg/day, such as 0.001-10 mg/kg/day, for example, 0.01-1 mg/kg/day. Unit dosage forms can contain, for example, 0.1-10 mg of at least one compound, or pharmaceutically acceptable salt thereof, described herein.

A labeled form of a compound, or pharmaceutically acceptable salt thereof, described herein can be used as a diagnostic for identifying and/or obtaining compounds that have the function of modulating an activity of HDAC as described herein. The compound, or pharmaceutically acceptable salt thereof, described herein may additionally be used for validating, optimizing, and standardizing bioassays.

By "labeled" herein is meant that the compound is either directly or indirectly labeled with a label which provides a detectable signal, e.g., radioisotope, fluorescent tag, enzyme, antibodies, particles such as magnetic particles, chemiluminescent tag, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In carrying out the procedures of the methods described herein, it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

EXAMPLES

The compounds, or pharmaceutically acceptable salts thereof, compositions, and methods described herein are further illustrated by the following non-limiting examples.

As used herein, the following abbreviations have the following meanings. If an abbreviation is not defined, it has its generally accepted meaning.

Abbreviations aq. Aqueous
DBU: 1,8-Diazabicyclo[5.4.0]undec-7-ene
DCM: Dichloromethane
DDQ: 2,3-Dichloro-5,6-dicyano-1,4-benzoquinone
DME: Dimethoxyethane
DIPEA: Diisopropylethylamine
DMAP: Dimethylaminopyridine
DMF: Dimethylformamide
DMSO: Dimethylsulfoxide
ES+: Electrospray Positive Ionisation
ES−: Electrospray Negative Ionisation
$Et_2O$: Diethyl ether
EtOAc: Ethyl acetate
h: Hour(s)
HPLC: High Performance Liquid Chromatography
i-hex: iso-Hexane
IPA: iso-Propyl alcohol
LCMS: Liquid Chromatography Mass Spectrometry
LiHMDS: Lithium bis(trimethylsilyl)amide
M: Mass
MeCN: Acetonitrile
MeOH: Methanol
min: Minute(s)
MS: Mass spectrum
NBS: N-Bromosuccinimide
NMR: Nuclear Magnetic Resonance
RT: Retention time
r.t.: Room temperature
sat.: Saturated
SFC: Supercritical Fluid Chromatography
TBAF: Tetrabutylammonium fluoride
tBu: tert-Butyl
TFA: Trifluoroacetic acid
TFFH: Fluoro-N,N,N',N'-tetramethylformamidinium hexafluorophosphate
THF: Tetrahydrofuran Compounds were named with the aid of the Cambridgesoft Chemistry Cartridge (v. 9.0.0.182) software.

All reactions involving air- or moisture-sensitive reagents were performed under a nitrogen atmosphere using dried solvents and glassware.

Analytical Conditions

| Analytical Method # | Description |
|---|---|
| Analytical method 1 | Solvents: Acetonitrile (far UV grade) with 0.1% (v/v) formic acid. Water (high purity via PureLab Option unit) with 0.1% formic acid Column: Phenomenex Luna 5 µm C18 (2), 100 × 4.6 mm (Plus guard cartridge) Flow Rate: 2 mL/min gradient: A: Water/formic acid B: MeCN/formic acid |
| | Time    A %    B % |
| | 0.00    95    5 |
| | 3.50    5    95 |
| | 5.50    5    95 |
| | 5.60    95    5 |
| | 6.50    95    5 |
| | Typical Injections 2-7 µL (concentration~0.2-1.0 mg/mL) |
| Analytical method 2 | Solvents: Acetonitrile (Far UV grade) with 0.1% (V/V) formic acid Water (High purity via PureLab Ultra unit) with 0.1% formic acid Column: Hichrom ACE 3 C18-AR mixed mode column 100 × 4.6 mm Flow Rate: 1 mL/min gradient: A: Water/formic B: MeCN/formic |
| | Time    A %    B % |
| | 0.00    98    2 |
| | 3.00    98    2 |
| | 12.00    0    100 |
| | 15.4    0    100 |
| | 15.5    98    2 |
| | 17    98    2 |
| | Typical Injections 0.2-10 µL |
| Analytical method 3 | Solvents: - Acetonitrile (Far UV grade) with 0.1% (V/V) formic acid Water (High purity via PureLab Ultra unit) with 0.1% formic acid Column. Supelco, Ascentis ® Express C18 or Hichrom Halo C18, 2.7 µm C18, 150 × 4.6 mm. Both latest technology fused core columns Flow Rate: 1 ml/min Gradient: A: Water/formic B: MeCN/formic |
| | Time    A %    B % |
| | 0.00    96    4 |
| | 3.00    96    4 |
| | 9.00    0    100 |
| | 13.6    0    100 |
| | 13.7    96    4 |
| | 15    96    4 |
| | Typical Injections 0.2-10 ul |

Preparation of Intermediates 1 and 2: (1S,4R)-4-(3-Fluoro-2-methylphenyl)-2-oxabicyclo[2.2.1]heptan-3-one and (R)-methyl-1-(3-fluoro-2-methylphenyl)-3-oxocyclopentanecarboxylate Method 1

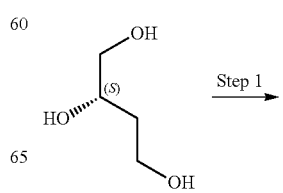

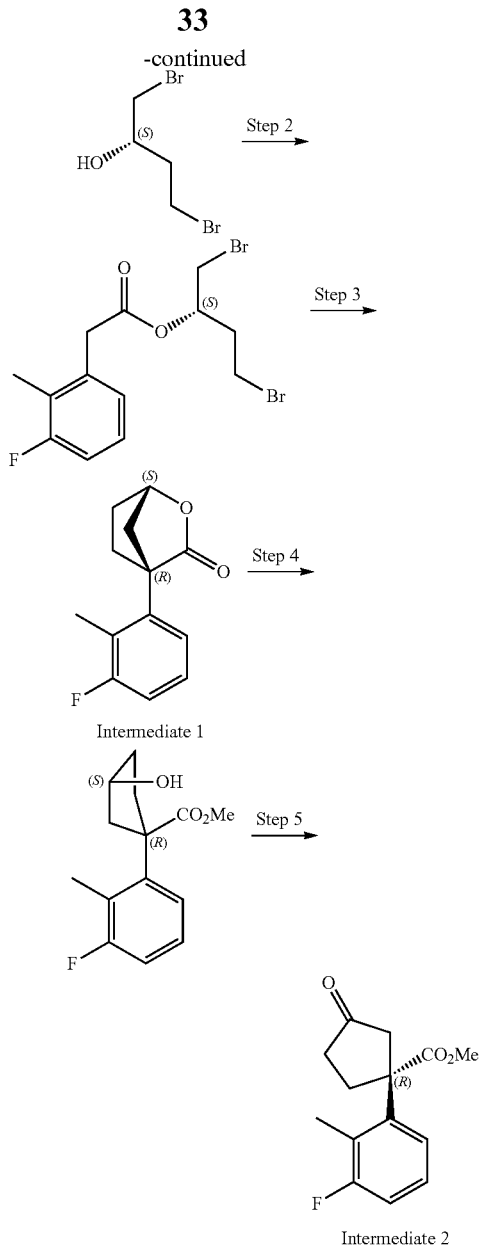

Intermediate 1

Intermediate 2

Step 1: (S)-1,4-Dibromobutan-2-ol

To a stirred solution of (S)-butane-1,2,4-triol (2 g, 18.9 mmol) and triphenylphosphine (9.9 g, 37.7 mmol) in DCM (100 mL) at 0° C. was added NBS (6.7 g, 37.7 mmol) portionwise. The mixture was allowed to warm to r.t. and stirred for 17 h. The reaction mixture was washed with water (2×100 mL) and sat. brine solution (100 mL) and the organics passed through a phase separator before concentrating in vacuo. The residue was dissolved in DCM (10 mL) and added to rapidly stirred Et$_2$O (200 mL). The resulting solid was removed by vacuum filtration. Additional solid precipitated in the filtrate during filtration, so this process was repeated several times to remove residual triphenylphosphine oxide. The filtrate was concentrated and the resulting oil purified by flash silica column chromatography (gradient elution 5% EtOAc in i-hex to 10% EtOAc in i-hex) to give the title compound as a colorless oil (1.5 g, 35%). $^1$H NMR δ (ppm)(CHCl$_3$-d): 4.09-4.01 (1H, m), 3.61-3.50 (3H, m), 3.42 (1H, dd, J=10.4, 6.7 Hz), 2.18 (1H, dd, J=5.4, 0.8 Hz), 2.13-2.01 (2H, m).

Step 2: (S)-1,4-Dibromobutan-2-yl 2-(3-fluoro-2-methylphenyl)acetate

To a stirred solution of (S)-1,4-dibromobutan-2-ol (1.43 g, 6.16 mmol) in DCM (30 mL) was added 2-(3-fluoro-2-methylphenyl)acetic acid (941 mg, 5.60 mmol), dicyclohexylcarbodiimide (1.27 g, 6.16 mmol) and DMAP (20 mg, catalytic) and the mixture stirred at r.t. for 17 h. The reaction was filtered and a white solid was removed by filtration and washed with DCM (3×25 mL). The filtrate was collected and washed with 1 M HCl$_{(aq)}$ (30 mL), sat. brine solution (30 mL) and the organics passed through a phase separator and concentrated. Purification by flash silica chromatography (gradient elution i-hex to 20% EtOAc in i-hex) gave the title compound as a white crystalline solid (2.06 g, 96%). $^1$H NMR δ (ppm)(CHCl$_3$-d): 7.15-7.07 (1H, m), 7.02-6.93 (2H, m), 5.20-5.12 (1H, m), 3.70 (2H, s), 3.58 (1H, dd, J=11.1, 4.7 Hz), 3.45 (1H, dd, J=11.1, 4.3 Hz), 3.34 (1H, ddd, J=10.3, 6.6, 5.5 Hz), 3.25 (1H, ddd, J=10.3, 8.4, 6.1 Hz), 2.35-2.26 (1H, m), 2.24 (3H, d, J=2.7 Hz), 2.26-2.12 (1H, m).

Step 3: (1S,4R)-4-(3-Fluoro-2-methylphenyl)-2-oxabicyclo[2.2.1]heptan-3-one (Intermediate 1)

To a stirred solution of (S)-1,4-dibromobutan-2-yl 2-(3-fluoro-2-methylphenyl)acetate (2.05 g, 5.37 mmol) in 1,4-dioxane (50 mL) at r.t., was added LiHMDS (11.8 mL, 11.8 mmol, 1 M in THF) at a rate of 1 mL/min. After complete addition, the mixture was stirred for 1 h and quenched with 1 M aq. HCl (20 mL) and then extracted into EtOAc (3×50 mL). The combined organics were washed with water (50 mL) and sat. brine solution (50 mL), separated, dried (MgSO$_4$), filtered and concentrated. Purification by flash silica chromatography (gradient elution i-hex to 5% EtOAc in i-hex) gave the title compound as a white crystalline solid (890 mg, 75%). MS (ES+) 221 (M+H)$^+$; $^1$H NMR δ (ppm) (CHCl$_3$-d): 7.17-7.08 (1H, m), 7.07-6.97 (2H, m), 5.00 (1H, d, J=2.10 Hz), 2.81 (1H, dd, J=10.4, 2.4 Hz), 2.40-2.18 (2H, m), 2.30 (3H, d, J=2.3 Hz), 2.13-2.07 (2H, m), 1.93 (1H, d, J=10.3 Hz).

Step 4: (1R,3S)-Methyl-1-(3-fluoro-2-methylphenyl)-3-hydroxycyclopentanecarboxylate To a stirred solution of (1R,4S)-4-(3-fluoro-2-methylphenyl)-2-oxabicyclo[2.2.1]heptan-3-one (890 mg, 4.05 mmol) in MeOH (30 mL) was added 4 M HCl in dioxane (1 mL). The mixture was heated to 60° C. for 17 h and then concentrated. Purification by flash silica chromatography (gradient elution i-hex to 30% EtOAc in i-hex) gave the title compound as a white crystalline solid (766 mg, 75% [95% based on recovered starting material]). $^1$H NMR δ (ppm) (CHCl$_3$-d): 7.18-7.06 (2H, m), 6.98-6.89 (1H, m), 4.42-4.37 (1H, m), 3.66 (3H, s), 2.74-2.69 (1H, m), 2.66-2.58 (1H, m), 2.55 (1H, d, J=7.85 Hz), 2.29-2.13 (3H, m), 2.13 (3H, d, J=2.7 Hz), 1.83-1.72 (1H, m).

Step 5: (R)-Methyl-1-(3-fluoro-2-methylphenyl)-3-oxocyclopentanecarboxylate (Intermediate 2)

To a solution of (1S,3R)-methyl-1-(3-fluoro-2-methylphenyl)-3-hydroxycyclopentanecarboxylate (766 mg, 3.04 mmol) in anhydrous DCM (20 mL) was added Dess-Martin Periodinane (1.55 g, 3.64 mmol). The reaction mixture was stirred at r.t. for 4 h. Reaction mixture was quenched with a mixture of 10% $Na_2S_2O_3$ and sat. $NaHCO_3$ solution (1:1, 50 mL) and then rapidly stirred for 30 min. Organic layers were extracted with further DCM (2×50 mL), then dried, filtered (phase separation cartridge) and concentrated to give a pale yellow oil. The residue was purified by flash silica column chromatography (gradient elution i-hex to 20% EtOAc in i-hex) to give the title compound as a colorless solid (656 mg, 86%). MS (ES+) 251 (M+H)+; $^1$H NMR δ (ppm) ($CHCl_3$-d): 7.28-7.19 (1H, m), 7.17-7.02 (2H, m), 3.76 (3H, s), 3.23 (1H, d, J=17.9 Hz), 2.88-2.79 (1H, m), 2.69-2.33 (4H, m), 2.19 (3H, d, J=2.7 Hz). SFC (Analytical) (Chiralpak IA 5/95 IPA/$CO_2$, 5.0 mL/min, 120 bar, 40° C.) RT 2.4 min; Chiral HPLC (Chiralpak IC 10/90 IPA/MeOH (50/50/0.1% formic acid)/heptane, 1.0 mL/min) RT 10.35 min (95.7% ee). Double recrystallization from hot heptane gave enantioenriched product (1.5 g, >99.5% ee).

Preparation of Intermediate 3: (S)-Methyl 1-(3-fluoro-2-methylphenyl)-3-oxocyclopentane-carboxylate Following Method 1 starting from (S)-butane-1,2,4-triol. Method 2

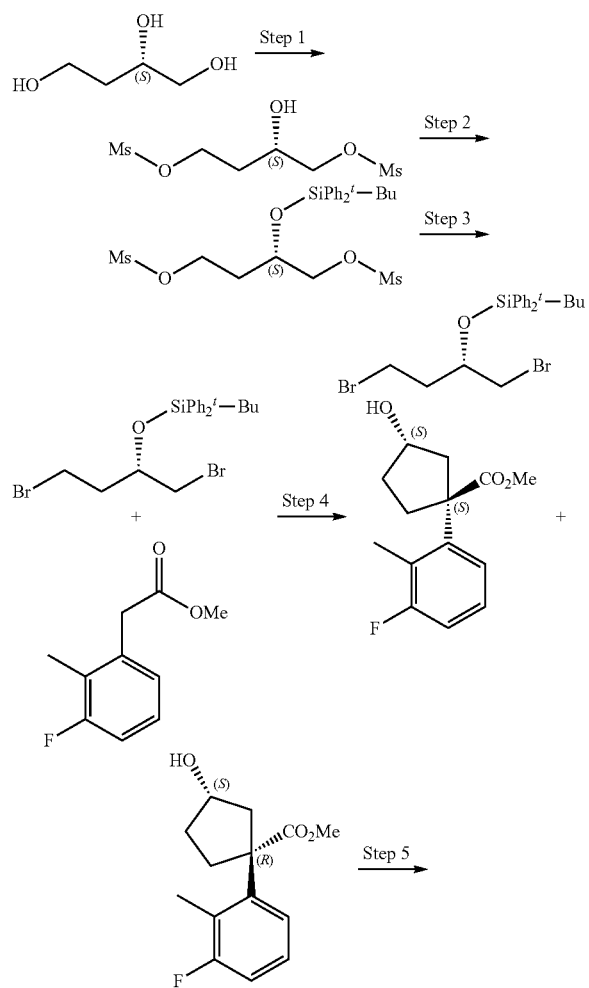

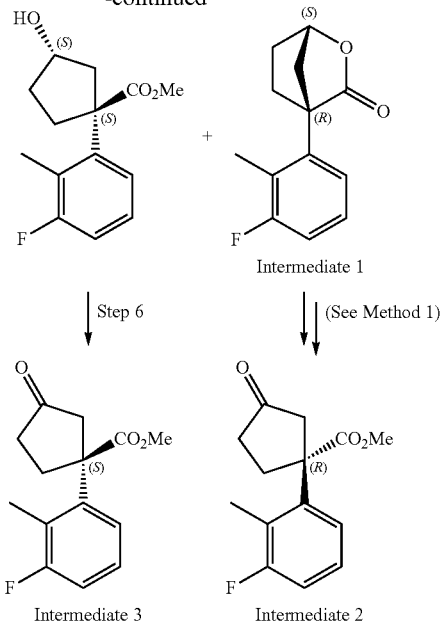

Step 1: (S)-2-Hydroxybutane-1,4-diyl dimethanesulfonate (S)-Butane-1,2,4-triol (20.0 g, 0.19 mol) was dissolved in anhydrous pyridine (85 mL). The reaction mixture was rapidly stirred whilst being cooled to −10° C. (NaCl/ice bath). Methanesulfonyl chloride (44.3 g, 30 mL, 0.40 mol) was then added drop-wise whilst maintaining internal flask temperature at <4° C. (~3 h). Once addition was complete the reaction mixture was stirred at r.t. for a further 1 h. After this time reaction was cooled to 4° C. and 2 M aq. HCl (200 mL) was added over 20 min. The resulting solution was partitioned with EtOAc (300 mL), washed with further 2 M aq. HCl (200 mL), dried, filtered (phase separation cartridge) and concentrated to give a yellow oil which partially solidified on standing. The residue was dissolved in the minimum hot EtOAc and left to stand at −20° C. for 16 h. Precipitated solids were filtered and washed with cold $Et_2O$/i-hex (1:9, 50 mL) to give the title compound as colorless crystals (26.8 g, 55%). [Purification can also be achieved via flash silica column chromatography ($Et_2O$ to EtOAc)—this gives a close running impurity which can be easily separated at the next step.] $R_f$=0.2 (66% EtOAc/i-hex); MS (ES+) 263 (M+H)+; $^1$H NMR δ (ppm): (DMSO-$d_6$): 5.33 (1H, s), 4.35-4.23 (2H, m), 4.19-3.99 (2H, m), 3.89-3.81 (1H, m), 3.19 (3H, s), 3.18 (3H, s), 1.94-1.84 (1H, m), 1.77-1.66 (1H, m).

Step 2: (S)-2-((tert-Butyldiphenylsilyl)oxy)butane-1,4-diyldimethanesulfonate

To a 4° C. solution of (S)-2-hydroxybutane-1,4-diyl dimethanesulfonate (23.2 g, 0.09 mol) in anhydrous DMF (75 mL) was added tert-butylchlorodiphenylsilane (36.5 g, 34.5 mL, 0.11 mol) followed by imidazole (10.0 g, 0.15 mol). The reaction mixture was stirred at 4° C. for 1 h then at r.t. for a further 16 h. The reaction mixture was quenched using ice water (200 mL) with rapid stirring for 30 min. The corresponding solution was partitioned with EtOAc (300 mL), washed with water (2×200 mL), and then sat. NaCl solution (250 mL). The combined organic layers were dried, filtered (phase separation cartridge) and concentrated to give a yellow oil. Purification by flash silica column chromatography (gradient elution i-hex to 50% EtOAc in i-hex) gave the title compound as a colorless glass (42.0 g, 93%). $R_f$=0.55 (66% EtOAc/i-hex); MS (ES+) 501 (M+H)$^+$; $^1$H NMR δ (ppm)(DMSO-d$_6$): 7.67-7.63 (4H, m), 7.52-7.41 (6H, m), 4.31-4.16 (2H, m), 4.13-4.01 (3H, m), 3.08 (3H, s), 3.02 (3H, s), 1.92 (2H, dd, J=12.2, 6.1 Hz), 1.02 (9H, s).

Step 3: (S)-tert-Butyl((1,4-dibromobutan-2-yl)oxy) diphenylsilane

To a solution of (S)-2-((tert-butyldiphenylsilyl)oxy)butane-1,4-diyl dimethanesulfonate (42.0 g, 0.08 mol) in anhydrous DMF (320 mL) was added lithium bromide (22.0 g, 0.25 mol). The reaction mixture was stirred at 105° C. for 1.5 h. The reaction mixture was cooled to r.t. and partitioned between EtOAc (500 mL) and water (300 mL). Organic layers were washed with further water (2×300 mL) and sat. NaCl solution (400 mL). The combined organic layers were dried, filtered (phase separation cartridge) and concentrated to give a yellow oil. Purification by flash silica column chromatography (gradient elution i-hex to 10% EtOAc in i-hex) gave the title compound as a colorless oil which darkens upon standing (30.0 g, 80%). $R_f$=0.80 (60% EtOAc/i-hex); MS (ES+) 471 (M+H)$^+$; $^1$H NMR δ (ppm)(DMSO-d$_6$): 7.69-7.63 (4H, m), 7.52-7.41 (6H, m), 4.07-3.99 (1H, m), 3.53-3.40 (4H, m), 2.10 (2H, dd, J=13.0, 6.5 Hz), 1.04 (9H, s).

Step 4: (1S,3S)-Methyl 1-(3-fluoro-2-methylphenyl)-3-hydroxycyclopentanecarboxylate To a solution of (S)-tert-butyl((1,4-dibromobutan-2-yl)oxy)diphenylsilane (6.43 g, 0.014 mol) and methyl 2-(3-fluoro-2-methylphenyl)acetate (2.0 g, 0.011 mol) in anhydrous DMF (80 mL) was added 18-crown-6 (0.2 g, catalytic). The reaction mixture was stirred at r.t. for 10 min then sodium hydride (60% dispersion in mineral oil 1.05 g, 0.03 mol) was added portion-wise over 1.5 h. Reaction mixture was stirred at r.t. for a further 16 h. The reaction mixture was cooled to 4° C. and quenched by drop-wise addition of 5% NaH$_2$PO$_4$ solution (15 mL). The solution was then partitioned between EtOAc (250 mL) and water (200 mL). The organic layer was washed with further water (2×150 mL), sat. NaCl solution (200 mL), then dried, filtered (phase separation cartridge) and concentrated to give a yellow oil. The resultant oil was dissolved in anhydrous THF (80 mL) and TBAF (1M in THF, 0.03 mol, 30 mL) was added. Reaction mixture was then stirred at r.t. for 3 h. After this time the reaction mixture was concentrated under reduced pressure and purified by flash silica column chromatography (gradient elution i-hex to 33% EtOAc in i-hex) to give the title compound as a colorless oil (2.10 g, 78%, 5:1 mixture of isomers). $R_f$=0.1 (20% EtOAc/i-hex); MS (ES+) 253 (M+H)$^+$.

Step 5: (1S,4R)-4-(3-Fluoro-2-methylphenyl)-2-oxabicyclo[2.2.1]heptan-3-one

To a solution of (1S,3S)-methyl 1-(3-fluoro-2-methylphenyl)-3-hydroxycyclopentanecarboxylate (5:1 (1S, 3S):(1R: 3S) mixture of isomers, 2.10 g, 0.0086 mol) in anhydrous acetonitrile (100 mL) was added DBU (1.44 g, 1.42 mL, 0.0095 mol). The reaction mixture was stirred at 80° C. for 20 h. The reaction mixture was cooled to r.t. and partitioned between DCM (125 mL) and 1 M HCl (100 mL). Organic layers were extracted, washed with water (100 mL), then dried, filtered (phase separation cartridge) and concentrated to give a yellow oil. The residue was purified by flash silica column chromatography (gradient elution i-hex to 40% EtOAc in i-hex) to give the title compound (1S,4R)-4-(3-fluoro-2-methylphenyl)-2-oxabicyclo[2.2.1]heptan-3-one as a colorless oil (256 mg); $R_f$=0.3 (33% EtOAc/i-hex); MS (ES+) 221 (M+H)$^+$; $^1$H NMR δ (ppm)(CHCl$_3$-d): 7.18-7.10 (1H, m), 7.09-6.98 (2H, m), 5.00 (1H, d, J=2.1 Hz), 2.81 (1H, dd, J=10.4, 2.4 Hz), 2.39-2.32 (1H, m), 2.32 (3H, d, J=2.8 Hz), 2.30-2.21 (1H, m), 2.15-2.07 (2H, m), 1.93 (1H, d, J=10.3 Hz); $^{19}$F NMR: −114.43; and unreacted starting material (1S,3S)-methyl 1-(3-fluoro-2-methylphenyl)-3-hydroxycyclopentanecarboxylateas a colorless oil (1.63 g); $R_f$=0.15 (33% EtOAc/i-hex); MS (ES+) consistent with target (M+H)$^+$; $^1$H NMR δ (ppm)(CHCl$_3$-d): 7.24 (1H, d, J=8.03 Hz), 7.19-7.11 (1H, m), 6.97-6.90 (1H, m), 4.56-4.49 (1H, m), 3.62 (3H, s), 3.07 (1H, dd, J=13.8, 6.6 Hz), 2.47-2.42 (2H, m), 2.11 (3H, d, J=2.8 Hz), 2.10-2.01 (1H, m), 1.92 (1H, ddd, J=13.9, 4.5, 1.1 Hz), 1.79-1.70 (1H, m), 1.38 (1H, d, J=4.2 Hz); $^{19}$F NMR: −114.83.

Step 6: (S)-Methyl 1-(3-fluoro-2-methylphenyl)-3-oxocyclopentanecarboxylate (Intermediate 3)

To a solution of (1S,3S)-methyl 1-(3-fluoro-2-methylphenyl)-3-hydroxycyclopentanecarboxylate (1.60 g, 6.5 mmol) in anhydrous DCM (100 mL) was added Dess-Martin Periodinane (3.32 g, 7.8 mmol). The reaction mixture was stirred at r.t. for 4 h. Reaction mixture was quenched with a mixture of 10% Na$_2$S$_2$O$_3$ and sat. NaHCO$_3$ solution (1:1, 100 mL) and then rapidly stirred for 30 min. Organic layers were extracted with further DCM (2×50 mL), then dried, filtered (phase separation cartridge) and concentrated to give a pale yellow oil. The residue was purified by flash silica column chromatography (gradient elution i-hex to 20% EtOAc in i-hex) to give the title compound as a colorless solid (1.42 g, 84%). $R_f$=0.25 (33% EtOAc/i-hex); $^1$H NMR δ (ppm) (CHCl$_3$-d): 7.28-7.19 (1H, m), 7.17-7.02 (2H, m), 3.76 (3H, s), 3.28 (1H, d, J=17.9 Hz), 2.88-2.79 (1H, m), 2.69-2.33 (4H, m), 2.19 (3H, d, J=2.7 Hz); SFC (Analytical) (Chiralpak IA 5/95 IPA/CO$_2$, 50 mL/min, 120 bar, 40° C.) RT 2.1 min (>99.5% ee); Chiral HPLC (Chiralpak IC 10/90 IPA/MeOH (50/50/0.1% formic acid)/heptane, 1.0 mL/min) RT 9.48 min.

Preparation of Intermediates 4-8: 3-tert-butyl 1-methyl 3'-fluoro-4-hydroxy-2'-methyl-1,2,5,6-tetrahydro-[1,1'-biphenyl]-1,3-dicarboxylate, methyl 1-(3-fluoro-2-methylphenyl)-4-oxocyclohexanecarboxylate, methyl 1-(3-fluoro-2-methylphenyl)-3-formyl-4-oxocyclohexanecarboxylate, methyl 2-amino-6-(3-fluoro-2-methylphenyl)-4,5,6,7-tetrahydrobenzo[d]thiazole-6-carboxylate and methyl 2-bromo-6-(3-fluoro-2-methylphenyl)-4,5,6,7-tetrahydrobenzo[d]thiazole-6-carboxylate was extracted with EtOAc which was then washed with water, brine and evaporated to dryness onto silica, then purified by flash chromatography to give 3-tert-butyl 1-methyl 3'-fluoro-4-hydroxy-2'-methyl-1,2,5,6-tetrahydro-[1,1'-biphenyl]-1,3-dicarboxylate as a white solid (2.14 g, 34%). $^1$H NMR δ (ppm)(CHCl$_3$-d): 7.20-7.05 (1H, m), 7.00-6.85 (2H, m), 3.70 (3H, s), 2.75 (2H, m), 2.4-2.15 (3H, m), 2.13 (3H, d, J=2.4 Hz), 1.85-1.70 (1H, m), 1.55 (9H, s). OH resonance not observed.

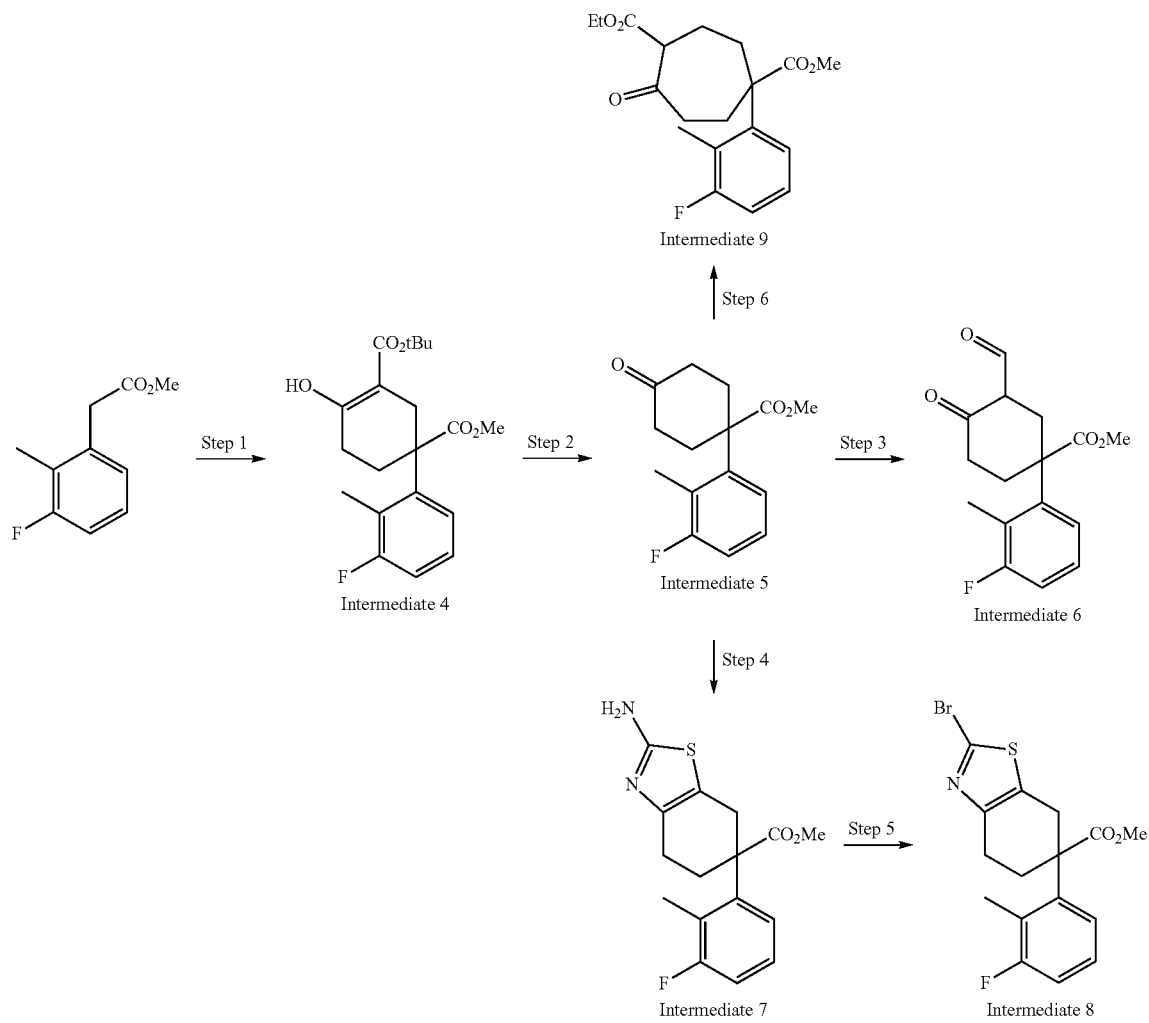

Step 1: 3-tert-Butyl 1-methyl 3'-fluoro-4-hydroxy-2'-methyl-1,2,5,6-tetrahydro-[1,1'-biphenyl]-1,3-dicarboxylate (Intermediate 4)

Methyl 2-(3-fluoro-2-methylphenyl)acetate (3.13 g, 17.2 mmol), DMF (30 mL) and t-butyl acrylate (5.22 mL, 36.12 mmol) were combined at room temperature under a nitrogen atmosphere. Reaction mixture was cooled with an ice bath and NaH (60% in oil) (3.44 g, 86 mmol) was added portionwise. Reaction mixture was stirred at room temperature for 20 h and then carefully quenched with sat. aq. NH$_4$Cl solution, with ice bath cooling. The reaction mixture Step 2: Methyl 1-(3-fluoro-2-methylphenyl)-4-oxocyclohexanecarboxylate (Intermediate 5)

Intermediate 4 (2.14 g, 5.88 mmol) and TFA (10 mL) were combined and stirred at room temperature for 20 h. The TFA was then removed by evaporation in vacuo and the residue was azeotroped with toluene. Toluene (100 mL), MeOH (10 mL) and NaHCO$_3$ (200 mg) were added and the mixture was heated to 105° C. for 20 h. The reaction mixture was then evaporated to dryness onto silica and purified by flash chromatography to give the title compound as a white solid (799 mg, 52%). LCMS (ES+) 265 (M+H)$^+$; $^1$H NMR δ (ppm)(CHCl$_3$-d): 7.22-7.15 (2H, m), 7.05-6.95 (1H, m), 3.72 (3H, s), 2.77-2.64 (4H, m), 2.46-2.41 (2H, m), 2.27-2.20 (2H, m), 2.21 (3H, d, J=2.4 Hz).

Step 3: Methyl 1-(3-fluoro-2-methylphenyl)-3-formyl-4-oxocyclohexanecarboxylate (Intermediate 6)

tBuOK (233 mg, 2.08 mmol) and THF were combined under a nitrogen atmosphere. The reaction mixture was cooled with an ice bath and ethyl formate (0.61 mL, 7.56 mmol) was added dropwise—care: effervescence. After 20 min intermediate 5 (500 mg, 1.89 mmol) was added dropwise as a solution in ethyl formate (2.5 mL). The reaction mixture was stirred for a further 1 h with ice bath cooling then diluted with EtOAc and washed with 1 N HCl, dried (MgSO$_4$) and evaporated to dryness to give the title compound as a brown gum (516 mg, 94%). LCMS (ES−) 291 (M−H)$^-$.

Step 4: Methyl 2-amino-6-(3-fluoro-2-methylphenyl)-4,5,6,7-tetrahydrobenzo[d]thiazole-6-carboxylate (Intermediate 7)

Intermediate 5 (550 mg, 2.08 mmol), thiourea (228 mg, 3 mmol) and AcOH (10 mL) were combined in a sealed tube. Bromine (0.107 mL, 2.08 mmol) was added and the mixture was heated to 65° C. for 18 h. Reaction mixture was cooled and evaporated to dryness. Residue was partitioned between 2 N NaOH soln. and EtOAc. Extracted with EtOAc (2x), organics were then dried (MgSO$_4$) and evaporated to dryness to give the title compound as a tan solid (641 mg, 96%). LCMS (ES+) 321 (M+H)$^+$.

Step 5: Methyl 2-bromo-6-(3-fluoro-2-methylphenyl)-4,5,6,7-tetrahydrobenzo[d]thiazole-6-carboxylate (Intermediate 8)

Intermediate 7 (1.94 g, 6.06 mmol), CuBr$_2$ (1.49 g, 6.67 mmol) and MeCN (100 mL) were combined. t-Butyl nitrite (0.94 mL, 7.88 mmol) was added dropwise—care: exotherm. After stirring for 2 h the reaction mixture was quenched with 1N HCl and extracted with EtOAc (2x), dried (MgSO$_4$) and evaporated to dryness to give the title compound as a brown solid (2.08 g, 89%). LCMS (ES+) 384/386 (M+H)$^+$.

Step 6: 4-Ethyl 1-methyl 1-(3-fluoro-2-methylphenyl)-5-oxocycloheptane-1,4-dicarboxylate (Intermediate 9)

Intermediate 5 (1.0 g, 3.79 mmol) was dissolved in dry DCM (11 mL) and cooled to 0° C. under a nitrogen atmosphere. Triethyloxonium tetrafluoroborate (4.6 mL, 4.55 mmol, 1.0 M in DCM) was added in one portion. Ethyl diazoacetate (0.48 mL, 4.55 mmol) was added dropwise over 10 min maintaining the internal temperature at 0° C. The reaction was stirred at 0° C. for 3 h then quenched with saturated sodium bicarbonate solution. The reaction mixture was transferred to a separating funnel and extracted with DCM (x2). The combined organic extracts were washed with water, dried (magnesium sulfate), filtered and evaporated to dryness to afford the title compound as a yellow oil (1.47 g, >100%). NMR indicated a mixture of enol and ketone forms. Used without further purification in the next step.

Preparation of Intermediate 10: (S)-Methyl 2-bromo-6-(3-fluoro-2-methylphenyl)-5,6-dihydro-4H-cyclopenta[d]thiazole-6-carboxylate

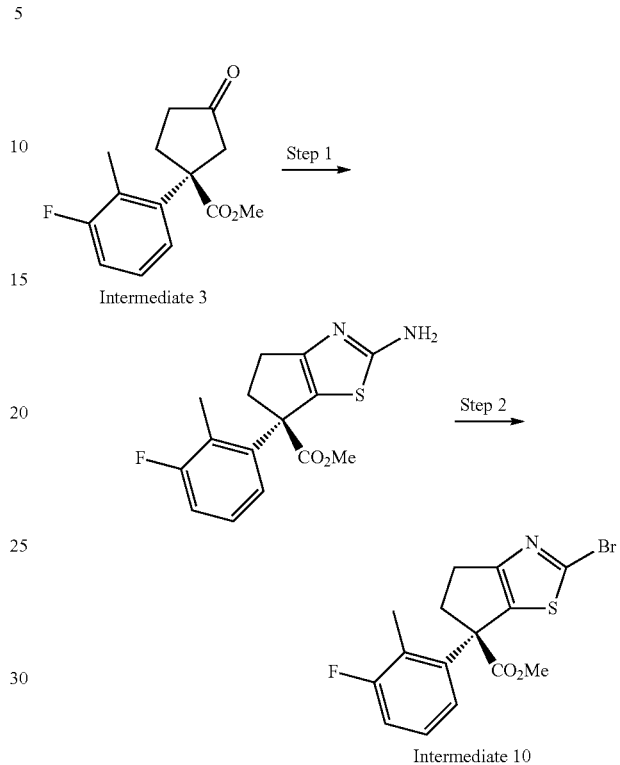

Step 1: (S)-Methyl 2-amino-6-(3-fluoro-2-methylphenyl)-5,6-dihydro-4H-cyclopenta[d]thiazole-6-carboxylate Intermediate 3 (0.75 g, 3.0 mmol), thiourea (0.25 g, 3.3 mmol) and bromine (0.52 g, 3.3 mmol) were added to acetic acid (10 mL) and heated to 100° C. for 16.5 h. The reaction was cooled, diluted with EtOAc (50 mL) and washed with NaOH (2N, 2x50 mL), water then brine followed by concentration under vacuum to give the title compound (0.66 g) which was used in the next step without further purification. LCMS (ES+) 307 (M+H)$^+$.

Step 2: (S)-Methyl 2-bromo-6-(3-fluoro-2-methylphenyl)-5,6-dihydro-4H-cyclopenta[d]thiazole-6-carboxylate To a solution of (S)-methyl 2-amino-6-(3-fluoro-2-methylphenyl)-5,6-dihydro-4H-cyclopenta[d]thiazole-6-carboxylate (0.54 g, 1.79 mmol) and copper (II) bromide (0.44 g, 1.96 mmol) in MeCN (10 mL) was added tert-butyl nitrite, drop-wise and the reaction mixture stirred at 20° C. for 0.6 h. The reaction was quenched on HCl (1 N, 50 mL), extracted into DCM (75 mL) and subjected to an aqueous workup. Separation of the organic and concentration under vacuum gave crude the title compound (0.63 g) which was used in the next step without further purification. LCMS (ES+) 370/372 (M+H)$^+$.

Preparation of Intermediates 11 and 12: Methyl 3-bromo-1-(3-fluoro-2-methylphenyl)-4-oxocyclopentanecarboxylate and methyl 2-bromo-5-(3-fluoro-2-methylphenyl)-5,6-dihydro-4H-cyclopenta[d]thiazole-5-carboxylate

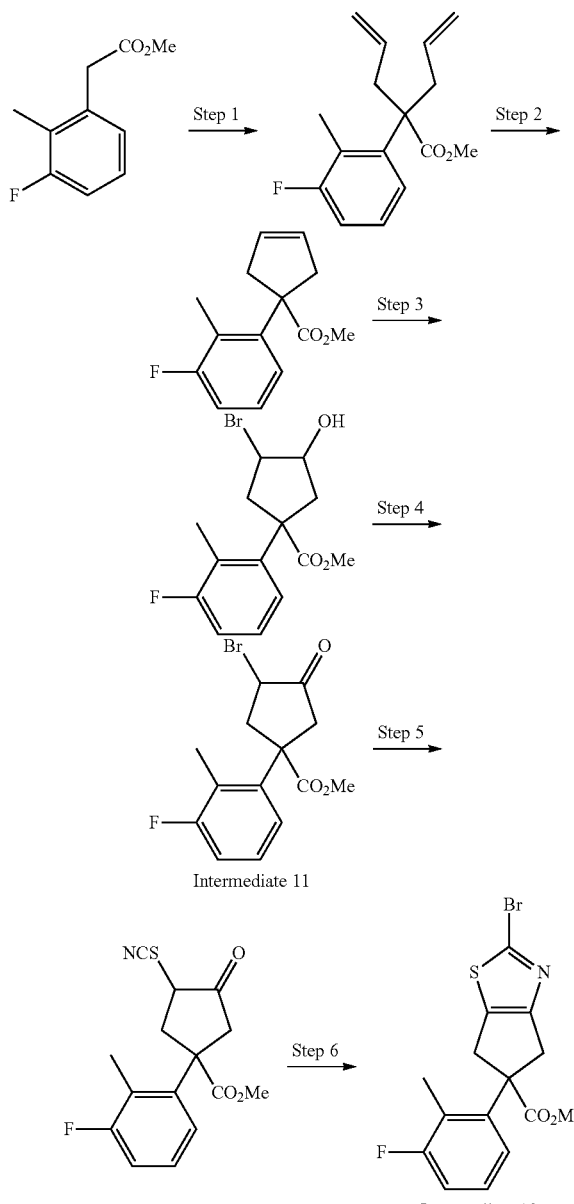

Step 1: Methyl 2-allyl-2-(3-fluoro-2-methylphenyl)pent-4-enoate

A solution of methyl 2-(3-fluoro-2-methylphenyl)acetate (1.95 g, 10.7 mmol) and allyl bromide (0.96 mL, 10.7 mmol) in dry DMF (20 mL) was treated at r.t under $N_2$ with NaH (60 wt % in oil, 448 mg, 10.7 mmol) and stirred for 2 h. After this time a further equivalent of allyl bromide and NaH were added, followed by a final addition of 0.5 equivalents of allyl bromide and NaH 1 h later. 1 h after the final addition the reaction was quenched with $H_2O$ (1 mL), diluted with EtOAc (100 mL) and washed with water (4×20 mL) and brine (20 mL). The organic layer was dried ($Na_2SO_4$) and concentrated to give 2.96 g yellow liquid that was used without further purification.

Step 2: Methyl 1-(3-fluoro-2-methylphenyl)cyclopent-3-enecarboxylate

A solution of methyl 2-allyl-2-(3-fluoro-2-methylphenyl)pent-4-enoate (2.96 g from previous step, ~10.7 mmol) and Grubbs $2^{nd}$ generation catalyst (210 mg, 0.25 mmol) in DCM (300 mL) was stirred under $N_2$ at r.t for 24 h. The mixture was concentrated onto silica and purified by flash silica chromatography (gradient elution, 0-50% EtOAc in i-hex) to give the title compound (1.85 g) as a pale brown liquid of approximately 80% purity.

Step 3: Methyl 3-bromo-1-(3-fluoro-2-methylphenyl)-4-hydroxycyclopentanecarboxylate A solution of methyl 1-(3-fluoro-2-methylphenyl)cyclopent-3-enecarboxylate (1.66 g, 7.09 mmol), NBS (1.39 g, 7.81 mmol) and ammonium acetate (80.3 mg, 1.04 mmol) in acetone (25 mL) and water (6 mL) was stirred at r.t for 2 h. After evaporating solvents the mixture was partitioned between water (20 mL) and DCM (40 mL) and the organic layer concentrated. The residue was purified by flash silica chromatography (gradient elution of 0% to 100% EtOAc in i-hex) to give the title compound as a colorless liquid (1.74 g, 5.25 mmol, 74%) as a mixture of stereoisomers.

Step 4: Methyl 3-bromo-1-(3-fluoro-2-methylphenyl)-4-oxocyclopentanecarboxylate (Intermediate 11)

A suspension of methyl 3-bromo-1-(3-fluoro-2-methylphenyl)-4-hydroxycyclopentanecarboxylate (1.74 g, 5.25 mmol) and Dess-Martin periodinane (2.44 g, 5.75 mmol) in DCM (50 mL) was stirred at r.t for 16 h. The reaction mixture was concentrated onto silica and purified by flash silica chromatography (gradient elution of 0% to 100% EtOAc in i-hex) to give the title compound as a colorless liquid (1.58 g, 4.80 mmol, 91%) as a mixture of stereoisomers.

Step 5: Methyl 1-(3-fluoro-2-methylphenyl)-3-oxo-4-thiocyanatocyclopentanecarboxylate A solution of intermediate 11 (800 mg, 2.43 mmol) and potassium thiocyanate (500 mg, 5.15 mmol) in dry acetonitrile (8 mL) was heated at 100° C. under microwave irradiation for 10 min. After cooling to r.t. the mixture was combined with two other identical reactions and partitioned between water (20 mL) and DCM (60 mL), dried (phase separator) and concentrated. Purification by flash silica chromatography (gradient elution, 0-100% EtOAc in i-hex) gave the title compound (2.07 g, 6.74 mmol, 93%) as white prisms in a 2:1 diastereomeric mixture.

Step 6: Methyl 2-bromo-5-(3-fluoro-2-methylphenyl)-5,6-dihydro-4H-cyclopenta[d]thiazole-5-carboxylate (Intermediate 12)

A solution of methyl 1-(3-fluoro-2-methylphenyl)-3-oxo-4-thiocyanatocyclopentanecarboxylate (338 mg, 1.10 mmol) in HBr (33 wt % in AcOH, 1 mL) and AcOH (3 mL) was heated at 100° C. under microwave irradiation for 10 min. After cooling to rt, the mixture was combined with three other identical reactions and poured into water (30 mL). DCM (50 mL) was added and the mixture was stirred vigorously at r.t for 5 min. The DCM layer was washed with sat. aq. NaHCO₃ (40 mL), dried (phase separator) and concentrated. Purification by flash silica chromatography (gradient elution, 0-50% EtOAc in i-hex) gave the title compound (620 mg, 1.67 mmol, 51%) as a colorless liquid.

Preparation of Intermediates 13-16: (1R)-Methyl 3-bromo-1-(3-fluoro-2-methylphenyl)-4-oxocyclopentanecarboxylate

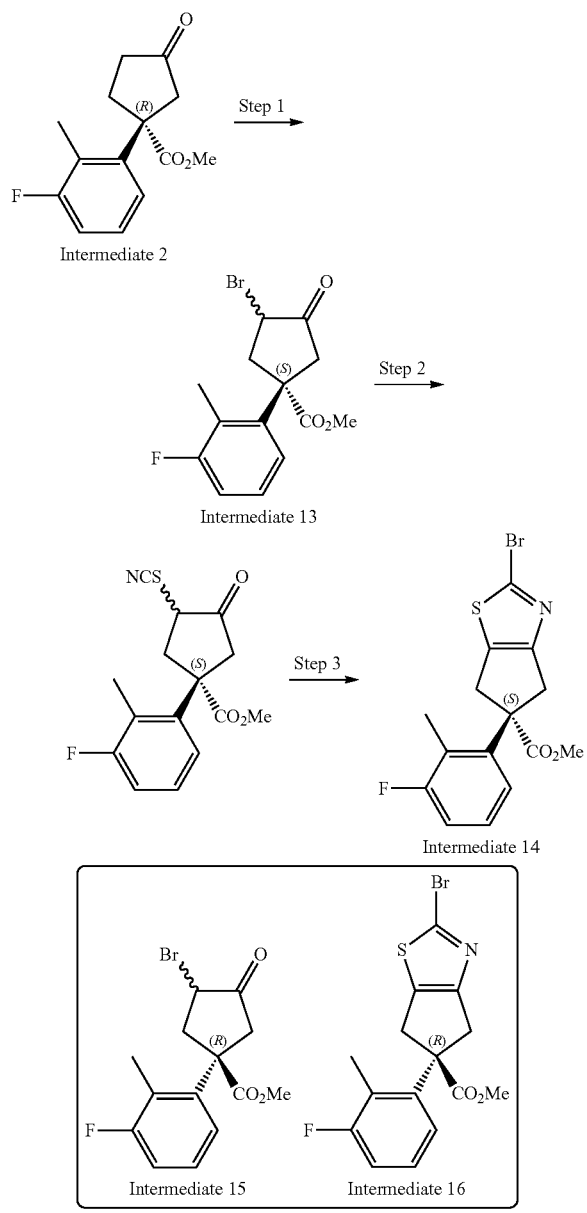

Step 1: (1R)-Methyl 3-bromo-1-(3-fluoro-2-methylphenyl)-4-oxocyclopentanecarboxylate (Intermediate 13)

To a cooled solution of Intermediate 2 (4.5 g, 18 mmol) in DCM (100 mL) at −78° C. was added 4 M HCl in dioxane (0.45 mL). This was stirred for 5 min before dropwise addition of bromine (2.88 g, 18 mmol). The reaction was stirred at −78° C. for 1 h then removed from the ice-bath. After an additional 1 h at r.t the reaction was diluted with water (100 mL) and the organics collected. The aqueous portion was re-extracted with DCM (100 mL), and the combined organics passed through a phase separator and concentrated. Purification by flash chromatography (10% EtOAc in i-hex) gave the title compound as a colorless oil which crystallized on standing (2.37 g, 40%). LCMS (ES+) 329/331 (M+H)⁺.

Step 2: (S)-Methyl 1-(3-fluoro-2-methylphenyl)-3-oxo-4-thiocyanatocyclopentanecarboxylate A solution of Intermediate 13 (800 mg, 2.43 mmol) and potassium thiocyanate (500 mg, 5.15 mmol) in dry acetonitrile (8 mL) was heated at 100° C. under microwave irradiation for 10 min. After cooling to r.t. the mixture was combined with two other identical reactions and partitioned between water (20 mL) and DCM (60 mL), dried (phase separator) and concentrated. Purification by flash silica chromatography (gradient elution, 0-100% EtOAc in i-hex) gave the title compound (2.07 g, 6.74 mmol, 93%) as white prisms in a 2:1 diastereomeric mixture. LCMS (ES+) 308 (M+H)⁺.

Step 3: (S)-Methyl 2-bromo-5-(3-fluoro-2-methylphenyl)-5,6-dihydro-4H-cyclopenta[d]thiazole-5-carboxylate (Intermediate 14)

A solution of (S)-methyl 1-(3-fluoro-2-methylphenyl)-3-oxo-4-thiocyanatocyclopentanecarboxylate (338 mg, 1.10 mmol) in HBr (33 wt % in AcOH, 1 mL) and AcOH (3 mL) was heated at 100° C. under microwave irradiation for 10 min. After cooling to r.t. the mixture was combined with three other identical reactions and poured into water (30 mL). DCM (50 mL) was added and the mixture was stirred vigorously at r.t. for 5 min. The DCM layer was washed with sat. aq. NaHCO₃ (40 mL), dried (phase separator) and concentrated. Purification by flash silica chromatography (gradient elution, 0-50% EtOAc in i-hex) gave the title compound (620 mg, 1.67 mmol, 51%) as a colorless liquid.

Steps 1-3 can be performed starting from Intermediate 3 to access Intermediate 15 and Intermediate 16.

PREPARATION OF EXAMPLES

Example 1: (S)-5-(3-Fluoro-2-methylphenyl)-N-hydroxy-1-phenyl-1,4,5,6-tetrahydrocyclopenta[c]pyrazole-5-carboxamide

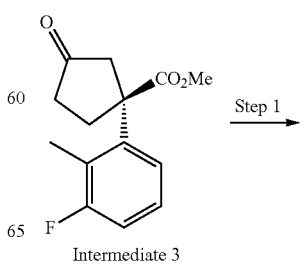

Intermediate 3

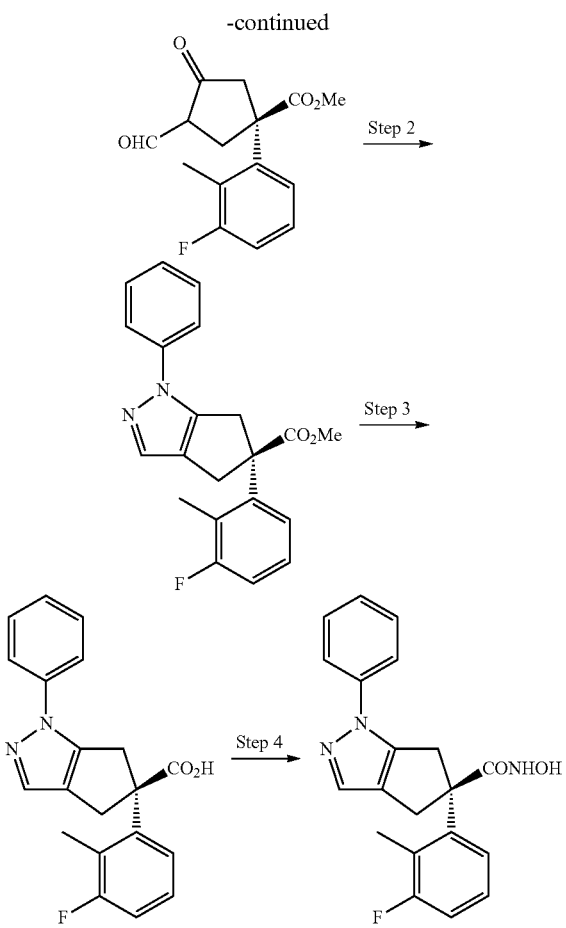

Step 1: (1S)-Methyl 1-(3-fluoro-2-methylphenyl)-3-formyl-4-oxocyclopentanecarboxylate tBuOK (247 mg, 2.2 mmol) and THF (15 mL) were combined under a nitrogen atmosphere. The reaction mixture was cooled with an ice bath and ethyl formate (0.64 mL, 8 mmol) was added dropwise—care effervescence. After 15 min, Intermediate 3 (500 mg, 2 mmol) was added dropwise as a solution in ethyl formate (2.5 mL). The reaction mixture was stirred for a further 1 h with ice bath cooling then diluted with EtOAc and washed with 1N HCl, dried (MgSO$_4$) and evaporated to dryness to give the title compound as a tan oil (569 mg, 100%). LCMS (ES+) 279 (M+H)$^+$.

Step 2: (S)-Methyl 5-(3-fluoro-2-methylphenyl)-1-phenyl-1,4,5,6-tetrahydrocyclopenta[c]pyrazole-5-carboxylate (1S)-Methyl 1-(3-fluoro-2-methylphenyl)-3-formyl-4-oxocyclopentanecarboxylate (569 mg, 2 mmol), acetic acid (10 mL) and phenylhydrazine (0.2 mL, 2 mmol) were combined in a sealed tube and heated to 70° C. for 1 h. Reaction mixture was then evaporated to dryness onto silica and purified by flash chromatography to give the title compound as a brown gum (451 mg, 64%). LCMS (ES+) 351 (M+H)$^+$.

Step 3: (S)-5-(3-Fluoro-2-methylphenyl)-1-phenyl-1,4,5,6-tetrahydrocyclopenta[c]pyrazole-5-carboxylic acid (S)-Methyl 5-(3-fluoro-2-methylphenyl)-1-phenyl-1,4,5,6-tetrahydrocyclopenta[c]pyrazole-5-carboxylate (451 mg, 1.29 mmol), MeOH (15 mL) and 15% aq. NaOH soln. (4 mL) were combined in a sealed tube and heated to 70° C. for 1 day. Reaction mixture was evaporated to dryness, diluted with EtOAc, washed with 1N HCl and evaporated to dryness once more to give the title compound as a brown gum (315 mg, 73%). LCMS (ES+) 337 (M+H)$^+$.

Step 4: (S)-5-(3-Fluoro-2-methylphenyl)-N-hydroxy-1-phenyl-1,4,5,6-tetrahydrocyclopenta[c]pyrazole-5-carboxamide (S)-5-(3-Fluoro-2-methylphenyl)-1-phenyl-1,4,5,6-tetrahydrocyclopenta[c]pyrazole-5-carboxylic acid (315 mg, 0.94 mmol), TFFH (264 mg, 1 mmol), DMF (2 mL) and triethylamine (0.5 mL) were combined and stirred at room temperature for 1.5 h. O-(Tetrahydro-2H-pyran-2-yl)hydroxylamine (234 mg, 2 mmol) was then added and stirring continued for 1 day. Volatile solvents were removed in vacuo. MeOH (5 mL) and 2N HCl in Et$_2$O (2 mL) were added and reaction mixture was stirred for 2 h. Volatile solvents were removed in vacuo and remaining crude material was purified by preparative HPLC to give the title compound as an off white solid (256 mg). LCMS (ES+) 352 (M+H)$^+$, RT 3.52 min (Analytical method 1); $^1$H NMR δ (ppm)(DMSO-d$_6$): 10.26 (1H, s), 8.80 (1H, br s), 7.70-7.60 (2H, m), 7.55-7.45 (3H, m), 7.30 (1H, m), 7.25-7.00 (3H, m), 4.12 (1H, d), 3.40 (1H, d), 3.25 (1H, d), 3.20 (1H, d), 2.20 (3H, d, J=2.4 Hz).

Example 2: (S)-5-(3-Fluoro-2-methylphenyl)-N-hydroxy-1-(o-tolyl)-1,4,5,6-tetrahydrocyclopenta[c]pyrazole-5-carboxamide Prepared following the method described for Example 1. Preparative HPLC gave the title compound as a tan solid (64 mg). LCMS (ES+) 366 (M+H)$^+$, RT 9.93 min (Analytical method 2); $^1$H NMR δ (ppm)(DMSO-d$_6$): 10.23 (1H, s), 8.79 (1H, br s), 7.45-7.00 (8H, m), 3.76 (1H, d, 16 Hz), 3.45 (1H, d, J=15 Hz), 3.25 (1H, d, J=15 Hz), 2.51 (1H, d, J=16 Hz), 2.11 (3H, d, J=2.4 Hz), 2.01 (3H, s).

Example 3: (S)-5-(3-Fluoro-2-methylphenyl)-1-(2-fluorophenyl)-N-hydroxy-1,4,5,6-tetrahydrocyclopenta[c]pyrazole-5-carboxamide Prepared following the method described for Example 1. Preparative HPLC gave the title compound as a white solid (115 mg). LCMS (ES+) 370 (M+H)$^+$, RT 3.43 min (Analytical method 1); $^1$H NMR δ (ppm)(DMSO-d$_6$): 10.22 (1H, s), 8.81 (1H, s), 7.70-7.30 (5H, m), 7.25-6.95 (3H, m), 3.83 (1H, d, J=16 Hz), 3.45 (1H, d, J=15 Hz), 3.13 (1H, d, J=15 Hz), 3.03 (1H, d, J=16 Hz), 2.12 (3H, d, J=2.8 Hz).

Example 4: (S)-1-(3-Chlorophenyl)-5-(3-fluoro-2-methylphenyl)-N-hydroxy-1,4,5,6-tetrahydrocyclopenta[c]pyrazole-5-carboxamide Prepared following the method described for Example 1. Preparative HPLC gave the title compound as a white solid (85 mg). LCMS (ES+) 386/388 (M+H)$^+$, RT 3.78 min (Analytical method 1); $^1$H NMR δ (ppm)(DMSO-d$_6$): 10.27 (1H, s), 8.85 (1H, s), 7.75-7.45 (5H, m), 7.25-7.00 (3H, m), 4.11 (1H, d, J=16 Hz), 3.41 (1H, d, J=16 Hz), 3.33 (1H, d, J=16 Hz), 3.15 (1H, d, J=16 Hz), 2.17 (3H, d, J=2.4 Hz).

Example 5: (S)-5-(3-Fluoro-2-methylphenyl)-1-(4-fluorophenyl)-N-hydroxy-1,4,5,6-tetrahydrocyclopenta[c]pyrazole-5-carboxamide Prepared following the method described for Example 1. Preparative HPLC gave the title compound as an off white solid (41 mg). LCMS (ES+) 370 (M+H)+, RT 3.65 min (Analytical method 1); $^1$H NMR δ (ppm)(DMSO-d$_6$): 10.24 (1H, s), 8.81 (1H, s), 810 (1H, s), 7.78-7.74 (2H, m), 7.35-7.25 (2H, m) 7.25-7.00 (3H, m), 3.65 (1H, d, J=16 Hz), 3.50 (1H, d, J=16 Hz), 3.10 (1H, d, J=16 Hz), 3.05 (1H, d, J=16 Hz), 2.17 (3H, d, J=2.4 Hz).

Example 6: (S)-5-(3-Fluoro-2-methylphenyl)-1-(3-fluorophenyl)-N-hydroxy-1,4,5,6-tetrahydrocyclopenta[c]pyrazole-5-carboxamide Prepared following the method described for Example 1. Preparative HPLC gave the title compound as a tan solid (129 mg). LCMS (ES+) 370 (M+H)+, RT 3.67 min (Analytical method 1); $^1$H NMR δ (ppm)(DMSO-d$_6$): 10.26 (1H, s), 8.83 (1H, br s), 7.60-7.45 (4H, m), 7.25-7.00 (4H, m), 4.13 (1H, d, J=16 Hz), 3.39 (1H, d, J=16 Hz), 3.31 (1H, d, J=16 Hz), 3.17 (1H, d, J=16 Hz), 2.18 (3H, d, J=2.4 Hz).

Example 7: (S)-1-(2-Chlorophenyl)-5-(3-fluoro-2-methylphenyl)-N-hydroxy-1,4,5,6-tetrahydrocyclopenta[c]pyrazole-5-carboxamide Prepared following the method described for Example 1. Preparative HPLC gave the title compound as an off white solid (108 mg). LCMS (ES+) 386/388 (M+H)+, RT 3.37 min (Analytical method 1); $^1$H NMR δ (ppm)(DMSO-d$_6$): 10.22 (1H, s), 8.80 (1H, br s), 7.75-7.45 (5H, m), 7.25-7.00 (3H, m), 3.7 (1H, d, J=16 Hz), 3.45 (1H, d, J=16 Hz), 3.5 (1H, d, J=15 Hz), 2.89 (1H, d, J=16 Hz), 2.11 (3H, d, J=2.8 Hz).

Example 8: (S)-1-(4-Chlorophenyl)-5-(3-fluoro-2-methylphenyl)-N-hydroxy-1,4,5,6-tetrahydrocyclopenta[c]pyrazole-5-carboxamide Prepared following the method described for Example 1. Preparative HPLC gave the title compound as an off white solid (15 mg). LCMS (ES+) 386/388 (M+H)+, RT 3.52 min (Analytical method 1); $^1$H NMR δ (ppm)(DMSO-d$_6$): 10.24 (1H, s), 8.81 (1H, s), 8.15 (1H, s), 7.80-7.70 (2H, m), 7.60-7.50 (2H, m), 7.25-7.00 (3H, m), 3.65 (1H, d, J=16 Hz), 3.50 (1H, d, J=16 Hz), 3.11 (1H, d, J=16 Hz), 3.06 (1H, d, J=16 Hz), 2.1 (3H, d, J=2.8 Hz).

Example 9: (S)-5-(3-Fluoro-2-methylphenyl)-N-hydroxy-1-(p-tolyl)-1,4,5,6-tetrahydrocyclopenta[c]pyrazole-5-carboxamide Prepared following the method described for Example 1. Preparative HPLC gave the title compound as a brown solid (60 mg). LCMS (ES+) 366 (M+H)+, RT 9.08 min (Analytical method 3); $^1$H NMR δ (ppm)(DMSO-d$_6$): 10.26 (1H, s), 8.80 (1H, br s), 7.52 (2H, d, J=8.4 Hz), 7.43 (1H, s), 7.28 (2H, d, J=8 Hz), 7.25-7.20 (3H, m), 4.10 (1H, d, J=16 Hz), 3.40 (1H, d, J=16 Hz), 3.22 (1H, d, J=16 Hz), 3.15 (1H, d, J=16 Hz), 2.32 (3H, s), 2.17 (3H, d, J=2.8 Hz).

Example 10: (S)-1-(3-Chloro-2-fluorophenyl)-5-(3-fluoro-2-methylphenyl)-N-hydroxy-1,4,5,6-tetrahydrocyclopenta[c]pyrazole-5-carboxamide Prepared following the method described for Example 1. Preparative HPLC gave the title compound as tan solid (124 mg). LCMS (ES+) 404/406 (M+H)+, RT 9.05 min (Analytical method 3); $^1$H NMR δ (ppm)(DMSO-d$_6$): 10.23 (1H, s), 8.80 (1H, br s), 7.70-7.60 (2H, m), 7.56 (1H, s), 7.40-7.30 (1H, m), 7.25-7.00 (3H, m), 3.84 (1H, d, J=15 Hz), 3.40 (1H, d, J=15 Hz), 3.15 (1H, d, J=15 Hz), 3.00 (1H, d, J=15 Hz), 2.12 (3H, d, J=2.8 Hz).

Example 11: (S)-1-(2,6-Difluorophenyl)-5-(3-fluoro-2-methylphenyl)-N-hydroxy-1,4,5,6-tetrahydrocyclopenta[c]pyrazole-5-carboxamide Prepared following the method described for Example 1. Preparative HPLC gave the title compound as beige solid (131 mg). LCMS (ES+) 388 (M+H)+, RT 8.52 min (Analytical method 3); $^1$H NMR δ (ppm)(DMSO-d$_6$): 10.21 (1H, s), 8.81 (1H, br s), 7.65-7.50 (2H, m), 7.45-7.30 (2H, m), 7.25-6.95 (3H, m), 3.73 (1H, d, J=16 Hz), 3.53 (1H, d, J=16 Hz), 3.15 (1H, d, J=16 Hz), 2.90 (1H, d, J=16 Hz), 2.10 (3H, d, J=2.8 Hz).

Example 12: (S)-1-(2,5-Dimethylphenyl)-5-(3-fluoro-2-methylphenyl)-N-hydroxy-1,4,5,6-tetrahydrocyclopenta[c]pyrazole-5-carboxamide Prepared following the method described for Example 1. Preparative HPLC gave the title compound as grey solid (108 mg). LCMS (ES+) 380 (M+H)+, RT 9.03 min (Analytical method 3); $^1$H NMR δ (ppm)(DMSO-d$_6$): 10.22 (1H, s), 8.80 (1H, br s), 7.39 (1H, s), 7.30-7.00 (6H, m), 3.76 (1H, d, J=16 Hz), 3.44 (1H, d, J=16 Hz), 3.17 (1H, d, J=16 Hz), 2.79 (1H, d, J=16 Hz), 2.33 (3H, s), 2.10 (3H, d, J=2.8 Hz), 2.00 (3H, s).

Example 13: (S)-1-(2,6-Dimethylphenyl)-5-(3-fluoro-2-methylphenyl)-N-hydroxy-1,4,5,6-tetrahydrocyclopenta[c]pyrazole-5-carboxamide Prepared following the method described for Example 1. Preparative HPLC gave the title compound as a tan solid (80 mg). LCMS (ES+) 380 (M+H)+, RT 3.50 min (Analytical method 1); $^1$H NMR δ (ppm)(DMSO-d$_6$): 10.23 (1H, s), 8.80 (1H, br s), 7.43 (1H, s), 7.30-7.00 (5H, m), 3.66 (1H, d, J=15.6 Hz), 3.39 (1H, d, J=15.2 Hz), 3.27 (1H, d, J=15.2 Hz), 2.54 (1H, d, J=15.6 Hz), 2.08 (3H, d, J=32.4 Hz), 2.01 (3H, s), 1.63 (1H, s).

Example 14: (S)-1-(2-Chloro-6-fluorophenyl)-5-(3-fluoro-2-methylphenyl)-N-hydroxy-1,4,5,6-tetrahydrocyclopenta[c]pyrazole-5-carboxamide Prepared following the method described for Example 1. Preparative HPLC gave the title compound as a tan solid (146 mg). LCMS (ES+) 404/406 (M+H)+, RT 9.86 min (Analytical method 2); $^1$H NMR δ (ppm)(DMSO-d$_6$): 10.22 (1H, s), 8.80 (1H, br s), 7.65-7.40 (4H, m), 7.25-7.00 (3H, m), 3.69 (1H, d, J=16 Hz), 3.43 (1H, d, J=15.2 Hz), 3.17 (1H, d, J=15.2 Hz), 2.80 (1H, d, J=16 Hz), 2.09 (3H, d, J=3.6 Hz).

Example 15: (S)-5-(3-Fluoro-2-methylphenyl)-1-(2-fluoro-6-methylphenyl)-N-hydroxy-1,4,5,6-tetrahydrocyclopenta[c]pyrazole-5-carboxamide Prepared following the method described for Example 1. Preparative HPLC gave the title compound as a tan solid (157 mg). LCMS (ES+) 384 (M+H)+, RT 10.13 min (Analytical method 2); $^1$H NMR δ (ppm)(DMSO-d$_6$): 10.22 (1H, s), 8.81 (1H, br s), 7.50-7.00 (7H, m), 3.81 (1H, d, J=16 Hz), 3.46 (1H, d, J=14.8 Hz), 3.12 (1H, d, J=15.2 Hz), 3.02 (1H, d, J=16 Hz), 2.32 (3H, d, J=2 Hz), 2.12 (3H, d, J=2.4 Hz).

Example 16: (S)-5-(3-Fluoro-2-methylphenyl)-1-(5-fluoropyridin-2-yl)-N-hydroxy-1,4,5,6-tetrahydrocyclopenta[c]pyrazole-5-carboxamide Prepared following the method described for Example 1. Preparative HPLC gave the title compound as an off white solid (126 mg). LCMS (ES+) 371 (M+H)+, RT 3.55 min (Analytical method 1); $^1$H NMR δ (ppm)(DMSO-d$_6$): 10.24 (1H, s), 8.80 (1H, br s), 8.46 (1H, s), 8.00-7.85 (2H, m), 7.52 (1H, s), 7.20-7.00 (3H, m), 4.03 (1H, d, J=16.8 Hz), 3.45 (1H, d, J=16.8 Hz), 3.42 (1H, d, J=15.6 Hz), 3.06 (1H, d, J=15.2 Hz), 2.15 (3H, d, J=2.8 Hz).

Example 17: (S)-1-(2,4-Difluorophenyl)-5-(3-fluoro-2-methylphenyl)-N-hydroxy-1,4,5,6-tetrahydrocyclopenta[c]pyrazole-5-carboxamide Prepared following the method described for Example 1. Preparative HPLC gave the title compound as an off white solid (118 mg). LCMS (ES+) 388 (M+H)+, RT 9.99 min (Analytical method 2); $^1$H NMR δ (ppm)(DMSO-d$_6$): 10.22 (1H, s), 8.80 (1H, br s), 7.70-7.60 (1H, m), 7.60-7.50 (2H, m), 7.30-7.00 (4H, m), 3.82 (1H, d, J=15 Hz), 3.45 (1H, d, J=15 Hz), 3.14 (1H, d, J=15 Hz), 3.01 (1H, d, J=16 Hz), 2.12 (3H, d, J=2.8 Hz).

Example 18: (S)-1-Cyclopentyl-5-(3-fluoro-2-methylphenyl)-N-hydroxy-1,4,5,6-tetrahydrocyclopenta[c]pyrazole-5-carboxamide Prepared following the method described for Example 1. Preparative HPLC gave the title compound as an off white solid (41 mg). LCMS (ES+) 344 (M+H)+, RT 3.31 min (Analytical method 1); $^1$H NMR δ (ppm)(DMSO-d$_6$): 10.18 (1H, s), 8.80 (1H, br s), 7.20-7.00 (4H, m), 4.60-4.50 (1H, m), 3.74 (1H, d, J=16 Hz), 3.37 (1H, d, J=16 Hz), 3.02 (1H, d, J=16 Hz), 2.98 (1H, d, J=16 Hz), 2.15 (3H, d, J=2.8 Hz), 2.10-1.90 (2H, m), 1.90-1.65 (4H, m), 1.65-1.52 (2H, m).

Example 19: (S)-5-(3-Fluoro-2-methylphenyl)-N-hydroxy-1-(pyrazin-2-yl)-1,4,5,6-tetrahydrocyclopenta[c]pyrazole-5-carboxamide Prepared following the method described for Example 1. Preparative HPLC gave the title compound as a brown solid (43 mg). LCMS (ES+) 354 (M+H)+, RT 3.09 min (Analytical method 1); $^1$H NMR δ (ppm)(DMSO-d$_6$): 10.25 (1H, s), 9.15 (1H, s), 8.82 (1H, br s), 8.56 (1H, d, J=2.8 Hz), 8.52 (1H, m), 7.64 (1H, s), 7.20-7.00 (3H, m), 4.06 (1H, d, J=16.8 Hz), 3.46 (1H, d, J=17.2 Hz), 3.43 (1H, d, J=15.2 Hz), 3.09 (1H, d, J=15.2 Hz), 2.18 (3H, d, J=2.8 Hz).

Examples 20 and 21: (S)-1-(4-(Difluoromethoxy)phenyl)-5-(3-fluoro-2-methylphenyl)-N-hydroxy-1,4,5,6-tetrahydrocyclopenta[c]pyrazole-5-carboxamide and (S)-2-(4-(difluoromethoxy)phenyl)-5-(3-fluoro-2-methylphenyl)-N-hydroxy-2,4,5,6-tetrahydrocyclopenta[c]pyrazole-5-carboxamide Prepared following the method described for Example 1. Two regioisomers observed. Preparative HPLC gave (S)-2-(4-(difluoromethoxy)phenyl)-5-(3-fluoro-2-methylphenyl)-N-hydroxy-2,4,5,6-tetrahydrocyclopenta[c]pyrazole-5-carboxamide as an off white solid (21 mg); LCMS (ES+) 418 (M+H)+, RT 3.7 min (Analytical method 1); $^1$H NMR δ (ppm)(DMSO-d$_6$): 10.25 (1H, s), 8.82 (1H, s), 8.13 (1H, s), 7.78 (2H, d, J=8.8 Hz), 7.26 (2H, d, J=9.2 Hz), 7.25 (1H, t, J=74 Hz), 7.20-7.05 (2H, m), 3.66 (1H, d, J=16 Hz), 3.52 (1H, d, J=16 Hz), 3.11 (1H, d, J=16 Hz), 3.06 (1H, d, J=16 Hz), 2.18 (3H, d, J=2.4 Hz) and also (S)-1-(4-(difluoromethoxy)phenyl)-5-(3-fluoro-2-methylphenyl)-N-hydroxy-1,4,5,6-tetrahydrocyclopenta[c]pyrazole-5-carboxamide as an off white solid (38 mg); LCMS (ES+) 418 (M+H)+, RT 10.55 min (Analytical method 2); $^1$H NMR δ (ppm)(DMSO-d$_6$): 10.27 (1H, s), 8.82 (1H, br s), 7.69 (2H, d, J=10 Hz), 7.46 (1H, s), 7.29 (2H, d, J=10 Hz), 7.26 (1H, t, J=74 Hz), 7.20-7.00 (2H, m), 4.12 (1H, d, J=16 Hz), 3.38 (1H, d, J=16 Hz), 3.23 (1H, d, J=16 Hz), 3.19 (1H, d, J=16 Hz), 2.17 (3H, d, J=2.4 Hz).

Examples 22 and 23: (S)-5-(3-Fluoro-2-methylphenyl)-1-(4-fluoro-2-methylphenyl)-N-hydroxy-1,4,5,6-tetrahydrocyclopenta[c]pyrazole-5-carboxamide and (S)-5-(3-fluoro-2-methylphenyl)-2-(4-fluoro-2-methylphenyl)-N-hydroxy-2,4,5,6-tetrahydrocyclopenta[c]pyrazole-5-carboxamide Prepared following the method described for Example 1. Two regioisomers observed. Preparative HPLC gave (S)-5-(3-fluoro-2-methylphenyl)-2-(4-fluoro-2-methylphenyl)-N-hydroxy-2,4,5,6-tetrahydrocyclopenta[c]pyrazole-5-carboxamide as an off white solid (4 mg); LCMS (ES+) 384 (M+H)+, RT 10.09 min (Analytical method 2); $^1$H NMR δ (ppm)(DMSO-d$_6$): 10.22 (1H, s), 8.80 (1H, br s), 7.62 (1H, s), 7.40-7.00 (6H, m), 3.64 (1H, d, J=16 Hz), 3.51 (1H, d, J=16 Hz), 3.08 (1H, d, J=16 Hz), 3.06 (1H, d, J=16 Hz), 2.18 (6H, s) and also (S)-5-(3-fluoro-2-methylphenyl)-1-(4-fluoro-2-methylphenyl)-N-hydroxy-1,4,5,6-tetrahydrocyclopenta[c]pyrazole-5-carboxamide as an off white solid (44 mg); LCMS (ES+) 384 (M+H)+, RT 3.62 min (Analytical method 1); $^1$H NMR δ (ppm)(DMSO-d$_6$): 10.23 (1H, s), 8.82 (1H, br s), 7.42 (1H, s), 7.38-7.00 (6H, m), 3.75 (1H, d, J=16 Hz), 3.43 (1H, d, J=16 Hz), 3.19 (1H, d, J=16 Hz), 2.79 (1H, d, J=16 Hz), 2.11 (3H, d, J=2.8 Hz), 2.04 (3H, s).

Examples 24 and 25: (S)-5-(3-Fluoro-2-methylphenyl)-N-hydroxy-1-(m-tolyl)-1,4,5,6-tetrahydrocyclopenta[c]pyrazole-5-carboxamide and (S)-5-(3-fluoro-2-methylphenyl)-N-hydroxy-2-(m-tolyl)-2,4,5,6-tetrahydrocyclopenta[c]pyrazole-5-carboxamide Prepared following the method described for Example 1. Two regioisomers observed. Preparative HPLC gave (S)-5-(3-fluoro-2-methylphenyl)-N-hydroxy-1-(m-tolyl)-1,4,5,6-tetrahydrocyclopenta[c]pyrazole-5-carboxamide as an off white solid (47 mg); LCMS (ES+) 366 (M+H)+, RT 3.62 min (Analytical method 1); $^1$H NMR δ (ppm)(DMSO-d$_6$): 10.26 (1H, s), 8.80 (1H, br s), 7.50-7.30 (4H, m), 7.25-7.00 (4H, m), 4.09 (1H, d, J=16 Hz), 3.50 (1H, d, J=16 Hz), 3.25 (1H, d, J=16 Hz), 3.14 (1H, d, J=16 Hz), 2.37 (3H, s), 2.16 (3H, d, J=2.8 Hz) and also (S)-5-(3-fluoro-2-methylphenyl)-N-hydroxy-2-(m-tolyl)-2,4,5,6-tetrahydrocyclopenta[c]pyrazole-5-carboxamide as an off white solid (39 mg); LCMS (ES+) 366 (M+H)+, RT 10.59 min (Analytical method 2); $^1$H NMR δ (ppm)(DMSO-d$_6$): 10.24 (1H, s), 8.09 (1H, s), 7.58 (1H, s), 7.55-7.50 (1H, m), 7.35-7.25 (1H, m), 7.20-7.00 (5H, m), 3.64 (1H, d, J=16 Hz), 3.50 (1H, d, J=16 Hz), 3.09 (1H, d, J=16 Hz), 3.05 (1H, d, J=16 Hz), 2.35 (3H, s), 2.17 (3H, d, J=2.4 Hz).

Examples 26 and 27: (S)-5-(3-Fluoro-2-methylphenyl)-N-hydroxy-1-(3-methylpyridin-4-yl)-1,4,5,6-tetrahydrocyclopenta[c]pyrazole-5-carboxamide and (S)-5-(3-fluoro-2-methylphenyl)-N-hydroxy-2-(3-methylpyridin-4-yl)-2,4,5,6-tetrahydrocyclopenta[c]pyrazole-5-carboxamide Prepared following the method described for Example 1. The two pyrazole regioisomers were separated by preparative HPLC at the carboxylic acid stage and both isomers progressed to the final step. Preparative HPLC gave (S)-5-(3-fluoro-2-methylphenyl)-N-hydroxy-1-(3-methylpyridin-4-yl)-1,4,5,6-tetrahydrocyclopenta[c]pyrazole-5-carboxamide as an off-white solid (27 mg); LCMS (ES+) 367 (M+H)$^+$, RT 2.32 min (Analytical method 1); $^1$H NMR δ (ppm) (DMSO-d$_6$): 10.25 (1H, s), 8.82 (1H, br s), 8.58 (1H, s), 8.51 (1H, d, J=5.2 Hz), 7.55 (1H, s), 7.37 (1H, d, J=5.2 Hz), 7.20-7.00 (3H, m), 3.94 (1H, d, J=16 Hz), 3.45 (1H, d, J=14.8 Hz), 3.20 (1H, d, J=13.6 Hz), 3.06 (1H, d, J=16 Hz), 2.31 (3H, s), 2.14 (3H, d, J=2.8 Hz). (S)-5-(3-Fluoro-2-methylphenyl)-N-hydroxy-2-(3-methylpyridin-4-yl)-2,4,5,6-tetrahydrocyclopenta[c]pyrazole-5-carboxamide as an off-white solid (29 mg). LCMS (ES+) 367 (M+H)$^+$, RT 2.46 min (Analytical method 1); $^1$H NMR δ (ppm)(DMSO-d$_6$): 10.25 (1H, s), 8.82 (1H, br s), 8.55 (1H, s), 8.47 (1H, d, J=5.2 Hz), 7.96 (1H, s), 7.48 (1H, d, J=5.2 Hz), 7.20-7.00 (3H, m), 3.68 (1H, d, J=16 Hz), 3.53 (1H, d, J=16 Hz), 3.14 (1H, d, J=16 Hz), 3.08 (1H, d, J=16 Hz), 2.42 (3H, s), 2.18 (3H, d, J=2.8 Hz).

Example 28: (S)-2-(3-Chloropyridin-2-yl)-5-(3-fluoro-2-methylphenyl)-N-hydroxy-2,4,5,6-tetrahydrocyclopenta[c]pyrazole-5-carboxamide Prepared following the method described for Example 1. The two pyrazole regioisomers were separated by preparative HPLC at the carboxylic acid stage and only one regioisomer was progressed. Preparative HPLC gave the title compound as an off-white solid (13 mg). LCMS (ES+) 387/389 (M+H)$^+$, RT 3.25 min (Analytical method 1); $^1$H NMR δ (ppm)(DMSO-d$_6$): 10.26 (1H, s), 8.80 (1H, br s), 8.46 (1H, dd, J=4.4 and 1.6 Hz), 8.15 (1H, dd, J=8 and 1.6 Hz), 7.95 (1H, s), 7.46 (1H, dd, J=8 and 4.4 Hz), 7.20-7.00 (3H, m), 3.69 (1H, d, J=16 Hz), 3.51 (1H, d, J=16 Hz), 3.14 (1H, d, J=16 Hz), 3.08 (1H, d, J=16 Hz), 2.18 (3H, d, J=2.4 Hz).

Example 29: (S)-5-(3-Fluoro-2-methylphenyl)-2-(3-fluoropyridin-2-yl)-N-hydroxy-2,4,5,6-tetrahydrocyclopenta[c]pyrazole-5-carboxamide Prepared following the method described for Example 1. Purification by preparative HPLC at the carboxylic acid and also the hydroxamic acid stage gave the title compound as an off-white solid (45 mg). LCMS (ES+) 371 (M+H)$^+$, RT 3.12 min (Analytical method 1); $^1$H NMR δ (ppm)(DMSO-d$_6$): 10.26 (1H, s), 8.82 (1H, br s), 8.32-8.28 (1H, m), 8.10 (1H, s), 7.98-7.90 (1H, m), 7.45-7.40 (1H, m), 7.20-7.00 (3H, m), 3.69 (1H, d, J=16 Hz), 3.51 (1H, d, J=16 Hz), 3.14 (1H, d, J=16 Hz), 3.08 (1H, d, J=16 Hz), 2.18 (3H, d, J=2.4 Hz).

Example 30: (R)-5-(3-Fluoro-2-methylphenyl)-N-hydroxy-1-phenyl-1,4,5,6-tetrahydrocyclopenta[c]pyrazole-5-carboxamide Prepared following the method described for Example 1 starting from Intermediate 2. Preparative HPLC gave the title compound as a tan solid (12 mg). LCMS (ES+) 352 (M+H)$^+$, RT 3.53 min (Analytical method 1); $^1$H NMR δ (ppm)(DMSO-d$_6$): 10.26 (1H, s), 8.80 (1H, br s), 7.70-7.60 (2H, m), 7.55-7.45 (3H, m), 7.30 (1H, m), 7.25-7.00 (3H, m), 4.12 (1H, d), 3.40 (1H, d), 3.25 (1 h, d), 3.20 (1H, d), 2.20 (3H, d, J=2.4 Hz).

Examples 31 and 32: E1-(abs)-5-(3-Fluoro-2-methylphenyl)-N-hydroxy-1-phenyl-4,5,6,7-tetrahydro-1H-indazole-5-carboxamide and E2-(abs)-5-(3-fluoro-2-methylphenyl)-N-hydroxy-1-phenyl-4,5,6,7-tetrahydro-1H-indazole-5-carboxamide

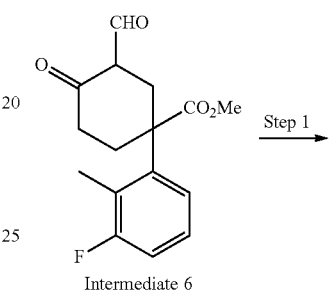

Intermediate 6

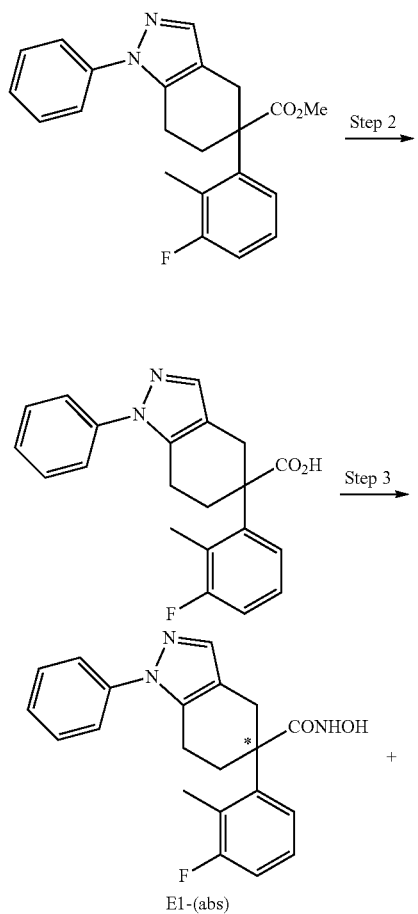

E1-(abs)

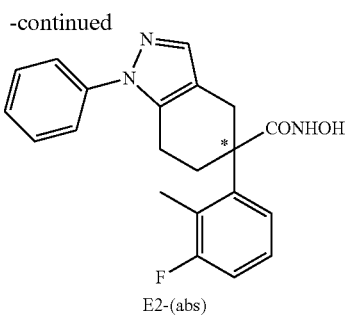

E2-(abs)

Step 1: Methyl 5-(3-fluoro-2-methylphenyl)-1-phenyl-4,5,6,7-tetrahydro-1H-indazole-5-carboxylate Intermediate 6 (515 mg, 1.76 mmol), AcOH (10 mL) and phenylhydrazine (0.174 mL, 1.76 mmol) were combined in a sealed tube and heated to 70° C. for 1 h. Reaction mixture was then evaporated to dryness onto silica and purified by flash chromatography to give the title compound as a yellow gum (288 mg, 45%). LCMS (ES+) 365 (M+H)+; $^1$H NMR δ (ppm)(CHCl$_3$-d) 7.58 (1H, s), 7.45-7.35 (4H, m), 7.35-7.25 (1H, m), 7.10-6.85 (3H, m), 3.73 (3H, s), 3.31 (1H, d, J=16.4 Hz), 3.12 (1H, d, J=16.4 Hz), 2.75-2.65 (1H, m), 2.55-2.30 (2H, m), 2.25-2.10 (1H, m), 2.20 (3H, d, J=2.4 Hz).

Step 2: 5-(3-Fluoro-2-methylphenyl)-1-phenyl-4,5,6,7-tetrahydro-1H-indazole-5-carboxylic acid Methyl 5-(3-fluoro-2-methylphenyl)-1-phenyl-4,5,6,7-tetrahydro-1H-indazole-5-carboxylate (280 mg), MeOH (10 mL) and 15% aq. NaOH soln. (2 mL) were combined in a sealed tube and heated to 70° C. for 5 days. Reaction was cooled and evaporated to dryness. Residue was partitioned between 1N HCl and EtOAc. Organics were dried (MgSO$_4$) and evaporated to dryness to give the title compound as a tan gum (225 mg, 84%). LCMS (ES+) 351 (M+H)+.

Step 3: E1-(abs)-5-(3-Fluoro-2-methylphenyl)-N-hydroxy-1-phenyl-4,5,6,7-tetrahydro-1H-indazole-5-carboxamide and E2-(abs)-5-(3-fluoro-2-methylphenyl)-N-hydroxy-1-phenyl-4,5,6,7-tetrahydro-1H-indazole-5-carboxamide 5-(3-Fluoro-2-methylphenyl)-1-phenyl-4,5,6,7-tetrahydro-1H-indazole-5-carboxylic acid (225 mg, 0.64 mmol), TFFH (185 mg, 0.7 mmol), DMF (2 mL) and triethylamine (0.28 mL) were combined and stirred for 1 h. O-(Tetrahydro-2H-pyran-2-yl)hydroxylamine (117 mg, 1 mmol) was then added and stirring continued for 2 days. Volatile solvents were removed in vacuo. MeOH (5 mL) and 2N HCl in Et$_2$O (2 mL) were added and reaction mixture was stirred for 4 h. Volatile solvents were removed in vacuo and remaining crude material was purified by preparative HPLC. Chiral preparative HPLC gave the E1 and E2 enantiomers (Chiralpak IA, Method 50/50 THF (0.1% formic acid)/heptane 5.0 mL/min, RT 5.4 (E1-(abs)) and 10.1 min (E2-(abs))). E1-enantiomer was obtained as a white solid (22 mg). LCMS (ES+) 366 (M+H)+, RT 3.45 min (Analytical method 1); $^1$H NMR δ (ppm)(DMSO-d$_6$): 10.21 (1H, s), 8.74 (1H, s), 7.58 (1H, s), 7.50-7.40 (4H, m), 7.33-7.27 (1H, m), 7.15-6.95 (3H, m), 3.15-2.98 (2H, m), 2.75-2.65 (1H, m), 2.45-2.10 (3H, m), 2.20 (3H, d, J=2.4 Hz). E2-enantiomer was obtained as a white solid (23 mg). LCMS (ES+) 366 (M+H)+, RT 3.39 min (Analytical method 1); $^1$H NMR δ (ppm)(DMSO-d$_6$): 10.21 (1H, s), 8.74 (1H, s), 7.58 (1H, s), 7.50-7.40 (4H, m), 7.33-7.27 (1H, m), 7.15-6.95 (3H, m), 3.15-2.98 (2H, m), 2.75-2.65 (1H, m), 2.45-2.10 (3H, m), 2.20 (3H, d, J=2.4 Hz).

Examples 33 and 34: E1-(abs)-5-(3-Fluoro-2-methylphenyl)-2-(2-fluorophenyl)-N-hydroxy-4,5,6,7-tetrahydro-2H-indazole-5-carboxamide and E2-(abs)-5-(3-fluoro-2-methylphenyl)-2-(2-fluorophenyl)-N-hydroxy-4,5,6,7-tetrahydro-2H-indazole-5-carboxamide Prepared following the method described for Example 31 and 32. The two observed pyrazole regioisomers were separated by flash chromatography at the carboxylic ester stage and only one regioisomer was progressed. Purification by preparative HPLC followed by chiral preparative HPLC gave the E1 and E2 enantiomers. (Chiralpak IC, Method 10/90 EtOH (0.1% formic acid)/Heptane 5.0 mL/min, RT 21.0 (E1-(abs)) and 15.6 min (E2-(abs))). E1-enantiomer was obtained as an off-white solid (8 mg). LCMS (ES+) 384 (M+H)+, RT 3.57 (Analytical method 1); $^1$H NMR δ (ppm) (DMSO-d$_6$): 10.22 (1H, br s), 8.73 (1H, s), 8.01 (1H, d, J=2.8 Hz), 7.79-7.75 (1H, m), 7.50-7.40 (1H, m), 7.40-7.25 (2H, m), 7.20-7.00 (3H, m), 3.10 (2H, s), 2.70-2.60 (1H, m), 2.45-2.30 (2H, m), 2.20 (3H, d, J=2.8 Hz), 2.15-2.05 (1H, m). E2-enantiomer was obtained as an off-white solid (7 mg). LCMS (ES+) 384 (M+H)+, RT 3.55 (Analytical method 1); $^1$H NMR δ (ppm)(DMSO-d$_6$): 10.22 (1H, br s), 8.73 (1H, s), 8.01 (1H, d, J=2.8 Hz), 7.79-7.75 (1H, m), 7.50-7.40 (1H, m), 7.40-7.25 (2H, m), 7.20-7.00 (3H, m), 3.10 (2H, s), 2.70-2.60 (1H, m), 2.45-2.30 (2H, m), 2.20 (3H, d, J=2.8 Hz), 2.15-2.05 (1H, m).

Example 35: 5-(3-Fluoro-2-methylphenyl)-N-hydroxy-1-(2,2,2-trifluoroethyl)-4,5,6,7-tetrahydro-1H-indazole-5-carboxamide and 5-(3-fluoro-2-methylphenyl)-N-hydroxy-2-(2,2,2-trifluoroethyl)-4,5,6,7-tetrahydro-2H-indazole-5-carboxamide Prepared following the method described for Example 31 and 32. The two observed pyrazole regioisomers were obtained as an inseparable mixture. Preparative HPLC gave a regioisomeric racemic mixture of the title compounds as an off-white solid (105 mg). LCMS (ES+) 372 (M+H)+, RT 9.33 (Analytical method 2). $^1$H NMR δ (ppm)(DMSO-d$_6$): 10.18 (0.5H, s), 10.16 (0.5H, s), 8.73 (1H, br s), 7.59 (0.5H, s), 7.42 (0.5H, s), 7.15-6.80 (3H, m), 5.04-4.86 (2H, m), 3.15-2.85 (2H, m), 2.70-2.50 (1H, m), 2.40-2.15 (2H, m), 2.17 (3H, d, J=2.8 Hz), 2.00-1.75 (1H, m).

Example 36: 5-(3-Fluoro-2-methylphenyl)-1-(4-fluorobenzyl)-N-hydroxy-4,5,6,7-tetrahydro-1H-indazole-5-carboxamide and 5-(3-fluoro-2-methylphenyl)-2-(4-fluorobenzyl)-N-hydroxy-4,5,6,7-tetrahydro-2H-indazole-5-carboxamide Prepared following the method described for Example 31 and 32. The two observed pyrazole regioisomers were obtained as an inseparable mixture. Purification by preparative HPLC gave a regioisomeric racemic mixture of the title compounds as a white solid (29 mg). LCMS (ES+) 398 (M+H)+, RT 3.36 (Analytical method 1); $^1$H NMR δ (ppm) (DMSO-d$_6$): 10.17 (0.5H, s), 10.14 (0.5H, s), 8.70 (1H, br s), 7.57 (0.5H, s), 7.36 (0.5H, s), 7.30-6.80 (6H, m), 5.19 (1H, s), 5.14 (1H, s), 3.20-2.80 (2H, m), 2.65-2.40 (1H, m), 2.40-2.15 (2H, m), 2.16 (1.5H, d, J=2.8 Hz), 2.14 (1.5H, d, J=2.8 Hz), 1.90-1.80 (1H, m), 1.65-1.50 (1H, m).

Examples 37 and 38: E1-(abs)-5-(3-Fluoro-2-methylphenyl)-N-hydroxy-1-(o-tolyl)-4,5,6,7-tetrahydro-1H-indazole-5-carboxamide and E2-(abs)-5-(3-fluoro-2-methylphenyl)-N-hydroxy-1-(o-tolyl)-4,5,6,7-tetrahydro-1H-indazole-5-carboxamide Prepared following the method described for Example 31 and 32. Purification by preparative HPLC followed by chiral preparative HPLC gave the E1 and E2 enantiomers. (Chiralpak IA, Method 20/80 EtOH (0.1% formic acid)/heptane 5.0 mL/min, RT 9.4 (E1-(abs)) and 17.0 min (E2-(abs))). E1-enantiomer was obtained as an off white solid (43 mg). LCMS (ES+) 380 (M+H)$^+$, RT 3.49 (Analytical method 1); $^1$H NMR δ (ppm)(DMSO-d$_6$): 10.19 (1H, s), 8.74 (1H, s), 7.54 (1H, s), 7.35-7.20 (3H, m), 7.15-7.00 (3H, m), 7.00-6.90 (1H, m), 3.21 (1H, d, J=16 Hz), 2.96 (1H, d, J=16 Hz), 2.40-2.20 (3H, m), 2.15 (3H, d, J=2.8 Hz), 1.79 (3H, s), 1.65-1.50 (1H, m). E2-enantiomer was obtained as an off white solid (43 mg). LCMS (ES+) 380 (M+H)$^+$, RT 3.49 (Analytical method 1); $^1$H NMR δ (ppm)(DMSO-d$_6$): 10.19 (1H, s), 8.74 (1H, s), 7.54 (1H, s), 7.35-7.20 (3H, m), 7.15-7.00 (3H, m), 7.00-6.90 (1H, m), 3.21 (1H, d, J=16 Hz), 2.96 (1H, d, J=16 Hz), 2.40-2.20 (3H, m), 2.15 (3H, d, J=2.8 Hz), 1.79 (3H, s), 1.65-1.50 (1H, m).

Example 39: 3-Cyclopropyl-5-(3-fluoro-2-methylphenyl)-N-hydroxy-2-(2,2,2-trifluoroethyl)-4,5,6,7-tetrahydro-2H-indazole-5-carboxamide Step 1: Methyl 5-(3-fluoro-2-methylphenyl)-3-hydroxy-2-(2,2,2-trifluoroethyl)-4,5,6,7-tetrahydro-2H-indazole-5-carboxylate and methyl 5-(3-fluoro-2-methylphenyl)-3-hydroxy-1-(2,2,2-trifluoroethyl)-4,5,6,7-tetrahydro-1H-indazole-5-carboxylate Intermediate 4 (1.12 g, 3.07 mmol), acetic acid (10 mL) and 2, 2, 2-trifluoroethyl hydrazine (70% in water) (0.5 mL, 3.1 mmol) were combined and heated to 65° C. for 19 h. Reaction mixture was evaporated to dryness onto silica and purified by flash chromatography to give a mixture of the title compounds as a clear gum (1.04 g, 88%). LCMS (ES+) 387 (M+H)$^+$.

Step 2: Methyl 5-(3-fluoro-2-methylphenyl)-1-(2,2,2-trifluoroethyl)-3-(((trifluoromethyl)sulfonyl)oxy)-4,5,6,7-tetrahydro-1H-indazole-5-carboxylate and methyl 5-(3-fluoro-2-methylphenyl)-2-(2,2,2-trifluoroethyl)-3-(((trifluoromethyl)sulfonyl)oxy)-4,5,6,7-tetrahydro-2H-indazole-5-carboxylate The crude mixture of methyl 5-(3-fluoro-2-methylphenyl)-3-hydroxy-2-(2,2,2-trifluoroethyl)-4,5,6,7-tetrahydro-2H-indazole-5-carboxylate and methyl 5-(3-fluoro-2-methylphenyl)-3-hydroxy-1-(2,2,2-trifluoroethyl)-4,5,6,7-tetrahydro-1H-indazole-5-carboxylate (0.925 mg, 2.39 mmol) from reaction above was combined with DCM (80 mL) and triethylamine (0.5 mL) under nitrogen. The reaction mixture was ice bath cooled and trifluoromethanesulfonic anhydride (0.4 mL, 2.4 mmol) was added dropwise. The reaction mixture was stirred with continued ice bath cooling for 1 h then evaporated to dryness in vacuo onto

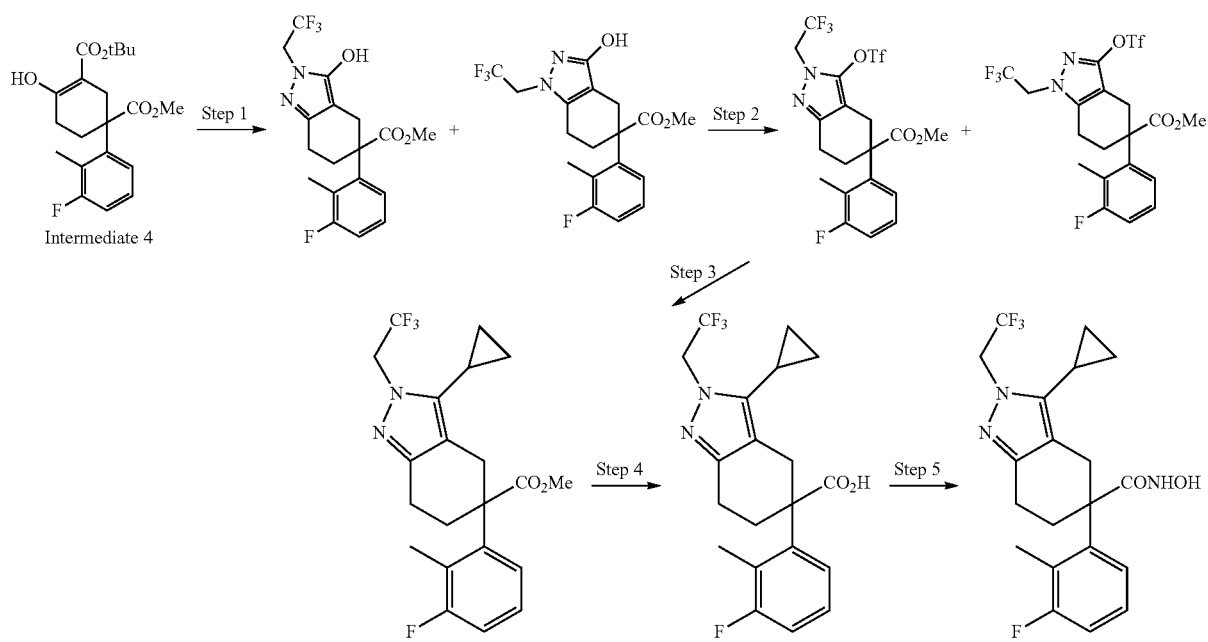

silica and purified by flash chromatography to give methyl 5-(3-fluoro-2-methylphenyl)-1-(2,2,2-trifluoroethyl)-3-(((trifluoromethyl)sulfonyl)oxy)-4,5,6,7-tetrahydro-1H-indazole-5-carboxylate as a clear oil (48 mg). LCMS (ES+) 519 (M+H)+; and methyl 5-(3-fluoro-2-methylphenyl)-2-(2,2,2-trifluoroethyl)-3-(((trifluoromethyl)sulfonyl)oxy)-4,5,6,7-tetrahydro-2H-indazole-5-carboxylate as a clear oil (639 mg). LCMS (ES+) 519 (M+H)+.

Step 3: 3-Cyclopropyl-5-(3-fluoro-2-methylphenyl)-2-(2,2,2-trifluoroethyl)-4,5,6,7-tetrahydro-2H-indazole-5-carboxylate Methyl 5-(3-fluoro-2-methylphenyl)-2-(2,2,2-trifluoroethyl)-3-(((trifluoromethyl)sulfonyl)oxy)-4,5,6,7-tetrahydro-2H-indazole-5-carboxylate (205 mg, 0.397 mmol), THF (10 mL), cyclopropyl zinc bromide (0.5N in THF) (4 mL, 2 mmol) and palladium tetrakis triphenylphosphine (10 mg) were combined under a nitrogen atmosphere and heated to 70° C. for 3 days. The reaction mixture was then diluted with EtOAc, washed with sat. aq. NH4Cl soln. and evaporated to dryness in vacuo. The crude product was purified by preparative HPLC to give the title compound as a tan solid (17.9 mg). LCMS (ES+) 411 (M+H)+.

Step 4: 3-Cyclopropyl-5-(3-fluoro-2-methylphenyl)-2-(2,2,2-trifluoroethyl)-4,5,6,7-tetrahydro-2H-indazole-5-carboxylic acid Methyl 3-cyclopropyl-5-(3-fluoro-2-methylphenyl)-2-(2,2,2-trifluoroethyl)-4,5,6,7-tetrahydro-2H-indazole-5-carboxylate (17.9 mg), MeOH (7 mL) and 15% NaOH soln. (0.5 mmol) were combined and heated to 70° C. for 15 days. Reaction mixture was then evaporated to dryness in vacuo, then partitioned between EtOAc and 1N HCl. Organic layer was dried (MgSO4) and evaporated to dryness in vacuo to give the title compound (16 mg) as a clear glass. LCMS (ES+) 397 (M+H)+.

Step 5: 3-Cyclopropyl-5-(3-fluoro-2-methylphenyl)-N-hydroxy-2-(2,2,2-trifluoroethyl)-4,5,6,7-tetrahydro-2H-indazole-5-carboxamide 3-Cyclopropyl-5-(3-fluoro-2-methylphenyl)-2-(2,2,2-trifluoroethyl)-4,5,6,7-tetrahydro-2H-indazole-5-carboxylic acid (16 mg), TFFH (100 mg), DMF (1 mL) and triethylamine (0.5 mL) were combined and stirred at room temperature for 1 h. 0-(Tetrahydro-2H-pyran-2-yl)hydroxylamine (60 mg, 0.5 mmol) was then added and stirring continued for 1 day. Volatile solvents were removed in vacuo. MeOH (5 mL) and 2N HCl in Et2O (2 mL) were added and reaction mixture was stirred for 1 h. Volatile solvents were removed in vacuo and remaining crude material was purified by preparative HPLC to give the title compound as a white solid (4 mg). LCMS (ES+) 412 (M+H)+, RT 9.89 (Analytical method 2); 1H NMR δ (ppm)(DMSO-d6): 10.15 (1H, s), 8.75 (1H, br s), 7.15-6.95 (2H, m), 6.85-6.80 (1H, m), 5.05-4.85 (2H, m), 3.08 (1H, d, J=16 Hz), 2.86 (1H, d, J=16 Hz), 2.50-2.40 (1H, m), 2.35-2.25 (1H, m), 2.25-2.15 (1H, m), 2.17 (3H, d, J=2.8 Hz), 1.85-1.70 (2H, m), 1.05-0.90 (2H, m), 0.85-0.65 (2H, m).

Example 40: 2-Cyclopropyl-6-(3-fluoro-2-methylphenyl)-N-hydroxy-4-oxo-3,4,5,6,7,8-hexahydroquinazoline-6-carboxamide

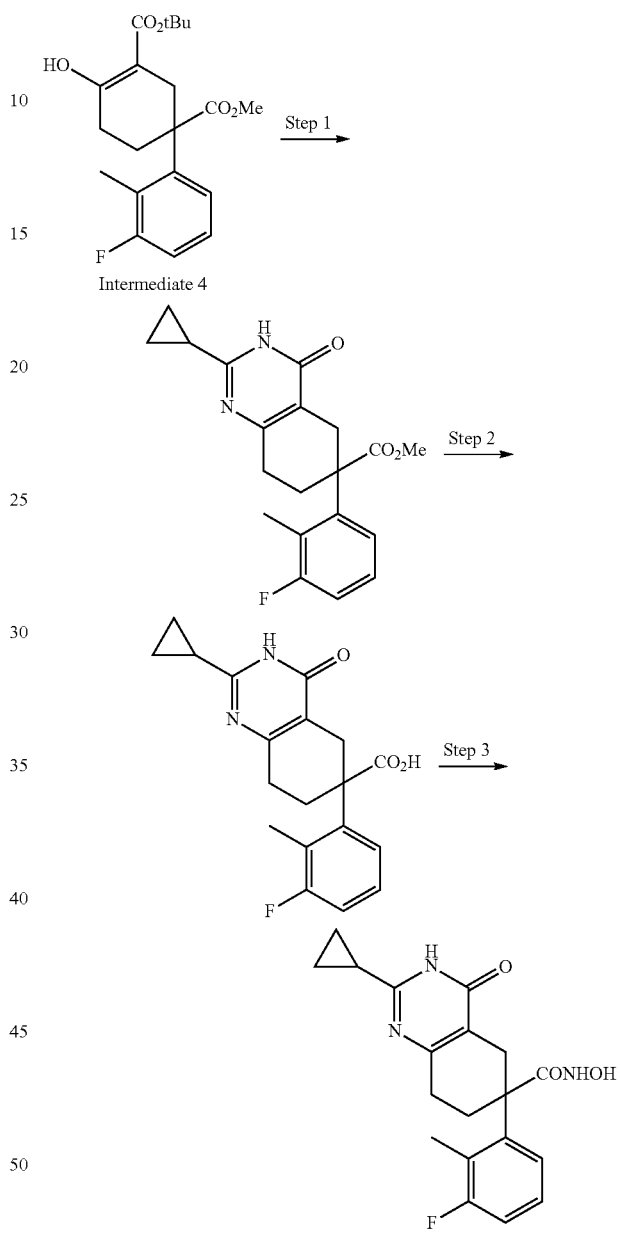

Step 1: Methyl 2-cyclopropyl-6-(3-fluoro-2-methylphenyl)-4-oxo-3,4,5,6,7,8-hexahydroquinazoline-6-carboxylate Intermediate 4 (1 g, 2.74 mmol), cyclopropylcarbamidine. HCl (361 mg, 3 mmol), MeOH (20 mL) and DIPEA (1 mL) were combined in a sealed tube and heated to 65° C. for 14 days. Reaction mixture was then evaporated to dryness in vacuo onto silica and purified by flash chromatography to give the title compound as a clear glass (99 mg). LCMS (ES+) 357 (M+H)+.

61

Step 2: 2-Cyclopropyl-6-(3-fluoro-2-methylphenyl)-4-oxo-3,4,5,6,7,8-hexahydroquinazoline-6-carboxylic acid Methyl 2-cyclopropyl-6-(3-fluoro-2-methylphenyl)-4-oxo-3,4,5,6,7,8-hexahydroquinazoline-6-carboxylate (99 mg), MeOH (10 mL) and 15% aq. NaOH soln. (2 mL) were combined in a sealed tube and heated to 65° C. for 19 days. The reaction mixture was then evaporated to dryness in vacuo, then partitioned between EtOAc and 1N HCl. The organic layer was dried (MgSO$_4$) and evaporated to dryness in vacuo to give the title compound as a clear glass (25 mg). LCMS (ES+) 343 (M+H)$^+$.

Step 3: 2-Cyclopropyl-6-(3-fluoro-2-methylphenyl)-N-hydroxy-4-oxo-3,4,5,6,7,8-hexahydroquinazoline-6-carboxamide 2-Cyclopropyl-6-(3-fluoro-2-methylphenyl)-4-oxo-3,4,5,6,7,8-hexahydroquinazoline-6-carboxylic acid (25 mg), TFFH (25 mg), DMF (1 mL) and triethylamine (0.1 mL) were combined and stirred at room temperature for 2 h. 0-(Tetrahydro-2H-pyran-2-yl)hydroxylamine (30 mg, 0.25 mmol) was then added and stirring was continued for 2 days. Volatile solvents were removed in vacuo. MeOH (2 mL) and 2N HCl in Et$_2$O (2 mL) were added and the reaction mixture was stirred for 1.5 h. Volatile solvents were removed in vacuo and remaining crude material was purified by preparative HPLC to give the title compound as an off-white solid (4 mg). LCMS (ES+) 358 (M+H)$^+$, RT 2.65 (Analytical method 1); $^1$H NMR δ (ppm)(DMSO-d$_6$): 12.44 (1H, s), 10.17 (1H, s), 8.71 (1H, s), 7.20-6.95 (2H, m), 6.90-6.80 (1H, m), 3.55-3.40 (1H, m), 2.70-2.60 (1H, m0, 2.40-2.30 (1H, m), 2.30-2.15 (2H, m), 2.17 (3H, d, J=2.8 Hz), 1.95-1.75 (2H, m), 1.00-0.85 (4H, m).

Example 41: 6-(3-Fluoro-2-methylphenyl)-N-hydroxy-2-(phenylsulfonamido)-4,5,6,7-tetrahydrobenzo[d]thiazole-6-carboxamide

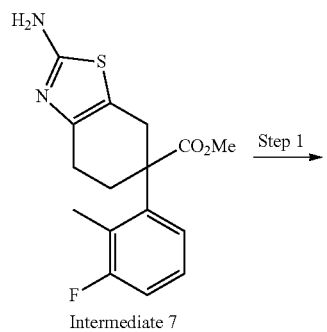

Intermediate 7

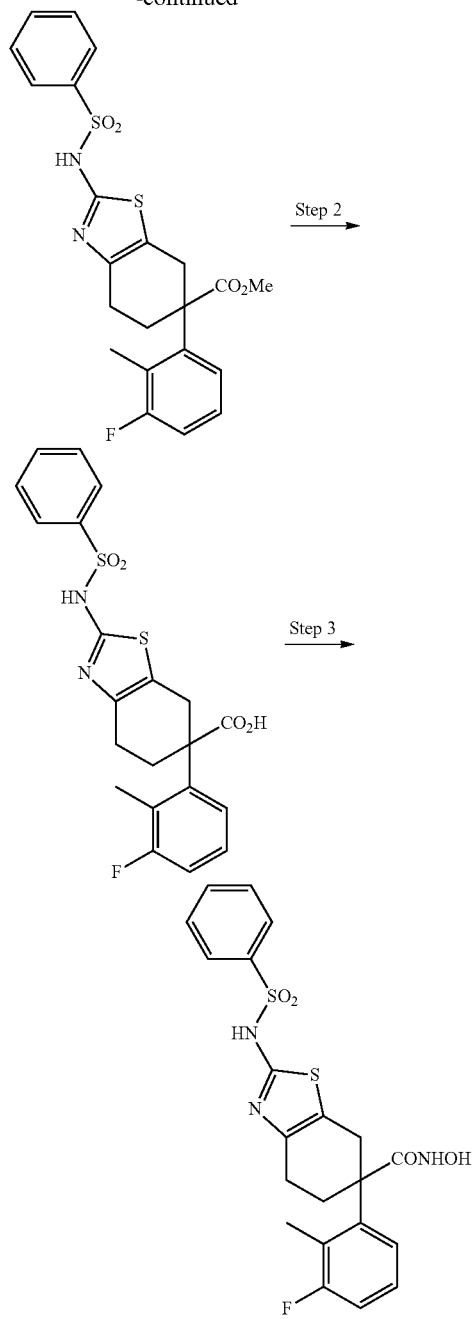

Step 1: Methyl 6-(3-fluoro-2-methylphenyl)-2-(phenylsulfonamido)-4,5,6,7-tetrahydrobenzo[d]thiazole-6-carboxylate Intermediate 7 (200 mg, 0.625 mmol), pyridine (5 mL), and phenylsulfonyl chloride (0.091 mL, 0.65 mmol) were combined and stirred for 4 days. Reaction mixture was then diluted with EtOAc, washed with 1N HCl (2×), dried (MgSO$_4$) and evaporated to dryness to give the title compound as a tan solid (234 mg, 81%). LCMS (ES+) 461 (M+H)$^+$.

Step 2: 6-(3-Fluoro-2-methylphenyl)-2-(phenylsulfonamido)-4,5,6,7-tetrahydrobenzo[d]thiazole-6-carboxylic acid Methyl 6-(3-fluoro-2-methylphenyl)-2-(phenylsulfonamido)-4,5,6,7-tetrahydrobenzo[d]thiazole-6-carboxylate (230 mg, 0.5 mmol), MeOH (10 mL) and 15% aq. NaOH soln. (2 mL) were combined in a sealed tube and heated to 70° C. for 5 days. Reaction was cooled and evaporated to dryness. Residue was partitioned between 1N HCl and EtOAc. Organics were dried (MgSO$_4$) and evaporated to dryness to give the title compound as a yellow gum (181 mg, 81%). LCMS (ES+) 447 (M+H)$^+$.

Step 3: 6-(3-Fluoro-2-methylphenyl)-N-hydroxy-2-(phenylsulfonamido)-4,5,6,7-tetrahydrobenzo[d]thiazole-6-carboxamide 6-(3-Fluoro-2-methylphenyl)-2-(phenylsulfonamido)-4,5,6,7-tetrahydrobenzo[d]thiazole-6-carboxylic acid (181 mg, 0.4 mmol), TFFH (127 mg, 0.48 mmol), DMF (2 mL) and triethylamine (0.5 mL) were combined and stirred for 16 h. O-(Tetrahydro-2H-pyran-2-yl)hydroxylamine (117 mg, 1 mmol) was then added and stirring continued for 2 days. Volatile solvents were removed in vacuo. MeOH (5 mL) and 2N HCl in Et$_2$O (2 mL) were added and reaction mixture was stirred for 2 h. Volatile solvents were removed in vacuo and remaining crude material was purified by preparative HPLC to give the title compound as an off-white solid (26 mg). LCMS (ES+) 462 (M+H)$^+$, RT 9.49 (Analytical method 2); $^1$H NMR δ (ppm)(DMSO-d$_6$): 12.45 (1H, br s), 10.22 (1H, s), 8.77 (1H, s), 7.82 (2H, m), 7.65-7.50 (3H, m), 7.25-7.10 (1H, m), 7.10-7.00 (1H, m), 6.95-6.85 (1H, m), 3.10-2.95 (1H, m), 2.85-2.75 (1H, m), 2.45-2.25 (3H, m), 2.15 (3H, d, J=2.4 Hz), 1.95-1.75 (1H, m).

Example 42: 2-Cyclopropyl-6-(3-fluoro-2-methylphenyl)-N-hydroxy-4,5,6,7-tetrahydrobenzo[d]thiazole-6-carboxamide

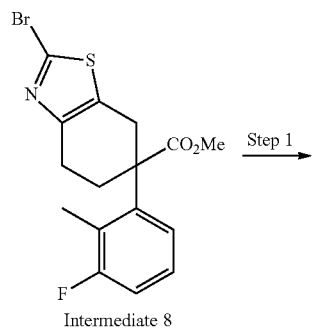

Intermediate 8

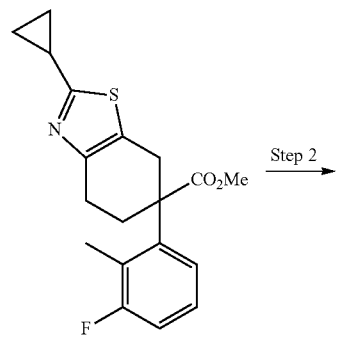

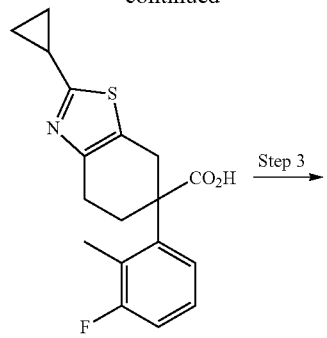

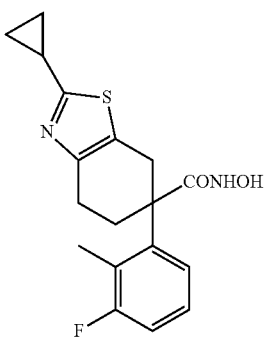

Step 1: Methyl 2-cyclopropyl-6-(3-fluoro-2-methylphenyl)-4,5,6,7-tetrahydrobenzo[d]thiazole-6-carboxylate Intermediate 8 (300 mg, 0.78 mmol), THF (10 mL), tetrakis(triphenylphosphine)palladium(0) (10 mg) and cyclopropylzinc bromide (0.5N in THF) (3 mL, 1.5 mmol) were combined under a nitrogen atmosphere and heated to 60° C. for 16 h. Further tetrakis(triphenylphosphine)palladium(0) (20 mg) and cyclopropylzinc bromide (0.5N in THF) (3 mL, 1.5 mmol) were added and heating continued for 23 h. The reaction mixture was evaporated to dryness onto silica and purified by flash chromatography to give the title compound as a tan solid (177 mg, 66%). LCMS (ES+) 346 (M+H)+.

Step 2: 2-Cyclopropyl-6-(3-fluoro-2-methylphenyl)-4,5,6,7-tetrahydrobenzo[d]thiazole-6-carboxylic acid Methyl 2-cyclopropyl-6-(3-fluoro-2-methylphenyl)-4,5,6,7-tetrahydrobenzo[d]thiazole-6-carboxylate (170 mg, 0.49 mmol), MeOH (10 mL) and 15% aq. NaOH soln. (1 mL) were combined in a sealed tube and heated to 65° C. for 5 days. Reaction was cooled and evaporated to dryness. Residue was partitioned between 1N HCl and EtOAc. The organic phase was dried (MgSO$_4$) and evaporated to dryness to give the title compound as a grey solid (136 mg, 84%). LCMS (ES+) 332 (M+H)$^+$.

Step 3: 2-Cyclopropyl-6-(3-fluoro-2-methylphenyl)-N-hydroxy-4,5,6,7-tetrahydrobenzo[d]thiazole-6-carboxamide 2-Cyclopropyl-6-(3-fluoro-2-methylphenyl)-4,5,6,7-tetrahydrobenzo[d]thiazole-6-carboxylic acid (136 mg, 0.41 mmol), TFFH (132 mg, 0.5 mmol), DMF (2 mL) and triethylamine (2 mL) were combined and stirred for 1.5 h. O-(Tetrahydro-2H-pyran-2-yl)hydroxylamine (117 mg, 1 mmol) was then added and stirring continued for 1 day. Volatile solvents were removed in vacuo. MeOH (2 mL) and 2N HCl in Et$_2$O (2 mL) were added and reaction mixture was stirred for 2 h. Volatile solvents were removed in vacuo and remaining crude material was purified by preparative HPLC to give the title compound as a yellow glass (54 mg). LCMS (ES+) 347 (M+H)$^+$, RT 3.2 (Analytical method 1); $^1$H NMR δ (ppm)(DMSO-d$_6$): 10.21 (1H, s), 8.80 (1H, br s), 7.15-7.05 (2H, m), 6.90 (1H, m), 3.30-3.05 (2H, m), 2.65-2.50 (1H, m), 2.40-2.25 (3H, m), 2.20 (3H, d, J=2.4 Hz), 2.10-2.00 (1H, m), 1.10-1.00 (2H, m), 1.90-1.80 (2H, m).

Example 43: 6-(3-Fluoro-2-methylphenyl)-N-hydroxy-2-(pyrimidin-5-yl)-4,5,6,7-tetrahydrobenzo[d]thiazole-6-carboxamide

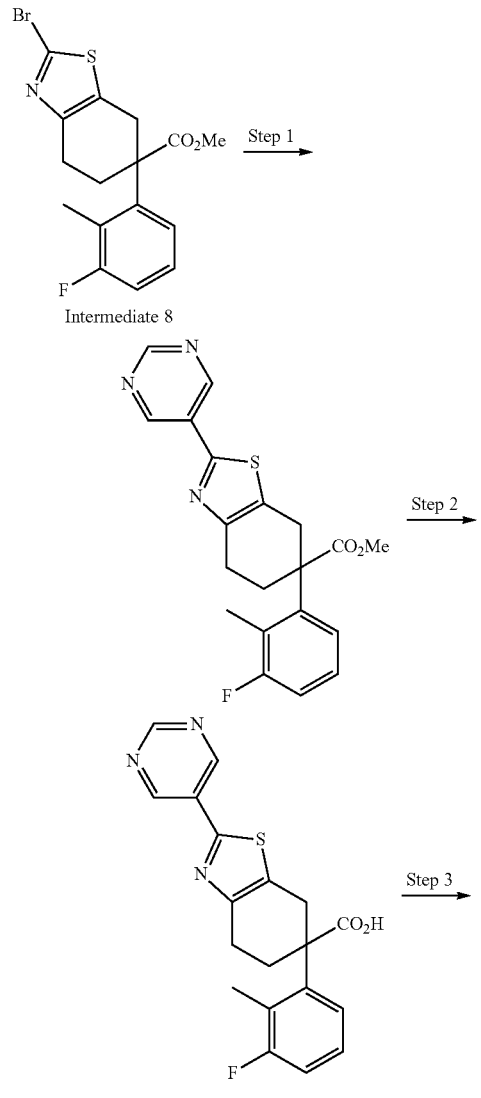

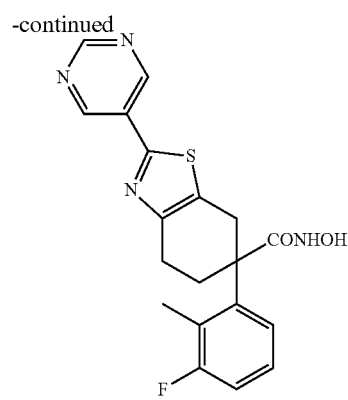

Step 1: Methyl 6-(3-fluoro-2-methylphenyl)-2-(pyrimidin-5-yl)-4,5,6,7-tetrahydrobenzo[d]thiazole-6-carboxylate Intermediate 8 (275 mg, 0.716 mmol), pyrimidine-5-boronic acid (99 mg, 0.8 mmol), CsF (150 mg), DME (15 mL), MeOH (2 mL) and tetrakis(triphenylphosphine)palladium(0) (10 mg) were combined in a sealed tube and microwave heated to 120° C. for 2 h. Reaction mixture was evaporated to dryness onto silica and purified by flash chromatography to give the title compound as a tan glass (217 mg, 79%). LCMS (ES+) 384 (M+H)$^+$.

Step 2: 6-(3-Fluoro-2-methylphenyl)-2-(pyrimidin-5-yl)-4,5,6,7-tetrahydrobenzo[d]thiazole-6-carboxylic acid Methyl 6-(3-fluoro-2-methylphenyl)-2-(pyrimidin-5-yl)-4,5,6,7-tetrahydrobenzo[d]thiazole-6-carboxylate (200 mg, 0.52 mmol), MeOH (10 mL) and 15% aq. NaOH soln. (1 mL) were combined in a sealed tube and heated to 65° C. for 2 days. The reaction mixture was cooled and evaporated to dryness. Residue was partitioned between AcOH/H$_2$O and EtOAc. The organic phase was dried (MgSO$_4$) and evaporated to dryness to give the title compound as a pale yellow glass (151 mg) which was used crude in next step.

Step 3: 6-(3-Fluoro-2-methylphenyl)-N-hydroxy-2-(pyrimidin-5-yl)-4,5,6,7-tetrahydrobenzo[d]thiazole-6-carboxamide 6-(3-Fluoro-2-methylphenyl)-2-(pyrimidin-5-yl)-4,5,6,7-tetrahydrobenzo[d]thiazole-6-carboxylic acid (151 mg, 0.4 mmol), TFFH (132 mg, 0.5 mmol), DMF (2 mL) and triethylamine (2 mL) were combined and stirred for 1 h. O-(Tetrahydro-2H-pyran-2-yl)hydroxylamine (117 mg, 1 mmol) was then added and stirring continued for 1 day. Volatile solvents were removed in vacuo. MeOH (2 mL) and 2N HCl in Et$_2$O (2 mL) were added and reaction mixture was stirred for 30 min. Volatile solvents were removed in vacuo and remaining crude material was purified by preparative HPLC to give the title compound as an off white solid (11 mg). LCMS (ES+) 385 (M+H)$^+$, RT 9.03 (Analytical method 2); $^1$H NMR δ (ppm)(DMSO-d$_6$): 10.30 (1H, s), 9.25 (1H, s), 9.24 (2H, s), 8.80 (1H, s), 7.20-6.95 (3H, m), 3.55-3.45 (1H, m), 3.30-3.15 (1H, m), 2.80-2.70 (1H, m), 2.60-2.40 (2H, m), 2.40-2.30 (1H, m), 2.20 (3H, d, J=2.4 Hz).

Example 44: 6-(3-Fluoro-2-methylphenyl)-N-hydroxy-4,5,6,7-tetrahydrobenzo[d]thiazole-6-carboxamide

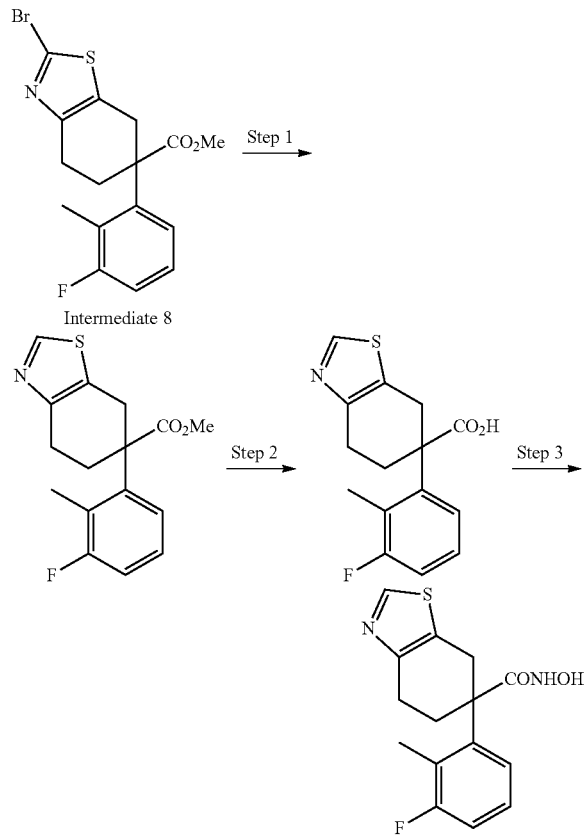

Intermediate 8

Step 1: Methyl 6-(3-fluoro-2-methylphenyl)-4,5,6,7-tetrahydrobenzo[d]thiazole-6-carboxylate Intermediate 8 (300 mg, 0.78 mmol), AcOH (10 mL) and Zn dust (300 mg) were combined and heated to 65° C. for 1 h. Zn residues were removed by filtering through a celite plug washing through with EtOAc. Organics were then evaporated to dryness to give the title compound as a tan solid which was used crude in next step. LCMS (ES+) 306 (M+H)+.

Step 2: 6-(3-Fluoro-2-methylphenyl)-4,5,6,7-tetrahydrobenzo[d]thiazole-6-carboxylic acid Methyl 6-(3-fluoro-2-methylphenyl)-4,5,6,7-tetrahydrobenzo[d]thiazole-6-carboxylate (0.78 mmol), MeOH (15 mL) and 15% aq. NaOH soln. (3 mL) were combined in a sealed tube and heated to 65° C. for 19 h. Reaction was cooled and evaporated to dryness. The residue was partitioned between 1N HCl and EtOAc. Organics were dried (MgSO4) and evaporated to dryness to give the title compound as a tan glass (191 mg, 84% over two steps). LCMS (ES+) 292 (M+H)+.

Step 3: 6-(3-Fluoro-2-methylphenyl)-N-hydroxy-4,5,6,7-tetrahydrobenzo[d]thiazole-6-carboxamide 6-(3-Fluoro-2-methylphenyl)-4,5,6,7-tetrahydrobenzo[d]thiazole-6-carboxylic acid (196 mg, 0.67 mmol), TFFH (264 mg, 1 mmol), DMF (2 mL) and triethylamine (0.3 mL) were combined and stirred for 1 h. O-(Tetrahydro-2H-pyran-2-yl)hydroxylamine (117 mg, 1 mmol) was then added and stirring continued for 2 days. Volatile solvents were removed in vacuo. MeOH (2 mL) and 2N HCl in Et2O (2 mL) were added and reaction mixture was stirred for 5 h. Volatile solvents were removed in vacuo and remaining crude material was purified by preparative HPLC to give the title compound as an off-white solid (43 mg). LCMS (ES+) 307 (M+H)+, RT 2.87 (Analytical method 1); $^1$H NMR δ (ppm) (DMSO-$d_6$): 10.24 (1H, s), 8.86 (1H, s), 8.77 (1H, s), 7.15-7.00 (2H, m), 6.90 (1H, m), 3.40-3.30 (1H, m), 3.25-3.15 (1H, m), 2.75-2.65 (1H, m), 2.60-2.50 (1H, m), 2.45-2.35 (1H, m), 2.25-2.10 (1H, m), 2.20 (3H, d, J=2.4 Hz).

Example 45: 6-(3-Fluoro-2-methylphenyl)-N-hydroxy-5,6,7,8-tetrahydroquinazoline-6-carboxamide

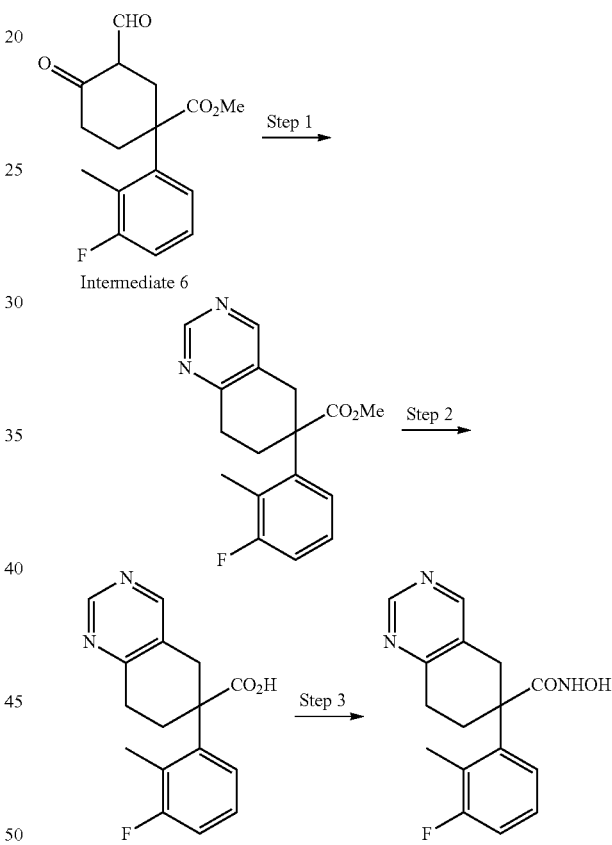

Intermediate 6

Step 1: Methyl 6-(3-fluoro-2-methylphenyl)-5,6,7,8-tetrahydroquinazoline-6-carboxylate Intermediate 6 (516 mg, 1.77 mmol), formamidine.AcOH (198 mg, 1.9 mmol), MeOH (10 mL) and DIPEA (2 mL) were combined in a sealed tube and heated to 70° C. for 2.5 h. The reaction mixture was then evaporated to dryness onto silica and purified by flash chromatography to give the title compound as a clear gum (264 mg, 50%). LCMS (ES+) 301 (M+H)+.

Step 2: 6-(3-Fluoro-2-methylphenyl)-5,6,7,8-tetrahydroquinazoline-6-carboxylic acid Methyl 6-(3-fluoro-2-methylphenyl)-5,6,7,8-tetrahydroquinazoline-6-carboxylate (264 mg, 0.88 mmol), MeOH (10 mL) and 15% aq. NaOH soln. (2 mL) were combined in a sealed tube and heated to 70° C. for 4 days. The reaction mixture was cooled and evaporated to dryness. The residue was partitioned between 1N HCl and EtOAc. Organics were dried (MgSO$_4$) and evaporated to dryness to give the title compound as a pale yellow gum (194 mg, 77%). LCMS (ES+) 287 (M+H)$^+$.

Step 3: 6-(3-Fluoro-2-methylphenyl)-N-hydroxy-5,6,7,8-tetrahydroquinazoline-6-carboxamide 6-(3-Fluoro-2-methylphenyl)-5,6,7,8-tetrahydroquinazoline-6-carboxylic acid (194 mg, 0.68 mmol), TFFH (211 mg, 0.8 mmol), DMF (2 mL) and triethylamine (0.28 mL) were combined and stirred for 4 h. O-(Tetrahydro-2H-pyran-2-yl)hydroxylamine (117 mg, 1 mmol) was then added and stirring continued for 16 h. Volatile solvents were removed in vacuo. MeOH (5 mL) and 2N HCl in Et$_2$O (2 mL) were added and reaction mixture was stirred for 2.5 h. Volatile solvents were removed in vacuo and remaining crude material was purified by preparative HPLC to give the title compound as a white solid (17 mg). LCMS (ES+) 302 (M+H)$^+$, RT 2.59 (Analytical method 1); $^1$H NMR δ (ppm) (DMSO-d$_6$): 10.28 (1H, s), 8.85 (1H, s), 8.76 (1H, s), 8.57 (1H, s), 7.25-7.00 (3H, m), 3.50-3.35 (1H, m), 3.00-2.90 (1H, m), 2.80-2.70 (1H, m), 2.65-2.55 (1H, m), 2.50-2.40 (2H, m), 2.21 (3H, d, J=2.4 Hz).

Example 46: 2-Cyclopropyl-6-(3-fluoro-2-methylphenyl)-N-hydroxy-5,6,7,8-tetrahydroquinazoline-6-carboxamide Prepared following the method described for Example 45. Preparative HPLC gave the title compound as a white solid (90 mg). LCMS (ES+) 342 (M+H)$^+$, RT 2.96 (Analytical method 1); $^1$H NMR δ (ppm)(DMSO-d$_6$): 10.28 (1H, s), 8.75 (1H, br s), 8.39 (1H, s), 7.20-6.95 (3H, m), 3.40-3.30 (2H, m), 2.9 (1H, m), 2.75-2.65 (1H, m), 2.50-2.35 (2H, m), 2.21 (3H, d, J=2.4 Hz), 2.10 (1H, m), 1.00-0.85 (4H, m).

Example 47: 6-(3-Fluoro-2-methylphenyl)-N-hydroxy-2-phenyl-5,6,7,8-tetrahydroquinazoline-6-carboxamide Prepared following the method described for Example 45. Preparative HPLC gave the title compound as a white solid (53 mg). LCMS (ES+) 378 (M+H)$^+$, RT 3.66 (Analytical method 1); $^1$H NMR δ (ppm)(DMSO-d$_6$): 10.31 (1H, s), 8.78 (1H, br s), 8.68 (1H, s), 8.35 (2H, m), 7.55-7.45 (3H, m), 7.25-7.00 (3H, m), 3.50-3.40 (2H, m), 3.05-2.95 (1H, m), 2.90-2.80 (1H, m), 2.70-2.55 (2H, m), 2.24 (3H, d, J=2.4 Hz).

Examples 48 and 49: (S)-2-(2-Chlorophenyl)-6-(3-fluoro-2-methylphenyl)-N-hydroxy-6,7-dihydro-5H-cyclopenta[d]pyrimidine-6-carboxamide and (R)-2-(2-chlorophenyl)-5-(3-fluoro-2-methylphenyl)-N-hydroxy-6,7-dihydro-5H-cyclopenta[d]pyrimidine-5-carboxamide

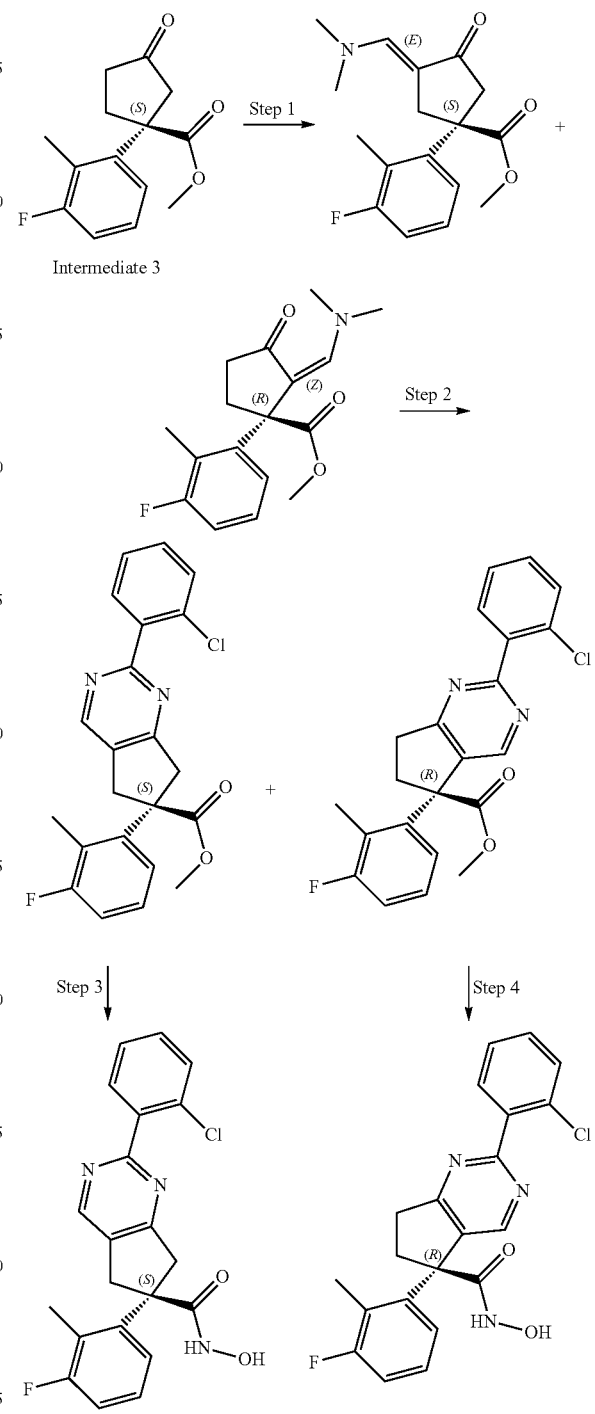

Step 1: (S)-Methyl-3-((dimethylamino)methylene)-1-(3-fluoro-2-methylphenyl)-4-oxocyclopentane carboxylate and (R)-methyl-2-(dimethylaminomethylene)-1-(3-fluoro-2-methyl-phenyl)-3-oxo-cyclopentanecarboxylate Intermediate 3 (2.5 g, 1.0 mmol) was dissolved in dimethylformamide dimethylacetal (5.0 mL) and heated to 80° C. for 16 h. The cooled mixture was concentrated onto silica and purified by flash silica column chromatography (gradient elution i-hex to 100% EtOAc in i-hex) to yield the title compounds as a pale yellow oil (1.8 g, 58%). LCMS (ES+) 306 (M+H)⁺.

Step 2: Methyl (6S)-2-(2-chlorophenyl)-6-(3-fluoro-2-methyl-phenyl)-5,7-dihydrocyclopenta[d]pyrimidine-6-carboxylate and methyl (5R)-2-(2-chlorophenyl)-5-(3-fluoro-2-methyl-phenyl)-6,7-dihydrocyclopenta[d]pyrimidine-5-carboxylate A mixture of (S)-methyl-3-((dimethylamino)methylene)-1-(3-fluoro-2-methylphenyl)-4-oxocyclopentane carboxylate and (R)-methyl-2-(dimethylaminomethylene)-1-(3-fluoro-2-methyl-phenyl)-3-oxo-cyclopentanecarboxylate (0.305 g, 1 mmol) and 2-chlorobenzamidine hydrochloride (0.28 g, 1.5 mmol) in methanol (5 mL) was heated to 130° C. for 30 min. The solvent was removed under reduced pressure and the residue was partitioned between DCM (15 mL) and water (15 mL). The DCM was separated (phase separator) and evaporated under reduced pressure to give an oil which was purified by flash chromatography to give (S)-methyl 2-(2-chlorophenyl)-6-(3-fluoro-2-methylphenyl)-6,7-dihydro-5H-cyclopenta[d]pyrimidine-6-carboxylate as a colorless oil. LCMS (ES+) 397 (M+H)⁺; ¹H NMR δ (ppm)(CHCl₃-d): 8.68 (1H, s), 7.74-7.68 (1H, m), 7.53-7.47 (1H, m), 7.40-7.33 (2H, m), 7.19-7.06 (1H, m), 7.07-6.94 (2H, m), 4.07-3.94 (2H, m), 3.73 (3H, s), 3.63 (1H, s), 3.59-3.48 (1H, m), 2.23 (3H, s). (R)-Methyl 2-(2-chlorophenyl)-5-(3-fluoro-2-methylphenyl)-6,7-dihydro-5H-cyclopenta[d]pyrimidine-5-carboxylate was obtained as a colorless oil. LCMS (ES+) 398 (M+H)⁺; ¹H NMR δ (ppm)(CHCl₃-d): 8.83 (1H, s), 7.81-7.75 (1H, m), 7.55-7.48 (1H, m), 7.48-7.26 (2H, m), 7.16-7.04 (1H, m), 7.01 (1H, m), 6.56 (1H, m), 3.79 (3H, s), 3.51 (1H, m), 3.30 (1H, m), 3.12 (1H, m), 2.27-2.18 (4H, m).

Step 3: (S)-2-(2-Chlorophenyl)-6-(3-fluoro-2-methylphenyl)-N-hydroxy-6,7-dihydro-5H-cyclopenta[d]pyrimidine-6-carboxamide Trimethylaluminum (1.56 mL, 2 M in toluene, 3.12 mmol) was added to a stirred solution of hydroxylamine hydrochloride (240 mg, 10.1 mmol) in dry DCM (5 mL) under nitrogen and the resulting solution was stirred for 30 min at room temperature under nitrogen. A solution of (6S)-2-(2-chlorophenyl)-6-(3-fluoro-2-methyl-phenyl)-5,7-dihydrocyclopenta[d]pyrimidine-6-carboxylate (0.234 g, 0.59 mmol) in DCM (8 mL) was added and stirring was continued for 1 h. Saturated ammonium chloride solution (1 mL) was added followed by water (2.5 mL) and the resulting mixture was evaporated to dryness, the residue was stirred with methanol (25 mL) for 10 min. and filtered. The filtrate was evaporated to dryness under reduced pressure and the residue was stirred with EtOAc (30 mL) and filtered. The EtOAc was evaporated and the resulting oil was purified by preparative HPLC to give the title compound (78 mg, 33%) as a colorless solid. LCMS (ES+) 398 (M+H)⁺, RT 3.44 (Analytical method 1); ¹H NMR δ (ppm)(DMSO-d₆): 10.30 (1H, br), 8.86 (1H, br), 8.81-8.69 (1H, m), 7.73-7.65 (1H, m), 7.59-7.53 (1H, m), 7.51-7.42 (2H, m), 7.24-7.05 (3H, m), 3.98-3.93 (1H, m), 3.84-3.78 (1H, m), 3.53-3.47 (1H, m), 3.43-3.23 (1H, m), 2.27-2.19 (3H, m).

Step 4: (R)-2-(2-Chlorophenyl)-5-(3-fluoro-2-methylphenyl)-N-hydroxy-6,7-dihydro-5H-cyclopenta[d]pyrimidine-5-carboxamide The same method as for Step 3 from (R)-methyl 2-(2-chlorophenyl)-5-(3-fluoro-2-methylphenyl)-6,7-dihydro-5H-cyclopenta[d]pyrimidine-5-carboxylate. Preparative HPLC gave the title compound (14 mg) as a colorless solid. LCMS (ES+) 398 (M+H)⁺, RT 8.91 (Analytical method 3); ¹H NMR δ (ppm)(DMSO-d₆): 8.95 (1H, s), 7.79-7.75 (1H, m), 7.63-7.58 (1H, m), 7.55-7.46 (2H, m), 7.21-7.11 (2H, m), 6.63 (1H, s), 3.5-3.30 (1H, m), 3.20-3.05 (1H, m), 3.05-2.96 (1H, m), 2.19 (3H, d, J=2 Hz), 2.07-1.98 (1H, m), two exchangeable protons not seen.

Examples 50 and 51: (R)-2-Cyclopropyl-6-(3-fluoro-2-methylphenyl)-N-hydroxy-6,7-dihydro-5H-cyclopenta[d]pyrimidine-6-carboxamide and (S)-2-cyclopropyl-5-(3-fluoro-2-methylphenyl)-N-hydroxy-6,7-dihydro-5H-cyclopenta[d]pyrimidine-5-carboxamide
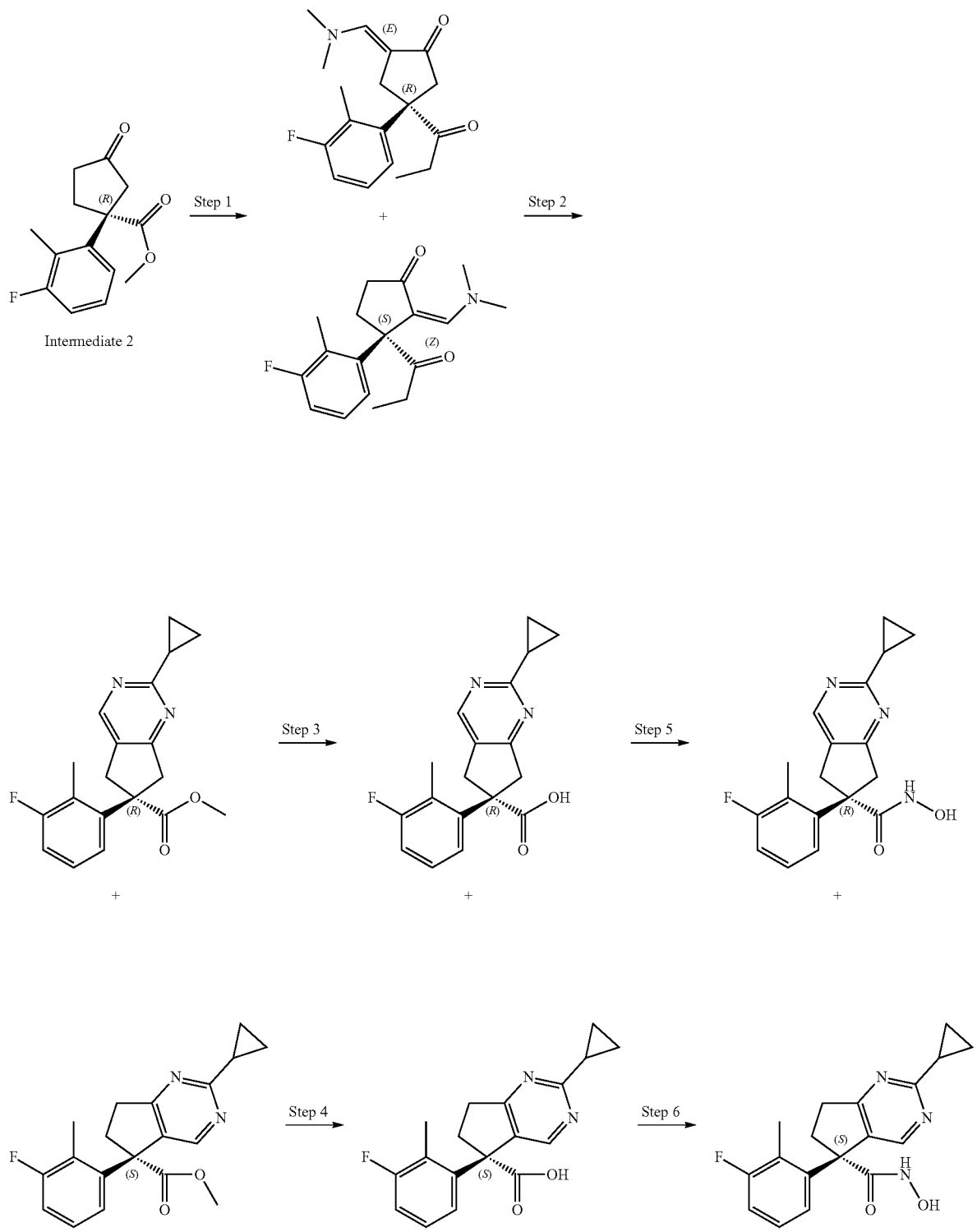

Step 1: (R)-Methyl-3-((dimethylamino)methylene)-1-(3-fluoro-2-methylphenyl)-4-oxocyclopentane carboxylate and (S)-methyl-2-(dimethylaminomethylene)-1-(3-fluoro-2-methyl-phenyl)-3-oxo-cyclopentanecarboxylate Intermediate 2 (2.5 g, 1.0 mmol) was dissolved in dimethylformamide dimethylacetal (5.0 mL) and heated to 80° C. for 16 h. Concentrated onto silica and purified by flash silica column chromatography (gradient elution i-hex to 100% EtOAc in i-hex) to yield the title compounds as a pale yellow oil (1.8 g, 58.8%). LCMS (ES+) 306 (M+H)+.

Step 2: (R)-Methyl 2-cyclopropyl-6-(3-fluoro-2-methylphenyl)-6,7-dihydro-5H-cyclopenta[d]pyrimidine-6-carboxylate and (S)-methyl 2-cyclopropyl-5-(3-fluoro-2-methylphenyl)-6,7-dihydro-5H-cyclopenta[d]pyrimidine-5-carboxylate To a solution of (R)-methyl-3-((dimethylamino)methylene)-1-(3-fluoro-2-methylphenyl)-4-oxocyclopentane carboxylate and (S)-methyl-2-(dimethylaminomethylene)-1-(3-fluoro-2-methyl-phenyl)-3-oxo-cyclopentanecarboxylate (0.23 g, 0.75 mmol) in methanol (10 mL) was added cyclopropanecarboximidamide (91 mg, 0.755 mmol) and NaOMe (41 mg, 0.755 mmol) and the reaction mixture was stirred at 100° C. overnight. The mixture was concentrated onto silica and purified by flash silica column chromatography (gradient elution i-hex to 70% EtOAc in i-hex) to yield (R)-methyl 2-cyclopropyl-6-(3-fluoro-2-methylphenyl)-6,7-dihydro-5H-cyclopenta[d]pyrimidine-6-carboxylateas a yellow oil (0.12 g, 50%). LCMS (ES+) 327 (M+H)+. (S)-Methyl 2-cyclopropyl-5-(3-fluoro-2-methylphenyl)-6,7-dihydro-5H-cyclopenta[d]pyrimidine-5-carboxylatewas obtained as a yellow oil (68 mg, 28%). LCMS (ES+) 327 (M+H)+.

Step 3: (R)-2-Cyclopropyl-6-(3-fluoro-2-methylphenyl)-6,7-dihydro-5H-cyclopenta[d]pyrimidine-6-carboxylic acid (R)-Methyl 2-cyclopropyl-6-(3-fluoro-2-methylphenyl)-6,7-dihydro-5H-cyclopenta[d]pyrimidine-6-carboxylate (68 mg, 0.19 mmol), MeOH (3 mL) and 15% aq. NaOH soln. (0.5 mL) were combined in a sealed tube and heated to 70° C. for 4 days. The reaction mixture was cooled and evaporated to dryness. The residue was partitioned between 1N HCl and EtOAc. Organics were dried (MgSO4) and evaporated to dryness to give the title compound as an off white solid. LCMS (ES+) 313 (M+H)+.

Step 4: (S)-2-Cyclopropyl-5-(3-fluoro-2-methylphenyl)-6,7-dihydro-5H-cyclopenta[d]pyrimidine-5-carboxylic acid Following the same method as Step 3. Preparative HPLC gave the title compound as a white solid. LCMS (ES+) 313 (M+H)+.

Step 5: (R)-2-Cyclopropyl-6-(3-fluoro-2-methylphenyl)-N-hydroxy-6,7-dihydro-5H-cyclopenta[d]pyrimidine-6-carboxamide (R)-2-Cyclopropyl-6-(3-fluoro-2-methylphenyl)-6,7-dihydro-5H-cyclopenta[d]pyrimidine-6-carboxylic acid (51 mg, 0.19 mmol), TFFH (58 mg, 0.22 mmol), DMF (1 mL) and triethylamine (1 mL) were combined and stirred for 1 h. O-(Tetrahydro-2H-pyran-2-yl)hydroxylamine (51 mg, 0.28 mmol) was then added and stirring continued for 1 day. Volatile solvents were removed in vacuo. MeOH (1 mL) and 2N HCl in Et2O (1 mL) were added and reaction mixture was stirred for 30 min. Volatile solvents were removed in vacuo and remaining crude material was purified by preparative HPLC to give the title compound as an off white solid (29 mg). LCMS (ES+) 328 (M+H)+, RT 2.90 (Analytical method 1); $^1$H NMR δ (ppm)(CH3OH-d4): 8.39 (1H, s), 7.19-7.10 (1H, m), 7.09-6.97 (2H, m), 3.90 (1H, d, J=17.2 Hz), 3.80 (1H, d, J=16.4 Hz), 3.44 (1H, d, J=16.4 Hz), 3.29 (1H, d, J=17.2 Hz), 2.26 (3H, s), 2.22-2.13 (1H, m), 1.12-1.04 (4H, m) two exchangeable protons not seen.

Step 6: (S)-2-Cyclopropyl-5-(3-fluoro-2-methylphenyl)-N-hydroxy-6,7-dihydro-5H-cyclopenta[d]pyrimidine-5-carboxamide Following the same method as Step 5. Preparative HPLC gave the title compound as a white solid (28 mg). LCMS (ES+) 328 (M+H)+, RT 9.15 (Analytical method 2). $^1$H NMR δ (ppm)(CH3OH-d4): 8.59 (1H, s), 7.16-7.08 (1H, m), 7.05 (1H, t, J=9.0 Hz), 6.54 (1H, d, J=7.78 Hz), 3.50 (1H, ddd, J=13.20, 9.30, 7.12 Hz), 3.16-3.05 (1H, m), 2.92 (1H, ddd, J=17.9, 9.2, 7.2 Hz), 2.32-2.23 (4H, m), 2.11 (1H, ddd, J=13.1, 9.2, 4.9 Hz), 1.22-1.10 (4H, m) two exchangeable protons not seen.

Example 52: (S)-2-Cyclopropyl-6-(3-fluoro-2-methylphenyl)-N-hydroxy-6,7-dihydro-5H-cyclopenta[d]pyrimidine-6-carboxamide Prepared following the method described for Examples 50 and 51, from Intermediate 3. Purification by preparative HPLC gave the title compound as a white solid (12 mg). LCMS (ES+) 328 (M+H)+, RT 8.81 (Analytical method 2). $^1$H NMR δ (ppm)(DMSO-d6): 10.24 (1H, s), 8.81 (1H, s), 8.43 (1H, s), 7.19-7.12 (1H, m), 7.09-7.03 (2H, m), 3.81 (1H, d, J=17.1 Hz), 3.65 (1H, d, J=16.3 Hz), 3.38 (1H, obscured by water), 3.17 (1H, d, J=17.2 Hz), 2.18 (3H, d, J=2.8 Hz), 2.16-2.11 (1H, m), 1.00-0.92 (4H, m).

Example 53: (S)-5-(3-Fluoro-2-methylphenyl)-N-hydroxy-1-isopropyl-1,4,5,6-tetrahydrocyclopenta[c]pyrazole-5-carboxamide Prepared following the method described for Example 50 and 51, starting from intermediate 3. Only one regioisomer was isolated. Preparative HPLC gave the title compound as a white solid (5 mg). LCMS (ES+) 318 (M+H)+, RT 8.89 (Analytical method 2); $^1$H NMR δ (ppm)(DMSO-d6): 10.18 (1H, s), 8.77 (1H, br s), 7.20-6.90 (4H, m), 4.40-4.30 (1H, m), 3.74 (1H, d, J=16 Hz), 3.30 (1H, d, J=16 Hz), 3.02 (1H, d, J=16 Hz), 2.98 (1H, d, J=16 Hz), 2.15 (3H, d, J=2.8 Hz), 1.35 (6H, d, J=6.8 Hz).

Example 54: (R)-4-(3-Fluoro-2-methylphenyl)-N-hydroxy-1-phenyl-1,4,5,6-tetrahydrocyclopenta[c]pyrazole-4-carboxamide Prepared following the method described for Example 48 and 49. Only one regioisomer was isolated. Preparative HPLC gave the title compound as a white solid (11 mg). LCMS (ES+) 352 (M+H)+, RT 9.08 (Analytical method 3). $^1$H NMR δ (ppm)(DMSO-d6): 10.21 (1H, s), 8.80 (1H, br s), 8.78 (1H, s), 7.76-7.66 (3H, m), 7.55-7.47 (2H, m), 7.35-

7.30 (1H, m), 7.22-7.14 (1H, m), 7.13-7.04 (2H, m), 3.95-3.80 (1H, m), 3.22-3.12 (1H, m), 3.11-3.02 (1H, m), 2.42-2.33 (1H, m), 2.15 (3H, s).

Example 55: (S)-6-(3-Fluoro-2-methylphenyl)-2-(4-fluorophenyl)-N-hydroxy-6,7-dihydro-5H-cyclopenta[d]pyrimidine-6-carboxamide Prepared following the method described for Example 50 and 51 starting from intermediate 3. Only one regioisomer was isolated. Preparative HPLC gave the title compound as an off white solid (23 mg). LCMS (ES+) 382 (M+H)$^+$, RT 10.55 (Analytical method 2); $^1$H NMR δ (ppm)(DMSO-d$_6$): 10.30 (1H, s), 8.80 (1H, br s), 8.72 (1H, s), 8.44-8.37 (2H, m), 7.38-7.28 (2H, m), 7.21-7.04 (3H, m), 3.95 (1H, d, J=17.2 Hz), 3.76 (1H, d, J=16.8 Hz), 3.47 (1H, d, 16.8 Hz), 3.29 (1H, d, J=17.2 Hz), 2.26-2.20 (3H, s).

Example 56: (S)-6-(3-Fluoro-2-methylphenyl)-N-hydroxy-2-(trifluoromethyl)-6,7-dihydro-5H-cyclopenta[d]pyrimidine-6-carboxamide Prepared following the method described for Example 50 and 51 starting from intermediate 3. Only one regioisomer was isolated. Preparative HPLC gave the title compound as a colorless solid (35 mg). LCMS (ES+) 356 (M+H)$^+$, RT 3.40 (Analytical method 1); $^1$H NMR δ (ppm)(DMSO-d$_6$): 10.30 (1H, s), 8.87 (2H, s), 7.23-7.14 (1H, m), 7.14-7.05 (2H, m), 4.02-3.97 (1H, m), 3.85-3.80 (1H, m), 3.60-3.56 (1H, m), 3.46-3.42 (1H, m), 2.20 (3H, s).

Example 57: (R)-2-Cyclopropyl-5-(3-fluoro-2-methylphenyl)-N-hydroxy-6,7-dihydro-5H-cyclopenta[d]pyrimidine-5-carboxamide Prepared following the method described for Example 50 and 51 starting from intermediate 3. Only one regioisomer was isolated. Preparative HPLC gave the title compound as a colorless solid (21 mg). LCMS (ES+) 328 (M+H)$^+$, RT 3.17 (Analytical method 1), $^1$H NMR δ (ppm)(CH$_3$OH-d$_4$): 8.59 (1H, s), 7.16-7.00 (2H, m), 6.54 (1H, d, J=7.8 Hz), 3.56-3.44 (1H, m), 3.18-3.06 (1H, m), 2.98-2.85 (1H, m), 2.32-2.23 (4H, m), 2.11-2.05 (1H, m), 1.22-1.09 (4H, m) two exchangeable protons not seen.

Examples 58 and 59: (S)-1-Cyclopropyl-5-(3-fluoro-2-methylphenyl)-N-hydroxy-1,4,5,6-tetrahydrocyclopenta[c]pyrazole-5-carboxamide and (R)-1-cyclopropyl-4-(3-fluoro-2-methylphenyl)-N-hydroxy-1,4,5,6-tetrahydrocyclopenta[c]pyrazole-4-carboxamide Prepared following the method described for Example 50 and 51 starting from intermediate 3. Preparative HPLC gave(S)-1-cyclopropyl-5-(3-fluoro-2-methylphenyl)-N-hydroxy-1,4,5,6-tetrahydrocyclopenta[c]pyrazole-5-carboxamide was obtained as a white solid (10 mg). LCMS (ES+) 316 (M+H)$^+$, RT 7.86 (Analytical method 3). $^1$H NMR δ (ppm)(DMSO-d$_6$): 10.19 (1H, s), 8.78 (1H, s), 7.20-7.01 (4H, m), 3.76 (1H, d, J=16 Hz), 3.53-3.45 (1H, m), 3.26 (1H, d, J=14.8 Hz), 3.05 (1H, d, J=16 Hz), 2.95 (1H, d, J=14.8 Hz), 2.18-2.11 (3H, m), 0.97-0.87 (4H, m). (R)-1-Cyclopropyl-4-(3-fluoro-2-methylphenyl)-N-hydroxy-1,4,5,6-tetrahydrocyclopenta[c]pyrazole-4-carboxamide was obtained as a white solid (8 mg). LCMS (ES+) 316 (M+H)$^+$, RT 8.22 (Analytical method 3). $^1$H NMR δ (ppm)(DMSO-d$_6$): 10.07 (1H, s), 8.68 (1H, s), 7.39 (1H, s), 7.18-7.09 (1H, m), 7.09-7.02 (2H, m), 3.80 (1H, ddd, J=13.1, 8.7, 3.9 Hz), 3.56-3.48 (1H, m), 2.91-2.81 (1H, m), 2.77-2.67 (1H, m), 2.31-2.21 (1H, m), 2.10 (3H, d, =16 Hz), 1.04-0.90 (4H, m).

Example 60: (S)-6-(3-Fluoro-2-methylphenyl)-N-hydroxy-2-(pyridin-3-yl)-6,7-dihydro-5H-cyclopenta[d]pyrimidine-6-carboxamide Prepared following the method described for Example 50 and 51, starting from intermediate 3. Only one regioisomer was isolated. Preparative HPLC gave the title compound as a white solid (9 mg). LCMS (ES+) 365 (M+H)$^+$, RT 2.50 (Analytical method 1); $^1$H NMR δ (ppm)(DMSO-d$_6$): 10.32 (1H, s), 9.5 (1H, s), 8.89 (1H, s), 8.8 (1H, s), 8.72-8.64 (2H, m), 8.64 (1H, s), 7.60-7.53 (1H, m), 7.21-7.06 (2H, m), 4.03-3.97 (1H, m), 3.84-3.76 (1H, m), 3.57-3.41 (2H, m), 2.24-2.19 (3H, s).

Examples 61 and 62: E1-(abs)-5-(3-Fluoro-2-methylphenyl)-2-(2-fluorophenyl)-N-hydroxy-5,6-dihydro-4H-cyclopenta[d]thiazole-5-carboxamide and E2-(abs)-5-(3-fluoro-2-methylphenyl)-2-(2-fluorophenyl)-N-hydroxy-5,6-dihydro-4H-cyclopenta[d]thiazole-5-carboxamide

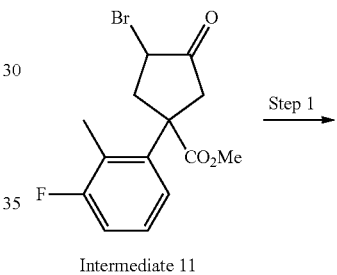

Intermediate 11

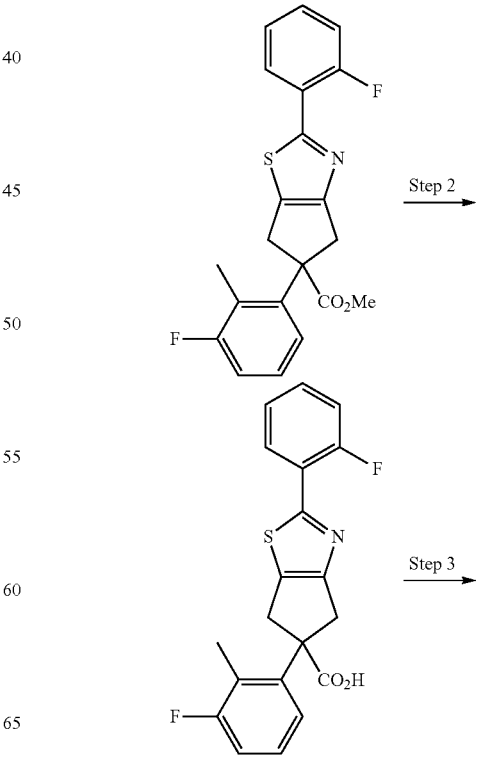

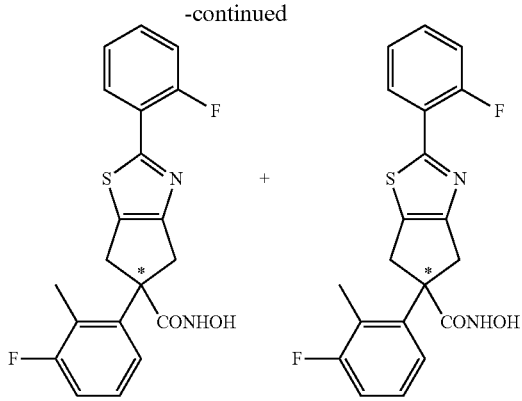

Step 1: (±)-Methyl 5-(3-fluoro-2-methylphenyl)-2-(2-fluorophenyl)-5,6-dihydro-4H-cyclopenta[d]thiazole-5-carboxylate To a solution of Intermediate 11 (500 mg, 1.52 mmol) in ethanol (5 mL) was added 2-fluorobenzothioamide (283 mg, 1.82 mmol). The reaction mixture was heated to 110° C. under microwave irradiation for 1 h. The reaction mixture was concentrated to give a yellow gum. The crude reaction material was purified by flash silica chromatography (gradient elution, 0-40% EtOAc in iso-hexane) to give the title compound as a pale yellow gum (190 mg, 0.49 mmol, 32%). LCMS (ES+) 386 (M+H)$^+$; $^1$H NMR δ (ppm)(400 MHz, CDCl$_3$): 8.20 (1H, dt, J=7.9, 7.5 Hz), 7.24-7.10 (5H, m), 7.00-6.96 (1H, m), 4.01 (1H, d, J=16.0 Hz), 3.85 (1H, d, J=16.0 Hz), 3.74 (3H, s), 3.49 (1H, d, J=16.0 Hz), 3.39 (1H, d, J=16.0 Hz), 2.20 (3H, d, J=2.7 Hz).

Step 2: (±)-5-(3-Fluoro-2-methylphenyl)-2-(2-fluorophenyl)-5,6-dihydro-4H-cyclopenta[d]thiazole-5-carboxylic acid (±)-Methyl 5-(3-fluoro-2-methylphenyl)-2-(2-fluorophenyl)-5,6-dihydro-4H-cyclopenta[d]thiazole-5-carboxylate (180 mg, 0.46 mmol), methanol (5 mL) and NaOH (3.75 M in water, 1.25 mL, 4.69 mmol) were combined in a sealed tube and heated to 65° C. for 18 h. The yellow reaction mixture was concentrated in vacuo. The residue was dissolved in H$_2$O (20 mL) and the solution adjusted to pH 7 with 1 M HCl. The aqueous mixture was extracted with EtOAc (2×20 mL); the organic extracts were dried (MgSO$_4$) and concentrated in vacuo. The residue was purified by flash silica chromatography (gradient elution, 0-100% EtOAc in iso-hexane) to give the title compound as a yellow gum (180 mg, 0.49 mmol, 98%), which was used without further purification.

Step 3: E2-(abs)-5-(3-fluoro-2-methylphenyl)-2-(2-fluorophenyl)-N-hydroxy-5,6-dihydro-4H-cyclopenta[d]thiazole-5-carboxamide and E1-(abs)-5-(3-fluoro-2-methylphenyl)-2-(2-fluorophenyl)-N-hydroxy-5,6-dihydro-4H-cyclopenta[d]thiazole-5-carboxamide 5-(3-fluoro-2-methylphenyl)-2-(2-fluorophenyl)-5,6-dihydro-4H-cyclopenta[d]thiazole-5-carboxylic acid (180 mg, 0.485 mmol), TFFH (148 mg, 0.56 mmol), DMF (2 mL) and triethylamine (2 mL) were combined and stirred for 1 h. O-(Tetrahydro-2H-pyran-2-yl)hydroxylamine (130 mg, 0.71 mmol) was then added and stirring continued for 1 day. Volatile solvents were removed in vacuo. MeOH (2 mL) and 2N HCl in Et$_2$O (2 mL) were added and the reaction mixture was stirred for 30 min. Volatile solvents were removed in vacuo and remaining crude material was purified by preparative HPLC and chiral HPLC to give the title compounds as off-white solids. (Chiralpak IA, Method 50/50 IPA/MeOH (50/50/0.1% formic acid)/Heptane 1.0 mL/min, RT 5.55 min (proposed (E2-(abs)) enantiomer) and 20.58 min. (proposed (E1-(abs)-enantiomer)). (E2-(abs)-5-(3-fluoro-2-methylphenyl)-2-(2-fluorophenyl)-N-hydroxy-5,6-dihydro-4H-cyclopenta[d]thiazole-5-carboxamide (27 mg). LCMS (ES+) 387 (M+H)$^+$, RT 10.82 min (Analytical method 2); $^1$H NMR δ (ppm)(400 MHz, DMSO-d$_6$): 10.27 (1H, s), 8.82 (1H, s), 8.13 (1H, td, J=7.8, 1.8 Hz), 7.51-7.44 (1H, m), 7.41-7.28 (2H, m), 7.19-7.02 (3H, m), 3.77 (2H, dd, J=16.0, 11.9 Hz), 3.40 (1H, d, J=16.5 Hz), 3.21 (1H, d, J=16.0 Hz), 2.15 (3H, d, J=2.7 Hz). And (E1-(abs)-5-(3-fluoro-2-methylphenyl)-2-(2-fluorophenyl)-N-hydroxy-5,6-dihydro-4H-cyclopenta[d]thiazole-5-carboxamide (32 mg). LCMS (ES+) 387 (M+H)$^+$, RT 10.82 min (Analytical method 2); $^1$H NMR δ (ppm)(400 MHz, DMSO-d$_6$): 10.27 (1H, s), 8.82 (1H, s), 8.13 (1H, td, J=7.8, 1.8 Hz), 7.51-7.44 (1H, m), 7.41-7.28 (2H, m), 7.19-7.02 (3H, m), 3.77 (2H, dd, J=16.0, 11.9 Hz), 3.40 (1H, d, J=16.5 Hz), 3.21 (1H, d, J=16.0 Hz), 2.15 (3H, d, J=2.7 Hz).

Example 63: 5-(3-Fluoro-2-methylphenyl)-N-hydroxy-2-(3-(trifluoromethyl)benzyl)-5,6-dihydro-4H-cyclopenta[d]thiazole-5-carboxamide Prepared following the same method as for Example 61 and 62. Purification by preparative HPLC gave the title compound as an off-white solid (12 mg). LCMS (ES+) 451 (M+H)$^+$, RT 11.05 min (Analytical method 2); $^1$H NMR δ (ppm)(DMSO-d$_6$): 10.22 (1H, s), 8.80 (1H, s), 7.72 (1H, s), 7.67-7.61 (2H, m), 7.61-7.54 (1H, m), 7.19-7.11 (1H, m), 7.11-7.01 (2H, m), 4.41 (2H, s), 3.65 (2H, d, J=15.6 Hz), 3.26 (1H, d, J=16.0 Hz), 3.09 (1H, d, J=15.6 Hz), 2.13 (3H, d, J=2.7 Hz).

Examples 64 and 65: E1-(abs)-5-(3-Fluoro-2-methylphenyl)-2-(3-fluorophenyl)-N-hydroxy-5,6-dihydro-4H-cyclopenta[d]thiazole-5-carboxamide and E2-(abs)-5-(3-fluoro-2-methylphenyl)-2-(3-fluorophenyl)-N-hydroxy-5,6-dihydro-4H-cyclopenta[d]thiazole-5-carboxamide Prepared following the same method as for Example 61 and 62. Purification by preparative HPLC and chiral HPLC gave the title compounds as off-white solids (30 mg and 24 mg, respectively). (Chiralpak IA, Method 50/50 IPA/MeOH (50/50/0.1% formic acid)/Heptane 1.0 mL/min, RT 6.73 min (proposed E2-(abs) enantiomer) and 17.40 min. (proposed E1-(abs) enantiomer)); E2-(abs)-enantiomer: LCMS (ES+) 387 (M+H)$^+$, RT 10.90 min (Analytical method 2); $^1$H NMR δ (ppm)(DMSO-d$_6$): 10.27 (1H, s), 8.82 (1H, s), 7.71-7.61 (2H, m), 7.54-7.47 (1H, m), 7.28 (1H, td, J=8.5, 2.7 Hz), 7.18-7.02 (3H, m), 3.75 (2H, dd, J=21.0, 16.4 Hz), 3.31 (1H, d, J=16.4 Hz), 3.20 (1H, d, J=15.6 Hz), 2.15 (3H, d, J=2.7 Hz). E1-(abs)-enantiomer: LCMS (ES+) 387 (M+H)$^+$, RT 10.90 min (Analytical method 2); $^1$H NMR δ (ppm)(DMSO-d$_6$): 10.27 (1H, s), 8.82 (1H, s), 7.71-7.61 (2H, m), 7.54-7.47 (1H, m), 7.28 (1H, td, J=8.5, 2.7 Hz), 7.18-7.02 (3H, m), 3.75 (2H, dd, J=21.0, 16.4 Hz), 3.31 (1H, d, J=16.4 Hz), 3.20 (1H, d, J=15.6 Hz), 2.15 (3H, d, J=2.7 Hz).

Example 66: (R)-5-(3-Fluoro-2-methylphenyl)-2-(4-fluorophenyl)-N-hydroxy-5,6-dihydro-4H-cyclopenta[d]thiazole-5-carboxamide Prepared following the same method as for Example 61 and 62 starting from Intermediate 15. Purification by preparative HPLC gave the title compound as a white solid(54 mg). LCMS (ES+) 387 (M+H)+, RT 10.85 min (Analytical method 2); $^1$H NMR δ (ppm)(DMSO-$d_6$): 10.29 (1H, s), 8.84 (1H, s), 7.95-7.89 (2H, m), 7.32 (2H, t, J=8.8 Hz), 7.21-7.05 (3H, m), 3.76 (2H, t, J=17.7 Hz), 3.37 (1H, d, J=16.5 Hz), 3.20 (1H, d, J=15.5 Hz), 2.17 (3H, d, J=2.7 Hz).

Examples 66 and 67: (R)-5-(3-Fluoro-2-methylphenyl)-2-(4-fluorophenyl)-N-hydroxy-5,6-dihydro-4H-cyclopenta[d]thiazole-5-carboxamide and (S)-5-(3-fluoro-2-methylphenyl)-2-(4-fluorophenyl)-N-hydroxy-5,6-dihydro-4H-cyclopenta[d]thiazole-5-carboxamide

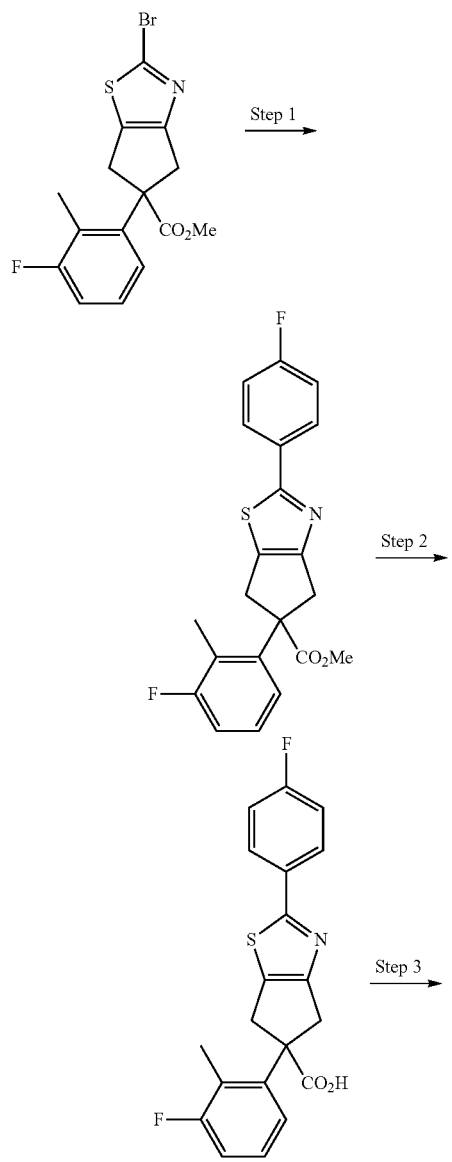

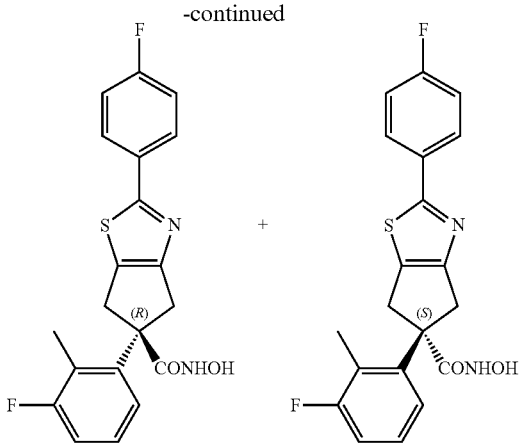

Step 1: Methyl 5-(3-fluoro-2-methylphenyl)-2-(4-fluorophenyl)-5,6-dihydro-4H-cyclopenta[d]thiazole-5-carboxylate A suspension of Intermediate 12 (50 mg, 0.14 mmol), 4-fluorophenyl boronic acid (20.6 mg, 0.15 mmol), tetrakis(triphenylphosphine)palladium(0) (23.6 mg, 0.02 mmol) and $Cs_2CO_3$ (278 mg, 0.85 mmol) in dioxane (0.6 mL) and water (0.1 mL) was purged with $N_2$ and stirred at 100° C. for 17 h. The mixture was purified by flash silica chromatography (gradient elution of 0% to 100% EtOAc in i-hex) to give the title compound as a pale yellow liquid (15 mg, 39 μmol, 29%).

Step 2: 5-(3-Fluoro-2-methylphenyl)-2-(4-fluorophenyl)-5,6-dihydro-4H-cyclopenta[d]thiazole-5-carboxylic acid A suspension of methyl 5-(3-fluoro-2-methylphenyl)-2-(4-fluorophenyl)-5,6-dihydro-4H-cyclopenta[d]thiazole-5-carboxylate (50 mg, 0.13 mmol) and KOH (111 mg, 1.98 mmol) in MeOH (1 mL) was stirred at 65° C. for 16 h. The reaction was acidified to pH 1 using 1 M HCl, then extracted with DCM (20 mL). The organic layer was dried by passage through a phase separator and concentrated to yield 40 mg of a yellow liquid that was used without further purification.

Step 3: (R)-5-(3-fluoro-2-methylphenyl)-2-(4-fluorophenyl)-N-hydroxy-5,6-dihydro-4H-cyclopenta[d]thiazole-5-carboxamide and (S)-5-(3-fluoro-2-methylphenyl)-2-(4-fluorophenyl)-N-hydroxy-5,6-dihydro-4H-cyclopenta[d]thiazole-5-carboxamide A stirred solution of 5-(3-fluoro-2-methylphenyl)-2-(4-fluorophenyl)-5,6-dihydro-4H-cyclopenta[d]thiazole-5-carboxylic acid (~40 mg of mixture from previous step) in DCM (1 mL) at r.t was treated with oxalyl chloride (10 μL, 0.12 mmol) and DMF (10 μL) and stirred for 30 min until effervescence ceased. MeCN (1 mL) and aqueous hydroxylamine (50 wt % hydroxylamine, 20 μL, 0.33 mmol) were added and the reaction heated to 100° C. under microwave irradiation for 10 min. The mixture was concentrated and purification by preparative HPLC and chiral preparative HPLC gave the title compounds (15 mg and 19 mg, respectively). (Chiralpak IA, Method 50/50 IPA/MeOH (50/50/0.1% formic acid)/heptane 1.0 mL/min, RT 6.1 min ((R) enantiomer) and 18.0 min ((S) enantiomer). (R)-Enantiomer LCMS (ES+) 387 (M+H)+, RT 10.85 min (Analytical method 2); ¹H NMR δ (ppm)(DMSO-d₆): 10.29 (1H, s), 8.84 (1H, s), 7.95-7.89 (2H, m), 7.32 (2H, t, J=8.8 Hz), 7.21-7.05 (3H, m), 3.76 (2H, t, J=17.7 Hz), 3.37 (1H, d, J=16.5 Hz), 3.20 (1H, d, J=15.5 Hz), 2.17 (3H, d, J=2.7 Hz). (S)-Enantiomer: LCMS (ES+) 387 (M+H)+, RT 10.85 min (Analytical method 2); ¹H NMR δ (ppm)(DMSO-d₆): 10.29 (1H, s), 8.84 (1H, s), 7.96-7.90 (2H, m), 7.32 (2H, t, J=8.8 Hz), 7.20-7.05 (3H, m), 3.76 (2H, t, J=17.7 Hz), 3.37 (2H, d, J=16.5 Hz), 3.20 (1H, d, J=15.5 Hz), 2.17 (3H, d, J=2.7 Hz).

Example 68: (S)-5-(3-Fluoro-2-methylphenyl)-N-hydroxy-2-(1-methyl-1H-pyrazol-5-yl)-5,6-dihydro-4H-cyclopenta[d]thiazole-5-carboxamide

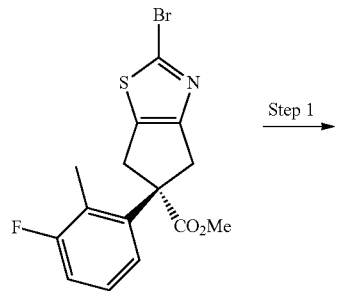

Intermediate 14

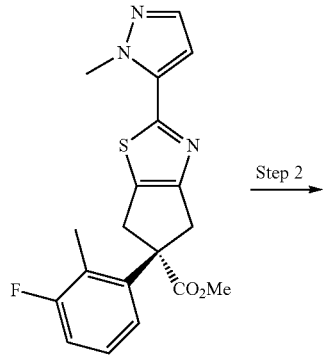

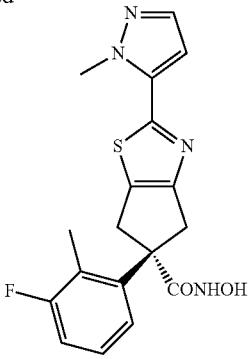

Step 1: (S)-Methyl 5-(3-fluoro-2-methylphenyl)-2-(1-methyl-1H-pyrazol-5-yl)-5,6-dihydro-4H-cyclopenta[d]thiazole-5-carboxylate A suspension of 1-methyl-5-(4,4,5,5-tetramethyl-1,3,2-dioxaborolan-2-yl)-1H-pyrazole (529 mg, 2.54 mmol), Intermediate 14 (620 mg, 1.67 mmol), tetrakis(triphenylphosphine)palladium(0) (93 mg, 80 µmol) and CsF (398 mg, 2.62 mmol) in DME (11 mL) and MeOH (2.7 mL) was purged with N₂ and stirred in a microwave reactor at 120° C. for 10 min. The mixture was concentrated and purified by flash silica chromatography (gradient elution of 0% to 100% EtOAc in i-hex) to give the title compound as an impure brown oil (548 mg), which was used without further purification.

Step 2: (S)-5-(3-Fluoro-2-methylphenyl)-2-(1-methyl-1H-pyrazol-5-yl)-5,6-dihydro-4H-cyclopenta[d]thiazole-5-carboxylic acid A solution of (S)-methyl 5-(3-fluoro-2-methylphenyl)-2-(1-methyl-1H-pyrazol-5-yl)-5,6-dihydro-4H-cyclopenta[d]thiazole-5-carboxylate (548 mg from previous step) and KOH (876 mg, 15.6 mmol) in MeOH (6 mL) was stirred in a sealed tube at 70° C. for 17 h. The mixture was acidified to pH 0 using 10% HCl, extracted with DCM (2×20 mL), dried (phase separator) and concentrated. The title compound was obtained as an impure brown oil (451 mg), which was used without further purification.

Step 3: (S)-5-(3-Fluoro-2-methylphenyl)-N-hydroxy-2-(1-methyl-1H-pyrazol-5-yl)-5,6-dihydro-4H-cyclopenta[d]thiazole-5-carboxamide A stirred solution of (S)-5-(3-fluoro-2-methylphenyl)-2-(1-methyl-1H-pyrazol-5-yl)-5,6-dihydro-4H-cyclopenta[d]thiazole-5-carboxylic acid (451 mg from previous step) and triethylamine (0.53 mL, 3.80 mmol) in dry DMF (12 mL) was treated with TFFH (451 mg, 1.71 mmol) at 0° C. under N₂. After stirring at r.t for 40 min, the mixture was cooled to 0° C. and O-(tetrahydro-2H-pyran-2-yl)hydroxylamine (240 mg, 2.05 mmol) was added. The mixture was stirred at r.t for 18 h before being diluted with MeOH (15 mL) and treated with HCl (4 M in dioxane, 6 mL). After 1.5 h at r.t., the reaction mixture was diluted with EtOAc (30 mL) and washed with H₂O (2×20 mL). The combined aqueous washes were extracted with EtOAc (2×20 mL); the combined organic layers were washed with H₂O (20 mL), dried (phase separator) and concentrated. LCMS analysis showed target material remained in the aqueous washes, which were therefore treated with brine (30 mL) and extracted with EtOAc (3×20 mL). LCMS analysis of the aqueous layer showed no target material now remained. The organic extracts were dried (phase separator), concentrated and combined with the earlier organic residue. This mixture was purified by preparative HPLC to give the title compound (140 mg) as a white solid. LCMS (ES+) 373 (M+H)$^+$, RT 9.75 min (Analytical method 3); $^1$H NMR δ (ppm)(400 MHz, DMSO-d$_6$): 10.30 (1H, s), 8.85 (1H, s), 7.50 (1H, d, J=2.1 Hz), 7.23-7.12 (2H, m), 7.10-7.05 (1H, m), 6.75 (1H, d, J=2.1 Hz), 4.12 (3H, s), 3.79 (2H, d, J=16.0 Hz), 3.41 (1H, d, J=16.6 Hz), 3.21 (1H, d, J=15.5 Hz), 2.18 (3H, d, J=2.7 Hz).

Example 69: (R)-5-(3-Fluoro-2-methylphenyl)-N-hydroxy-2-(1-methyl-1H-pyrazol-5-yl)-5,6-dihydro-4H-cyclopenta[d]thiazole-5-carboxamide Prepared following the same method as for Example 68 starting from Intermediate 16. Preparative HPLC gave the title compound as a white solid (133 mg). LCMS (ES+) 373 (M+H)$^+$, RT 9.55 min (Analytical method 2); $^1$H NMR δ (ppm)(400 MHz, DMSO-d$_6$): 10.30 (1H, s), 8.85 (1H, s), 7.50 (1H, d, J=2.1 Hz), 7.23-7.12 (2H, m), 7.10-7.05 (1H, m), 6.75 (1H, d, J=2.1 Hz), 4.12 (3H, s), 3.79 (2H, d, J=16.0 Hz), 3.41 (1H, d, J=16.6 Hz), 3.21 (1H, d, J=15.5 Hz), 2.18 (3H, d, J=2.7 Hz).

Example 70: (R)-2-(1,3-Dimethyl-1H-pyrazol-5-yl)-5-(3-fluoro-2-methylphenyl)-N-hydroxy-5,6-dihydro-4H-cyclopenta[d]thiazole-5-carboxamide Prepared following the method described for Example 68 starting from Intermediate 16. Preparative HPLC gave the title compound (54 mg). LCMS (ES+) 387 (M+H)$^+$, RT 9.35 min (Analytical method 2); $^1$H NMR δ (ppm)(DMSO-d$_6$): 10.27 (1H, s), 8.82 (1H, d, J=1.6 Hz), 7.22-7.04 (3H, m), 6.48-6.44 (1H, m), 3.83-3.61 (5H, m), 3.28 (1H, dd, J=4.9, 1.2 Hz), 3.18 (1H, dd, J=13.5, 11.0 Hz), 2.49-2.14 (3H, m), 2.18-2.14 (3H, m).

Example 71: (R)-5-(3-Fluoro-2-methylphenyl)-N-hydroxy-2-(5-methoxypyridin-2-yl)-5,6-dihydro-4H-cyclopenta[d]thiazole-5-carboxamide

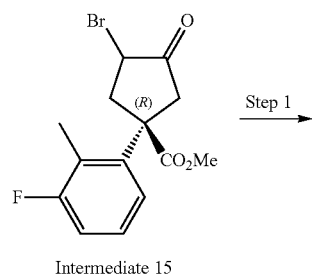

Intermediate 15

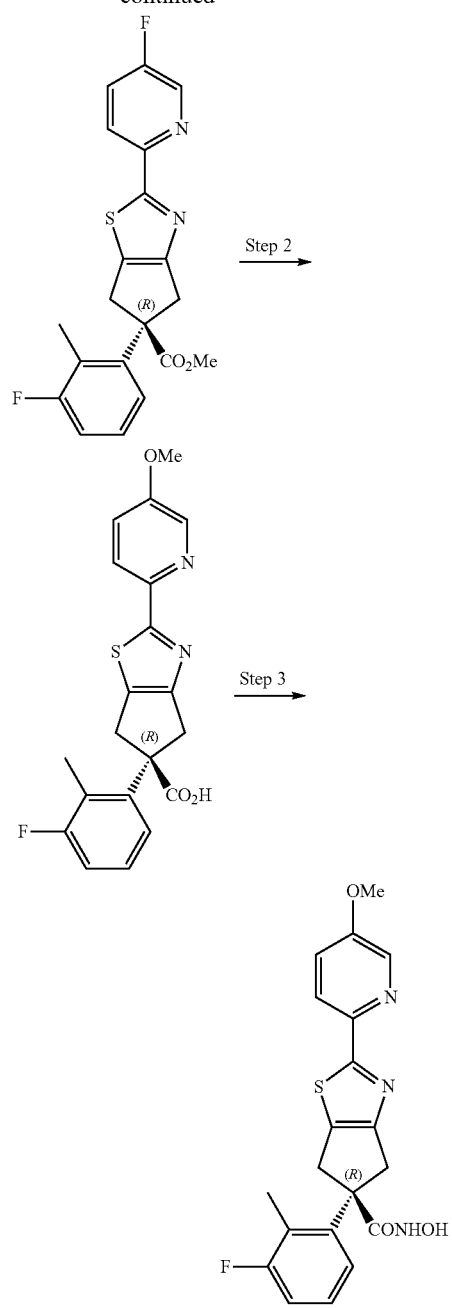

Step 1: (R)-5-(3-Fluoro-2-methylphenyl)-2-(5-fluoropyridin-2-yl)-5-((methylperoxy)methyl)-5,6-dihydro-4H-cyclopenta[d]thiazole To a solution of Intermediate 15 (500 mg, 1.52 mmol) in ethanol (5 mL) was added 5-fluoropyridine-2-carbothioamide (356 mg, 2.28 mmol). The reaction mixture was heated to 110° C. under microwave conditions for 1 h. The reaction mixture was concentrated to give a dark red gum. The crude reaction material was purified by flash silica chromatography (gradient elution i-hex to 40% EtOAc in i-hex) to give the title compound as a bright orange gum (200 mg, 34%). Progressed without further purification.

Step 2: (R)-5-(3-Fluoro-2-methylphenyl)-2-(5-methoxypyridin-2-yl)-5,6-dihydro-4H-cyclopenta[d]thiazole-5-carboxylic acid (R)-5-(3-fluoro-2-methylphenyl)-2-(5-fluoropyridin-2-yl)-5-((methylperoxy)methyl)-5,6-dihydro-4H-cyclopenta[d]thiazole (160 mg, 0.41 mmol), methanol (5 mL) and 15% aq. NaOH solution (1.10 mL, 4.1 mmol) were combined in a sealed tube and heated to 65° C. for 18 h. The orange reaction mixture was evaporated in vacuo then diluted with EtOAc and H$_2$O. The aqueous layer was adjusted to pH 7 with 1 M HCl and the layers separated. The organic layer was dried (MgSO$_4$) and evaporated in vacuo. The residue was purified by flash silica chromatography (gradient elution i-hex to 100% EtOAc in i-hex) to give the title compound as an orange solid (85 mg, 53%). $^1$H NMR δ (ppm)(CH$_3$OH-d$_4$): 8.26 (1H, dd, J=20.1, 2.9 Hz), 8.04 (1H, dd, J=20.1, 8.8 Hz), 7.46 (1H, dt, J=8.8, 3.0 Hz), 7.18-7.13 (2H, m), 7.01-6.94 (1H, m), 3.95-3.82 (5H, m), 3.53-3.42 (1H, m), 3.35 (1H, d, J=7.7 Hz), 2.27 (3H, d, J=2.7 Hz). Acid OH not seen Used crude without further purification.

Step 3: (R)-5-(3-Fluoro-2-methylphenyl)-N-hydroxy-2-(5-methoxypyridin-2-yl)-5,6-dihydro-4H-cyclopenta[d]thiazole-5-carboxamide A stirred solution of (R)-5-(3-Fluoro-2-methylphenyl)-2-(5-methoxypyridin-2-yl)-5,6-dihydro-4H-cyclopenta[d]thiazole-5-carboxylic acid (82 mg, 0.21 mmol) and triethylamine (0.096 mL, 0.68 mmol) in dry DMF (2 mL) was treated with TFFH (81 mg, 0.31 mmol) at 0° C. under N$_2$. After stirring at r.t. for 40 min, the mixture was cooled to 0° C. and O-(tetrahydro-2H-pyran-2-yl)hydroxylamine (43 mg, 0.37 mmol) was added. The mixture was stirred at r.t. for 18 h before being diluted with MeOH (2 mL) and treated with HCl (4 M in dioxane, 1 mL). After 1.5 h at rt, the reaction mixture was diluted with EtOAc (10 mL) and washed with H$_2$O (2×10 mL). The combined aqueous washes were extracted with EtOAc (2×10 mL); the combined organic layers were washed with H$_2$O (20 mL), dried (phase separator) and concentrated. Preparative HPLC gave the title compound as an off-white solid (36 mg). LCMS (ES+) 400 (M+H)$^+$, RT 3.51 min (Analytical method 1). $^1$H NMR δ (ppm)(DMSO-d$_6$): 10.26 (1H, s), 8.82 (1H, s), 8.30 (1H, dd, J=2.9, 0.6 Hz), 7.97 (1H, dd, J=8.8, 0.6 Hz), 7.50 (1H, dd, J=8.8, 2.9 Hz), 7.21-7.03 (3H, m), 3.87 (3H, s), 3.73 (2H, t, J=15.6 Hz), 3.34 (1H, d, J=13.7 Hz), 3.18 (1H, d, J=15.6 Hz), 2.18-2.14 (3H, m).

Example 72: (S)-2-Cyclopropyl-6-(3-fluoro-2-methylphenyl)-N-hydroxy-5,6-dihydro-4H-cyclopenta[d]thiazole-6-carboxamide

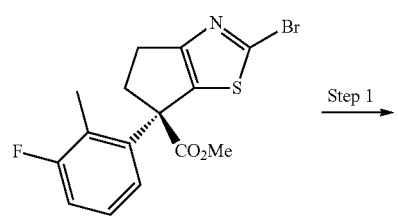

Intermediate 10

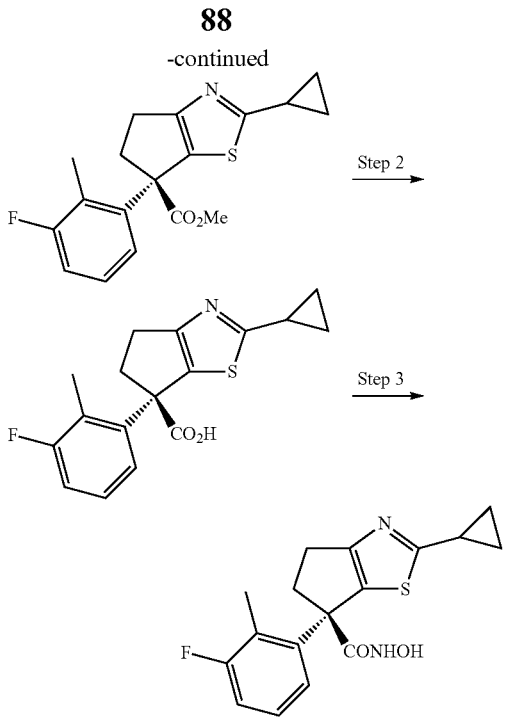

Step 1: (S)-Methyl 2-cyclopropyl-6-(3-fluoro-2-methylphenyl)-5,6-dihydro-4H-cyclopenta[d]thiazole-6-carboxylate A suspension of intermediate 10 (0.114 g, 0.31 mmol), cyclopropyl boronic acid (0.029 g, 0.34 mmol), palladium tetrakis(triphenylphosphine) (0.015 g) and cesium carbonate (0.5 g, 1.54 mmol) in a mixture of degassed dioxane/water (9:1, 10 mL) was stirred at 110° C. for 16 h. The reaction was cooled to r.t., diluted with EtOAc (75 mL) and subjected to an aqueous workup. The organic layer was concentrated under vacuum to give the title compound as an impure yellow oil, which was used without further purification in the next step. LCMS (ES+) 332 (M+H)$^+$.

Step 2: (S)-2-Cyclopropyl-6-(3-fluoro-2-methylphenyl)-5,6-dihydro-4H-cyclopenta[d]thiazole-6-carboxylic acid (S)-Methyl 2-cyclopropyl-6-(3-fluoro-2-methylphenyl)-5,6-dihydro-4H-cyclopenta[d]thiazole-6-carboxylate (26 mg, 0.07 mmol), MeOH (2 mL) and 15% aq. NaOH soln. (0.5 mL) were combined in a sealed tube and heated to 70° C. for 4 days. The reaction mixture was cooled and evaporated to dryness. Residue was partitioned between 1N HCl and EtOAc. Organics were dried (MgSO$_4$) and evaporated to dryness to give the title compound as an off white solid. LCMS (ES+) 318 (M+H)$^+$.

Step 3: (S)-2-Cyclopropyl-6-(3-fluoro-2-methylphenyl)-N-hydroxy-5,6-dihydro-4H-cyclopenta[d]thiazole-6-carboxamide (S)-2-Cyclopropyl-6-(3-fluoro-2-methylphenyl)-5,6-dihydro-4H-cyclopenta[d]thiazole-6-carboxylic acid (53 mg, 0.16 mmol), TFFH (49 mg, 0.18 mmol), DMF (2 mL) and triethylamine (0.12 mL) were combined and stirred for 1 h. O-(Tetrahydro-2H-pyran-2-yl)hydroxylamine (22 mg, 0.184 mmol) was then added and stirring continued for 1 day.

Volatile solvents were removed in vacuo. MeOH (1 mL) and 2N HCl in Et₂O (1 mL) were added and reaction mixture was stirred for 30 min. Volatile solvents were removed in vacuo and remaining crude material was purified by preparative HPLC to give (S)-2-cyclopropyl-6-(3-fluoro-2-methylphenyl)-N-hydroxy-5,6-dihydro-4H-cyclopenta[d]thiazole-6-carboxamide (1 mg). LCMS (ES+) 333 (M+H)⁺, 331 (M–H)⁻, RT 9.68 min (Analytical method 2); ¹H NMR (400 MHz, CHCl₃-d) 8.19 (1H, s) 7.03-6.86 (3H, m), 3.85-3.70 (1H, m) 3.05-2.95 (1H, m) 2.92-2.75 (1H, m) 2.50-2.38 (1H, m), 2.41-2.17 (4H, m) 1.20-0.90 (4H, m). OH resonance not observed.

Example 73: (S)-6-(3-Fluoro-2-methylphenyl)-N-hydroxy-2-(o-tolyl)-5,6-dihydro-4H-cyclopenta[d]thiazole-6-carboxamide Prepared following the method described for Example 72. Preparative HPLC gave the title compound as an off-white solid (4 mg). LCMS (ES+) 383 (M+H)⁺, RT 11.0 min. (Analytical method 2); ¹H NMR δ (ppm)(400 MHz, DMSO-d₆): 10.55 (1H, s), 8.92 (1H, s), 7.76 (1H, d, J=7.4 Hz), 7.40-7.34 (3H, m), 7.21-7.09 (2H, m), 7.02 (1H, dd, J=7.8, 7.8 Hz), 3.77-3.60 (1H, m), 3.06-2.83 (2H, m), 2.59 (3H, s), 2.43-2.31 (1H, m), 2.17 (3H, d, J=2.4 Hz).

Examples 74 and 75: E1-(abs)-5-(3-Fluoro-2-methylphenyl)-2-(4-fluoro-2-methylphenyl)-N-hydroxy-5,6-dihydro-4H-cyclopenta[d]thiazole-5-carboxamide and E2-(abs)-5-(3-Fluoro-2-methylphenyl)-2-(4-fluoro-2-methylphenyl)-N-hydroxy-5,6-dihydro-4H-cyclopenta[d]thiazole-5-carboxamide

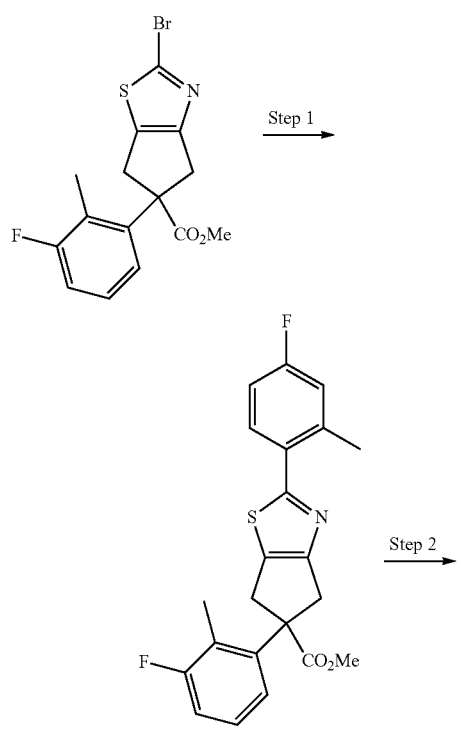

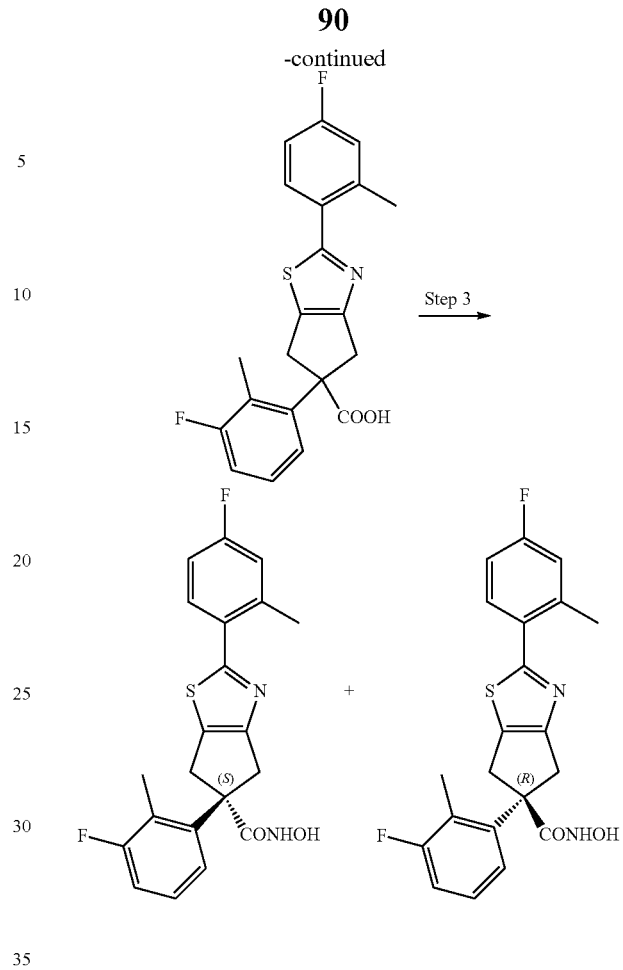

Step 1: Methyl 5-(3-fluoro-2-methylphenyl)-2-(4-fluoro-2-methylphenyl)-5,6-dihydro-4H-cyclopenta[d]thiazole-5-carboxylate A suspension of 4-fluoro-2-methylphenylboronic acid (105 mg, 0.68 mmol), Intermediate 12 (188 mg, 0.51 mmol), tetrakis(triphenylphosphine)palladium(0) (93 mg, 80 μmol) and CsF (100 mg, 0.66 mmol) in DME (3 mL) and MeOH (0.75 mL) was purged with N₂ and stirred in a microwave reactor at 120° C. for 10 min. The mixture was concentrated and purified by flash silica chromatography (gradient elution of 0% to 100% EtOAc in i-hex) to give the title compound (79 mg) in 75% purity as a colorless oil, which was used without further purification.

Step 2: 5-(3-fluoro-2-methylphenyl)-2-(4-fluoro-2-methylphenyl)-5,6-dihydro-4H-cyclopenta[d]thiazole-5-carboxylic acid To a solution of methyl 5-(3-fluoro-2-methylphenyl)-2-(4-fluoro-2-methylphenyl)-5,6-dihydro-4H-cyclopenta[d]thiazole-5-carboxylate (79 mg mixture from previous step) in methanol (2 mL) was added KOH (122 mg). The reaction mixture was capped and heated at 70° C. for 20 h. After this time the contents were cooled to r.t. and acidified to pH 0 with 10% HCl. The mixture was extracted with DCM (2×20 mL), dried (phase separation cartridge) and concentrated to give the title compound (58 mg) in 85% purity as a brown oil, which was used without further purification.

Step 3: E1-(abs)-5-(3-Fluoro-2-methylphenyl)-2-(4-fluoro-2-methylphenyl)-N-hydroxy-5,6-dihydro-4H-cyclopenta[d]thiazole-5-carboxamide and E2-(abs)-5-(3-Fluoro-2-methylphenyl)-2-(4-fluoro-2-methylphenyl)-N-hydroxy-5,6-dihydro-4H-cyclopenta[d]thiazole-5-carboxamide A stirred solution of 5-(3-fluoro-2-methylphenyl)-2-(4-fluoro-2-methylphenyl)-5,6-dihydro-4H-cyclopenta[d]thiazole-5-carboxylic acid (58 mg, mixture from the previous step) in DCM (1 mL) at 20° C. was treated sequentially with oxalyl chloride (14 µL) and DMF (10 µL). The mixture was stirred for 25 min until gas evolution ceased. MeCN (1 mL) and hydroxylamine (28 µL) were added and the mixture heated to 100° C. in a microwave reactor for 10 min. Purification by preparative HPLC and chiral preparative HPLC gave the E1-(abs) and E2-(abs) enantiomers (1 mg and 2 mg respectively) which were arbitrarily assigned. (Chiralpak IA 50/50 EtOH (0.1% formic acid)/Heptane, 1.0 mL/min, r.t., RT 11.3 min (E2-(abs)) and 6.1 min (E1-(abs)). E2-(abs): LCMS (ES+) 401 (M+H)$^+$, RT 4.06 min (Analytical method 1); $^1$H NMR δ (ppm)(400 MHz, DMSO-d$_6$): 10.31 (1H, s), 8.82 (1H, s), 7.76-7.71 (1H, m), 7.25 (1H, dd, J=2.4, 10.0 Hz), 7.20-7.05 (4H, m), 3.90-3.76 (2H, m), 3.40-3.31 (1H, m), 3.26-3.17 (1H, m), 2.56 (3H, s), 2.21-2.18 (3H, m). E1-(abs): LCMS (ES+) 401 (M+H)$^+$, RT 4.06 min (Analytical method 1); $^1$H NMR δ (ppm)(400 MHz, DMSO-d$_6$): 10.31 (1H, s), 8.82 (1H, s), 7.76-7.71 (1H, m), 7.25 (1H, dd, J=2.4, 10.0 Hz), 7.20-7.05 (4H, m), 3.90-3.76 (2H, m), 3.40-3.31 (1H, m), 3.26-3.17 (1H, m), 2.56 (3H, s), 2.21-2.18 (3H, m).

Example 76 and 77: E1-(abs)-2-(1,5-Dimethyl-1H-pyrazol-4-yl)-5-(3-fluoro-2-methylphenyl)-N-hydroxy-5,6-dihydro-4H-cyclopenta[d]thiazole-5-carboxamide and E2-(abs)-2-(1,5-dimethyl-1H-pyrazol-4-yl)-5-(3-fluoro-2-methylphenyl)-N-hydroxy-5,6-dihydro-4H-cyclopenta[d]thiazole-5-carboxamide Prepared following the same method as for Example 74 and 75. Purification by preparative HPLC and chiral HPLC gave the E1-(abs) and E2-(abs) enantiomers (3 mg and 5 mg respectively) which were arbitrarily assigned. (Chiralpak IC 50/50 EtOH (0.1% formic acid)/heptane, 1.0 mL/min, RT 6.1 min (E1-(abs)) and 11.6 min (E2-(abs)). E1-(abs) Enantiomer: LCMS (ES+) 387 (M+H)$^+$, RT 3.15 min (Analytical method 1); $^1$H NMR δ (ppm)(400 MHz, DMSO-d$_6$): 10.28 (1H, s), 8.82 (1H, s), 7.74 (1H, s), 7.19-7.05 (3H, m), 3.78 (3H, s), 3.77-3.67 (2H, m), 3.14 (1H, d, J=15.8 Hz), 2.53 (3H, s), 2.21-2.16 (3H, m), 1H obscured by water. E2-(abs) Enantiomer: LCMS (ES+) 387 (M+H)$^+$, RT 3.16 min (Analytical method 1); $^1$H NMR δ (ppm)(400 MHz, DMSO-d$_6$): 10.28 (1H, s), 8.82 (1H, s), 7.74 (1H, s), 7.19-7.05 (3H, m), 3.78 (3H, s), 3.77-3.67 (2H, m), 3.14 (1H, d, J=15.8 Hz), 2.53 (3H, s), 2.21-2.16 (3H, m), 1H obscured by water resonance.

Example 78: (S)-6-(3-Fluoro-2-methylphenyl)-2-(4-fluorophenyl)-N-hydroxy-5,6-dihydro-4H-cyclopenta[d]thiazole-6-carboxamide Prepared following the same method as for Example 72. Preparative HPLC gave the title compound as a white solid (8 mg). LCMS (ES+) 387 (M+H)$^+$, RT 3.8 min (Analytical method 1); $^1$H NMR δ (ppm)(400 MHz, DMSO-d$_6$): 10.57 (1H, d, J=1.4 Hz), 8.93-8.91 (1H, m), 8.02-7.97 (2H, m), 7.38-7.33 (2H, m), 7.21-7.09 (2H, m), 6.98 (1H, d, J=7.5 Hz), 3.73-3.65 (1H, m), 3.02-2.94 (1H, m), 2.91-2.82 (1H, m), 2.40-2.32 (1H, m), 2.16 (3H, d, J=2.4 Hz) (data reported for major rotamer).

Example 79: (R)-5-(3-Fluoro-2-methylphenyl)-3-(4-fluorophenyl)-N-hydroxy-2-methyl-2,4,5,6-tetrahydrocyclopenta[c]pyrazole-5-carboxamide

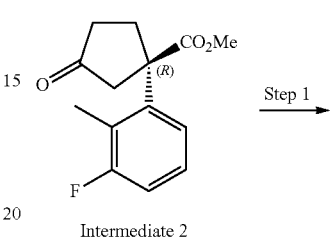

Intermediate 2

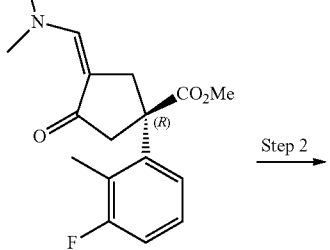

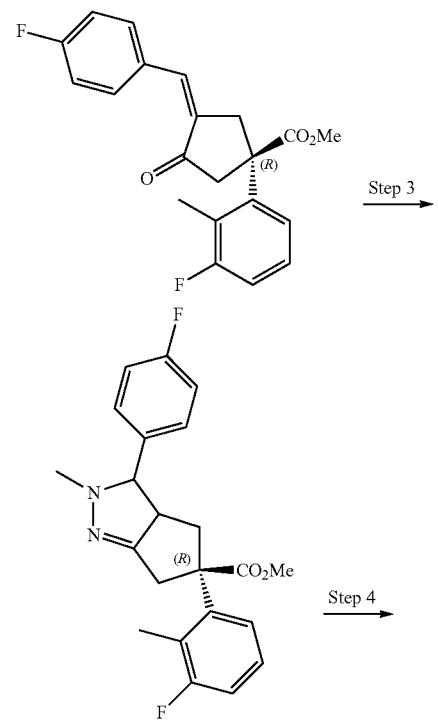

-continued

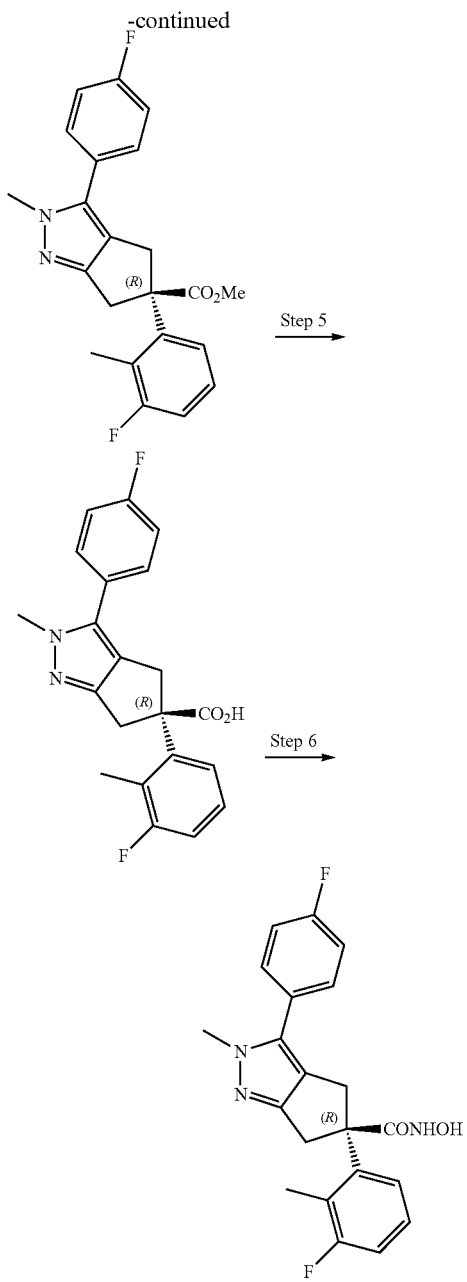

Step 1: (R)-Methyl 3-((dimethylamino)methylene)-1-(3-fluoro-2-methylphenyl)-4-oxocyclopentanecarboxylate tBuOK (124 mg, 1.1 mmol) and THF (6 mL) were combined under a nitrogen atmosphere. The reaction mixture was cooled with an ice bath and ethyl formate (0.24 mL, 4 mmol) was added drop-wise. After 15 min Intermediate 2 (250 mg, 1 mmol) was added drop-wise as a solution in ethyl formate (2 mL). The reaction mixture was stirred for a further 1 h with ice bath cooling then diluted with EtOAc, washed with 1N HCl, then brine, dried (phase separator) and evaporated to dryness to give the crude aldehyde as a pale brown oil. The crude residue was dissolved in anhydrous THF (6 mL) and dimethylamine (2 mL, 4 mmol, 2 M in THF) added. The reaction mixture was then stirred for a further 36 h. After this time the reaction mixture was concentrated under reduced pressure and purified by flash silica column chromatography (gradient elution i-hex to 66% EtOAc in i-hex) to give the title compound as a pale yellow solid (0.25 g, 83% over 2 steps). LCMS (ES+) 306 (M+H)$^+$.

Step 2: (R)-Methyl 1-(3-fluoro-2-methylphenyl)-3-(4-fluorobenzylidene)-4-oxocyclopentanecarboxylate (R)-Methyl 3-((dimethylamino)methylene)-1-(3-fluoro-2-methylphenyl)-4-oxocyclopentanecarboxylate (250 mg, 0.8 mmol) and THF (5 mL) were combined under a nitrogen atmosphere. The reaction mixture was cooled with an ice bath and 4-fluorophenyl magnesium bromide (2 mL, 2 mmol, 1 M in THF) was added drop-wise. The reaction mixture was stirred for 1 h with ice bath cooling then quenched with aq. NH$_4$Cl (2 mL). The solution was then diluted with EtOAc, washed with water, then brine, dried (phase separator) and evaporated to dryness and purified by flash silica column chromatography (gradient elution i-hex to 20% EtOAc in i-hex) to give the title compound as a colorless solid (0.28 g, 95%). LCMS (ES+) 357 (M+H)$^+$.

Step 3: (5R)-Methyl 5-(3-fluoro-2-methylphenyl)-3-(4-fluorophenyl)-2-methyl-2,3,3a,4,5,6-hexahydro-cyclopenta[c]pyrazole-5-carboxylate (R)-Methyl 1-(3-fluoro-2-methylphenyl)-3-(4-fluorobenzylidene)-4-oxocyclopentanecarboxylate (130 mg, 0.4 mmol), indium chloride (20 mg, 0.15 mmol), methylhydrazine (25 µL, 0.44 mmol) and ethanol (6 mL) were combined under a nitrogen atmosphere. The reaction mixture was then refluxed for 2 h. After this time the reaction mixture was cooled to room temperature and passed through a pad of silica gel eluting with 50% EtOAc in i-hex to give crude hydrazide as a 3:1 mixture of syn/anti isomers. LCMS (ES+) 385 (M+H)$^+$.

Step 4: (R)-Methyl 5-(3-fluoro-2-methylphenyl)-3-(4-fluorophenyl)-2-methyl-2,4,5,6-tetrahydrocyclo-penta[c]pyrazole-5-carboxylate (5R)-Methyl 5-(3-fluoro-2-methylphenyl)-3-(4-fluorophenyl)-2-methyl-2,3,3a,4,5,6-hexahydro cyclopenta[c]pyrazole-5-carboxylate (80 mg, 0.2 mmol), DDQ (52 mg, 0.23 mmol) and anhydrous dioxane (3 mL) were combined under a nitrogen atmosphere. The reaction mixture was then refluxed for 2 h. After this time the reaction mixture was cooled to r.t., concentrated under reduced pressure and purified by flash silica column chromatography (gradient elution i-hex to 60% EtOAc in i-hex) to give the title compound as a pale yellow oil (53 mg, 66%). LCMS (ES+) 383 (M+H)$^+$.

Step 5: (R)-5-(3-Fluoro-2-methylphenyl)-3-(4-fluorophenyl)-2-methyl-2,4,5,6-tetrahydrocyclopenta[c]pyrazole-5-carboxylic acid To a solution of (R)-methyl 5-(3-fluoro-2-methylphenyl)-3-(4-fluorophenyl)-2-methyl-2,4,5,6-tetrahydrocyclopenta[c]pyrazole-5-carboxylate (52 mg, 0.14 mmol) in THF/methanol/water (1:1:0.5, 2.5 mL) was added lithium hydroxide hydrate (0.03 g, 0.70 mmol). The reaction mixture was capped and heated at 65° C. for 18 h. After this time the contents were cooled to r.t. and methanol was removed under reduced pressure. Aqueous residues were partitioned between EtOAc (15 mL) and 1 M aqueous HCl (15 mL). Organic layers were extracted, washed with brine (20 mL), dried, filtered (phase separation cartridge) and concentrated to give the title compound as a pale yellow oil which was used directly (42 mg, 84%).

Step 6: (R)-5-(3-Fluoro-2-methylphenyl)-3-(4-fluorophenyl)-N-hydroxy-2-methyl-2,4,5,6-tetrahydrocyclopenta[c]pyrazole-5-carboxamide To a solution of (R)-5-(3-fluoro-2-methylphenyl)-3-(4-fluorophenyl)-2-methyl-2,4,5,6-tetrahydrocyclopenta[c]pyrazole-5-carboxylic acid (0.40 g, 1.1 mmol), and triethylamine (0.33 g, 468 µL, 3.3 mmol) in anhydrous DMF (10 mL) was added TFFH (0.36 g, 1.42 mmol) at 0° C. The reaction mixture was stirred at this temperature for 15 min, then O-(tetrahydro-2H-pyran-2-yl)hydroxylamine (0.2 g, 1.67 mmol) was added in a single portion. The reaction mixture was then stirred at r.t. for 24 h. After this time the reaction mixture was quenched by the addition of 1 M HCl solution (5 mL). The reaction was partitioned between EtOAc (30 mL) and 1 M HCl (15 mL). The organic layer was separated, washed with brine (40 mL), dried, filtered (phase separation cartridge) and concentrated to give the crude THP protected hydroxamic acid as a pale yellow oil. To this oil was added anhydrous methanol (3 mL) and 4 M HCl in dioxane (2 mL). The reaction mixture was stirred at r.t. for 30 min. After this time solvents were removed under reduced pressure to give crude hydroxamic acid which was purified by preparative HPLC to give the title compound as a colorless solid (20 mg). LCMS (ES+) 384 (M+H)$^+$, RT 3.43 min (Analytical method 1); $^1$H NMR δ (ppm)(DMSO-$d_6$): 10.19 (1H, s), 8.76 (1H, s), 7.58-7.53 (2H, m), 7.38-7.32 (2H, m), 7.14 (1H, t, J=7.3 Hz), 7.04 (2H, t, J=7.8 Hz), 3.78 (3H, s), 3.64-3.53 (2H, m), 3.02 (1H, d, J=7.2 Hz), 2.98 (1H, d, J=7.6 Hz), 2.16 (3H, d, J=2.7 Hz).

Examples 80 and 81: E1-(abs)-5-(3-Fluoro-2-methylphenyl)-N-hydroxy-3-phenyl-5,6-dihydro-4H-cyclopenta[d]isothiazole-5-carboxamide and E2-(abs)-5-(3-Fluoro-2-methylphenyl)-N-hydroxy-3-phenyl-5,6-dihydro-4H-cyclopenta[d]isothiazole-5-carboxamide

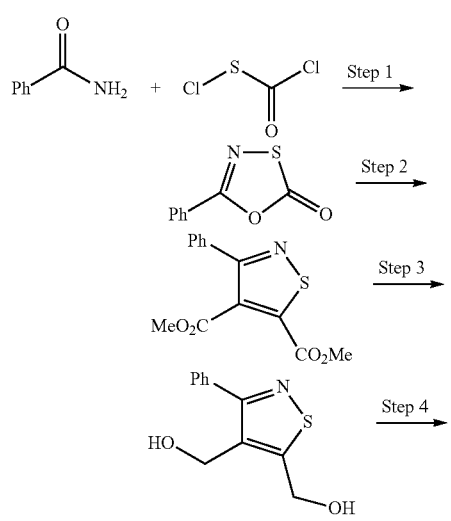

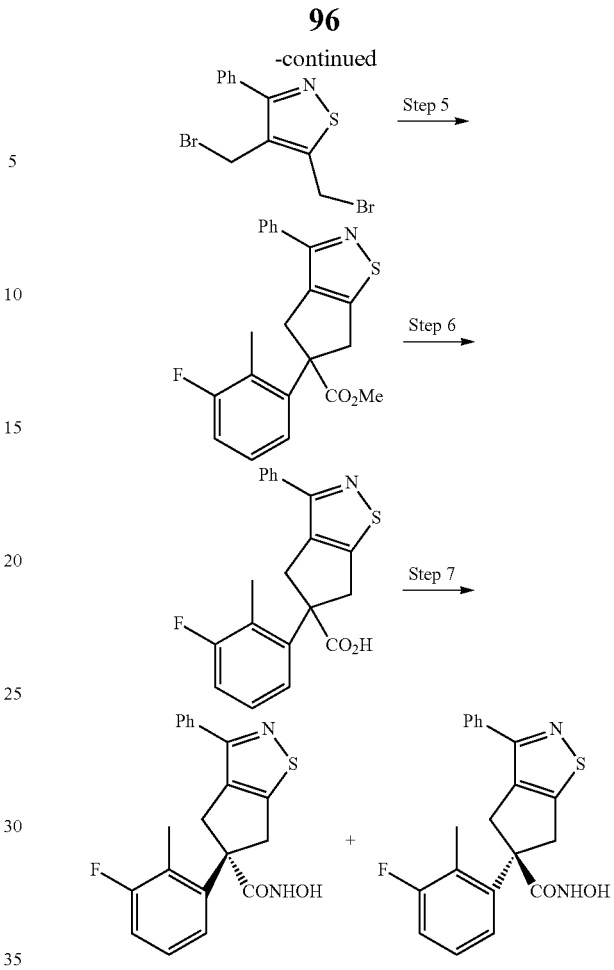

Step 1: 5-Phenyl-1,3,4-oxathiazol-2-one

To a stirred solution of amide (24.8 mmol) in THF (50 mL) was added chlorocarbonylsulfenyl chloride (29.8 mmol). The solution was stirred at r.t for 17 h, concentrated in vacuo. Purification by flash chromatography (5% EtOAc in i-hex) gave the title compound as an off-white solid (3.9 g, 88%). LCMS (ES+) 180 (M+H)$^+$ Step 2: Dimethyl 3-phenylisothiazole-4,5-dicarboxylate A solution of 5-phenyl-1,3,4-oxathiazol-2-one (12.7 mmol) and dimethyl acetylenedicarboxylate (38.1 mmol) in CHCl$_3$ (10 mL) was heated in the microwave at 160° C. for 1 h, or until evolution of gas stopped. The mixture was then concentrated and purified by flash chromatography (5% EtOAc in i-hex) to give the title compound as a colorless oil (3.09 g, 88%). LCMS (ES+) 278 (M+H)$^+$ Step 3: (3-Phenylisothiazole-4,5-diyl)dimethanol To a cooled solution of dimethyl 3-phenylisothiazole-4,5-dicarboxylate (10.7 mmol) in THF (180 mL) was added Super-Hydride (53.3 mmol) over a 10 min period and the reaction then stirred at r.t for 1.5 h. The mixture was quenched with 1M HCl (70 mL), the volume reduced to half and extracted into EtOAc. The aqueous was re-extracted with further portions of EtOAc and the organics combined, dried (MgSO$_4$), filtered and concentrated. Purification by flash chromatography (5% to 15% MeOH in DCM gradient) gave the title compound as a colorless oil (2.36 g, >99%). LCMS (ES+) 222 (M+H)+

Step 4: 4,5-Bis(bromomethyl)-3-phenylisothiazole

To a stirred solution of (3-phenylisothiazole-4,5-diyl) dimethanol (13.6 mmol) in DCM/Et$_2$O (1:1, 100 mL) was added phosphorous tribromide (27.2 mmol) dropwise. The mixture was heated to 30° C. for 3 h. The mixture was diluted with H$_2$O (50 mL) and the volatiles concentrated before extraction with DCM (2×50 mL). The combined organics were passed through a phase separator and concentrated. Purification by flash chromatography (5% EtOAc in i-hex) gave the title compound as a colorless oil (3.02 g, 64%). LCMS (ES+) 348 (M+H)+

Step 5: Methyl 5-(3-fluoro-2-methylphenyl)-3-phenyl-5,6-dihydro-4H-cyclopenta[d]isothiazole-5-carboxylate To a stirred solution of methyl 2-(3-fluoro-2-methylphenyl)acetate (5.4 mmol) in DMF (200 mL) was added NaH (5.4 mmol). This was stirred for 1 h with occasional heating until no more H$_2$ gas evolution was observed. This solution was then added slowly dropwise to a stirred solution of 4,5-bis(bromomethyl)-3-phenylisothiazole (4.9 mmol) in DMF (200 mL) at 0° C. A further portion of NaH (5.4 mmol) was added and the reaction mixture heated to 60° C. for 1 h. An additional portion of NaH (5.4 mmol) was added and stirring continued for 1 h. The reaction was quenched with H$_2$O (in ice-bath) and the volatiles removed under reduced pressure. The remaining residue was partitioned between EtOAc and H$_2$O. The organics were collected, dried (MgSO$_4$), filtered and concentrated. Purification by flash chromatography (3% to 5% EtOAc in i-hex) gave the title compound (125 mg, 7%). LCMS (ES+) 367 (M+H)+

Step 6: 5-(3-Fluoro-2-methylphenyl)-3-phenyl-5,6-dihydro-4H-cyclopenta[d]isothiazole-5-carboxylic acid To a solution of methyl 5-(3-fluoro-2-methylphenyl)-3-phenyl-5,6-dihydro-4H-cyclopenta[d]isothiazole-5-carboxylate (97 mg, 0.26 mmol) in THF/methanol (1:1, 2 mL) was added sodium hydroxide (2.0 mL, 2 M aqueous solution). The reaction mixture was capped and heated at 70° C. for 18 h. After this time the contents were cooled to r.t. and methanol was removed under reduced pressure. Aqueous residues were partitioned between EtOAc (15 mL) and 1 M aqueous HCl (15 mL). Organic layers were extracted, washed with brine (20 mL), dried, filtered (phase separation cartridge) and concentrated to give the title compound as a colorless oil which was used directly in the next step (60 mg, 65%).

Step 7: E1-(abs)-5-(3-Fluoro-2-methylphenyl)-N-hydroxy-3-phenyl-5,6-dihydro-4H-cyclopenta[d]isothiazole-5-carboxamide and E2-(abs)-5-(3-Fluoro-2-methylphenyl)-N-hydroxy-3-phenyl-5,6-dihydro-4H-cyclopenta[d]isothiazole-5-carboxamide To a solution of 5-(3-fluoro-2-methylphenyl)-3-phenyl-5,6-dihydro-4H-cyclopenta[d]isothiazole-5-carboxylic acid (60 mg from previous step), triethylamine (92 µl, 0.65 mmol) in anhydrous DMF (1 mL) was added TFFH (49 mg, 0.19 mmol) at 0° C. The reaction mixture was stirred at this temperature for 15 min, then O-(tetrahydro-2H-pyran-2-yl) hydroxylamine (39 mg, 0.34 mmol) was added in a single portion. Reaction mixture was then stirred at r.t. for 24 h. After this time the reaction mixture was quenched by the addition of 1 M HCl solution (2 mL). The reaction was partitioned between EtOAc (5 mL) and 1 M HCl (5 mL). The organic layer was separated, washed with brine (10 mL), dried, filtered (phase separation cartridge) and concentrated to give the crude THP protected hydroxamic acid as a pale yellow oil. To this oil was added anhydrous methanol (2 mL) and 4 M HCl in dioxane (1 mL). The reaction mixture was stirred at r.t. for 30 min. After this time solvents were removed under reduced pressure to give crude hydroxamic acid which was purified by preparative HPLC and chiral HPLC to give the E1-(abs) and E2-(abs) enantiomers (2 mg and 3 mg respectively) which were arbitrarily assigned. (Chiralpak IC 40/60 IPA/MeOH (50/50/0.1% formic acid)/Heptane, 1.0 mL/min, RT 13.2 min (E1-(abs)) and 4.9 min (E2-(abs)). E1-(abs) LCMS (ES+) 369 (M+H)+, RT 3.77 min (Analytical method 1); $^1$H NMR δ (ppm)(DMSO-d$_6$): 10.3 (1H, s), 8.84 (1H, s), 7.90-7.85 (2H, m), 7.55-7.40 (3H, m), 7.20-7.00 (3H, m), 3.95 (1H, d, J=15.2 Hz), 3.92 (1H, d, J=17.2 Hz), 3.45 (1H, d, J=17.2 Hz), 3.42 (1H, d, J=15.2 Hz), 2.17 (3H, d, J=2.4 Hz). E2-(abs) LCMS (ES+) 369 (M+H)+, RT 3.77 min (Analytical method 1); $^1$H NMR δ (ppm)(DMSO-d$_6$): 10.3 (1H, s), 8.84 (1H, s), 7.90-7.85 (2H, m), 7.55-7.40 (3H, m), 7.20-7.00 (3H, m), 3.95 (1H, d, J=15.2 Hz), 3.92 (1H, d, J=17.2 Hz), 3.45 (1H, d, J=17.2 Hz), 3.42 (1H, d, J=15.2 Hz), 2.17 (3H, d, J=2.4 Hz).

Example 82: 2-(3-Fluoro-2-methylphenyl)-N-hydroxy-2,3-dihydro-1H-indene-2-carboxamide

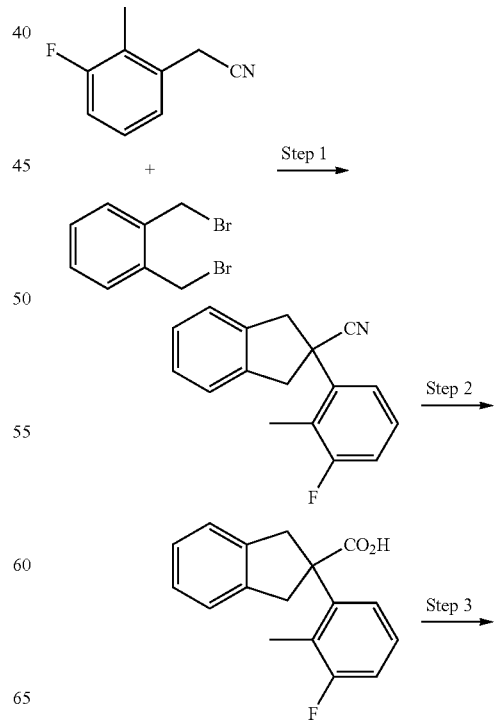

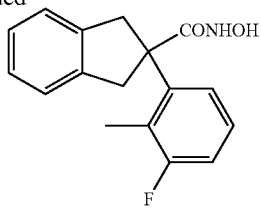

Step 1: 2-(3-Fluoro-2-methylphenyl)-2,3-dihydro-1H-indene-2-carbonitrile

To a solution of 2-(3-fluoro-2-methylphenyl)acetonitrile (0.298 g, 2.0 mmol) in DMF (30 mL) was added NaH (0.176 g, 4.4 mmol) stirred at RT under $N_2$ for 30 min, α,α'-dibromo-o-xylene (0.58 g, 2.2 mmol) added and the reaction mixture was stirred at RT under $N_2$ for 92 h. Saturated $NH_4Cl$ solution (30 mL) added extracted with EtOAc (3×30 mL). Combined organics were extracted with brine (20 mL). EtOAc layers were then dried, filtered (phase separation cartridge) and concentrated onto silica and purified by flash silica column chromatography (gradient elution i-hex to 100% EtOAc in i-hex) to yield the title compound as a pale yellow oil (0.098 g, 19%). LCMS (ES+) 252 (M+H)+

Step 2: 2-(3-Fluoro-2-methylphenyl)-2,3-dihydro-1H-indene-2-carboxylic acid 2-(3-Fluoro-2-methylphenyl)-2,3-dihydro-1H-indene-2-carbonitrile (98 mg, 0.39 mmol) was dissolved in dioxane (2 mL) and 4M HCl in dioxane (1 mL) was added. The mixture was stirred at 120° C. for 96 h to give the title compound as a white solid (63 mg, 97%) and used crude in next step. LCMS (ES+) 271 (M+H)+.

Step 3: 2-(3-Fluoro-2-methylphenyl)-N-hydroxy-2,3-dihydro-1H-indene-2-carboxamide To a solution of 2-(3-fluoro-2-methylphenyl)-2,3-dihydro-1H-indene-2-carboxylic acid (63 mg from previous step) and triethylamine (92 μl, 0.65 mmol) in anhydrous DMF (1 mL) was added TFFH (49 mg, 0.19 mmol) at 0° C. The reaction mixture was stirred at this temperature for 15 min, then O-(tetrahydro-2H-pyran-2-yl)hydroxylamine (39 mg, 0.34 mmol) was added in a single portion. The reaction mixture was then stirred at r.t. for 24 h. After this time the reaction mixture was quenched by the addition of 1 M HCl solution (2 mL). The reaction was partitioned between EtOAc (5 mL) and 1 M HCl (5 mL). The organic layer was separated, washed with brine (10 mL), dried, filtered (phase separation cartridge) and concentrated to give the crude THP protected hydroxamic acid as a pale yellow oil. To this oil was added anhydrous methanol (2 mL) and 4 M HCl in dioxane (1 mL). The reaction mixture was stirred at r.t. for 30 min. After this time solvents were removed under reduced pressure to give crude hydroxamic acid which was purified by preparative HPLC to give the title compound as a colorless solid (20 mg). LCMS (ES+) 285 (M+H)+, RT 3.58 min (Analytical method 1). $^1$H NMR δ (ppm)(DMSO-$d_6$): 10.19 (1H, s), 8.74 (1H, s), 7.30-7.15 (2H, m), 7.15-6.95 (5H, m), 3.71 (2H, d, J=16.8 Hz), 3.20 (2H, d, J=16.8 Hz), 2.17 (3H, d, J=2.4 Hz).

Example 83: 2-Cyclopropyl-7-(3-fluoro-2-methylphenyl)-N-hydroxy-6,7,8,9-tetrahydro-5H-cyclohepta[d]pyrimidine-7-carboxamide

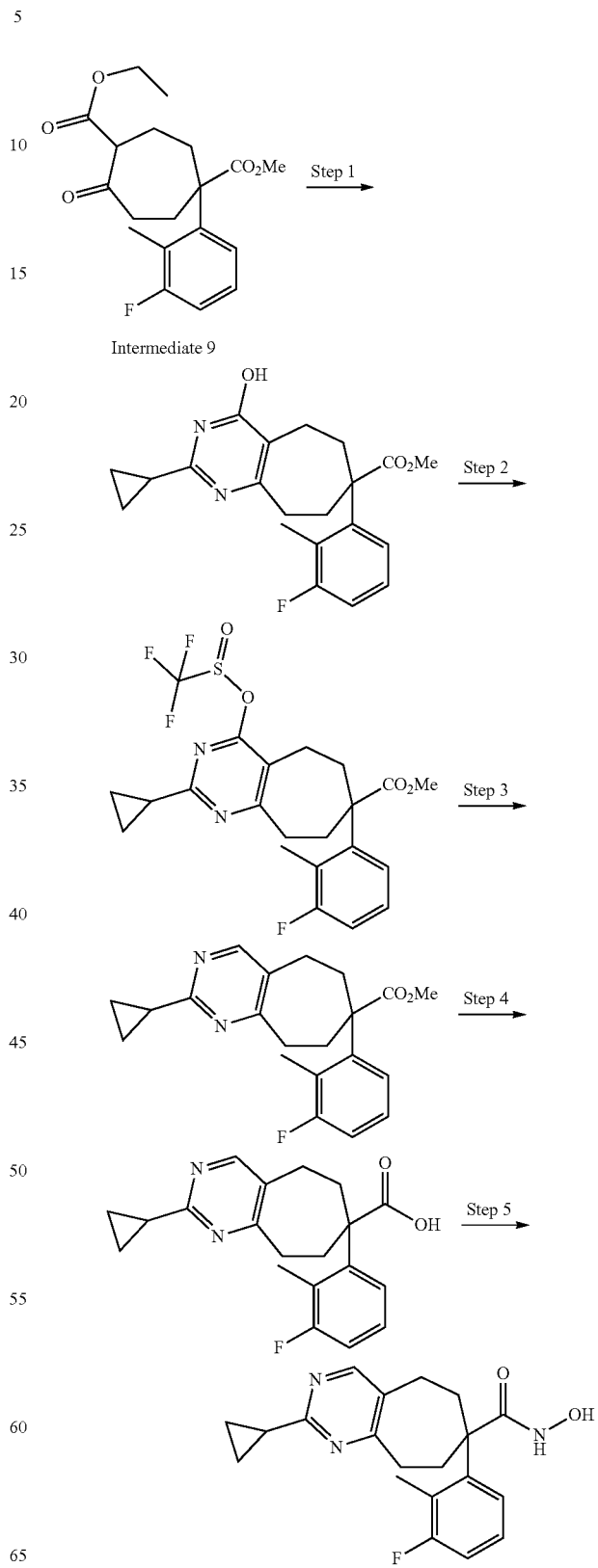

Step 1: Methyl 2-cyclopropyl-7-(3-fluoro-2-methylphenyl)-4-hydroxy-6,7,8,9-tetrahydro-5H-cyclohepta[d]pyrimidine-7-carboxylate Cyclopropanecarboximidamide hydrochloride (0.27 g, 2.2 mmol) was added to a solution of intermediate 9 (0.77 g, 2.2 mmol) in dry methanol (15 mL). Sodium methoxide (0.24 g, 4.44 mmol) was added and the reaction mixture heated at reflux for 3.25 h. Additional cyclopropanecarboximidamide hydrochloride (0.10 g, 0.83 mmol), sodium methoxide (0.10 g, 1.85 mmol) and methanol (3 mL) were added and the reaction heated at reflux for 3 h. Additional cyclopropanecarboximidamide hydrochloride (0.05 g, 0.41 mmol), sodium methoxide (0.06 g, 1.11 mmol) and methanol (10 mL) were added and the reaction stirred at room temperature. After 18 h the reaction mixture was quenched with saturated ammonium chloride solution. The reaction mixture was concentrated to a ¼ volume, diluted with DCM and water and transferred to a separating funnel. The mixture was extracted with DCM (×3), dried (phase separating cartridge) and evaporated to dryness. The crude mixture was purified by silica gel column chromatography (25 g SNAP column), eluting with 0-70% EtOAc in i-hex to afford the title compound as a solid (0.44 g, 54%). $^1$H NMR δ (ppm)(CHCl$_3$-d): 12.32 (1H, br. s), 7.23-7.14 (2H, m), 7.04-6.95 (1H, m), 3.71 (3H, s), 3.02 (1H, dd, J=17.2, 10.3 Hz), 2.88-2.67 (3H, m), 2.64-2.53 (2H, m), 2.33-2.21 (2H, m), 2.16 (3H, d, J=3.1 Hz), 1.87-1.79 (1H, m), 1.20-1.14 (2H, m), 1.08-1.01 (2H, m).

Step 2: Methyl 2-cyclopropyl-7-(3-fluoro-2-methylphenyl)-4-(((trifluoromethyl)sulfinyl)oxy)-6,7,8,9-tetrahydro-5H-cyclohepta[d]pyrimidine-7-carboxylate Methyl 2-cyclopropyl-7-(3-fluoro-2-methylphenyl)-4-hydroxy-6,7,8,9-tetrahydro-5H-cyclohepta[d]pyrimidine-7-carboxylate (0.44 g, 1.19 mmol) was dissolved in DCM (15 mL) and cooled to 0° C. Pyridine (0.15 mL, 1.79 mmol) was added followed by dropwise addition of triflic anhydride (0.24 mL, 1.42 mmol). The reaction mixture was stirred at 0° C. for 2 h. The reaction mixture was transferred to a separating funnel with DCM and washed with water. The combined organic extracts were dried (phase separating cartridge), and concentrated under reduced pressure. Purified by silica gel column chromatography eluting with 0-100% EtOAc in i-hex to afford the title compound as a yellow oil (153 mg, 26%). $^1$H NMR δ (ppm)(CHCl$_3$-d): 7.23-7.12 (2H, m), 7.05-6.97 (1H, m), 3.75 (3H, s), 3.33 (1H, dd, J=16.6, 10.8 Hz), 3.09-2.97 (2H, m), 2.92-2.83 (1H, m), 2.71-2.62 (2H, m), 2.29-2.10 (5H, m), 1.17-1.06 (4H, m).

Step 3: Methyl 2-cyclopropyl-7-(3-fluoro-2-methylphenyl)-6,7,8,9-tetrahydro-5H-cyclohepta[d]pyrimidine-7-carboxylate Palladium on carbon (100 mg), triethylamine (0.06 mL, 0.43 mmol) and 3 Å molecular sieves were added to methyl 2-cyclopropyl-7-(3-fluoro-2-methylphenyl)-4-(((trifluoromethyl)sulfinyl)oxy)-6,7,8,9-tetrahydro-5H-cyclohepta[d]pyrimidine-7-carboxylate (153 mg, 0.30 mmol) in EtOAc (10 mL) at room temperature. The reaction mixture was placed under an atmosphere of hydrogen and stirred at room temperature for 21 h. The reaction mixture was filtered over celite washing with EtOAc and methanol. The filtrate was condensed and the resultant oil partitioned between water and DCM. The mixture was extracted with DCM (×2) and the combined organic extracts dried (phase separating cartridge) and evaporated to dryness to afford the title compound as a yellow oil (120 mg, >100%). Used without further purification in the next step.

Step 4: 2-Cyclopropyl-7-(3-fluoro-2-methylphenyl)-6,7,8,9-tetrahydro-5H-cyclohepta[d]pyrimidine-7-carboxylic acid Methyl 2-cyclopropyl-7-(3-fluoro-2-methylphenyl)-6,7,8,9-tetrahydro-5H-cyclohepta[d]pyrimidine-7-carboxylate (0.30 mmol), lithium hydroxide (100 mg), THF (2 mL), MeOH (2 mL) and water (1 mL) were combined in a sealed tube at 65° C. for 15 h. Additional LiOH (50 mg) was added and heated for a further 21 h. The reaction mixture was cooled to room temperature and partially concentrated under reduced pressure. Water was added and the aqueous mixture acidified with 1N hydrochloric acid. The resultant white precipitate was collected by filtration and dried. There was evidence of the target material in the filtrate. This was condensed, extracted with DCM (×3), dried (phase separating cartridge) and evaporated to dryness. This was combined with the filtered solid and used without further purification in the next step (58 mg, 57%).

Step 5: 2-Cyclopropyl-7-(3-fluoro-2-methylphenyl)-N-hydroxy-6,7,8,9-tetrahydro-5H-cyclohepta[d]pyrimidine-7-carboxamide 2-Cyclopropyl-7-(3-fluoro-2-methylphenyl)-6,7,8,9-tetrahydro-5H-cyclohepta[d]pyrimidine-7-carboxylic acid (58 mg, 0.17 mmol), TFFH (68 mg, 0.26 mmol), DMF (1.5 ml) and Triethylamine (47 µl) were combined and stirred at 0° C. for 0.5 h. Triethylamine (59 µl, 0.43 mmol) and hydroxylamine hydrochloride (24 mg, 0.34 mmol) were added and the reaction stirred at room temperature for 20 h. The reaction mixture was diluted with water (2-3 drops), filtered and purified by preparative HPLC to afford the title compound as a white solid (5 mg). LCMS (ES+) 356 (M+H)$^+$, RT 3.04 min (Analytical method 1); $^1$H NMR δ (ppm) (CH$_3$OH-d$_4$): 8.27 (1H, s), 7.20-7.18 (1H, m), 7.17-7.07 (1H, m), 6.96-6.87 (1H, m), 3.40-3.31 (1H, m), 3.12-2.99 (1H, m), 2.86 (1H, dd, J=16.7, 8.7 Hz), 2.79-2.66 (1H, m), 2.60-2.47 (2H, m), 2.22-2.01 (6H, m), 1.08-1.00 (4H, m).

Examples 84 and 85: E1-(abs)-6-(3-Fluoro-2-methylphenyl)-N-hydroxy-2-(2,2,2-trifluoroethyl)-2,4,5,6,7,8-hexahydrocyclohepta[c]pyrazole-6-carboxamide and E2-(abs)-6-(3-fluoro-2-methylphenyl)-N-hydroxy-2-(2,2,2-trifluoroethyl)-2,4,5,6,7,8-hexahydrocyclohepta[c]pyrazole-6-carboxamide

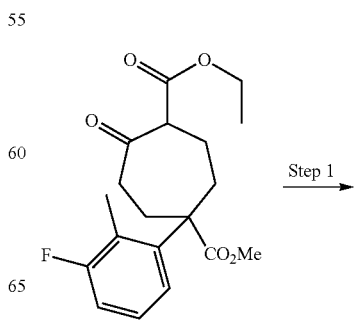

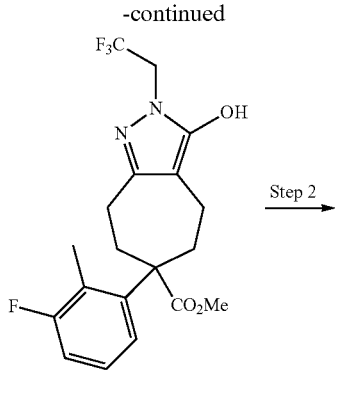

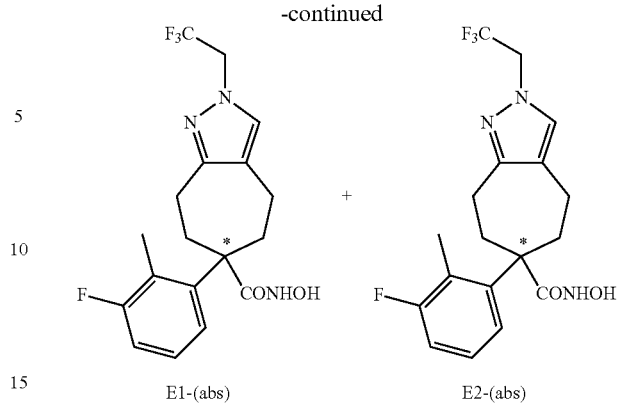

E1-(abs)      E2-(abs)

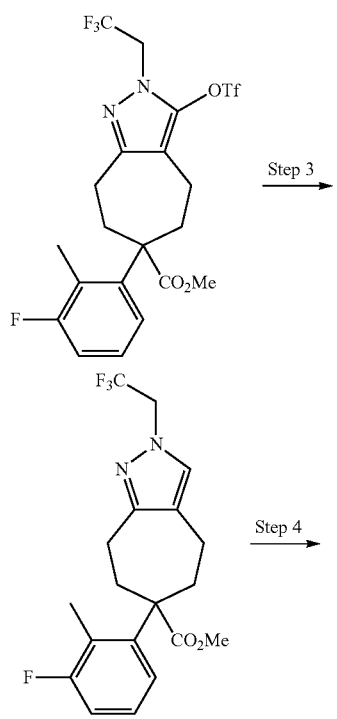

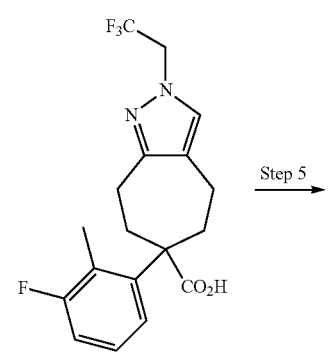

Step 1: Methyl 6-(3-fluoro-2-methylphenyl)-3-hydroxy-2-(2,2,2-trifluoroethyl)-2,4,5,6,7,8-hexahydrocyclohepta[c]pyrazole-6-carboxylate 2,2,2-Trifluoroethylhydrazine (0.32 mL, 70% aqueous solution) was added to a solution of intermediate 9 (0.64 g, 1.8 mmol) in dry ethanol (7 mL) in a sealed tube and heated at 95° C. for 16 h. The reaction mixture was cooled to room temperature and concentrated under reduced pressure. The resultant gum was allowed to stand at room temperature. Partial crystallization occurred over 2 weeks. The solid was triturated sequentially with EtOAc then 20% EtOAc in iso-hexane. The resultant solid was collected by filtration, washing with 20% EtOAc in i-hexane and dried in the vacuum oven to afford the title compound as an off-white solid (360 mg, 50%). $^1$H NMR δ (ppm)(DMSO-d$_6$): 10.55 (0.67H, s), 10.39 (0.33H, s), 7.35 (1H, d, J=8.08 Hz), 7.23 (1H, dd, J=14.82, 7.41 Hz), 7.13-7.04 (1H, m), 4.62 (1.33H, dd, J=18.38, 9.19 Hz), 4.40 (0.67H, d, J=10.33 Hz), 3.64 (3H, s), 2.72-2.58 (2H, m), 2.50-2.32 (4H, m), 2.25-2.12 (2H, m), 2.06 (3H, s). The NMR spectrum was consistent with a mixture of tautomers.

Step 2: Methyl 6-(3-fluoro-2-methylphenyl)-2-(2,2,2-trifluoroethyl)-3-(((trifluoromethyl)sulfonyl)oxy)-2,4,5,6,7,8-hexahydrocyclohepta[c]pyrazole-6-carboxylate Methyl 6-(3-fluoro-2-methylphenyl)-3-hydroxy-2-(2,2,2-trifluoroethyl)-2,4,5,6,7,8-hexahydrocyclohepta[c]pyrazole-6-carboxylate (0.36 g, 0.90 mmol) was dissolved in DCM (10 mL). Pyridine (0.11 mL, 1.35 mmol) was added at room temperature followed by dropwise addition of a triflic anhydride (0.06 mL, 0.36 mmol) in DCM (1 mL). The reaction mixture was cooled to 0° C. and triflic anhydride (0.12 mL, 0.72 mmol) in DCM (3 mL) was added dropwise. After 1.5 h the reaction mixture was transferred to a separating funnel with DCM and washed with water. The combined organic extracts were dried (phase separating cartridge) and evaporated to dryness. The crude material was purified by silica gel column chromatography eluting with 0-70% EtOAc in i-hex to afford the title compound as a colorless gum (380 mg, 80%). $^1$H NMR δ (ppm)(CHCl$_3$-d): 7.21-7.15 (2H, m), 7.03-6.95 (1H, m), 4.57 (2H, dd, J=16.20, 8.10 Hz), 3.70 (3H, s), 3.01-2.92 (1H, m), 2.84-2.72 (2H, m), 2.66-2.49 (3H, m), 2.31-2.18 (2H, m), 2.15 (3H, d, J=3.13 Hz).

Step 3: Methyl 6-(3-fluoro-2-methylphenyl)-2-(2,2,2-trifluoroethyl)-2,4,5,6,7,8-hexahydrocyclohepta[c]pyrazole-6-carboxylate Palladium on carbon (300 mg), triethylamine (0.14 mL, 1.00 mmol) and 3 Å molecular sieves were added to methyl 6-(3-fluoro-2-methylphenyl)-2-(2,2,2-trifluoroethyl)-3-(((trifluoromethyl)sulfonyl)oxy)-2,4,5,6,7,8-hexahydrocyclohepta[c]pyrazole-6-carboxylate (0.38 g, 0.70 mmol) in EtOAc (20 mL) at room temperature. The reaction mixture was placed under an atmosphere of hydrogen and stirred at room temperature for 20 h. The reaction mixture was filtered over celite washing with methanol. The filtrate was condensed and the resultant oil partitioned between water and DCM. The mixture was extracted with DCM (×2) and the combined organics dried (phase separating cartridge), filtered and evaporated to dryness to afford the title compound as a yellow oil (331 mg, >100%). Used without further purification in the next step. $^1$H NMR δ (ppm)(CHCl$_3$-d): 7.22-7.14 (3H, m), 7.02-6.95 (1H, m), 4.58 (2H, dd, J=16.98, 8.49 Hz), 3.72 (3H, s), 2.94-2.91 (1H, m), 2.86-2.73 (2H, m), 2.67-2.56 (3H, m), 2.34-2.19 (2H, m), 2.18 (3H, d, J=3.13 Hz).

Step 4: 6-(3-Fluoro-2-methylphenyl)-2-(2,2,2-trifluoroethyl)-2,4,5,6,7,8-hexahydrocyclohepta[c]pyrazole-6-carboxylic acid Methyl 6-(3-fluoro-2-methylphenyl)-2-(2,2,2-trifluoroethyl)-2,4,5,6,7,8-hexahydrocyclohepta[c]pyrazole-6-carboxylate (0.33 g, 0.86 mmol), lithium hydroxide (180 mg), THF (2 mL), MeOH (2 mL) and water (1 mL) were combined in a sealed tube at 65° C. for 18.5 h. Additional LiOH (135 mg) was added and heated for a further 54 h. The reaction mixture was cooled to room temperature and evaporated to dryness. The mixture was partitioned between water and DCM, acidified to pH 1 using 2N hydrochloric acid. The mixture was extracted with DCM (3 times), dried (phase separating cartridge) and evaporated to dryness to afford the title compound as a white solid (250 mg, 79%). $^1$H NMR δ (ppm)(DMSO-d$_6$): 12.72 (1H, s), 7.50-7.46 (1H, m), 7.32 (1H, d, J=8.1 Hz), 7.25-7.17 (1H, m), 7.11-7.04 (1H, m), 4.94 (2H, dd, J=18.4, 9.2 Hz), 2.81 (1H, dd, J=16.2, 10.5 Hz), 2.71-2.58 (3H, m), 2.56-2.47 (2H, m), 2.48-2.37 (2H, m), 2.17 (3H, d, J=3.1 Hz).

Step 5: E1-(abs)-6-(3-Fluoro-2-methylphenyl)-N-hydroxy-2-(2,2,2-trifluoroethyl)-2,4,5,6,7,8-hexahydrocyclohepta[c]pyrazole-6-carboxamide and E2-(abs)-6-(3-fluoro-2-methylphenyl)-N-hydroxy-2-(2,2,2-trifluoroethyl)-2,4,5,6,7,8-hexahydrocyclohepta[c]pyrazole-6-carboxamide 6-(3-Fluoro-2-methylphenyl)-2-(2,2,2-trifluoroethyl)-2,4,5,6,7,8-hexahydrocyclohepta[c]pyrazole-6-carboxylic acid (210 mg, 0.57 mmol) was suspended in dry DCM (4 mL). Oxalyl chloride (53 μL, 0.62 mmol) and DMF (1 drop) were added with stirring at room temperature. After 2 h MeCN (4 mL) was added and the reaction transferred to a 20 mL microwave tube. Hydroxylamine (200 μL, 50% aqueous solution) was added and the reaction heated in the microwave at 100° C. for 10 min. The reaction is evaporated to dryness and suspended in methanol. The slurry was triturated with water to afford a white powder which was purified by silica gel column chromatography (gradient elution 0-5% MeOH in DCM). Chiral preparative HPLC gave the E1-(abs)- and E2-(abs)-enantiomers which were arbitrarily assigned. (Chiralpak IA, Method 40/60 EtOH (0.1% formic acid)/Heptane 1.0 mL/min, RT 6.3 (E1-(abs)) and 17.3 min (E2-(abs)). E1-(abs)-enantiomer was obtained as a cream solid (34 mg). LCMS (ES+) 386 (M+H)$^+$, RT 9.85 (Analytical method 2). $^1$H NMR δ (ppm)(DMSO-d$_6$): 10.11 (1H, s), 8.68 (1H, s), 7.44 (1H, s), 7.36-7.30 (1H, m), 7.20 (1H, q, J=7.40 Hz), 7.10-7.03 (1H, m), 4.92 (2H, q, J=9.18 Hz), 2.82 (1H, dd, J=15.69, 10.24 Hz), 2.70-2.39 (7H, m), 2.13 (3H, d, J=2.8 Hz). E2-(abs)-enantiomer was obtained as a white solid (31 mg). LCMS (ES+) 386 (M+H)$^+$, RT 3.36 min (Analytical method 1). $^1$H NMR δ (ppm)(DMSO-d$_6$): 10.11 (1H, s), 8.68 (1H, s), 7.44 (1H, s), 7.32 (1H, d, J=8.1 Hz), 7.20 (1H, dd, J=14.8, 7.4 Hz), 7.10-7.03 (1H, m), 4.92 (2H, dd, J=18.4, 9.2 Hz), 2.82 (1H, dd, J=15.7, 10.2 Hz), 2.70-2.41 (7H, m), 2.13 (3H, d, J=3.2 Hz).

Example 86: N-Hydroxy-6-phenyl-2-(2,2,2-trifluoroethyl)-2,4,5,6,7,8-hexahydrocyclohepta[c]pyrazole-6-carboxamide The title compound was prepared according to Example 83 and 84, using the TFFH method of hydroxamic acid formation as in Step 5 of Example 82. Preparative HPLC gave the title compound as a white solid (38 mg). LCMS (ES+) 354 (M+H)$^+$, RT 9.44 min (Analytical method 2); $^1$H NMR δ (ppm)(DMSO-d$_6$): 10.46 (1H, s), 8.75 (1H, s), 7.46 (1H, s), 7.39-7.28 (4H, m), 7.25-7.18 (1H, m), 4.92 (2H, dd, J=18.4, 9.2 Hz), 2.78 (1H, dd, J=15.8, 10.8 Hz), 2.72-2.55 (3H, m), 2.48-2.39 (2H, m), 2.02-1.87 (2H, m).

Examples 87 and 88: E1-(abs)-N-Hydroxy-1-phenyl-2,3-dihydro-1H-indene-1-carboxamide and E2-(abs)-N-hydroxy-1-phenyl-2,3-dihydro-1H-indene-1-carboxamide

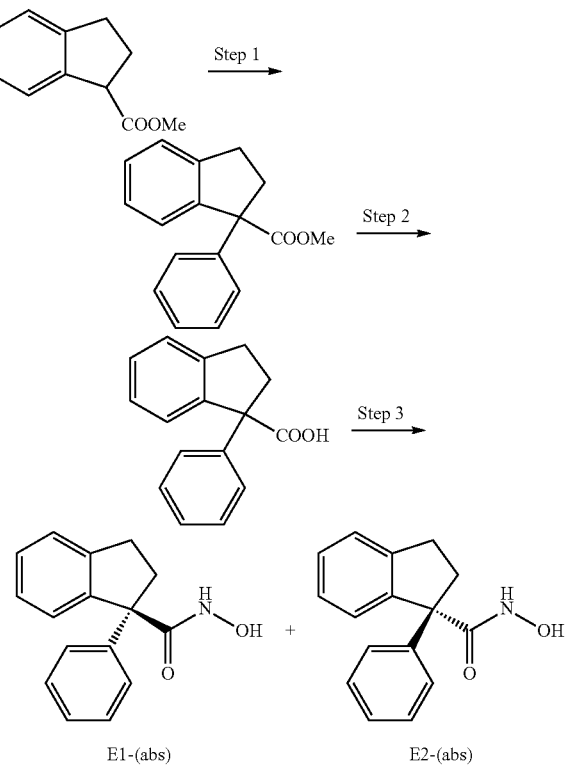

To a solution of methyl 2,3-dihydro-1H-indene-1-carboxylate (545 mg, 3.10 mmol) in toluene (3.8 mL) was added dicyclohexylamine (632 µL, 3.17 mmol) followed by BuLi (2 mL, 3.2 mmol, 1.6 M in hexane). In a seperate flask, Pd(OAc)$_2$ (8 mg, 0.037 mmol), P(tBu)$_3$·HBF$_4$ (24 mg, 0.084 mmol), bromobenzene (163 µL, 1.55 mmol) and toluene (2 mL) were combined sequentially and heated to 100° C. for 1 min. The enolate solution was then added to the reaction mixture via syringe. The combined mixture was heated at 100° C. for 1 h. The mixture was left to cool to r.t., then water (8 mL) and DCM (20 mL) added and the biphasic mixture passed through a phase separator. The organics were concentrated and purified by silica gel column chromatography (10% EtOAc in i-hex), to give the title compound as a yellow oil (277 mg, 77%). LCMS (ES+) 253 (M+H)$^+$.

Step 2:
1-Phenyl-2,3-dihydro-1H-indene-1-carboxylic acid

To a stirred suspension of tBuOK (813 mg, 7.25 mmol) in dry ether (14 mL) at 0° C., was added H$_2$O (33.5 µL, 1.86 mmol). To this was added methyl 1-phenyl-2,3-dihydro-1H-indene-1-carboxylate (211 mg, 0.84 mmol) and the reaction mixture was left to warm to r.t and stirred for 96 h. The mixture was cooled (ice-bath) and acidified with 2 M HCl (4 mL) and diluted with H$_2$O (15 mL). The reaction mixture was then extracted into EtOAc (2×50 mL) and the combined organic layer was dried (MgSO$_4$), filtered and evaporated to dryness to give the title compound as a yellow oil (213 mg, 80%).

Step 3: E1-(abs)-N-Hydroxy-1-phenyl-2,3-dihydro-1H-indene-1-carboxamide and E2-(abs)-N-hydroxy-1-phenyl-2,3-dihydro-1H-indene-1-carboxamide To a solution of 1-phenyl-2,3-dihydro-1H-indene-1-carboxylic acid (210 mg, 0.88 mmol) in DCM (7 mL) was added oxalyl chloride (149 µL, 1.76 mmol). The reaction mixture was stirred at r.t for 20 h under an atmosphere of nitrogen. The reaction mixture was concentrated to dryness and redissolved in DCM (8 mL). To this was added aqueous hydroxylamine (1.5 mL, 50% solution) and the mixture stirred at r.t for 4 h. The mixture was cooled (ice-bath) and acidified with 2 M HCl (4 mL) and diluted with H$_2$O (15 mL). The reaction mixture was then extracted into EtOAc (2×50 mL) and the combined organics washed with brine (10 mL), dried (MgSO$_4$), filtered and concentrated. Purification by preparative HPLC and chiral HPLC to give the E1-(abs) and E2-(abs) enantiomers (2 mg and 3 mg respectively) which were arbitrarily assigned. (Chiralpak IA 20/80 IPA/MeOH (50/50/0.1% formic acid)/Heptane, 1.0 mL/min, RT 7.8 min (E1-(abs)) and 10.9 min (E2-(abs)). E1-(abs) LCMS (ES+) 254 (M+H)$^+$, RT 3.40 min (Analytical method 1); $^1$H NMR δ (ppm)(DMSO-d$_6$): 10.36 (1H, s), 8.80 (1H, s), 7.55-7.51 (1H, m), 7.32-7.20 (6H, m), 7.11 (2H, d, J=7.3 Hz), 3.00-2.86 (2H, m), 2.80-2.67 (1H, m), 2.20-2.11 (1H, m). E2-(abs) LCMS (ES+) 254 (M+H)$^+$, RT 3.40 min (Analytical method 1); $^1$H NMR δ (ppm)(DMSO-d$_6$): 10.38 (1H, s), 8.82 (1H, s), 7.54-7.51 (1H, m), 7.32-7.20 (6H, m), 7.11 (2H, d, J=7.2 Hz), 2.99-2.86 (1H, m), 2.80-2.67 (1H, m), 2.20-2.11 (1H, m).

Example 89: N-Hydroxy-2-phenyl-2,3-dihydro-1H-indene-2-carboxamide

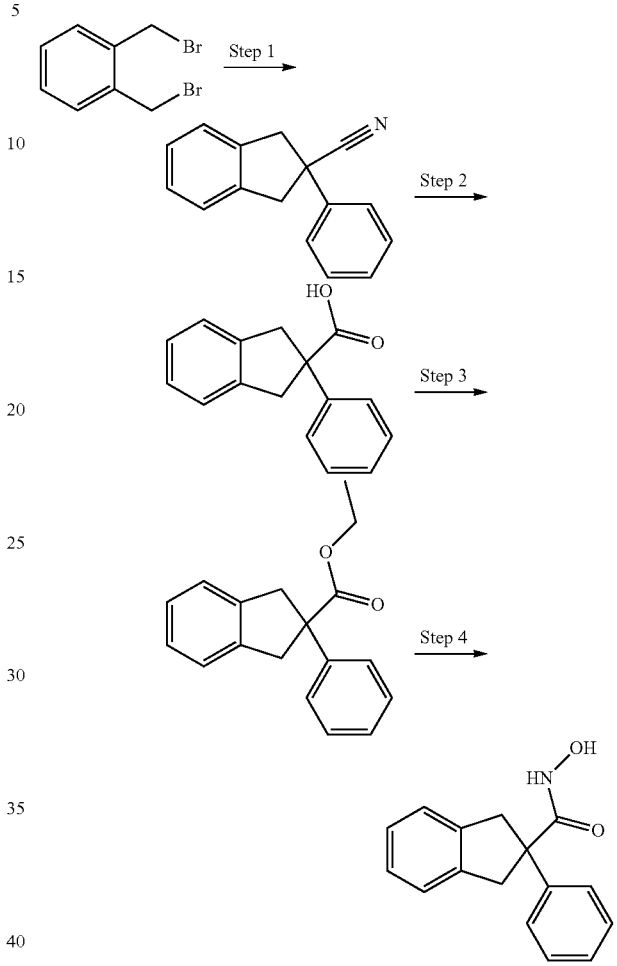

Step 1:
2-Phenyl-2,3-dihydro-1H-indene-2-carbonitrile

Benzyl cyanide (117 mg, 1.00 mmol), α,α'-dibromo-o-xylene (396 mg, 1.50 mmol), NaOH (2 mL, 2 M aqueous solution, 4.00 mmol), benzyl triethylammonium bromide (408 mg, 1.50 mmol) and toluene (10 mL) were combined and stirred at r.t. for 8 days. The reaction mixture was washed with H$_2$O and the organics concentrated. Purification by flash chromatography (33% EtOAc in i-hex) gave the title compound as a clear oil (110 mg, 50%). LCMS (ES+) 220 (M+H)$^+$.

Step 2:
2-Phenyl-2,3-dihydro-1H-indene-2-carboxylic acid

To a stirred solution of 2-phenyl-2,3-dihydro-1H-indene-2-carbonitrile (110 mg, 0.5 mmol) in EtOH/H$_2$O (5 mL, 3:2) was added NaOH (100 mg, 2.5 mmol), and the mixture stirred at reflux for 2 days. The mixture was diluted with H$_2$O and washed with DCM. The aqueous portion was collected, acidified with 2 M HCl and extracted into EtOAc. The organics were dried (MgSO$_4$), filtered and concentrated to give the title compound as a white solid (97 mg, 82 mmol). LCMS (ES+) 239 (M+H)+.

Step 3: Ethyl 2-phenyl-2,3-dihydro-1H-indene-2-carboxylate

A solution of 2-phenyl-2,3-dihydro-1H-indene-2-carboxylic acid (97 mg, 0.4 mmol) and conc. $H_2SO_4$ (1 drop) in EtOH (20 mL) was heated at reflux temperature overnight. The reaction mixture was allowed to cool to r.t., diluted with 2 M aqueous $K_2CO_3$ solution and extracted into DCM. The organics were passed through a phase separator and concentrated to give the title compound as a white solid (95 mg, 88%). LCMS (ES+) 267 (M+H)+.

Step 4: N-Hydroxy-2-phenyl-2,3-dihydro-1H-indene-2-carboxamide

Ethyl 2-phenyl-2,3-dihydro-1H-indene-2-carboxylate (96 mg, 0.37 mmol), aqueous hydroxylamine (2 mL, 50% solution) and sodium hydroxide (1 mL, 15% solution) in MeOH (20 mL) were stirred at r.t. for 6 h. The reaction mixture was extracted with DCM, passed through a phase separator and concentrated to give a white solid which was then triturated with petroleum ether 60-80/$Et_2O$ (1:1) to give the title compound as a white solid. LCMS (ES+) 254 (M+H)+. $^1$H NMR δ (ppm)(DMSO-$d_6$): 10.67 (1H, s), 8.69 (1H, s), 7.40 (2H, d, J=7.4 Hz), 7.36-7.29 (2H, m), 7.26-7.21 (3H, m), 7.14-7.10 (2H, m), 3.84 (2H, d, J=15.7 Hz), 3.18 (2H, d, J=15.7 Hz).

Example 90: (S)-1-(2-Chloro-4-fluorophenyl)-5-(3-fluoro-2-methylphenyl)-N-hydroxy-1,4,5,6-tetrahydrocyclopenta[c]pyrazole-5-carboxamide Prepared following the method described for Example 1. Preparative HPLC gave the title compound as an off-white solid (23 mg). LCMS (ES+) 404 (M+H)+, RT 3.48 min (Analytical method 1); $^1$H NMR δ (ppm)(DMSO-$d_6$): 10.25-10.18 (1H, br s), 8.83-8.77 (1H, br s), 7.68 (1H, dd, J=2.8, 8.6 Hz), 7.58 (1H, dd, J=5.6, 8.9 Hz), 7.47 (1H, s), 7.41-7.34 (1H, m), 7.20-7.13 (1H, m), 7.11-7.04 (2H, m), 3.77 (1H, d, J=15.9 Hz), 3.45 (1H, d, J=14.8 Hz), 3.19-3.13 (1H, m), 2.88 (1H, d, J=16.1 Hz), 2.11 (3H, d, J=2.6 Hz).

Example 91: (S)-2-(4,6-Dimethylpyrimidin-2-yl)-5-(3-fluoro-2-methylphenyl)-N-hydroxy-2,4,5,6-tetrahydrocyclopenta[c]pyrazole-5-carboxamide Prepared following the method described for Example 1. Preparative HPLC gave the title compound as an off-white solid (6 mg). LCMS (ES+) 382 (M+H)+, RT 3.16 min (Analytical method 1); $^1$H NMR δ (ppm)(DMSO-$d_6$): 10.24 (1H, s), 8.85 (1H, s), 8.24 (1H, s), 7.14-7.03 (4H, m), 3.62 (1H, d, J=16.2 Hz), 3.49 (1H, d, J=16.7 Hz), 3.08 (2H, dd, J=6.4, 16.1 Hz), 2.44 (6H, s), 2.17 (3H, d, J=2.6 Hz).

Examples 92, 93 and 94 (S)-1-Benzyl-5-(3-fluoro-2-methylphenyl)-N-hydroxy-1,4,5,6-tetrahydrocyclopenta[c]pyrazole-5-carboxamide, (R)-1-benzyl-4-(3-fluoro-2-methylphenyl)-N-hydroxy-1,4,5,6-tetrahydrocyclopenta[c]pyrazole-4-carboxamide and (R)-2-Benzyl-4-(3-fluoro-2-methylphenyl)-N-hydroxy-2,4,5,6-tetrahydrocyclopenta[c]pyrazole-4-carboxamide

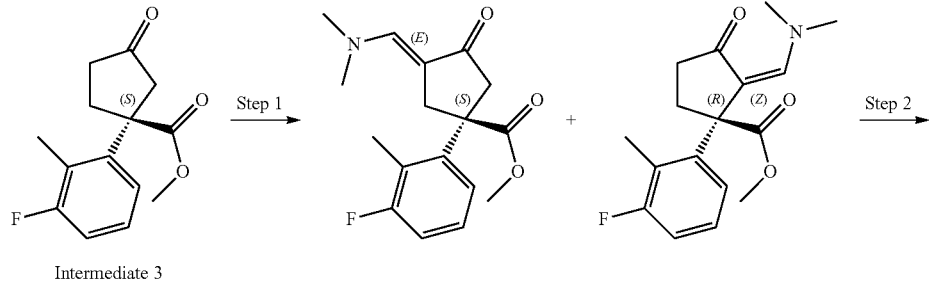

Intermediate 3

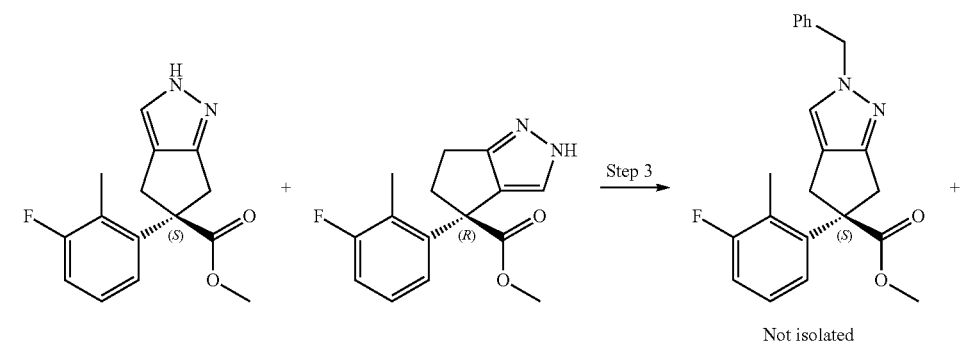

Not isolated

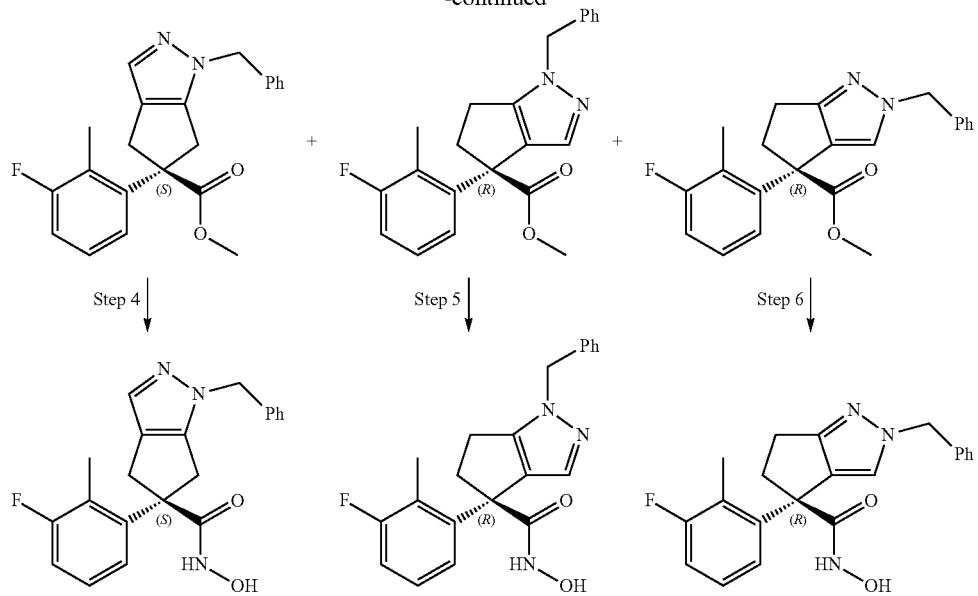

Step 1: (S)-Methyl-3-((dimethylamino)methylene)-1-(3-fluoro-2-methylphenyl)-4-oxocyclopentane carboxylate and (R)-methyl-2-(dimethylaminomethylene)-1-(3-fluoro-2-methyl-phenyl)-3-oxo-cyclopentanecarboxylate Intermediate 3 (2.5 g, 1.0 mmol) was dissolved in dimethylformamide dimethylacetal (5.0 mL) and heated to 80° C. for 16 h. The cooled mixture was concentrated onto silica and purified by flash silica column chromatography (gradient elution i-hex to 100% EtOAc in i-hex) to yield the title compounds as a pale yellow oil (1.8 g, 58%). LCMS (ES+) 306 (M+H)+.

Step 2: (S)-Methyl 5-(3-fluoro-2-methylphenyl-2,4,5,6-tetrahydrocyclopenta[c]pyrazole-5-carboxylate and (R)-methyl 4-(3-fluoro-2-methylphenyl)-2,4,5,6-tetrahydrocyclopenta[c]pyrazole-4-carboxylate To a solution of (S)-methyl-3-((dimethylamino)methylene)-1-(3-fluoro-2-methylphenyl)-4-oxocyclopentane carboxylate and (R)-methyl-2-(dimethylaminomethylene)-1-(3-fluoro-2-methyl-phenyl)-3-oxo-cyclopentanecarboxylate (2.75 g, 9.02 mmol) in acetic acid (9 mL) was added hydrazine (9 mL, 9.00 mmol, 1 M in THF), and the mixture stirred at r.t for 15 min before heating to 55° C. for 3 h. The solvent was removed in vacuo and water added and then extracted with DCM. The organics were passed through a phase separator and concentrated. Purification by flash silica chromatography (elution with Et₂O) gave the title compounds (1.7 g, 68%).

Step 3: (S)-Methyl 1-benzyl-5-(3-fluoro-2-methylplyl)-1,4,5,6-tetrahydrocyclopenta[c]pyrazole-5-carboxylate, (R)-methyl 1-benzyl-4-(3-fluoro-2-methylphenI-1,4,5,6-tetrahydrocyclopenta[c]pyrazole-4-carboxylate and (R)-methyl 2-benzyl-4-(3-fluoro-2-methylphenyl)-2,4,5,6-tetrahydrocyclopenta[c]pyrazole-4-carboxylate To a stirred suspension of (S)-methyl 5-(3-fluoro-2-methylphenyl-2,4,5,6-tetrahydrocyclopenta[c]pyrazole-5-carboxylate and (R)-methyl 4-(3-fluoro-2-methylphenyl)-2,4,5,6-tetrahydrocyclopenta[c]pyrazole-4-carboxylate (0.77 g, 2.8 mmol) in DMF (5 mL) was added benzyl chloride (0.38 g, 3.0 mmol) and cesium carbonate (1.0 g, 3.1 mmol) and the mixture stirred at r.t. for 3 days. The reaction was then diluted with water and extracted into Et₂O. The combined organics were dried (MgSO₄), filtered and concentrated. Purification by flash silica chromatography (elution with Et₂O) and preparative HPLC gave (S)-methyl 1-benzyl-5-(3-fluoro-2-methylphenyl)-1,4,5,6-tetrahydrocyclopenta[c]pyrazole-5-carboxylate (143 mg, 14%) and (R)-methyl 1-benzyl-4-(3-fluoro-2-methylphenyl)-1,4,5,6-tetrahydrocyclopenta[c]pyrazole-4-carboxylate (142 mg, 14%) and (R)-methyl 2-benzyl-4-(3-fluoro-2-methylphenyl)-2,4,5,6-tetrahydrocyclopenta[c]pyrazole-4-carboxylate (156 mg, 15%) as a separable mixture of isomers. LCMS (ES+) 365 (M+H)+.

Step 4: (S)-1-Benzyl-5-(3-fluoro-2-methylphenyl)-N-hydroxy-1,4,5,6-tetrahydrocyclopenta[c]pyrazole-5-carboxamide To a stirred suspension of hydroxylamine hydrochloride (180 mg, 2.61 mmol) in DCM (6 mL), under a nitrogen atmosphere, was added trimethyl aluminium (1.2 mL, 2.4 mmol, 2 M THF solution). The mixture was stirred at r.t. for 20 min before a solution of (S)-methyl 1-benzyl-5-(3-fluoro-2-methylphenyl)-1,4,5,6-tetrahydrocyclopenta[c]pyrazole-5-carboxylate (143 mg, 0.4 mmol) in DCM (4 mL) was added, and the mixture stirred for an additional 1.5 h. Additional hydroxylamine hydrochloride (180 mg, 2.61 mmol) and trimethyl aluminium (1.2 mL, 2.4 mmol, 2 M THF solution) were added and stirring continued for 2 h. The reaction mixture was quenched with 2 M HCl (3 mL), then the mixture concentrated to dryness, and partitioned between water and EtOAc. The organics were dried (MgSO₄), filtered and concentrated. Purification by preparative HPLC gave the title compound as a colorless solid (67 mg). LCMS (ES+) 366 (M+H)+, RT 3.29 min (Analytical method 1); ¹H NMR δ (ppm)(DMSO-d₆): 10.14 (1H, s), 8.76 (1H, s), 7.33-7.28 (3H, m), 7.15-7.11 (3H, m), 7.08-

7.02 (2H, m), 6.87 (1H, dd, J=2.1, 6.7 Hz), 5.27-5.20 (2H, m), 3.51 (1H, d, J=16 Hz), 3.34 (1H, d, J=16 Hz), 2.98 (1H, d, J=16 Hz), 2.83 (1H, d, J=16 Hz), 2.08 (3H, d, J=2.5 Hz).

Step 5: (R)-1-Benzyl-4-(3-fluoro-2-methylphenyl)-N-hydroxy-1,4,5,6-tetrahydrocyclopenta[c]pyrazole-4-carboxamide Following the same method as Step 4 starting from (R)-methyl 1-benzyl-4-(3-fluoro-2-methylphenyl)-1,4,5,6-tetrahydrocyclopenta[c]pyrazole-4-carboxylate (142 mg, 0.39 mmol). Purification by preparative HPLC gave the title compound as a colorless solid (99 mg). LCMS (ES+) 366 (M+H)$^+$, RT 10.11 min (Analytical method 2); $^1$H NMR δ (ppm)(DMSO-d$_6$): 10.09 (1H, s), 8.69 (1H, s), 7.46-7.45 (1H, m), 7.39-7.34 (2H, m), 7.33-7.27 (1H, m), 7.26-7.22 (2H, m), 7.17-7.10 (1H, m), 7.09-7.02 (2H, m), 5.23 (2H, s), 3.84-3.75 (1H, m), 2.78-2.68 (1H, m), 2.61-2.52 (1H, m), 2.30-2.20 (1H, m), 2.11 (3H, s).

Step 6: (R)-2-Benzyl-4-(3-fluoro-2-methylphenyl)-N-hydroxy-2,4,5,6-tetrahydrocyclopenta[c]pyrazole-4-carboxamide Following the same method as Step 4 starting from (R)-methyl 2-benzyl-4-(3-fluoro-2-methylphenyl)-2,4,5,6-tetrahydrocyclopenta[c]pyrazole-4-carboxylate (156 mg, 0.43 mmol). Purification by preparative HPLC gave the title compound as a colorless solid (104 mg). LCMS (ES+) 366 (M+H)$^+$, RT 9.94 min (Analytical method 2); $^1$H NMR δ (ppm)(DMSO-d$_6$): 10.11 (1H, s), 8.70 (1H, d, J=1.4 Hz), 7.68 (1H, s), 7.40-7.36 (2H, m), 7.33-7.28 (3H, m), 7.16-7.03 (2H, m), 6.99 (1H, d, J=7.5 Hz), 5.33 (2H, s), 3.67-3.58 (1H, m), 2.79-2.70 (1H, m), 2.60-2.56 (1H, m), 2.21-2.15 (1H, m), 2.14 (3H, d, J=2.4 Hz).

Example 95: (R)-4-(3-fluoro-2-methylphenyl)-2-(2-fluorobenzyl)-N-hydroxy-2,4,5,6-tetrahydrocyclopenta[c]pyrazole-4-carboxamide Prepared following the method described for Example 91, using 2-fluoro benzyl chloride (432 mg, 3.0 mmol) gave the title compound as a colorless solid (89 mg). LCMS (ES+) 384 (M+H)$^+$, RT 10.01 min (Analytical method 2); $^1$H NMR δ (ppm)(DMSO-d$_6$): 10.11 (1H, s), 8.71 (1H, s), 7.69 (1H, s), 7.43-7.36 (1H, m), 7.32-7.27 (1H, m), 7.25-7.20 (2H, m), 7.16-7.04 (2H, m), 6.99 (1H, d, J=7.5 Hz), 5.39 (2H, s), 3.67-3.58 (1H, m), 2.77-2.69 (1H, m), 2.59-2.53 (1H, m), 2.20-2.15 (1H, m), 2.13 (3H, d, J=2.5 Hz).

Example 96: (R)-5-(3-Fluoro-2-methylphenyl)-N-hydroxy-2-(5-fluoropyridin-2-yl)-5,6-dihydro-4H-cyclopenta[d]thiazole-5-carboxamide Step 1: Methyl 5-(3-fluoro-2-methylphenyl)-2-(5-fluoropyridin-2-yl)-5,6-dihydro-4H-cyclopenta[d]thiazole-5-carboxylate To a solution of methyl 3-bromo-1-(3-fluoro-2-methylphenyl)-4-oxocyclopentanecarboxylate (500 mg, 1.52 mmol) in ethanol (5 mL) was added 5-fluoropyridine-2-carbothioamide (356 mg, 2.28 mmol). The reaction mixture heated to 110° C. under microwave conditions for 1 h. The reaction mixture was concentrated to give a dark red gum. The crude reaction material was purified by flash silica chromatography (gradient elution i-hex to 40% EtOAc in i-hex) to give the title compound as a bright orange solid (226 mg, 34%). Used crude (45% pure) without further purification.

Step 2: 5-(3-Fluoro-2-methylphenyl)-2-(5-fluoropyridin-2-yl)-N-hydroxy-5,6-dihydro-4H-cyclopenta[d]thiazole-5-carboxamide To a solution of hydroxylamine hydrochloride (0.25 g, 3.68 mmol) in DCM (10 mL) was added trimethyl aluminum in heptane (1.6 mL, 3.3 mmol). Then a solution of methyl 5-(3-fluoro-2-methylphenyl)-2-(5-fluoropyridin-2-yl)-5,6-dihydro-4H-cyclopenta[d]thiazole-5-carboxylate (226 mg, 0.58 mmol) in DCM (7 mL) was added dropwise and stirred for 1 h. The reaction was treated with 2N HCl (6 mL) with cooling then MeOH (25 mL) was added and adjusted pH to 1 with 2N HCl. The solvent was evaporated to leave the aqueous which was added to pH 5 with NaHCO$_3$ to precipitate the aluminum which was filtered off through Celite washing well with ethyl acetate. The phases were separated and the organics evaporated to give a yellow solid which was purified by preparative HPLC to give the title compound as an off white solid (39 mg). LCMS (ES+) 388 (M+H)$^+$, RT 3.57 min (Analytical method 1); $^1$H NMR δ (ppm)(DMSO-d$_6$): 10.29 (1H, s), 8.84 (1H, s), 8.62 (1H, d, J=2.9 Hz), 8.09 (1H, dd, J=4.5, 8.9 Hz), 7.90-7.85 (1H, m), 7.19-7.06 (3H, m), 3.77 (2H, dd, J=15.6, 15.6 Hz), 3.42-3.36 (1H, m), 3.22 (1H, d, J=15.8 Hz), 2.17 (3H, d, J=2.6 Hz).

Table of Examples

| Example | Structure | IUPAC Name |
|---|---|---|
| 1 | 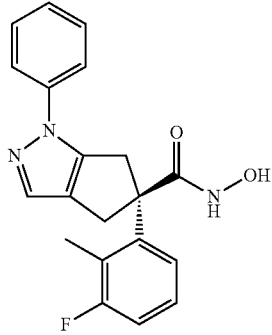 [SMILES: Cc1c(F)cccc1[C@]1(C(=O)NO)Cc2cnn(-c3ccccc3)c2C1] | (S)-5-(3-Fluoro-2-methylphenyl)-N-hydroxy-1-phenyl-1,4,5,6-tetrahydrocyclopenta[c]pyrazole-5-carboxamide |

-continued

| Table of Examples | | |
|---|---|---|
| Example | Structure | IUPAC Name |
| 2 | | (S)-5-(3-Fluoro-2-methylphenyl)-N-hydroxy-1-(o-tolyl)-1,4,5,6-tetrahydrocyclopenta[c]pyrazole-5-carboxamide |
| 3 | | (S)-5-(3-Fluoro-2-methylphenyl)-1-(2-fluorophenyl)-N-hydroxy-1,4,5,6-tetrahydrocyclopenta[c]pyrazole-5-carboxamide |
| 4 | | (S)-1-(3-Chlorophenyl)-5-(3-fluoro-2-methylphenyl)-N-hydroxy-1,4,5,6-tetrahydrocyclopenta[c]pyrazole-5-carboxamide |
| 5 | | (S)-5-(3-Fluoro-2-methylphenyl)-1-(4-fluorophenyl)-N-hydroxy-1,4,5,6-tetrahydrocyclopenta[c]pyrazole-5-carboxamide |

| Example | Structure | IUPAC Name |
|---|---|---|
| 6 | 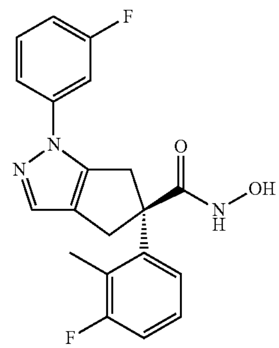 [SMILES: Cc1c(F)cccc1[C@]1(C(=O)NO)Cc2cnn(-c3cccc(F)c3)c2C1] | (S)-5-(3-Fluoro-2-methylphenyl)-1-(3-fluorophenyl)-N-hydroxy-1,4,5,6-tetrahydrocyclopenta[c]pyrazole-5-carboxamide |
| 7 | 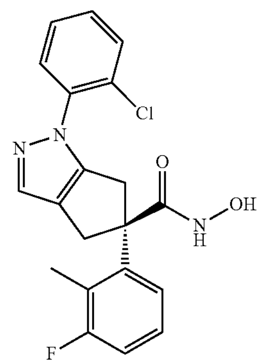 [SMILES: Cc1c(F)cccc1[C@]1(C(=O)NO)Cc2cnn(-c3ccccc3Cl)c2C1] | (S)-1-(2-Chlorophenyl)-5-(3-fluoro-2-methylphenyl)-N-hydroxy-1,4,5,6-tetrahydrocyclopenta[c]pyrazole-5-carboxamide |
| 8 | 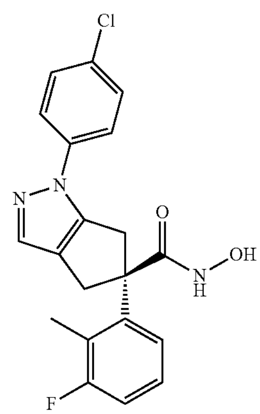 [SMILES: Cc1c(F)cccc1[C@]1(C(=O)NO)Cc2cnn(-c3ccc(Cl)cc3)c2C1] | (S)-1-(4-Chlorophenyl)-5-(3-fluoro-2-methylphenyl)-N-hydroxy-1,4,5,6-tetrahydrocyclopenta[c]pyrazole-5-carboxamide |
| 9 | 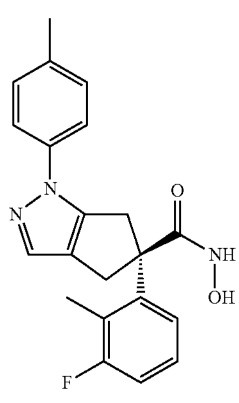 [SMILES: Cc1ccc(-n2ncc3c2C[C@](C(=O)NO)(c2cccc(F)c2C)C3)cc1] | (S)-5-(3-Fluoro-2-methylphenyl)-N-hydroxy-1-(p-tolyl)-1,4,5,6-tetrahydrocyclopenta[c]pyrazole-5-carboxamide |

-continued

| Example | Structure | IUPAC Name |
|---|---|---|
| 10 | 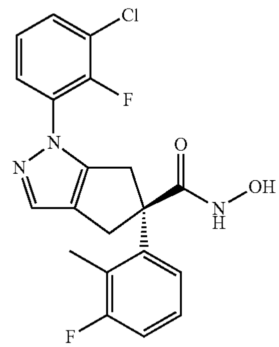 [SMILES: Cc1c(F)cccc1[C@]1(C(=O)NO)Cc2cnn(-c3cccc(Cl)c3F)c2C1] | (S)-1-(3-Chloro-2-fluorophenyl)-5-(3-fluoro-2-methylphenyl)-N-hydroxy-1,4,5,6-tetrahydrocyclopenta[c]pyrazole-5-carboxamide |
| 11 | 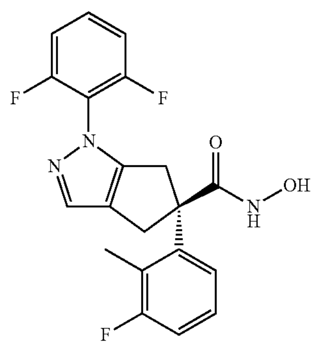 [SMILES: Cc1c(F)cccc1[C@]1(C(=O)NO)Cc2cnn(-c3c(F)cccc3F)c2C1] | (S)-1-(2,6-Difluorophenyl)-5-(3-fluoro-2-methylphenyl)-N-hydroxy-1,4,5,6-tetrahydrocyclopenta[c]pyrazole-5-carboxamide |
| 12 | 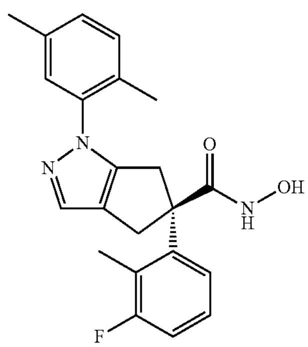 [SMILES: Cc1ccc(C)c(-n2ncc3c2C[C@](C(=O)NO)(c2cccc(F)c2C)C3)c1] | (S)-1-(2,5-Dimethylphenyl)-5-(3-fluoro-2-methylphenyl)-N-hydroxy-1,4,5,6-tetrahydrocyclopenta[c]pyrazole-5-carboxamide |
| 13 | 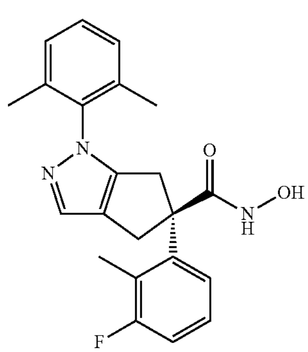 | (S)-1-(2,6-Dimethylphenyl)-5-(3-fluoro-2-methylphenyl)-N-hydroxy-1,4,5,6-tetrahydrocyclopenta[c]pyrazole-5-carboxamide |

| Example | Structure | IUPAC Name |
|---|---|---|
| 14 | 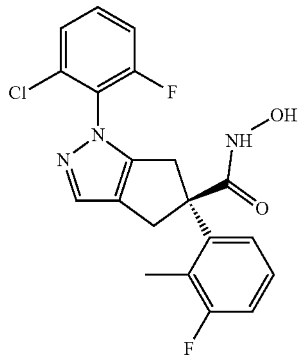 [SMILES: Cc1c(F)cccc1[C@]1(C(=O)NO)Cc2cnn(-c3c(F)cccc3Cl)c2C1] | (S)-1-(2-Chloro-6-fluorophenyl)-5-(3-fluoro-2-methylphenyl)-N-hydroxy-1,4,5,6-tetrahydrocyclopenta[c]pyrazole-5-carboxamide |
| 15 | 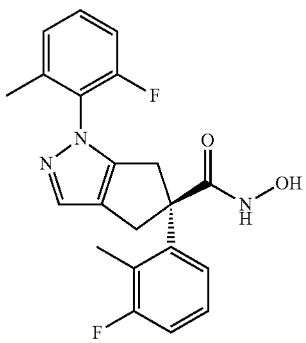 | (S)-5-(3-Fluoro-2-methylphenyl)-1-(2-fluoro-6-methylphenyl)-N-hydroxy-1,4,5,6-tetrahydrocyclopenta[c]pyrazole-5-carboxamide |
| 16 | 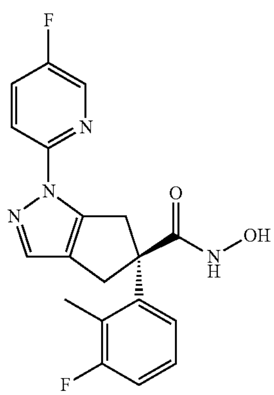 [SMILES: Cc1c(F)cccc1[C@]1(C(=O)NO)Cc2cnn(-c3ccc(F)cn3)c2C1] | (S)-5-(3-Fluoro-2-methylphenyl)-1-(5-fluoropyridin-2-yl)-N-hydroxy-1,4,5,6-tetrahydrocyclopenta[c]pyrazole-5-carboxamide |
| 17 | 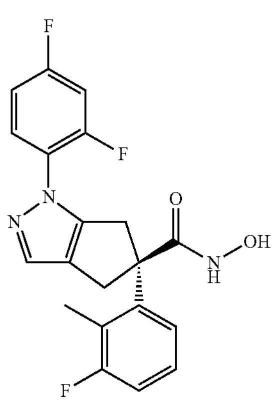 [SMILES: Cc1c(F)cccc1[C@]1(C(=O)NO)Cc2cnn(-c3ccc(F)cc3F)c2C1] | (S)-1-(2,4-Difluorophenyl)-5-(3-fluoro-2-methylphenyl)-N-hydroxy-1,4,5,6-tetrahydrocyclopenta[c]pyrazole-5-carboxamide |

-continued

Table of Examples

| Example | Structure | IUPAC Name |
|---|---|---|
| 18 | 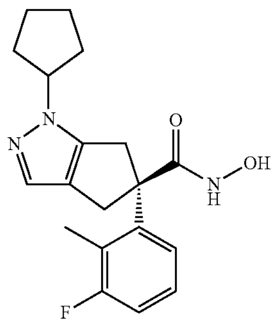 [SMILES: Cc1c(F)cccc1[C@]1(C(=O)NO)Cc2cnn(C3CCCC3)c2C1] | (S)-1-Cyclopentyl-5-(3-fluoro-2-methylphenyl)-N-hydroxy-1,4,5,6-tetrahydrocyclopenta[c]pyrazole-5-carboxamide |
| 19 | 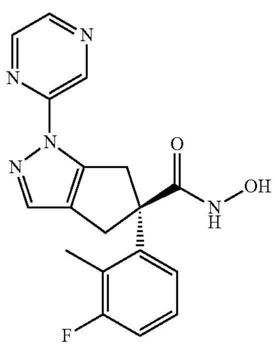 [SMILES: Cc1c(F)cccc1[C@]1(C(=O)NO)Cc2cnn(-c3cnccn3)c2C1] | (S)-5-(3-Fluoro-2-methylphenyl)-N-hydroxy-1-(pyrazin-2-yl)-1,4,5,6-tetrahydrocyclopenta[c]pyrazole-5-carboxamide |
| 20 | 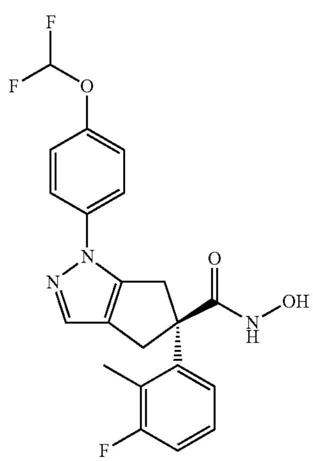 [SMILES: Cc1c(F)cccc1[C@]1(C(=O)NO)Cc2cnn(-c3ccc(OC(F)F)cc3)c2C1] | (S)-1-(4-(Difluoromethoxy)phenyl)-5-(3-fluoro-2-methylphenyl)-N-hydroxy-1,4,5,6-tetrahydrocyclopenta[c]pyrazole-5-carboxamide |
| 21 | 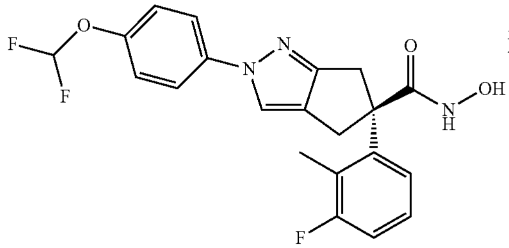 | (S)-2-(4-(Difluoromethoxy)phenyl)-5-(3-fluoro-2-methylphenyl)-N-hydroxy-2,4,5,6-tetrahydrocyclopenta[c]pyrazole-5-carboxamide |

-continued

Table of Examples

| Example | Structure | IUPAC Name |
|---|---|---|
| 22 | 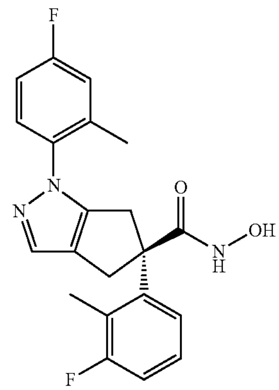 [SMILES: Cc1cc(F)ccc1-n1ncc2c1C[C@](C(=O)NO)(c1cccc(F)c1C)C2] | (S)-5-(3-Fluoro-2-methylphenyl)-1-(4-fluoro-2-methylphenyl)-N-hydroxy-1,4,5,6-tetrahydrocyclopenta[c]pyrazole-5-carboxamide |
| 23 | 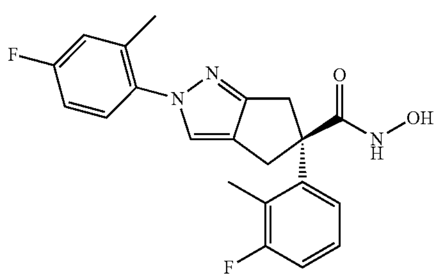 [SMILES: Cc1cc(F)ccc1-n1cc2c(n1)C[C@](C(=O)NO)(c1cccc(F)c1C)C2] | (S)-5-(3-Fluoro-2-methylphenyl)-2-(4-fluoro-2-methylphenyl)-N-hydroxy-2,4,5,6-tetrahydrocyclopenta[c]pyrazole-5-carboxamide |
| 24 | 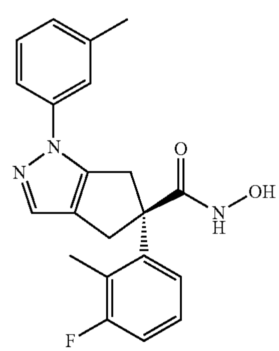 [SMILES: Cc1cccc(-n2ncc3c2C[C@](C(=O)NO)(c2cccc(F)c2C)C3)c1] | (S)-5-(3-Fluoro-2-methylphenyl)-N-hydroxy-1-(m-tolyl)-1,4,5,6-tetrahydrocyclopenta[c]pyrazole-5-carboxamide |
| 25 | 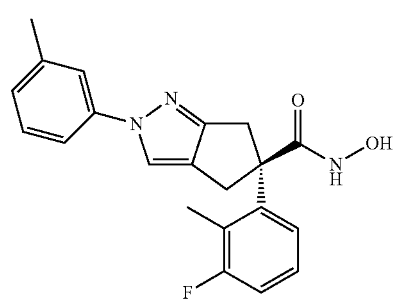 [SMILES: Cc1cccc(-n2cc3c(n2)C[C@](C(=O)NO)(c2cccc(F)c2C)C3)c1] | (S)-5-(3-Fluoro-2-methylphenyl)-N-hydroxy-2-(m-tolyl)-2,4,5,6-tetrahydrocyclopenta[c]pyrazole-5-carboxamide |

| Example | Structure | IUPAC Name |
|---|---|---|
| 26 | 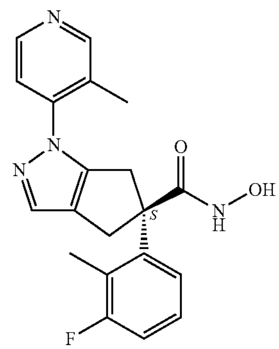 | (S)-5-(3-Fluoro-2-methylphenyl)-N-hydroxy-1-(3-methylpyridin-4-yl)-1,4,5,6-tetrahydrocyclopenta[c]pyrazole-5-carboxamide |
| 27 | 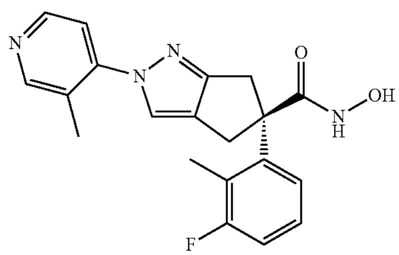 [SMILES: Cc1cnccc1-n1cc2c(n1)C[C@](C(=O)NO)(c1cccc(F)c1C)C2] | (S)-5-(3-Fluoro-2-methylphenyl)-N-hydroxy-2-(3-methylpyridin-4-yl)-2,4,5,6-tetrahydrocyclopenta[c]pyrazole-5-carboxamide |
| 28 | 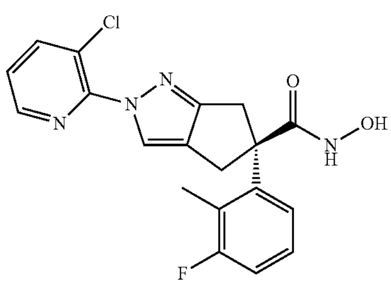 | (S)-2-(3-Chloropyridin-2-yl)-5-(3-fluoro-2-methylphenyl)-N-hydroxy-2,4,5,6-tetrahydrocyclopenta[c]pyrazole-5-carboxamide |
| 29 | 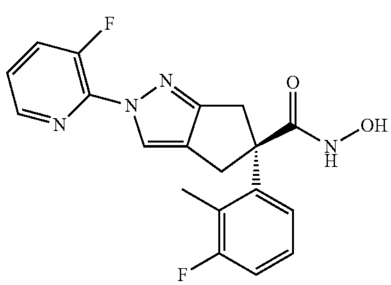 | (S)-5-(3-Fluoro-2-methylphenyl)-2-(3-fluoropyridin-2-yl)-N-hydroxy-2,4,5,6-tetrahydrocyclopenta[c]pyrazole-5-carboxamide |
| 30 | 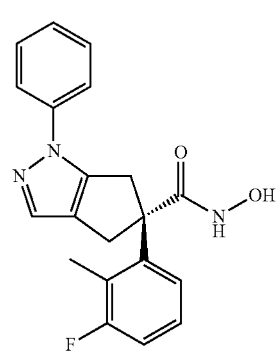 [SMILES: Cc1c(F)cccc1[C@@]1(C(=O)NO)Cc2cnn(-c3ccccc3)c2C1] | (R)-5-(3-Fluoro-2-methylphenyl)-N-hydroxy-1-phenyl-1,4,5,6-tetrahydrocyclopenta[c]pyrazole-5-carboxamide |

| Example | Structure | IUPAC Name |
|---|---|---|
| 31 | 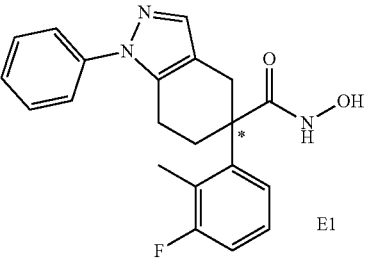 [SMILES: Cc1c(F)cccc1C1(C(=O)NO)CCc2c(cnn2-c2ccccc2)C1] | E1-(abs)-5-(3-Fluoro-2-methylphenyl)-N-hydroxy-1-phenyl-4,5,6,7-tetrahydro-1H-indazole-5-carboxamide |
| 32 | 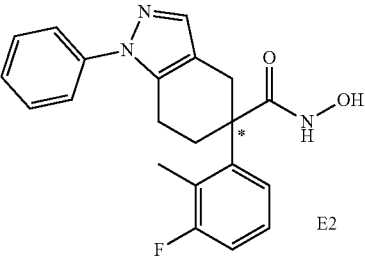 [SMILES: Cc1c(F)cccc1C1(C(=O)NO)CCc2c(cnn2-c2ccccc2)C1] | E2-(abs)-5-(3-Fluoro-2-methylphenyl)-N-hydroxy-1-phenyl-4,5,6,7-tetrahydro-1H-indazole-5-carboxamide |
| 33 | 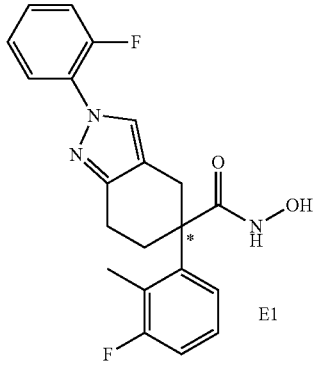 [SMILES: Cc1c(F)cccc1C1(C(=O)NO)CCc2nn(-c3ccccc3F)cc2C1] | E1-(abs)-5-(3-Fluoro-2-methylphenyl)-2-(2-fluorophenyl)-N-hydroxy-4,5,6,7-tetrahydro-2H-indazole-5-carboxamide |
| 34 | 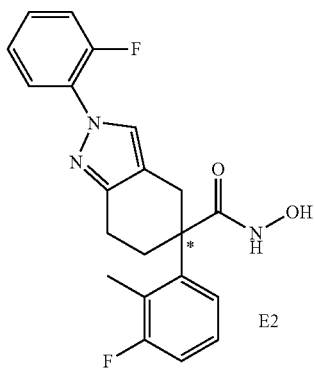 [SMILES: Cc1c(F)cccc1C1(C(=O)NO)CCc2nn(-c3ccccc3F)cc2C1] | E2-(abs)-5-(3-Fluoro-2-methylphenyl)-2-(2-fluorophenyl)-N-hydroxy-4,5,6,7-tetrahydro-2H-indazole-5-carboxamide |

-continued

Table of Examples

| Example | Structure | IUPAC Name |
|---|---|---|
| 35 | 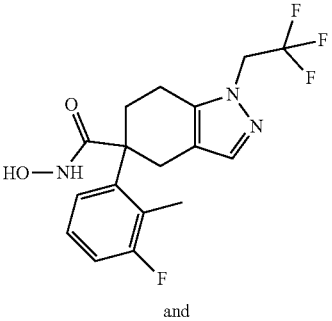 and 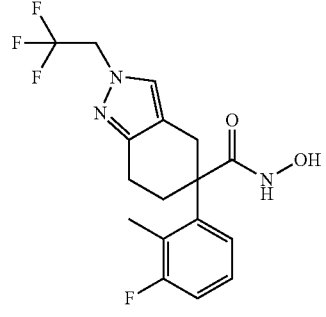 | 5-(3-Fluoro-2-methylphenyl)-N-hydroxy-1-(2,2,2-trifluoroethyl)-4,5,6,7-tetrahydro-1H-indazole-5-carboxamide and 5-(3-fluoro-2-methylphenyl)-N-hydroxy-2-(2,2,2-trifluoroethyl)-4,5,6,7-tetrahydro-2H-indazole-5-carboxamide |
| 36 | 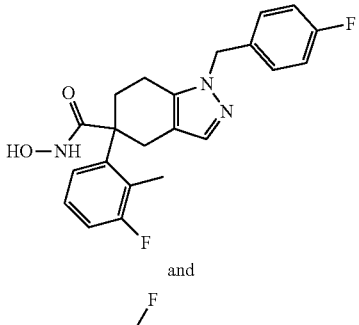 and 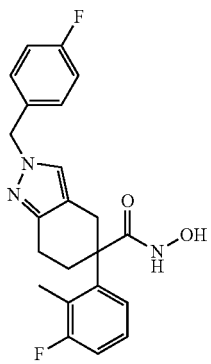 | 5-(3-Fluoro-2-methylphenyl)-1-(4-fluorobenzyl)-N-hydroxy-4,5,6,7-tetrahydro-1H-indazole-5-carboxamide and 5-(3-fluoro-2-methylphenyl)-2-(4-fluorobenzyl)-N-hydroxy-4,5,6,7-tetrahydro-2H-indazole-5-carboxamide |
| 37 | 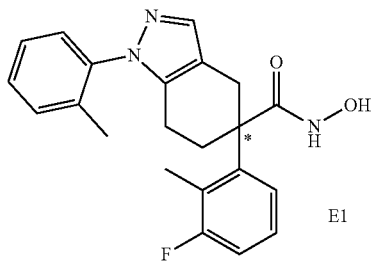 | E1-(abs)-5-(3-Fluoro-2-methylphenyl)-N-hydroxy-1-(o-tolyl)-4,5,6,7-tetrahydro-1H-indazole-5-carboxamide |

Table of Examples

| Example | Structure | IUPAC Name |
|---|---|---|
| 38 | 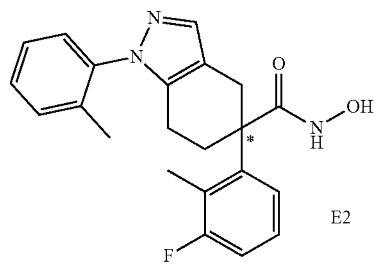 [SMILES: Cc1ccccc1-n1ncc2c1CCC(C(=O)NO)(c1cccc(F)c1C)C2] | E2-(abs)-5-(3-Fluoro-2-methylphenyl)-N-hydroxy-1-(o-tolyl)-4,5,6,7-tetrahydro-1H-indazole-5-carboxamide |
| 39 | 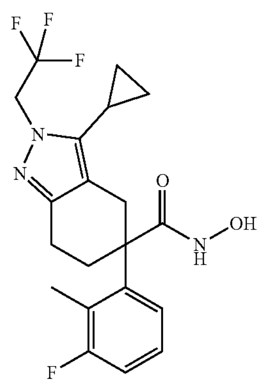 [SMILES: Cc1c(F)cccc1C1(C(=O)NO)CCc2nn(CC(F)(F)F)c(C3CC3)c2C1] | 3-Cyclopropyl-5-(3-fluoro-2-methylphenyl)-N-hydroxy-2-(2,2,2-trifluoroethyl)-4,5,6,7-tetrahydro-2H-indazole-5-carboxamide |
| 40 | 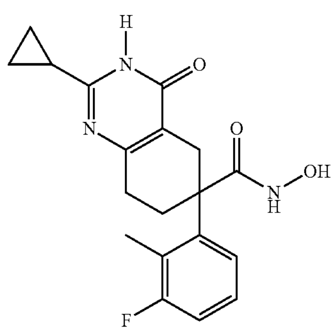 [SMILES: Cc1c(F)cccc1C1(C(=O)NO)CCc2nc(C3CC3)[nH]c(=O)c2C1] | 2-Cyclopropyl-6-(3-fluoro-2-methylphenyl)-N-hydroxy-4-oxo-3,4,5,6,7,8-hexahydroquinazoline-6-carboxamide |
| 41 | 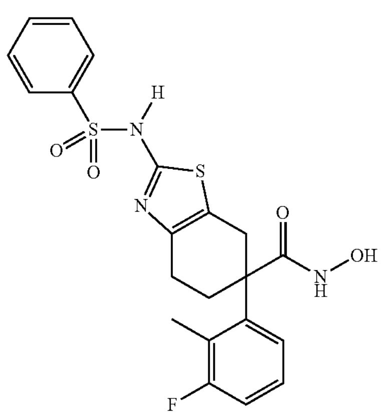 [SMILES: Cc1c(F)cccc1C1(C(=O)NO)CCc2nc(NS(=O)(=O)c3ccccc3)sc2C1] | 6-(3-Fluoro-2-methylphenyl)-N-hydroxy-2-(phenylsulfonamide)-4,5,6,7-tetrahydrobenzo[d]thiazole-6-carboxamide |

-continued

| Example | Structure | IUPAC Name |
|---|---|---|
| 42 | 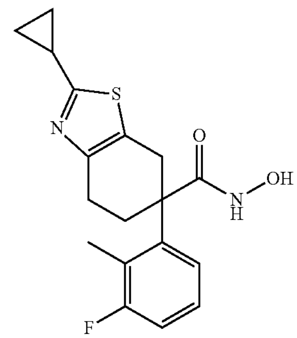 [SMILES: Cc1c(F)cccc1C1(C(=O)NO)CCc2nc(C3CC3)sc2C1] | 2-Cyclopropyl-6-(3-fluoro-2-methylphenyl)-N-hydroxy-4,5,6,7-tetrahydrobenzo[d]thiazole-6-carboxamide |
| 43 | 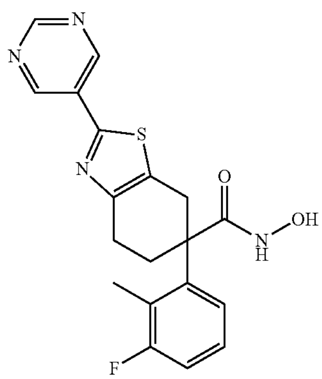 [SMILES: Cc1c(F)cccc1C1(C(=O)NO)CCc2nc(-c3cncnc3)sc2C1] | 6-(3-Fluoro-2-methylphenyl)-N-hydroxy-2-(pyrimidin-5-yl)-4,5,6,7-tetrahydrobenzo[d]thiazole-6-carboxamide |
| 44 | 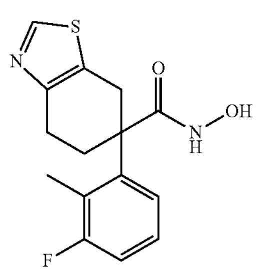 [SMILES: Cc1c(F)cccc1C1(C(=O)NO)CCc2ncsc2C1] | 6-(3-Fluoro-2-methylphenyl)-N-hydroxy-4,5,6,7-tetrahydrobenzo[d]thiazole-6-carboxamide |
| 45 | 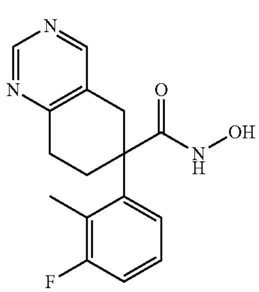 [SMILES: Cc1c(F)cccc1C1(C(=O)NO)CCc2ncncc2C1] | 6-(3-Fluoro-2-methylphenyl)-N-hydroxy-5,6,7,8-tetrahydroquinazoline-6-carboxamide |

-continued

| Example | Structure | IUPAC Name |
|---|---|---|
| 46 | 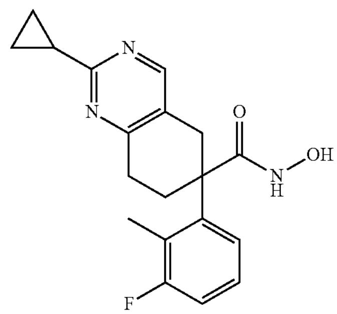 [SMILES: Cc1c(F)cccc1C1(C(=O)NO)CCc2nc(C3CC3)ncc2C1] | 2-Cyclopropyl-6-(3-fluoro-2-methylphenyl)-N-hydroxy-5,6,7,8-tetrahydroquinazoline-6-carboxamide |
| 47 | 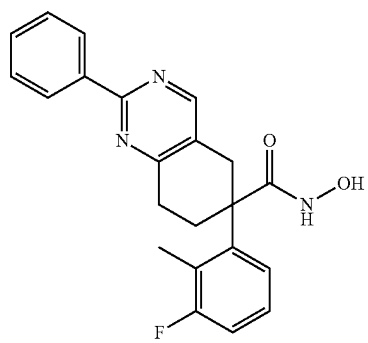 [SMILES: Cc1c(F)cccc1C1(C(=O)NO)CCc2nc(-c3ccccc3)ncc2C1] | 6-(3-Fluoro-2-methylphenyl)-N-hydroxy-2-phenyl-5,6,7,8-tetrahydroquinazoline-6-carboxamide |
| 48 | 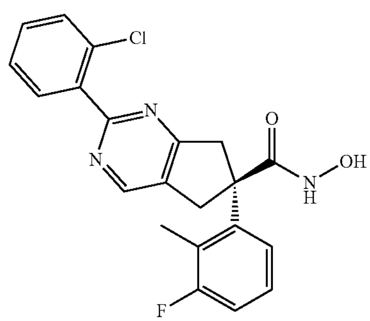 [SMILES: Cc1c(F)cccc1[C@]1(C(=O)NO)Cc2cnc(-c3ccccc3Cl)nc2C1] | (S)-2-(2-Chlorophenyl)-6-(3-fluoro-2-methylphenyl)-N-hydroxy-6,7-dihydro-5H-cyclopenta[d]pyrimidine-6-carboxamide |
| 49 | 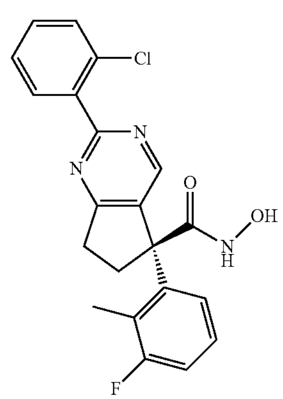 [SMILES: Cc1c(F)cccc1[C@]1(C(=O)NO)CCc2nc(-c3ccccc3Cl)ncc21] | (R)-2-(2-Chlorophenyl)-5-(3-fluoro-2-methylphenyl)-N-hydroxy-6,7-dihydro-5H-cyclopenta[d]pyrimidine-5-carboxamide |

-continued

| Example | Structure | IUPAC Name |
|---|---|---|
| 50 | 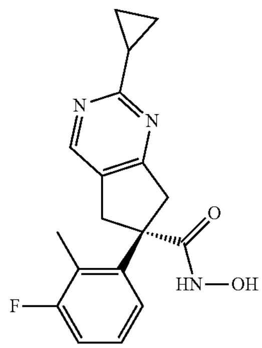 [SMILES: Cc1c(F)cccc1[C@@]1(C(=O)NO)Cc2cnc(C3CC3)nc2C1] | (R)-2-Cyclopropyl-6-(3-fluoro-2-methylphenyl)-N-hydroxy-6,7-dihydro-5H-cyclopenta[d]pyrimidine-6-carboxamide |
| 51 | 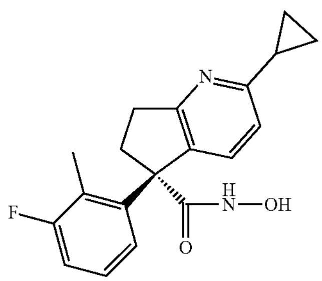 [SMILES: Cc1c(F)cccc1[C@@]1(C(=O)NO)CCc2nc(C3CC3)ccc21] | (S)-2-Cyclopropyl-5-(3-fluoro-2-methylphenyl)-N-hydroxy-6,7-dihydro-5H-cyclopenta[d]pyrimidine-5-carboxamide |
| 52 | 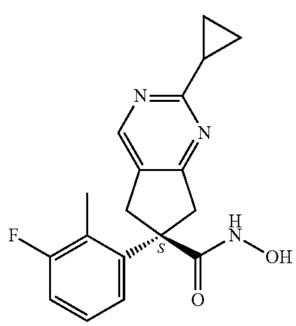 | (S)-2-Cyclopropyl-6-(3-fluoro-2-methylphenyl)-N-hydroxy-6,7-dihydro-5H-cyclopenta[d]pyrimidine-6-carboxamide |
| 53 | 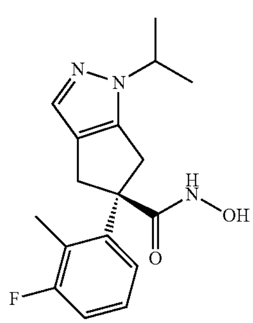 [SMILES: Cc1c(F)cccc1[C@]1(C(=O)NO)Cc2cnn(C(C)C)c2C1] | (S)-5-(3-Fluoro-2-methylphenyl)-N-hydroxy-1-isopropyl-1,4,5,6-tetrahydrocyclopenta[c]pyrazole-5-carboxamide |

Table of Examples

| Example | Structure | IUPAC Name |
|---|---|---|
| 54 | 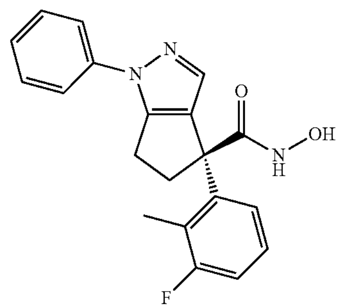 [SMILES: Cc1c(F)cccc1[C@]1(C(=O)NO)CCc2c1cnn2-c1ccccc1] | (R)-4-(3-Fluoro-2-methylphenyl)-N-hydroxy-1-phenyl-1,4,5,6-tetrahydrocyclopenta[c]pyrazole-4-carboxamide |
| 55 | 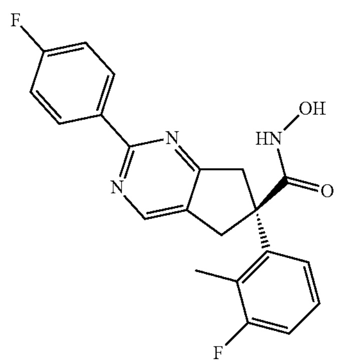 [SMILES: Cc1c(F)cccc1[C@]1(C(=O)NO)Cc2cnc(-c3ccc(F)cc3)nc2C1] | (S)-6-(3-fluoro-2-methylphenyl)-2-(4-fluorophenyl)-N-hydroxy-6,7-dihydro-5H-cyclopenta[d]pyrimidine-6-carboxamide |
| 56 | 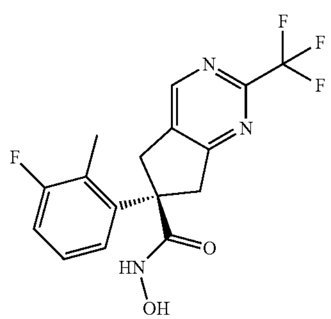 [SMILES: Cc1c(F)cccc1[C@]1(C(=O)NO)Cc2cnc(C(F)(F)F)nc2C1] | (S)-6-(3-Fluoro-2-methylphenyl)-N-hydroxy-2-(trifluoromethyl)-6,7-dihydro-5H-cyclopenta[d]pyrimidine-6-carboxamide |
| 57 | 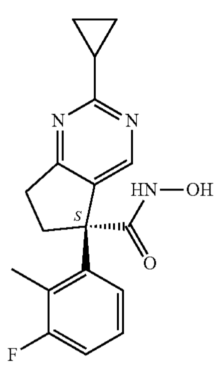 | (R)-2-Cyclopropyl-5-(3-fluoro-2-methylphenyl)-N-hydroxy-6,7-dihydro-5H-cyclopenta[d]pyrimidine-5-carboxamide |

Table of Examples

| Example | Structure | IUPAC Name |
|---|---|---|
| 58 | 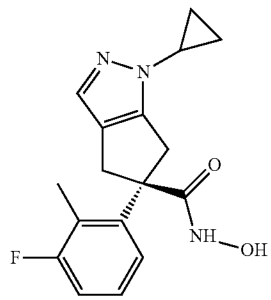 [SMILES: Cc1c(F)cccc1[C@]1(C(=O)NO)Cc2cnn(C3CC3)c2C1] | (S)-1-Cyclopropyl-5-(3-fluoro-2-methylphenyl)-N-hydroxy-1,4,5,6-tetrahydrocyclopenta[c]pyrazole-5-carboxamide |
| 59 | 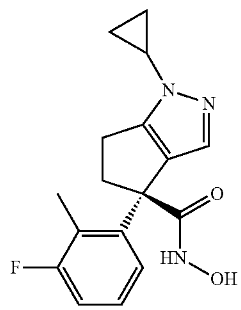 [SMILES: Cc1c(F)cccc1[C@]1(C(=O)NO)CCc2c1cnn2C1CC1] | (R)-1-Cyclopropyl-4-(3-fluoro-2-methylphenyl)-N-hydroxy-1,4,5,6-tetrahydrocyclopenta[c]pyrazole-4-carboxamide |
| 60 | 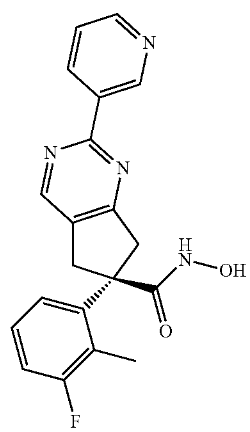 [SMILES: Cc1c(F)cccc1[C@]1(C(=O)NO)Cc2cnc(-c3cccnc3)nc2C1] | (S)-6-(3-Fluoro-2-methylphenyl)-N-hydroxy-2-(pyridin-3-yl)-6,7-dihydro-5H-cyclopenta[d]pyrimidine-6-carboxamide |
| 61 | 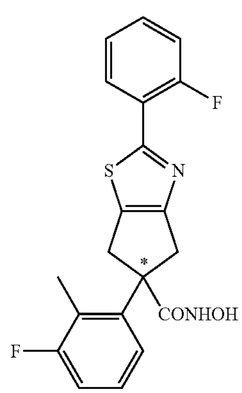 | E1-(abs)-5-(3-Fluoro-2-methylphenyl)-2-(2-fluorophenyl)-N-hydroxy-5,6-dihydro-4H-cyclopenta[d]thiazole-5-carboxamide |

Table of Examples

| Example | Structure | IUPAC Name |
|---|---|---|
| 62 | 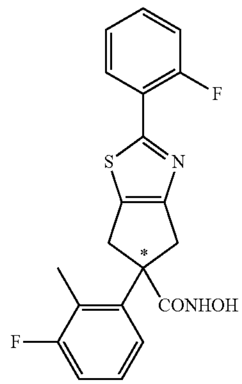 | E2-(abs)-5-(3-Fluoro-2-methylphenyl)-2-(2-fluorophenyl)-N-hydroxy-5,6-dihydro-4H-cyclopenta[d]thiazole-5-carboxamide |
| 63 | 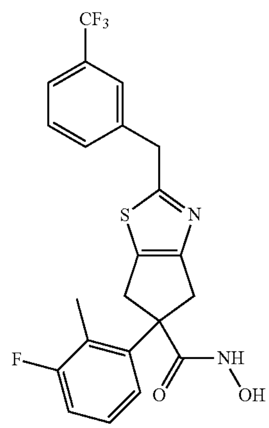 [SMILES: Cc1c(F)cccc1C1(C(=O)NO)Cc2nc(Cc3cccc(C(F)(F)F)c3)sc2C1] | 5-(3-Fluoro-2-methylphenyl)-N-hydroxy-2-(3-(trifluoromethyl)benzyl)-5,6-dihydro-4H-cyclopenta[d]thiazole-5-carboxamide |
| 64 | 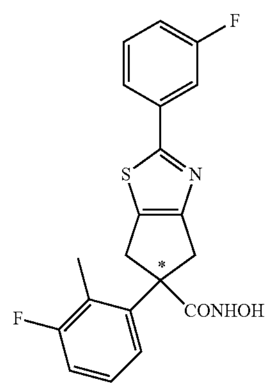 | E1-(abs)-5-(3-Fluoro-2-methylphenyl)-2-(3-fluorophenyl)-N-hydroxy-5,6-dihydro-4H-cyclopenta[d]thiazole-5-carboxamide |
| 65 | 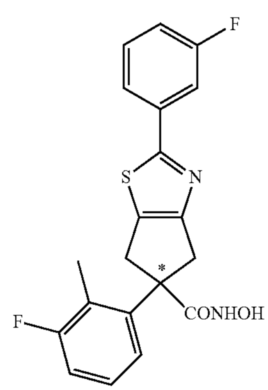 | E2-(abs)-5-(3-Fluoro-2-methylphenyl)-2-(3-fluorophenyl)-N-hydroxy-5,6-dihydro-4H-cyclopenta[d]thiazole-5-carboxamide |

Table of Examples

| Example | Structure | IUPAC Name |
|---|---|---|
| 66 | 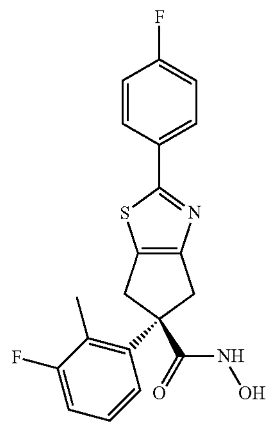 [SMILES: Cc1c(F)cccc1[C@@]1(C(=O)NO)Cc2nc(-c3ccc(F)cc3)sc2C1] | (R)-5-(3-Fluoro-2-methylphenyl)-2-(4-fluorophenyl)-N-hydroxy-5,6-dihydro-4H-cyclopenta[d]thiazole-5-carboxamide |
| 67 | 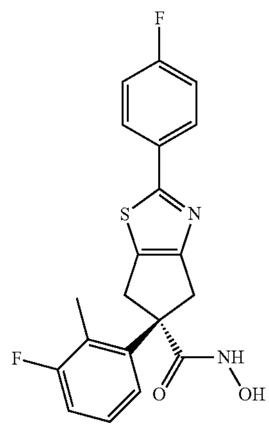 [SMILES: Cc1c(F)cccc1[C@]1(C(=O)NO)Cc2nc(-c3ccc(F)cc3)sc2C1] | (S)-5-(3-Fluoro-2-methylphenyl)-2-(4-fluorophenyl)-N-hydroxy-5,6-dihydro-4H-cyclopenta[d]thiazole-5-carboxamide |
| 68 | 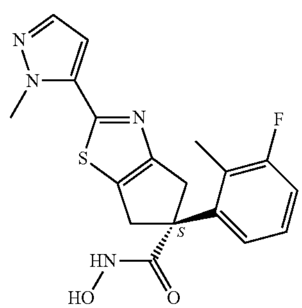 | (S)-5-(3-Fluoro-2-methylphenyl)-N-hydroxy-2-(1-methyl-1H-pyrazol-5-yl)-5,6-dihydro-4H-cyclopenta[d]thiazole-5-carboxamide |
| 69 | 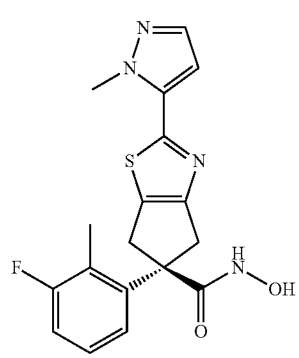 [SMILES: Cc1c(F)cccc1[C@@]1(C(=O)NO)Cc2nc(-c3ccnn3C)sc2C1] | (R)-5-(3-Fluoro-2-methylphenyl)-N-hydroxy-2-(1-methyl-1H-pyrazol-5-yl)-5,6-dihydro-4H-cyclopenta[d]thiazole-5-carboxamide |

| Example | Structure | IUPAC Name |
|---|---|---|
| 70 | 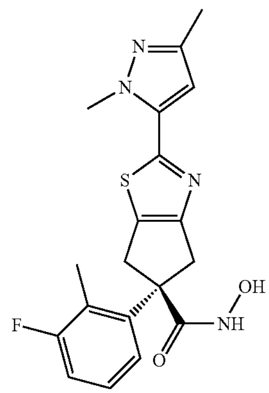 [SMILES: Cc1cc(-c2nc3c(s2)C[C@@](C(=O)NO)(c2cccc(F)c2C)C3)n(C)n1] | (R)-2-(1,3-Dimethyl-1H-pyrazol-5-yl)-5-(3-fluoro-2-methylphenyl)-N-hydroxy-5,6-dihydro-4H-cyclopenta[d]thiazole-5-carboxamide |
| 71 | 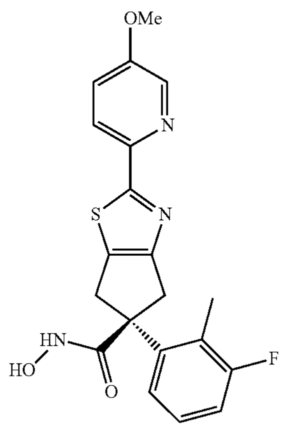 [SMILES: COc1ccc(-c2nc3c(s2)C[C@@](C(=O)NO)(c2cccc(F)c2C)C3)nc1] | (R)-5-(3-Fluoro-2-methylphenyl)-N-hydroxy-2-(5-methoxypyridin-2-yl)-5,6-dihydro-4H-cyclopenta[d]thiazole-5-carboxamide |
| 72 | 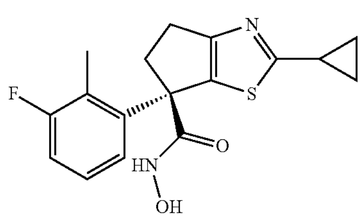 [SMILES: Cc1c(F)cccc1[C@]1(C(=O)NO)CCc2nc(C3CC3)sc21] | (S)-2-Cyclopropyl-6-(3-fluoro-2-methylphenyl)-N-hydroxy-5,6-dihydro-4H-cyclopenta[d]thiazole-6-carboxamide |
| 73 | 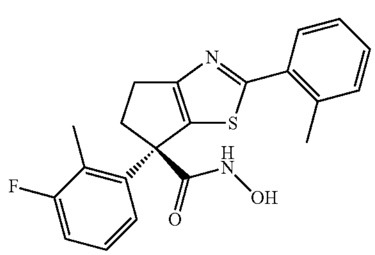 [SMILES: Cc1ccccc1-c1nc2c(s1)[C@](C(=O)NO)(c1cccc(F)c1C)CC2] | (S)-6-(3-Fluoro-2-methylphenyl)-N-hydroxy-2-(o-tolyl)-5,6-dihydro-4H-cyclopenta[d]thiazole-6-carboxamide |

-continued

Table of Examples

| Example | Structure | IUPAC Name |
|---|---|---|
| 74 | 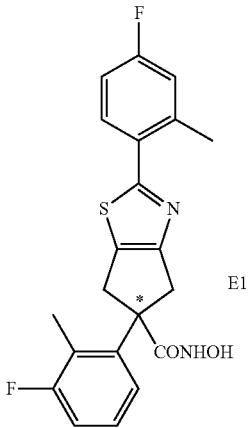 | E1-(abs)-5-(3-Fluoro-2-methylphenyl)-2-(4-fluoro-2-methylphenyl)-N-hydroxy-5,6-dihydro-4H-cyclopenta[d]thiazole-5-carboxamide |
| 75 | 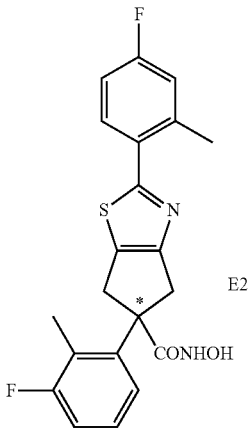 | E2-(abs)-5-(3-Fluoro-2-methylphenyl)-2-(4-fluoro-2-methylphenyl)-N-hydroxy-5,6-dihydro-4H-cyclopenta[d]thiazole-5-carboxamide |
| 76 | 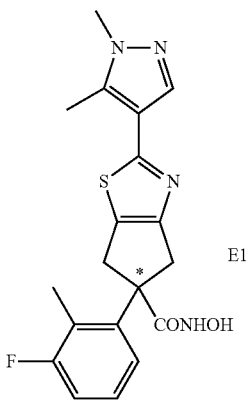 | E1-(abs)-2-(1,5-Dimethyl-1H-pyrazol-4-yl)-5-(3-fluoro-2-methylphenyl)-N-hydroxy-5,6-dihydro-4H-cyclopenta[d]thiazole-5-carboxamide |

-continued

| Table of Examples | | |
|---|---|---|
| Example | Structure | IUPAC Name |
| 77 | 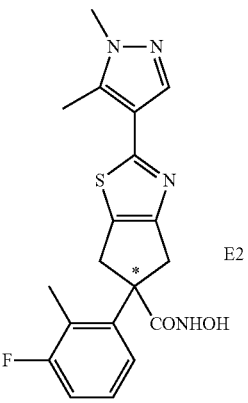 | E2-(abs)-2-(1,5-dimethyl-1H-pyrazol-4-yl)-5-(3-fluoro-2-methylphenyl)-N-hydroxy-5,6-dihydro-4H-cyclopenta[d]thiazole-5-carboxamide |
| 78 | 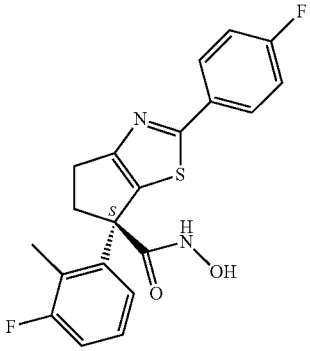 | (S)-6-(3-Fluoro-2-methylphenyl)-2-(4-fluorophenyl)-N-hydroxy-5,6-dihydro-4H-cyclopenta[d]thiazole-6-carboxamide |
| 79 | 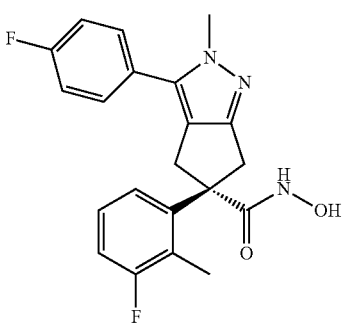 [SMILES: Cc1c(F)cccc1[C@]1(C(=O)NO)Cc2nn(C)c(-c3ccc(F)cc3)c2C1] | (R)-5-(3-Fluoro-2-methylphenyl)-3-(4-fluorophenyl)-N-hydroxy-2-methyl-2,4,5,6-tetrahydrocyclopenta[c]pyrazole-5-carboxamide |
| 80 | 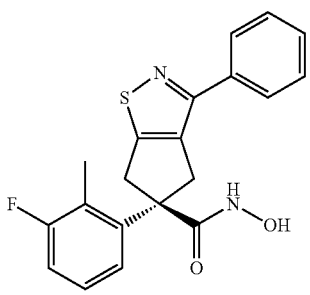 [SMILES: Cc1c(F)cccc1[C@]1(C(=O)NO)Cc2snc(-c3ccccc3)c2C1] | E1-(abs)-5-(3-fluoro-2-methylphenyl)-N-hydroxy-3-phenyl-5,6-dihydro-4H-cyclopenta[d]isothiazole-5-carboxamide |

Table of Examples

| Example | Structure | IUPAC Name |
|---|---|---|
| 81 | 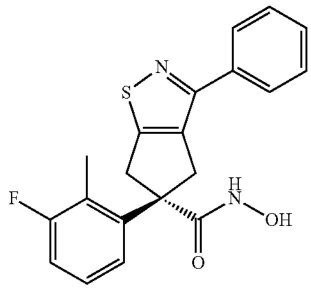 [SMILES: Cc1c(F)cccc1[C@@]1(C(=O)NO)Cc2snc(-c3ccccc3)c2C1] | E2-(abs)-5-(3-fluoro-2-methylphenyl)-N-hydroxy-3-phenyl-5,6-dihydro-4H-cyclopenta[d]isothiazole-5-carboxamide |
| 82 | 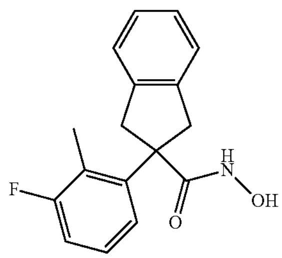 [SMILES: Cc1c(F)cccc1C1(C(=O)NO)Cc2ccccc2C1] | 2-(3-Fluoro-2-methylphenyl)-N-hydroxy-2,3-dihydro-1H-indene-2-carboxamide |
| 83 | 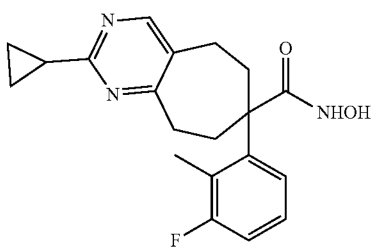 | 2-Cyclopropyl-7-(3-fluoro-2-methylphenyl)-N-hydroxy-6,7,8,9-tetrahydro-5H-cyclohepta[d]pyrimidine-7-carboxamide |
| 84 | 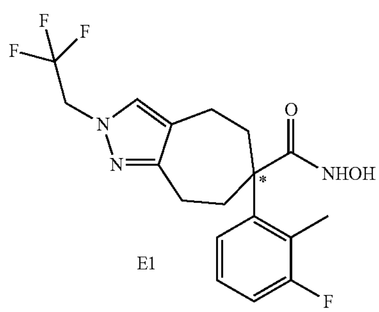 | E1-(abs)-6-(3-Fluoro-2-methylphenyl)-N-hydroxy-2-(2,2,2-trifluoroethyl)-2,4,5,6,7,8-hexahydrocyclohepta[c]pyrazole-6-carboxamide |
| 85 | 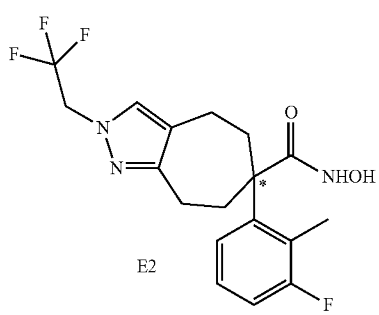 | E2-(abs)-6-(3-Fluoro-2-methylphenyl)-N-hydroxy-2-(2,2,2-trifluoroethyl)-2,4,5,6,7,8-hexahydrocyclohepta[c]pyrazole-6-carboxamide |

-continued

| Example | Structure | IUPAC Name |
|---|---|---|
| 86 | 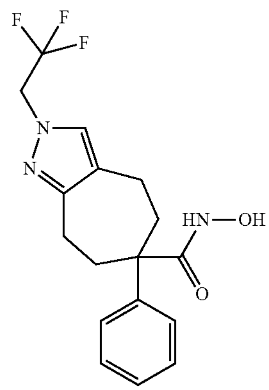 [SMILES: O=C(NO)C1(c2ccccc2)CCc2cn(CC(F)(F)F)nc2CC1] | N-Hydroxy-6-phenyl-2-(2,2,2-trifluoroethyl)-2,4,5,6,7,8-hexahydrocyclohepta[c]pyrazole-6-carboxamide |
| 87 | 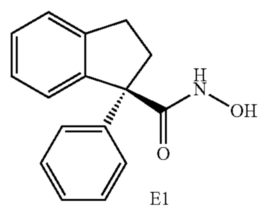 [SMILES: O=C(NO)[C@]1(c2ccccc2)CCc2ccccc21] | E1-(abs)-N-Hydroxy-1-phenyl-2,3-dihydro-1H-indene-1-carboxamide |
| 88 | 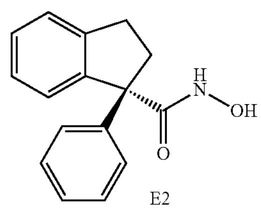 [SMILES: O=C(NO)[C@@]1(c2ccccc2)CCc2ccccc21] | E2-(abs)-N-hydroxy-1-phenyl-2,3-dihydro-1H-indene-1-carboxamide |
| 89 | 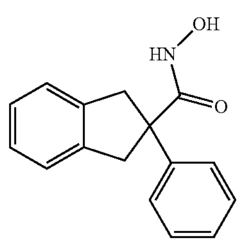 [SMILES: O=C(NO)C1(c2ccccc2)Cc2ccccc2C1] | N-Hydroxy-2-phenyl-2,3-dihydro-1H-indene-2-carboxamide |
| 96 | 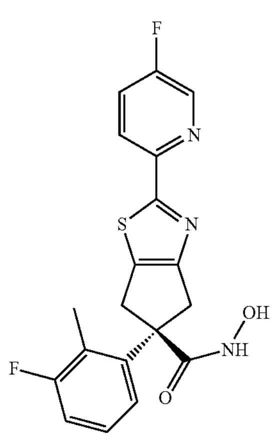 [SMILES: Cc1c(F)cccc1[C@@]1(C(=O)NO)Cc2nc(-c3ccc(F)cn3)sc2C1] | (R)-5-(3-Fluoro-2-methylphenyl)-N-hydroxy-2-(5-fluoropyridin-2-yl)-5,6-dihydroxy-4H-cyclopenta[d]thiazole-5-carboxamide |

| Example | Structure | IUPAC Name |
|---|---|---|
| 90 | 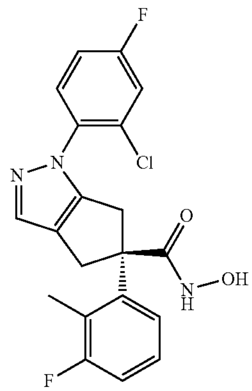 [SMILES: Cc1c(F)cccc1[C@]1(C(=O)NO)Cc2cnn(-c3ccc(F)cc3Cl)c2C1] | (S)-1-(2-Chloro-4-fluorophenyl)-5-(3-fluoro-2-methylphenyl)-N-hydroxy-1,4,5,6-tetrahydrocyclopenta[c]pyrazole-5-carboxamide |
| 91 | 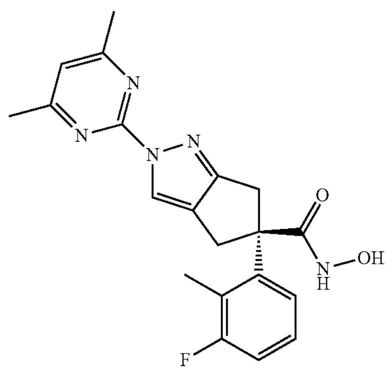 [SMILES: Cc1cc(C)nc(-n2cc3c(n2)C[C@](C(=O)NO)(c2cccc(F)c2C)C3)n1] | (S)-2-(4,6-Dimethylpyrimidin-2-yl)-5-(3-fluoro-2-methylphenyl)-N-hydroxy-2,4,5,6-tetrahydrocyclopenta[c]pyrazole-5-carboxamide |
| 92 | 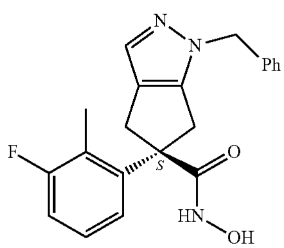 | (S)-1-Benzyl-5-(3-fluoro-2-methylphenyl)-N-hydroxy-1,4,5,6-tetrahydrocyclopenta[c]pyrazole-5-carboxamide |
| 93 | 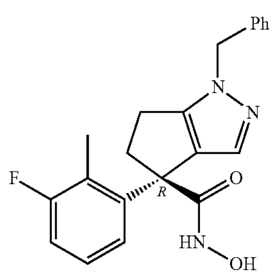 | (R)-1-Benzyl-4-(3-fluoro-2-methylphenyl)-N-hydroxy-1,4,5,6-tetrahydrocyclopenta[c]pyrazole-4-carboxamide |
| 94 | 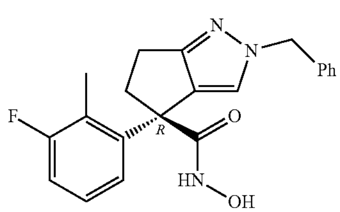 | (R)-2-Benzyl-4-(3-fluoro-2-methylphenyl)-N-hydroxy-2,4,5,6-tetrahydrocyclopenta[c]pyrazole-4-carboxamide |

-continued

Table of Examples

| Example | Structure | IUPAC Name |
|---|---|---|
| 95 | 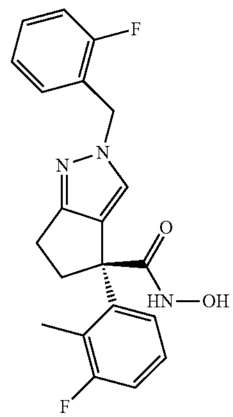 [SMILES: Cc1c(F)cccc1[C@]1(C(=O)NO)CCc2nn(Cc3ccccc3F)cc21] | (R)-4-(3-fluoro-2-methylphenyl)-2-(2-flurobenzyl)-N-hydroxy-2,4,5,6-tetrahydrocyclopenta[c]pyrazole-4-carboxamide |

BIOLOGICAL EXAMPLES

Example A: Analysis of Inhibition of HDAC4 with the Compounds

The potency of compounds is quantified by measuring the Histone Deacetylase 4 (HDAC4) catalytic domain enzymatic activity using the fluorogenic substrate, Boc-Lys(Tfa)-AMC. The substrate is deacetylated to Boc-Lys-AMC by HDAC4. Cleavage by trypsin results in the release of the fluorophore AMC from the deacetylated substrate. The fluorescence of the sample is directly related to the histone deacetylase activity in the sample.

Serially Dilute the Compounds.

Serial dilutions of the compounds being tested and control reference compound (1-(5-(3-((4-(1,3,4-oxadiazol-2-yl)phenoxy)methyl)-1,2,4-oxadiazol-5-yl)thiophen-2-yl)-2,2,2-trifluoroethanone) are made by first resuspending the lyophilized compound to a final concentration of 10 mM in 100% dimethyl sulfoxide (DMSO). Stocks of 60 µL aliquots of the 10 mM compound in DMSO are prepared and stored at −20° C. From one stock aliquot of each compound to be tested and the reference compound, a 16-point serial dilution is prepared according to Table 1 using a 125 µL 16-channel Matrix multi-channel pipette (Matrix Technologies Ltd).

TABLE 1

Serial Dilution of Compounds

| Diluted Solutions | Well | Concentration (µM) | Dilution ratio | Volumes |
|---|---|---|---|---|
| Concentration 1 | A | 10000 | — | 60 µL 10 mM Test compound/reference control |
| Concentration 2 | B | 5000 | 1:2 | 30 µL A + 30 µL DMSO |
| Concentration 3 | C | 2500 | 1:2 | 30 µL B + 30 µL DMSO |
| Concentration 4 | D | 1000 | 1:2.5 | 30 µL C + 45 µL DMSO |
| Concentration 5 | E | 500 | 1:2 | 30 µL D + 30 µL DMSO |
| Concentration 6 | F | 250 | 1:2 | 30 µL E + 30 µL DMSO |
| Concentration 7 | G | 125 | 1:2 | 30 µL F + 30 µL DMSO |
| Concentration 8 | H | 62.5 | 1:2 | 30 µL G + 30 µL DMSO |
| Concentration 9 | I | 31.25 | 1:2 | 30 µL H + 30 µL DMSO |
| Concentration 10 | J | 15.63 | 1:2 | 30 µL I + 30 µL DMSO |
| Concentration 11 | K | 7.81 | 1:2 | 30 µL J + 30 µL DMSO |
| Concentration 12 | L | 3.91 | 1:2 | 30 µL K + 30 µL DMSO |
| Concentration 13 | M | 1.95 | 1:2 | 30 µL L + 30 µL DMSO |
| Concentration 14 | N | 0.98 | 1:2 | 30 µL M + 30 µL DMSO |
| Concentration 15 | O | 0.49 | 1:2 | 30 µL N + 30 µL DMSO |
| Concentration 16 | P | 0.24 | 1:2 | 30 µL O + 30 µL DMSO |

2 µL (200×) of each diluted solution and each control (full activity: 100% DMSO alone or full inhibition 1 mM) is stamped into V-bottomed polypropylene 384-well compound plates using either the Bravo (384-well head from Agilent) or 12.5 µL 16-channel Matrix multi-channel pipette (Matrix Technologies Ltd). Each well with the 200× compound solution is diluted 1:20 by the addition of 38 µL assay buffer+DMSO (10.5% DMSO, 45 mM Tris-HCl, 123 mM NaCl, 2.4 mM KCl, and 0.9 mM MgCl$_2$ at pH 8.0 and equilibrated to room temperature).

Prepare HDAC4 Catalytic Domain Enzyme (0.2 µg/mL).

The HDAC4 catalytic domain enzyme is human catalytic domain HDAC4 protein (amino acids 648-1032) with a C-terminal 6× histidine tag, produced by BioFocus. A working solution of enzyme is prepared from a 500 µg/mL stock aliquot of HDAC4 catalytic domain (thawed on ice) diluted to 0.2 µg/mL with assay buffer (50 mM Tris-HCl, 137 mM NaCl, 2.7 mM KCl, and 1 mM MgCl$_2$ at pH 8 and equilibrated to room temperature) just prior to the addition of the enzyme to the assay.

Prepare 5× (50 µM) Boc-Lys(Tfa)-AMC Substrate.

5× (50 µM) substrate is prepared just prior to the addition to the assay. A 1 mM substrate stock is made by diluting a 100 mM Boc-Lys(Tfa)-AMC in DMSO solution 1:100 by adding it drop-wise to assay buffer (equilibrated to room temperature) while vortexing at slow speed to prevent precipitation. The 5× substrate is prepared by diluting the 1 mM substrate solution 1:20 by adding it drop-wise to assay buffer (equilibrated to room temperature) while vortexing at slow speed to prevent precipitation.

Prepare 3× (30 µM) Developer/Stop Solution.

3× (30 µM) Developer/Stop Solution is prepared just prior to addition to the plate by diluting a stock solution of 10 mM reference compound 1:333 in 25 mg/mL trypsin (PAA Laboratories Ltd.) equilibrated to room temperature.

Assay.

5 µL of each solution of 1:20 diluted compound from above is transferred to a clear bottomed, black, 384-well assay plate using the Bravo or the Janus (384-well MDT head from Perkin Elmer). Using a 16-channel Matrix multi-channel pipette, 35 µL of the working solution of HDAC4 catalytic domain enzyme (0.2 µg/mL in assay buffer) is transferred to the assay plate. The assay is then started by adding 10 µL of 5× (50 µM) substrate to the assay plates using either the Bravo, Janus or 16-channel Matrix multi-channel pipette. The assay plate is then shaken for two minutes on an orbital shaker at 900 rpm (rotations per minute). Next the plate is incubated for 15 minutes at 37° C. The reaction is stopped by adding 25 µL of 3× (30 µM) developer/stop solution to the assay plates using either the Bravo, Janus or a 16-channel Matrix multi-channel pipette. Assay plates are then shaken for 5 minutes on an orbital shaker at 1200 rpm. Next, the assay plates are incubated at 37° C. for 1 hour in a tissue culture incubator. Finally, the fluorescence is measured (Excitation: 355 nm, Emission: 460 nm) using PerkinElmer EnVision in top read mode.

Example B: Analysis of Inhibition of HDAC5 with the Compounds

The potency of the compounds is quantified by measuring the Histone Deacetylase 5 (HDAC5) enzymatic activity using the fluorogenic substrate, Boc-Lys(Tfa)-AMC. The substrate is deacetylated to Boc-Lys-AMC by HDAC5. Cleavage by trypsin results in the release of the fluorophore AMC from the deacetylated substrate. The fluorescence of the sample is directly related to the histone deacetylase activity in the sample.

Serially Dilute the Compounds.

Serial dilutions of the compounds and control reference compound (1-(5-(3-((4-(1,3,4-oxadiazol-2-yl)phenoxy)methyl)-1,2,4-oxadiazol-5-yl)thiophen-2-yl)-2,2,2-trifluoroethanone) are made by first resuspending the lyophilized compound to a final concentration of 10 mM in 100% DMSO. Stocks of 60 µL aliquots of the 10 mM compound in DMSO are prepared and stored at −20° C. From one stock aliquot of each compound to be tested and the reference compound, a 16-point serial dilution is prepared according to Table 1 using a 125 µL 16-channel Matrix multi-channel pipette.

2 µL (200×) of each diluted solution and each control (full activity: 100% DMSO alone or full inhibition 1 mM) is stamped into V-bottom polypropylene 384-well compound plates using either Bravo, Janus, or a 12.5 µL 16-channel Matrix multi-channel pipette. Each well with the 2 µL of the 200× stamped compound solution is diluted 1:20 by the addition of 38 µl assay buffer+DMSO (10.5% DMSO, 45 mM Tris-HCl, 123 mM NaCl, 2.4 mM KCl, and 0.9 mM MgCl$_2$ at pH 8.0 and equilibrated to 37° C.).

Prepare HDAC5 Catalytic Domain Enzyme (0.57 µg/mL).

The HDAC5 catalytic domain enzyme is human HDAC5 catalytic domain (GenBank Accession No. NM_001015053), amino acids 657-1123 with a C-terminal His tag and can be obtained from BPS BioScience. The protein is 51 kDa and is expressed in a baculovirus expression system. A working solution of enzyme is prepared from a 1.65 mg/mL stock aliquot of HDAC5 catalytic domain (thawed on ice) diluted to 0.57 µg/mL with assay buffer (50 mM Tris-HCl, 137 mM NaCl, 2.7 mM KCl, and 1 mM MgCl$_2$ at pH 8 and equilibrated to 37° C.) just prior to the addition of the enzyme to the assay.

Prepare 5× (40 µM) Boc-Lys(Tfa)-AMC Substrate.

5× (40 µM) substrate is prepared just prior to the addition to the assay. The 5× substrate is prepared by diluting the 100 mM Boc-Lys(Tfa)-AMC in DMSO solution 1:2500 by adding it drop-wise to assay buffer (equilibrated to 37° C.) while vortexing at slow speed to prevent precipitation.

Prepare 3× (30 µM) Developer/Stop Solution.

3× (30 µM) Developer/Stop Solution is prepared just prior to addition to the plate by diluting a stock solution of 10 mM reference compound 1:333 in 25 mg/mL trypsin equilibrated to 37° C.

Assay.

5 µL of each solution of the 1:20 diluted compounds and controls from above is transferred to a clear bottomed, black, 384-well assay plate using the Bravo or Janus. Using a 16-channel Matrix multi-channel pipette, 35 µL of the working solution of the HDAC5 catalytic domain enzyme (0.57 µg/mL in assay buffer) is transferred to the assay plate. The assay is then started by adding 10 µL of 5× (40 µM) substrate to the assay plates using either the Bravo, Janus or 16-channel Matrix multi-channel pipette. The assay plate is then shaken for one minute on an orbital shaker at 900 rpm. Next, the plates are incubated for 15 minutes at 37° C. The reaction is stopped by adding 25 µL of 3× (30 µM) developer/stop solution to the assay plates using either the Bravo, Janus or a 16-channel Matrix multi-channel pipette. Assay plates are then shaken for 2 minutes on an orbital shaker at 900 rpm. Next, the assay plates are incubated at 37° C. for 1 hour in a tissue culture incubator followed by shaking for 1 minute at the maximum rpm on an orbital shaker before reading on the EnVision. Finally, the fluorescence is measured (Excitation: 355 nm, Emission: 460 nm) using PerkinElmer EnVision in top read mode.

Example C: Analysis of Inhibition of HDAC7 with the Compounds

The potency of the compounds is quantified by measuring the Histone Deacetylase 7 (HDAC7) enzymatic activity using the fluorogenic substrate, Boc-Lys(Tfa)-AMC. The substrate is deacetylated to Boc-Lys-AMC by HDAC7. Cleavage by trypsin results in the release of the fluorophore AMC from the deacetylated substrate. The fluorescence of the sample is directly related to the histone deacetylase activity in the sample.

Serially Dilute HDAC Inhibitor Compounds.

Serial dilutions of the compounds to be tested and control reference compound (1-(5-(3-((4-(1,3,4-oxadiazol-2-yl)phenoxy)methyl)-1,2,4-oxadiazol-5-yl)thiophen-2-yl)-2,2,2-trifluoroethanone) are made by first resuspending the lyophilized compound to a final concentration of 10 mM in 100% DMSO. Stocks of 60 µL, aliquots of the 10 mM compound in DMSO are prepared and stored at −20° C. From one stock aliquot of each compound to be tested and the reference compound, a 16-point serial dilution is prepared according to Table 1 using a 125 µL, 16-channel Matrix multi-channel pipette.

2 µL (200×) of each diluted solution and each control (full activity: 100% DMSO alone or full inhibition 1 mM) is stamped into V-bottom polypropylene 384-well compound plates using either the Bravo, Janus, or a 12.5 µL, 16-channel Matrix multi-channel pipette. Each well with the 200× compound solution is diluted 1:20 by the addition of 38 µL assay buffer+DMSO (10.5% DMSO, 45 mM Tris-HCl, 123 mM NaCl, 2.4 mM KCl, and 0.9 mM $MgCl_2$ at pH 8.0 and equilibrated to 37° C.).

Prepare HDAC7 Enzyme (71 ng/mL).

The HDAC7 enzyme is human HDAC7 (GenBank Accession No. AY302468) amino acids 518-end with a N-terminal Glutathione S-transferase (GST) tag and can be obtained from BPS BioScience. The protein is 78 kDa and is expressed in a baculovirus expression system. A working solution of enzyme is prepared from a 0.5 mg/ml stock aliquot of HDAC7 (thawed on ice) diluted to 71 ng/mL with assay buffer (50 mM Tris-HCl, 137 mM NaCl, 2.7 mM KCl, and 1 mM $MgCl_2$ at pH 8 and equilibrated to 37° C.) just prior to the addition of enzyme to the assay.

Prepare 5× (50 µM) Boc-Lys(Tfa)-AMC Substrate.

5× (50 µM) substrate is prepared just prior to the addition to the assay. The 5× substrate is prepared by diluting a 100 mM Boc-Lys(Tfa)-AMC in DMSO solution 1:2000 by adding it drop-wise to assay buffer (equilibrated to 37° C.) while vortexing at slow speed to prevent precipitation.

Prepare 3× (30 µM) Developer/Stop Solution.

3× (30 µM) Developer/Stop Solution is prepared just prior to addition to the plate by diluting a stock solution of 10 mM reference compound 1:333 in 25 mg/mL trypsin equilibrated to 37° C.

Assay.

5 µL of each solution of 1:20 diluted compound from above is transferred to a clear bottomed, black, 384-well assay plate using the Bravo or Janus. Using a 16-channel Matrix multi-channel pipette, 35 µL of the working solution of the HDAC7 enzyme (71 ng/mL in assay buffer) is transferred to the assay plate. The assay is then started by adding 10 µL of 5× (50 µM) substrate to the assay plate using either the Bravo, Janus or 16-channel Matrix multi-channel pipette. The assay plate is then shaken for one minute on an orbital shaker at 900 rpm. Next, the plate is incubated for 15 minutes at 37° C. The reaction is then stopped by adding 25 µL of 3× (30 µM) developer/stop solution to the assay plates using either the Bravo, Janus or a 16-channel Matrix multi-channel pipette. The assay plate is then shaken for 2 minutes on an orbital shaker at 900 rpm. Next, the assay plate is incubated at 37° C. for 1 hour in a tissue culture incubator followed by shaking for 1 minute at maximum rpm on an orbital shaker. Finally, the fluorescence is measured (Excitation: 355 nm, Emission: 460 nm) using PerkinElmer EnVision in top read mode.

Example D: Analysis of Inhibition of HDAC9 with the Compounds

The potency of the compounds is quantified by measuring the Histone Deacetylase 9 (HDAC9) enzymatic activity using the fluorogenic substrate, Boc-Lys(Tfa)-AMC. The substrate is deacetylated to Boc-Lys-AMC by HDAC9. Cleavage by trypsin results in the release of the fluorophore AMC from the deacetylated substrate. The fluorescence of the sample is directly related to the histone deacetylase activity in the sample.

Serially Dilute the Compounds.

Serial dilutions of the compounds and control reference compound (1-(5-(3-((4-(1,3,4-oxadiazol-2-yl)phenoxy)methyl)-1,2,4-oxadiazol-5-yl)thiophen-2-yl)-2,2,2-trifluoroethanone) are made by first resuspending the lyophilized compound to a final concentration of 10 mM in 100% DMSO. Stocks of 60 µL aliquots of the 10 mM compound in DMSO are prepared and stored at −20° C. From one stock aliquot of each compound to be tested and the reference compound, a 16-point serial dilution is prepared according to Table 1 using a 125 µL 16-channel Matrix multi-channel pipette.

2 µL (200×) of each diluted solution and each control (full activity: 100% DMSO alone or full inhibition 1 mM) is stamped into V-bottom polypropylene 384-well compound plates using either the Bravo, Janus, or 12.5 µL 16-channel Matrix multi-channel pipette. Each well with the stamped 200× compound solution is diluted 1:20 by the addition of 38 µL assay buffer+DMSO (10.5% DMSO, 45 mM Tris-HCl, 123 mM NaCl, 2.4 mM KCl, and 0.9 mM $MgCl_2$ at pH 8.0 and equilibrated to 37° C.).

Prepare HDAC9 Enzyme (0.57 µg/mL).

The HDAC9 enzyme is human HDAC9 (GenBank Accession No. NM_178423) amino acids 604-1066 with a C-terminal His tag and can be obtained from BPS BioScience. The protein is 50.7 kDa and is expressed in a baculovirus expression system. A working solution of enzyme is prepared from a 0.5 mg/mL stock aliquot of HDAC9 (thawed on ice) diluted to 0.57 µg/mL with assay buffer (50 mM Tris-HCl, 137 mM NaCl, 2.7 mM KCl, and 1 mM $MgCl_2$ at pH 8 and equilibrated to 37° C.) just prior to the addition of enzyme to the assay.

Prepare 5× (125 µM) Boc-Lys(Tfa)-AMC Substrate.

5× (125 µM) substrate is prepared just prior to the addition to the assay. The 5× substrate is prepared by diluting a 100 mM Boc-Lys(Tfa)-AMC in DMSO solution 1:800 by adding it drop-wise to assay buffer (equilibrated to 37° C.) while vortexing at slow speed to prevent precipitation.

Prepare 3× (30 µM) Developer/Stop Solution.

3× (30 µM) Developer/Stop Solution is prepared just prior to addition to the plate by diluting a stock solution of 10 mM reference compound 1:333 in 25 mg/mL trypsin equilibrated to 37° C.

Assay.

5 µL of each solution of 1:20 diluted compound from above is transferred to a clear bottomed, black, 384-well assay plate using the Bravo or Janus. Using a 16-channel Matrix multi-channel pipette, 35 µL of the working solution of the HDAC9 enzyme (0.57 µg/mL in assay buffer) is transferred to the assay plate. The assay is then started by adding 10 µL of 5× (125 µM) substrate to the assay plate using either the Bravo, Janus or 16-channel Matrix multi-channel pipette. The assay plate is then shaken for one minute on an orbital shaker at 900 rpm. Next, the plate is incubated for 15 minutes at 37° C. The reaction is stopped by adding 25 µL of 3× developer/stop solution to the assay plates using either the Bravo, Janus or a 16-channel Matrix multi-channel pipette. The assay plate is then shaken for 2 minutes on an orbital shaker at 900 rpm. Next, the assay plate is incubated at 37° C. for 1 hour in a tissue culture incubator followed by shaking for 1 minute at maximum rpm on an orbital shaker before reading on the enVision. Finally, the fluorescence is measured (Excitation: 355 nm, Emission: 460 nm) using PerkinElmer EnVision in top read mode.

Example E: Analysis of Inhibition of Cellular HDAC Activity with the Compounds

The potency of the compounds is quantified by measuring the cellular histone deacetylase enzymatic activity using the fluorogenic substrate, Boc-Lys(Tfa)-AMC. After penetration in Jurkat E6-1 cells, the substrate is deacetylated to Boc-Lys-AMC. After cell lysis and cleavage by trypsin, the fluorophore AMC is released from the deacetylated substrate only. The fluorescence of the sample is directly related to the histone deacetylase activity in the sample.

Jurkat E6.1 Cell Culture and Plating.

Jurkat E6.1 cells are cultured according to standard cell culture protocols in Jurkat E6.1 Growth Media (RPMI without phenol red, 10% FBS, 10 mM HEPES, and 1 mM Sodium Pyruvate). Jurkat E6.1 cells are counted using a Coulter Counter and resuspended in Jurkat E6.1 growth media at a concentration of 75,000 cells/35 µL. 35 µL or 75,000 cells is seeded into Greiner microtitre assay plates. The plates are then incubated at 37° C. and 5% $CO_2$ while other assay components are being prepared.

Serially Dilute the Compounds.

Serial dilutions of the compounds being tested and control reference compound (1-(5-(3-((4-(1,3,4-oxadiazol-2-yl)phenoxy)methyl)-1,2,4-oxadiazol-5-yl)thiophen-2-yl)-2,2,2-trifluoroethanone) are made by first resuspending the lyophilized compound to a final concentration of 10 mM in 100% DMSO. Stocks of 70 µL aliquots of the 10 mM compound in DMSO are prepared and stored at −20° C. From one stock aliquot of each compound to be tested and the reference compound, a 16-point serial dilution is prepared according to Table 1 using a 125 µL 16-channel Matrix multi-channel pipette.

2 µL (200×) of each diluted solution and each control (full activity: 100% DMSO alone or full inhibition 1 mM) is stamped into V-bottom polypropylene 384-well compound plates using either the Bravo, Janus, or 12.5 µL 16-channel Matrix multi-channel pipette. Each well with the 200× compound solution is diluted 1:20 by the addition of 38 µL Jurkat assay buffer+DMSO (9.5% DMSO, RPMI without phenol red, 0.09% FBS, 9 mM Hepes, and 0.9 mM Sodium Pyruvate equilibrated to room temperature)

Prepare 5× (500 µM) Boc-Lys(Tfa)-AMC Substrate.

5× (500 µM) substrate is prepared just prior to the addition to the assay. The 5× substrate is prepared by diluting a 100 mM Boc-Lys(Tfa)-AMC in DMSO solution 1:200 by adding it drop-wise to Jurkat assay medium (RPMI without phenol red, 0.1% FBS, 10 mM Hepes, and 1 mM Sodium Pyruvate equilibrated to 37° C.) while vortexing at slow speed to prevent precipitation.

Prepare 3× Lysis Buffer.

10 mL of 3× lysis buffer is prepared with 8.8 ml of 3× stock lysis buffer (50 mM Tris-HCl, pH 8.0, 137 mM NaCl, 2.7 mM KCl, 1 mM $MgCl_2$, 1% Nonidet P40 Substitute equilibrated to room temperature) and 1.2 mL of 3 mg/mL Trypsin equilibrated to room temperature.

Assay.

5 µL of each solution of 1:20 diluted compound from above is transferred to the Greiner microtitre assay plates with 75,000 cells/well using the Bravo. Cells are then incubated for 2 hours at 37° C. and 5% $CO_2$. The assay is then started by adding 10 µL of 5× (500 µM) substrate to the assay plate using either the Bravo or 16-channel Matrix multi-channel pipette. The cells are then incubated for 3 hours at 37° C. and 5% $CO_2$. Next, 25 µL of 3× lysis buffer is added to each well using either the 125 µL 16 channel pipette or the Bravo. The assay plate is then incubated overnight (15-16 hours) at 37° C. and 5% $CO_2$. The following day, the plates are shaken on an orbital shaker for 1 minute at 900 rpm. Finally the top read fluorescence (Excitation: 355 nm, Emission: 460 nm) is measured using PerkinElmer EnVision.

Example F

Using the assay protocols described above, the following compounds synthesized by the above synthetic methods were tested.

| Example | Structure | Biochemical $IC_{50}$ (µM) | Cell (Lys-TFA) $IC_{50}$ (µM) | Cell (Lys-Ac) $IC_{50}$ (µM) |
|---|---|---|---|---|
| 1 | 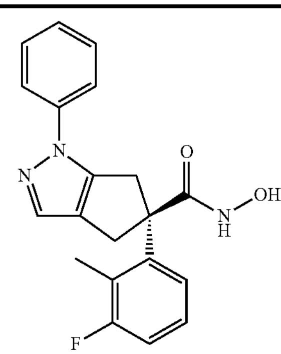 | 0.028 | 0.059 | >50 |
| 2 | 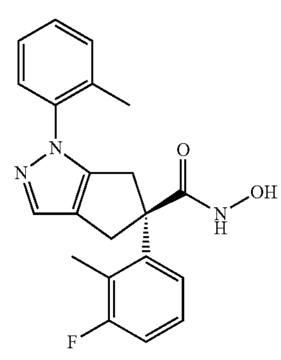 | 0.023 | 0.014 | >50 |

-continued

| Example | Structure | Biochemical IC$_{50}$ (μM) | Cell (Lys-TFA) IC$_{50}$ (μM) | Cell (Lys-Ac) IC$_{50}$ (μM) |
|---------|-----------|---------------------------|-------------------------------|------------------------------|
| 3 | 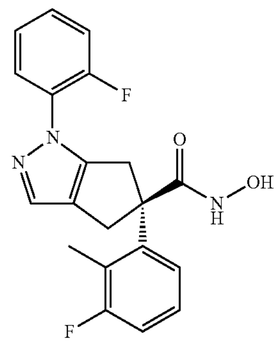 [SMILES: Cc1ccccc1-n1ncc2c1C[C@](C(=O)NO)(c1cccc(F)c1C)C2] | 0.017 | 0.033 | >50 |
| 4 | 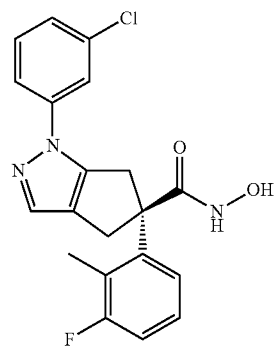 | 0.061 | 0.072 | >50 |
| 5 | 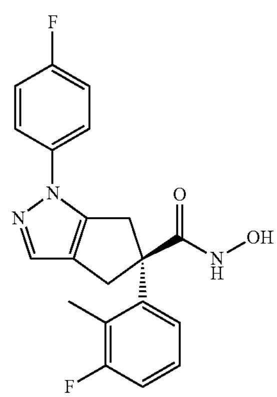 [SMILES: Cc1c(F)cccc1[C@]1(C(=O)NO)Cc2cnn(-c3ccc(F)cc3)c2C1] | 0.053 | 0.099 | >50 |
| 6 | 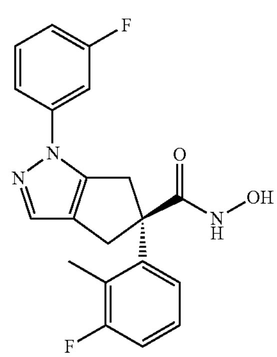 [SMILES: Cc1c(F)cccc1[C@]1(C(=O)NO)Cc2cnn(-c3cccc(F)c3)c2C1] | 0.044 | 0.067 | >50 |

| Example | Structure | Biochemical IC$_{50}$ (μM) | Cell (Lys-TFA) IC$_{50}$ (μM) | Cell (Lys-Ac) IC$_{50}$ (μM) |
|---|---|---|---|---|
| 7 | 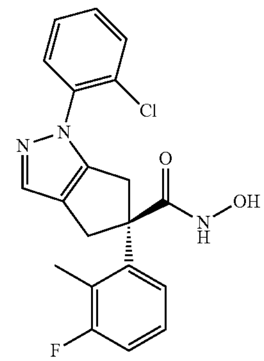 [SMILES: Cc1c(F)cccc1[C@]1(C(=O)NO)Cc2cnn(-c3ccccc3Cl)c2C1] | 0.015 | 0.013 | >50 |
| 8 | 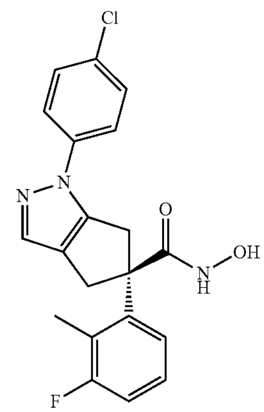 [SMILES: Cc1c(F)cccc1[C@]1(C(=O)NO)Cc2cnn(-c3ccc(Cl)cc3)c2C1] | 0.112 | 0.103 | >50 |
| 9 | 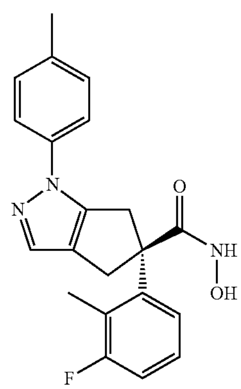 [SMILES: Cc1ccc(-n2ncc3c2C[C@](C(=O)NO)(c2cccc(F)c2C)C3)cc1] | 0.039 | 0.082 | >50 |
| 10 | 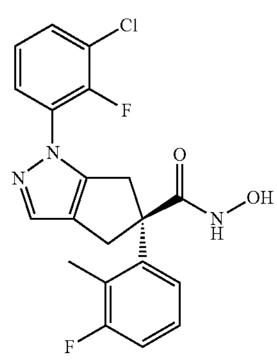 [SMILES: Cc1c(F)cccc1[C@]1(C(=O)NO)Cc2cnn(-c3cccc(Cl)c3F)c2C1] | 0.017 | 0.017 | >50 |

| Example | Structure | Biochemical IC$_{50}$ (µM) | Cell (Lys-TFA) IC$_{50}$ (µM) | Cell (Lys-Ac) IC$_{50}$ (µM) |
| --- | --- | --- | --- | --- |
| 11 | 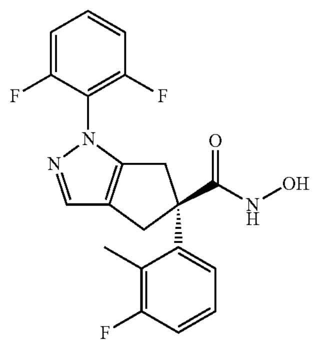 [SMILES: Cc1c(F)cccc1[C@]1(C(=O)NO)Cc2cnn(-c3c(F)cccc3F)c2C1] | 0.012 | 0.027 | >50 |
| 12 | 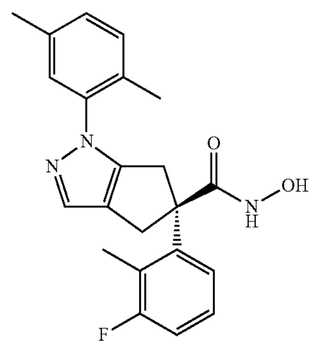 [SMILES: Cc1ccc(C)c(-n2ncc3c2C[C@](C(=O)NO)(c2cccc(F)c2C)C3)c1] | 0.021 | 0.018 | >50 |
| 13 | 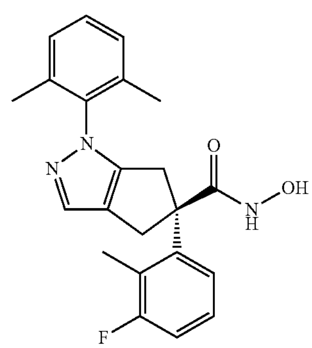 | 0.027 | 0.012 | >50 |
| 14 | 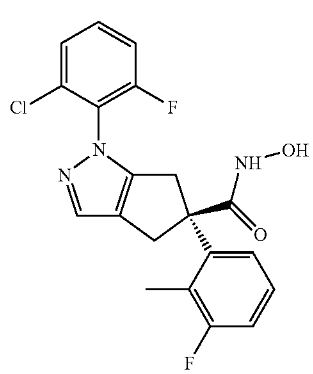 [SMILES: Cc1c(F)cccc1[C@]1(C(=O)NO)Cc2cnn(-c3c(F)cccc3Cl)c2C1] | 0.015 | 0.011 | >50 |

-continued

| Example | Structure | Biochemical IC$_{50}$ (μM) | Cell (Lys-TFA) IC$_{50}$ (μM) | Cell (Lys-Ac) IC$_{50}$ (μM) |
|---|---|---|---|---|
| 15 | 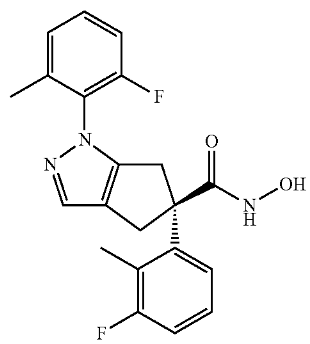 | 0.019 | 0.032 | >50 |
| 16 | 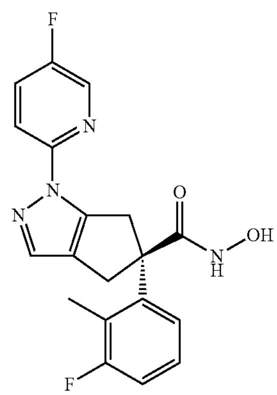 [SMILES: Cc1c(F)cccc1[C@]1(C(=O)NO)Cc2cnn(-c3ccc(F)cn3)c2C1] | 0.031 | 0.069 | >50 |
| 17 | 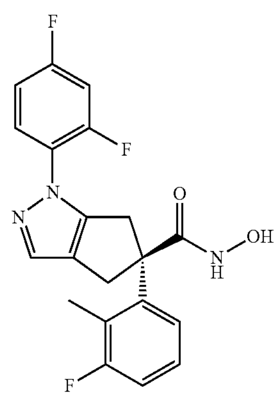 | 0.029 | 0.039 | >50 |
| 18 | 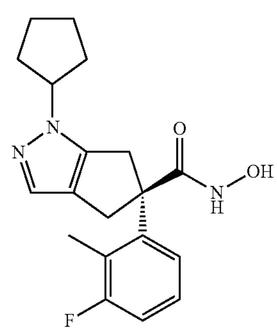 [SMILES: Cc1c(F)cccc1[C@]1(C(=O)NO)Cc2cnn(C3CCCC3)c2C1] | 0.037 | 0.163 | >50 |

-continued
| Example | Structure | Biochemical IC$_{50}$ (μM) | Cell (Lys-TFA) IC$_{50}$ (μM) | Cell (Lys-Ac) IC$_{50}$ (μM) |
| --- | --- | --- | --- | --- |
| 19 | 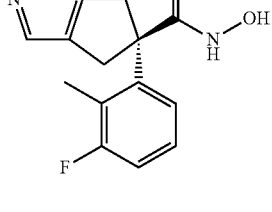 | 0.038 | 0.053 | >50 |
| 20 | 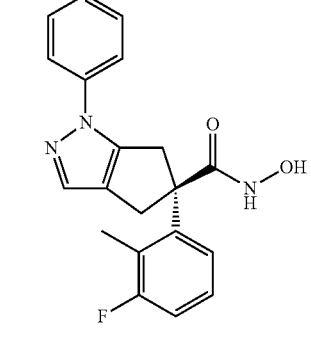 | 0.109 | 0.25 | >50 |
| 21 | 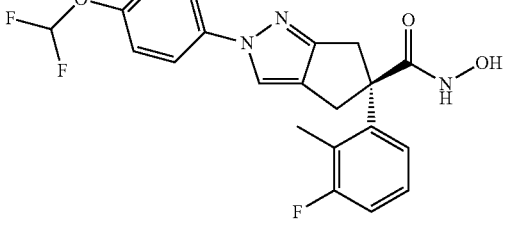 | 0.147 | 0.175 | >50 |
| 22 | 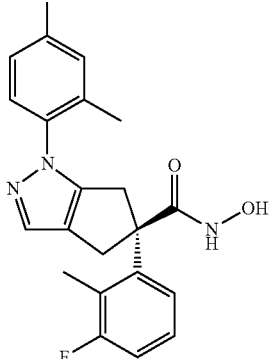 | 0.044 | 0.011 | >50 |

-continued

| Example | Structure | Biochemical IC$_{50}$ (μM) | Cell (Lys-TFA) IC$_{50}$ (μM) | Cell (Lys-Ac) IC$_{50}$ (μM) |
|---|---|---|---|---|
| 23 | 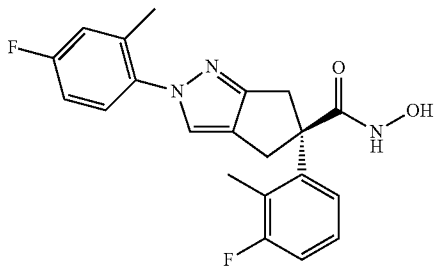 [SMILES: Cc1cc(F)ccc1-n1cc2c(n1)C[C@](C(=O)NO)(c1cccc(F)c1C)C2] | 0.197 | 0.134 | >50 |
| 24 | 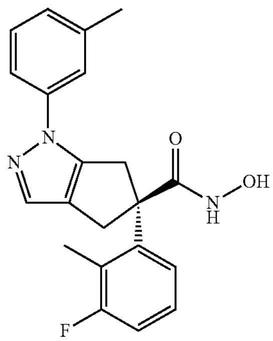 [SMILES: Cc1cccc(-n2ncc3c2C[C@](C(=O)NO)(c2cccc(F)c2C)C3)c1] | 0.028 | 0.064 | >50 |
| 25 | 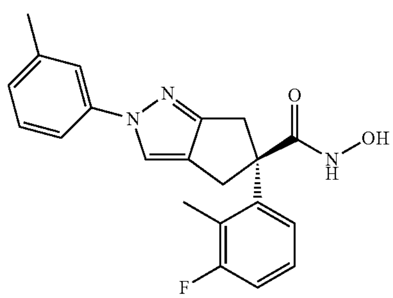 [SMILES: Cc1cccc(-n2cc3c(n2)C[C@](C(=O)NO)(c2cccc(F)c2C)C3)c1] | 0.076 | 0.160 | >50 |
| 26 | 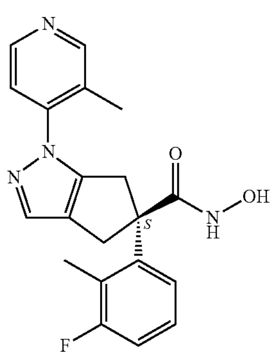 | 0.057 | 0.071 | >50 |
| 27 | 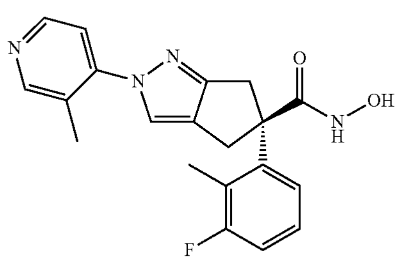 [SMILES: Cc1cnccc1-n1cc2c(n1)C[C@](C(=O)NO)(c1cccc(F)c1C)C2] | 0.053 | 0.116 | >50 |

-continued

| Example | Structure | Biochemical IC$_{50}$ (μM) | Cell (Lys-TFA) IC$_{50}$ (μM) | Cell (Lys-Ac) IC$_{50}$ (μM) |
| --- | --- | --- | --- | --- |
| 28 | 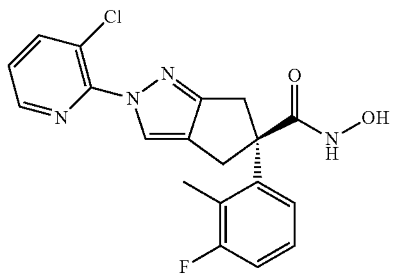 | 0.065 | 0.069 | >50 |
| 29 | 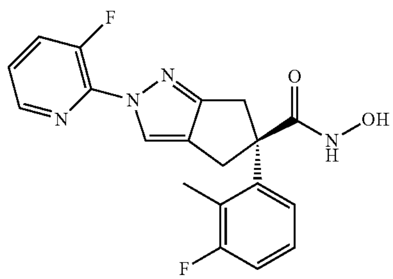 [SMILES: Cc1c(F)cccc1[C@]1(C(=O)NO)Cc2cn(-c3ncccc3F)nc2C1] | 0.104 | 0.069 | >50 |
| 30 | 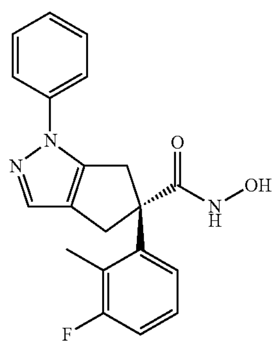 [SMILES: Cc1c(F)cccc1[C@@]1(C(=O)NO)Cc2cnn(-c3ccccc3)c2C1] | 1.0 | 1.7 | >50 |
| 31 | E1 | 0.82 | 0.072 | >50 |
| 32 | E2 | 17.3 | 2.9 | >50 |

-continued
| Example | Structure | Biochemical IC$_{50}$ (μM) | Cell (Lys-TFA) IC$_{50}$ (μM) | Cell (Lys-Ac) IC$_{50}$ (μM) |
| --- | --- | --- | --- | --- |
| 33 | 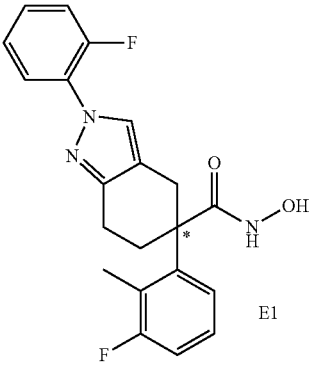 E1 | 0.71 | 0.41 | >50 |
| 34 | 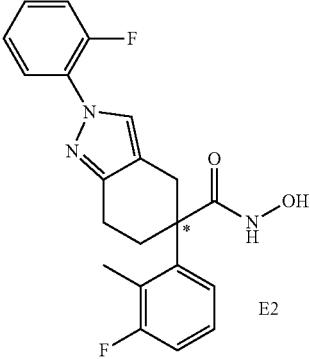 E2 | 19.8 | 26.7 | >50 |
| 35 | 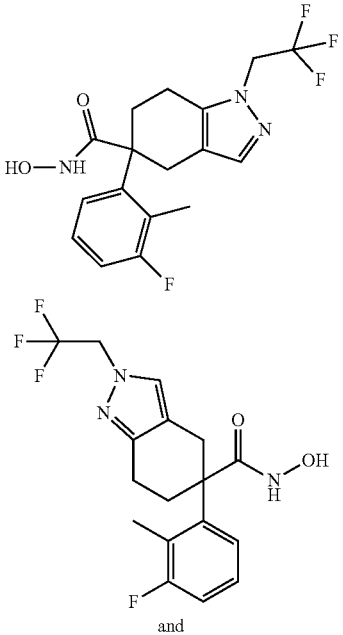 and | 1.7 | 0.77 | >50 |

-continued
| Example | Structure | Biochemical IC$_{50}$ (μM) | Cell (Lys-TFA) IC$_{50}$ (μM) | Cell (Lys-Ac) IC$_{50}$ (μM) |
|---|---|---|---|---|
| 36 | 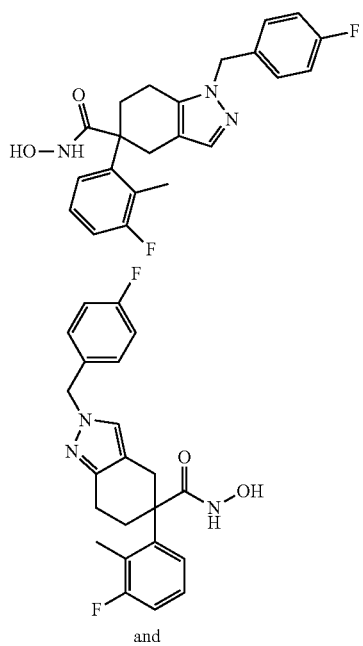 and | 0.60 | 0.37 | >50 |
| 37 | 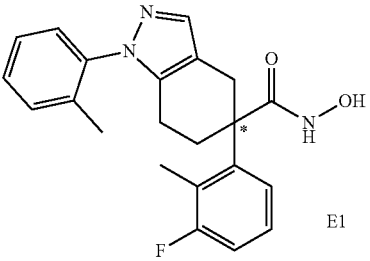 [SMILES: Cc1ccccc1-n1ncc2c1CCC(C(=O)NO)(c1cccc(F)c1C)C2] E1 | 1.1 | 0.086 | >50 |
| 38 | 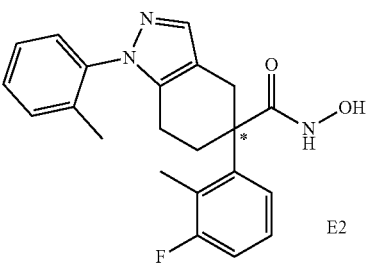 [SMILES: Cc1ccccc1-n1ncc2c1CCC(C(=O)NO)(c1cccc(F)c1C)C2] E2 | 7.9 | 11.2 | >50 |
| 39 | 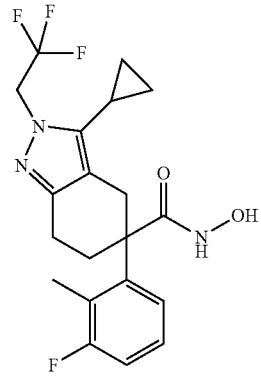 [SMILES: Cc1c(F)cccc1C1(C(=O)NO)CCc2nn(CC(F)(F)F)c(C3CC3)c2C1] | 4.4 | 1.8 | >50 |

-continued

| Example | Structure | Biochemical IC$_{50}$ (μM) | Cell (Lys-TFA) IC$_{50}$ (μM) | Cell (Lys-Ac) IC$_{50}$ (μM) |
|---|---|---|---|---|
| 40 | 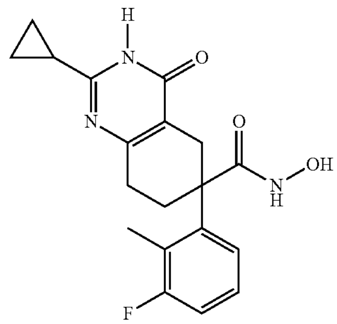 [SMILES: Cc1c(F)cccc1C1(C(=O)NO)CCc2nc(C3CC3)[nH]c(=O)c2C1] | 1.6 | 0.58 | >50 |
| 41 | 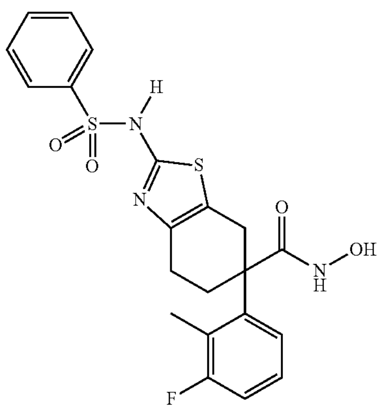 [SMILES: Cc1c(F)cccc1C1(C(=O)NO)CCc2nc(NS(=O)(=O)c3ccccc3)sc2C1] | 0.19 | 1.6 | >50 |
| 42 | 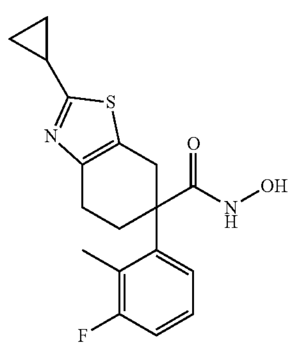 [SMILES: Cc1c(F)cccc1C1(C(=O)NO)CCc2nc(C3CC3)sc2C1] | 0.77 | 0.32 | >50 |
| 43 | 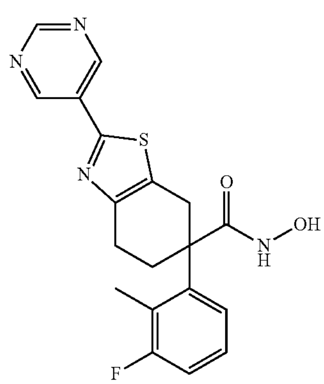 [SMILES: Cc1c(F)cccc1C1(C(=O)NO)CCc2nc(-c3cncnc3)sc2C1] | 1.9 | 0.66 | >50 |

-continued
| Example | Structure | Biochemical IC$_{50}$ (μM) | Cell (Lys-TFA) IC$_{50}$ (μM) | Cell (Lys-Ac) IC$_{50}$ (μM) |
|---|---|---|---|---|
| 44 | 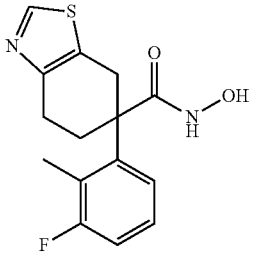 | 1.0 | 1.5 | >50 |
| 45 | 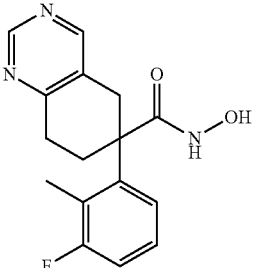 | 3.7 | 2.6 | >50 |
| 46 | 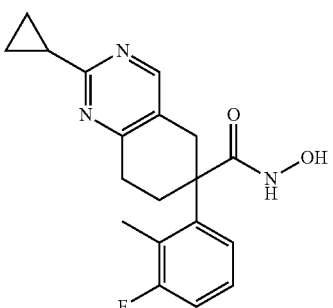 | 1.6 | 0.76 | >50 |
| 47 | 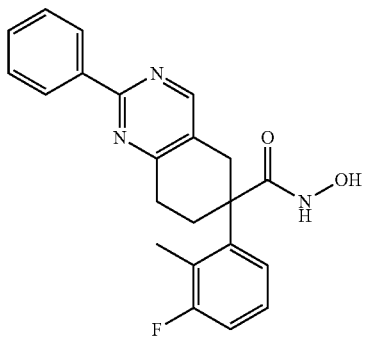 [SMILES: Cc1c(F)cccc1C1(C(=O)NO)CCc2nc(-c3ccccc3)ncc2C1] | 3.2 | 1.1 | >50 |
| 48 | 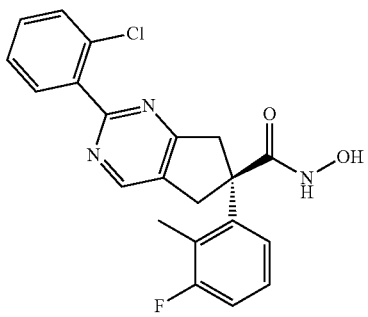 [SMILES: Cc1c(F)cccc1[C@]1(C(=O)NO)Cc2cnc(-c3ccccc3Cl)nc2C1] | 0.156 | 0.060 | >50 |

-continued

| Example | Structure | Biochemical IC$_{50}$ (μM) | Cell (Lys-TFA) IC$_{50}$ (μM) | Cell (Lys-Ac) IC$_{50}$ (μM) |
|---|---|---|---|---|
| 49 | 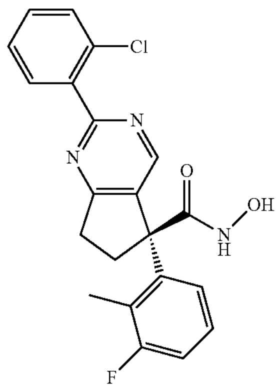 [SMILES: Cc1c(F)cccc1[C@]1(C(=O)NO)CCc2nc(-c3ccccc3Cl)ncc21] | 0.102 | 0.25 | >50 |
| 50 | 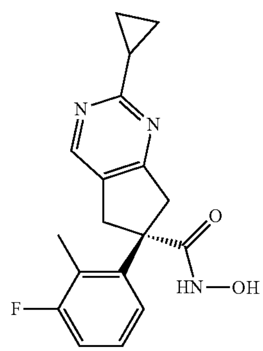 [SMILES: Cc1c(F)cccc1[C@@]1(C(=O)NO)Cc2cnc(C3CC3)nc2C1] | 0.22 | 0.12 | >50 |
| 51 | 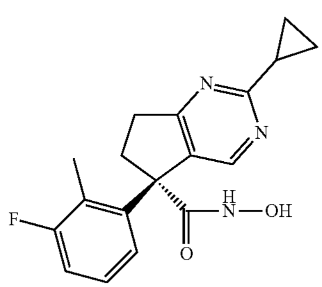 [SMILES: Cc1c(F)cccc1[C@@]1(C(=O)NO)CCc2nc(C3CC3)ncc21] | 0.27 | 1.4 | >50 |
| 52 | 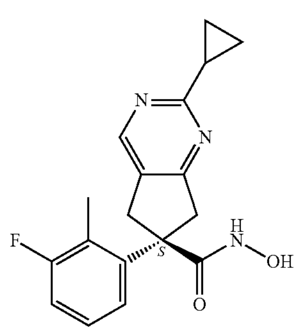 | 0.16 | 0.21 | >50 |

-continued
| Example | Structure | Biochemical IC$_{50}$ (μM) | Cell (Lys-TFA) IC$_{50}$ (μM) | Cell (Lys-Ac) IC$_{50}$ (μM) |
| --- | --- | --- | --- | --- |
| 53 | 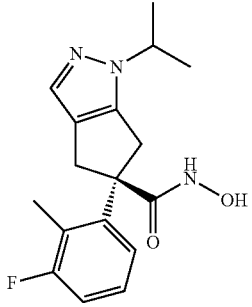 [SMILES: Cc1c(F)cccc1[C@]1(C(=O)NO)Cc2cnn(C(C)C)c2C1] | 0.067 | 0.23 | >50 |
| 54 | 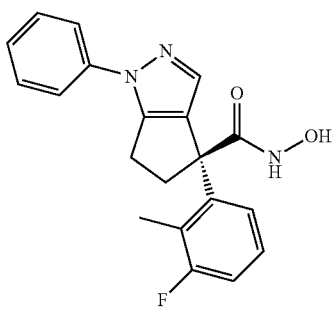 [SMILES: Cc1c(F)cccc1[C@]1(C(=O)NO)CCc2c1cnn2-c1ccccc1] | 0.072 | 0.32 | >50 |
| 55 | 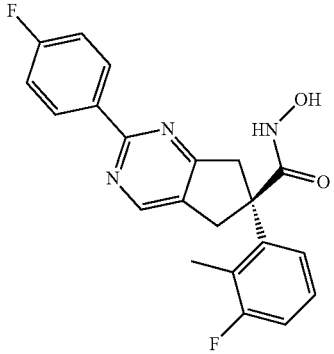 [SMILES: Cc1c(F)cccc1[C@]1(C(=O)NO)Cc2cnc(-c3ccc(F)cc3)nc2C1] | 0.29 | 0.26 | >50 |
| 56 | 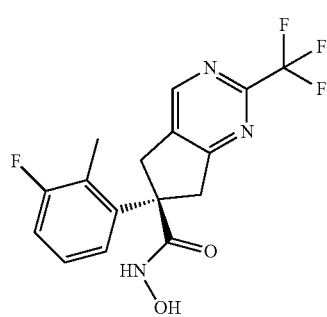 [SMILES: Cc1c(F)cccc1[C@]1(C(=O)NO)Cc2cnc(C(F)(F)F)nc2C1] | 0.88 | 1.8 | >50 |

| Example | Structure | Biochemical IC$_{50}$ (μM) | Cell (Lys-TFA) IC$_{50}$ (μM) | Cell (Lys-Ac) IC$_{50}$ (μM) |
| --- | --- | --- | --- | --- |
| 57 | 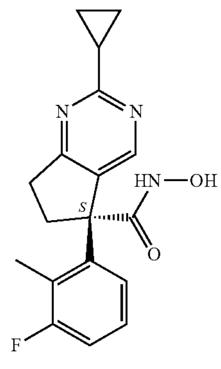 | 19.4 | >50 | >50 |
| 58 | 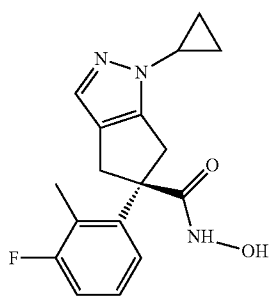 [SMILES: Cc1c(F)cccc1[C@]1(C(=O)NO)Cc2cnn(C3CC3)c2C1] | 0.048 | 0.125 | >50 |
| 59 | 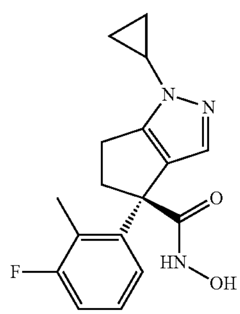 [SMILES: Cc1c(F)cccc1[C@]1(C(=O)NO)CCc2c1cnn2C1CC1] | 0.100 | 0.72 | >50 |
| 60 | 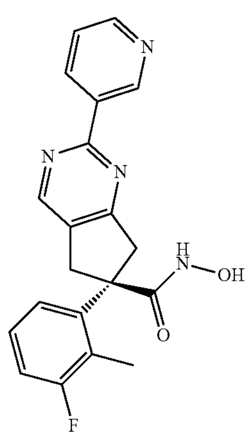 [SMILES: Cc1c(F)cccc1[C@]1(C(=O)NO)Cc2cnc(-c3cccnc3)nc2C1] | 0.22 | 0.20 | >50 |

-continued

| Example | Structure | Biochemical IC$_{50}$ (μM) | Cell (Lys-TFA) IC$_{50}$ (μM) | Cell (Lys-Ac) IC$_{50}$ (μM) |
|---------|-----------|---------------------------|-------------------------------|-------------------------------|
| 61 | 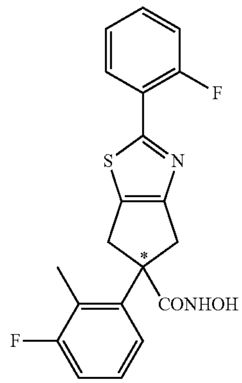 | 0.48 | 0.12 | >50 |
| 62 | 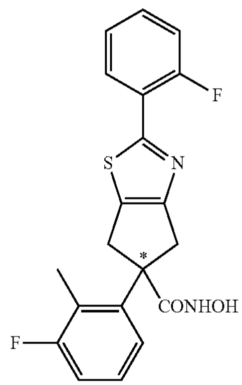 | 0.193 | 0.049 | >50 |
| 63 | 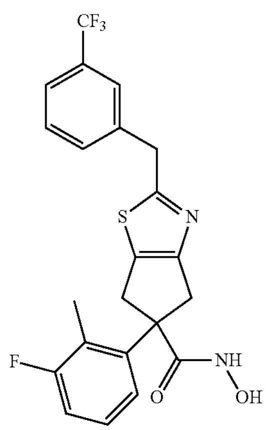 [SMILES: Cc1c(F)cccc1C1(C(=O)NO)Cc2nc(Cc3cccc(C(F)(F)F)c3)sc2C1] | 0.49 | 0.038 | >50 |
| 64 | 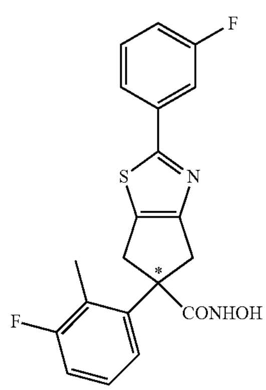 | 0.21 | 0.11 | >50 |

-continued

| Example | Structure | Biochemical IC$_{50}$ (μM) | Cell (Lys-TFA) IC$_{50}$ (μM) | Cell (Lys-Ac) IC$_{50}$ (μM) |
|---|---|---|---|---|
| 65 | 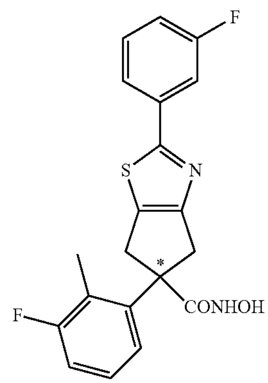 | 0.53 | 0.22 | >50 |
| 66 | 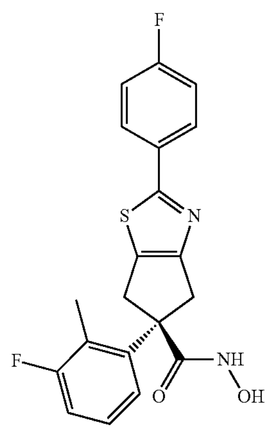 [SMILES: Cc1c(F)cccc1[C@@]1(C(=O)NO)Cc2nc(-c3ccc(F)cc3)sc2C1] | 0.081 | 0.098 | >50 |
| 67 | 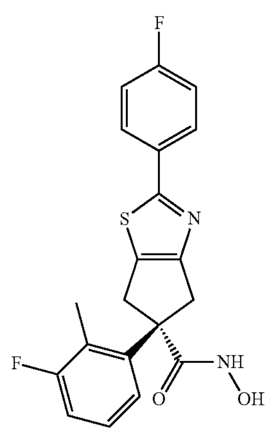 [SMILES: Cc1c(F)cccc1[C@]1(C(=O)NO)Cc2nc(-c3ccc(F)cc3)sc2C1] | 0.193 | 0.29 | >50 |
| 68 | 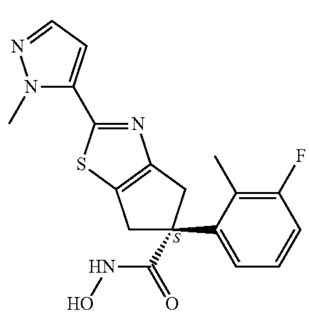 | 0.24 | 0.12 | >50 |

-continued

| Example | Structure | Biochemical IC$_{50}$ (μM) | Cell (Lys-TFA) IC$_{50}$ (μM) | Cell (Lys-Ac) IC$_{50}$ (μM) |
|---|---|---|---|---|
| 69 | 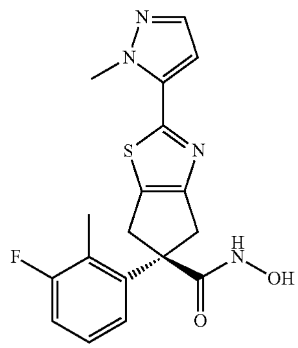 [SMILES: Cc1c(F)cccc1[C@@]1(C(=O)NO)Cc2nc(-c3ccnn3C)sc2C1] | 0.044 | 0.035 | >50 |
| 70 | 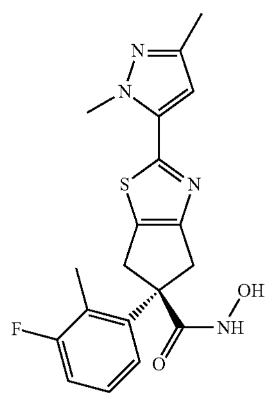 [SMILES: Cc1cc(-c2nc3c(s2)C[C@@](C(=O)NO)(c2cccc(F)c2C)C3)n(C)n1] | 0.122 | 0.079 | >50 |
| 71 | 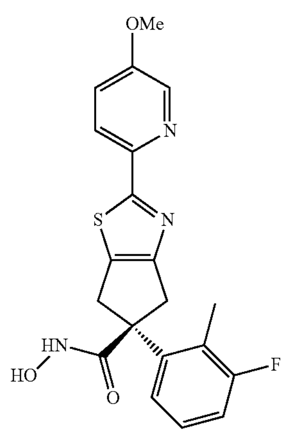 [SMILES: COc1ccc(-c2nc3c(s2)C[C@@](C(=O)NO)(c2cccc(F)c2C)C3)nc1] | 0.095 | 0.056 | >50 |
| 72 | 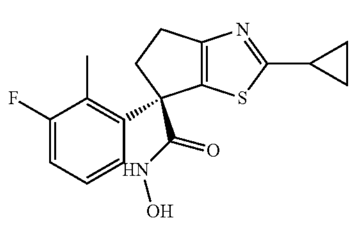 [SMILES: Cc1c(F)cccc1[C@]1(C(=O)NO)CCc2nc(C3CC3)sc21] | 0.094 | 0.79 | >50 |

-continued

| Example | Structure | Biochemical IC$_{50}$ (μM) | Cell (Lys-TFA) IC$_{50}$ (μM) | Cell (Lys-Ac) IC$_{50}$ (μM) |
|---------|-----------|---------------------------|-------------------------------|-------------------------------|
| 73 | 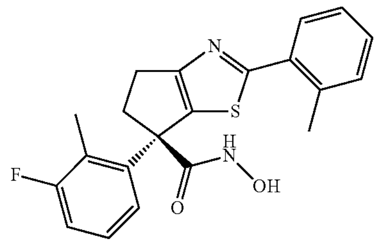 [SMILES: Cc1ccccc1-c1nc2c(s1)[C@](C(=O)NO)(c1cccc(F)c1C)CC2] | 0.143 | 0.63 | >50 |
| 74 | E1 | 0.78 | 0.54 | >50 |
| 75 | E2 | 0.27 | 0.051 | >50 |
| 76 | E1 | 0.068 | 0.036 | >50 |

| Example | Structure | Biochemical IC$_{50}$ (μM) | Cell (Lys-TFA) IC$_{50}$ (μM) | Cell (Lys-Ac) IC$_{50}$ (μM) |
|---|---|---|---|---|
| 77 | 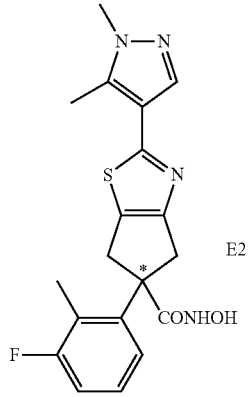 E2 | 0.20 | 0.128 | >50 |
| 78 | 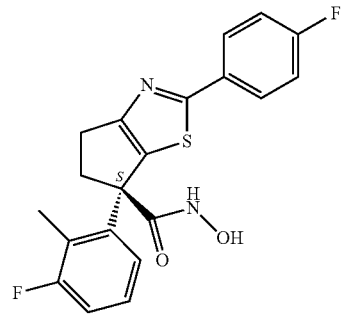 | 0.12 | 0.50 | >50 |
| 79 | 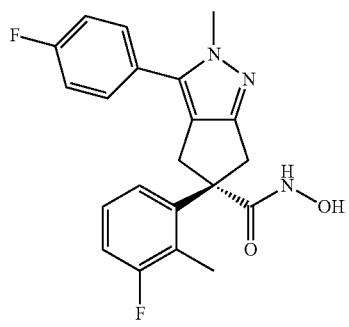 | 0.053 | 0.026 | 36.5 |
| 80 | 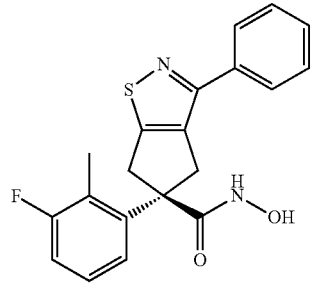 | 0.079 | 0.045 | >50 |

-continued

| Example | Structure | Biochemical IC$_{50}$ (μM) | Cell (Lys-TFA) IC$_{50}$ (μM) | Cell (Lys-Ac) IC$_{50}$ (μM) |
|---|---|---|---|---|
| 81 | 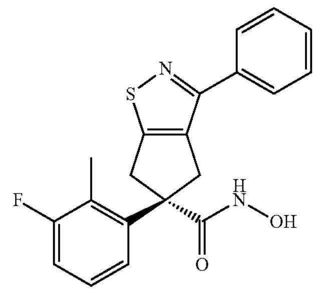 [SMILES: Cc1c(F)cccc1[C@@]1(C(=O)NO)Cc2snc(-c3ccccc3)c2C1] | 9.7 | 5.6 | >50 |
| 82 | 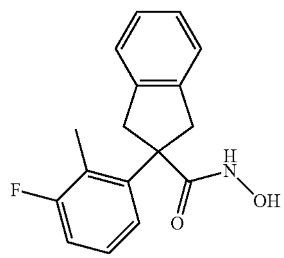 [SMILES: Cc1c(F)cccc1C1(C(=O)NO)Cc2ccccc2C1] | 0.11 | 1.8 | >50 |
| 83 | 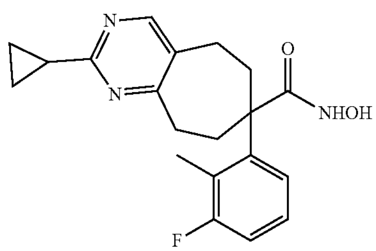 | 1.3 | 0.49 | >50 |
| 84 (E1) | | 0.48 | 1.4 | >50 |
| 85 (E2) | | 0.79 | 1.8 | >50 |

-continued

| Example | Structure | Biochemical IC$_{50}$ (μM) | Cell (Lys-TFA) IC$_{50}$ (μM) | Cell (Lys-Ac) IC$_{50}$ (μM) |
|---|---|---|---|---|
| 86 | 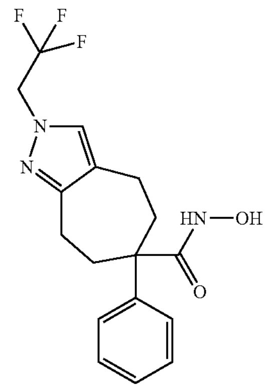 [SMILES: O=C(NO)C1(c2ccccc2)CCc2cn(CC(F)(F)F)nc2CC1] | 8.2 | 46.7 | >50 |
| 87 | E1 | 5.67 | 45.7 | >50 |
| 88 | E2 | >50 | >50 | >50 |
| 89 | 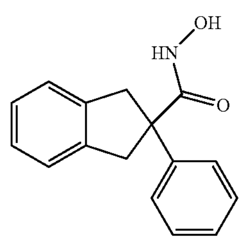 [SMILES: O=C(NO)C1(c2ccccc2)Cc2ccccc2C1] | 15.3 | >50 | >50 |
| 96 | 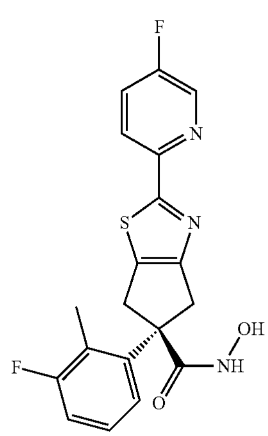 [SMILES: Cc1c(F)cccc1[C@@]1(C(=O)NO)Cc2nc(-c3ccc(F)cn3)sc2C1] | 0.051 | 0.060 | >50 |

-continued

| Example | Structure | Biochemical IC$_{50}$ (μM) | Cell (Lys-TFA) IC$_{50}$ (μM) | Cell (Lys-Ac) IC$_{50}$ (μM) |
|---|---|---|---|---|
| 90 | 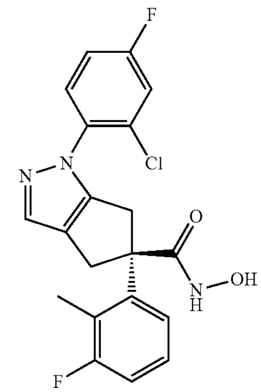 [SMILES: Cc1c(F)cccc1[C@]1(C(=O)NO)Cc2cnn(-c3ccc(F)cc3Cl)c2C1] | 0.036 | 0.015 | >50 |
| 91 | 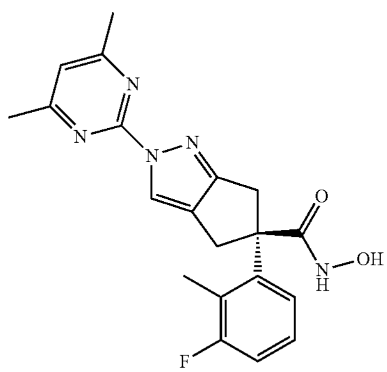 [SMILES: Cc1cc(C)nc(-n2cc3c(n2)C[C@](C(=O)NO)(c2cccc(F)c2C)C3)n1] | 0.28 | 0.46 | >50 |
| 92 | 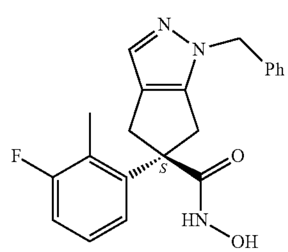 | 0.048 | 0.027 | >50 |
| 93 | 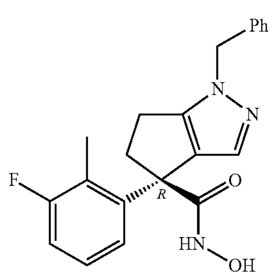 | 0.027 | 0.17 | >50 |
| 94 | 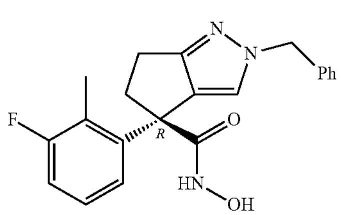 | 0.82 | 2.78 | >50 |

-continued

| Example | Structure | Biochemical IC$_{50}$ (µM) | Cell (Lys-TFA) IC$_{50}$ (µM) | Cell (Lys-Ac) IC$_{50}$ (µM) |
|---|---|---|---|---|
| 95 | 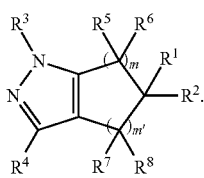 | 0.71 | 2.98 | >50 |

While some embodiments have been shown and described, various modifications and substitutions may be made thereto without departing from the spirit and scope of the invention. For example, for claim construction purposes, it is not intended that the claims set forth hereinafter be construed in any way narrower than the literal language thereof, and it is thus not intended that exemplary embodiments from the specification be read into the claims. Accordingly, it is to be understood that the present invention has been described by way of illustration and not limitations on the scope of the claims.

What is claimed is:

1. A compound of Formula I:

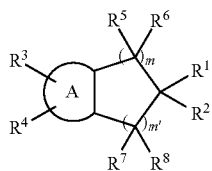

Formula I or a pharmaceutically acceptable salt thereof,
wherein:
$R^1$ is —C(O)NH(OH) or —N(OH)C(O)R$^9$;
$R^2$ is aryl, heteroaryl, or heterocycloalkyl, each of which is optionally substituted with 1 to 3 substituents independently chosen from halo, alkyl, cycloalkyl, haloalkyl, hydroxyl, alkoxy, and nitrile;
A is aryl or heteroaryl;
$R^3$ and $R^4$ are independently chosen from hydrogen, alkyl, halo, —NHSO$_2$R$^{10}$, C(O)NR$^{11}$R$^{12}$, NR$^{11}$R$^{12}$, nitrile, cycloalkyl, heterocycloalkyl, aryl, heteroaryl, aralkyl, and heteroaralkyl, each of which is optionally substituted with 1 to 3 substituents independently chosen from halo, alkyl, cycloalkyl, haloalkyl, hydroxyl, alkoxy, haloalkoxy, aryl, heteroaryl, and nitrile, wherein alkyl and alkoxy are optionally substituted with amino, (alkyl)amino or di(alkyl)amino;
for each occurrence, $R^5$, $R^6$, $R^7$, and $R^8$ are independently chosen from hydrogen and lower alkyl;
$R^9$ is hydrogen or lower alkyl;
$R^{10}$ is lower alkyl, cycloalkyl, heterocycloalkyl, aryl, or heteroaryl;
$R^{11}$ and $R^{12}$ are independently chosen from hydrogen, lower alkyl, alkoxy, lower haloalkyl and cycloalkyl, wherein alkyl and alkoxy are optionally substituted with amino, (alkyl)amino or di(alkyl)amino, and
m and m' are independently chosen from 0, 1, 2, 3 and 4, provided that 2≤(m+m')≤4.

2. The compound of claim 1, or a pharmaceutically acceptable salt thereof, wherein the compound of Formula I is a compound of Formula II:

Formula II

3. The compound of claim 2, or a pharmaceutically acceptable salt thereof, wherein $R^3$ is phenyl optionally substituted with one or two substituents independently chosen from alkyl, haloalkyl, alkoxy, haloalkoxy, and halo.

4. The compound of claim 3, or a pharmaceutically acceptable salt thereof, wherein $R^3$ is phenyl, 2-methylphenyl, 3-methylphenyl, 4-methylphenyl, 2-fluorophenyl, 3-fluorophenyl, 4-fluorophenyl, 2-chlorophenyl, 3-chlorophenyl, 4-chlorophenyl, 3-chloro-2-fluorophenyl, 2,6-difluorophenyl, 2,5-dimethylphenyl, 2,6-dimethylphenyl, 2-chloro-6-fluorophenyl, 2-fluoro-6-methylphenyl, 2,4-difluorophenyl, 4-(difluoromethoxy)phenyl, or 3-fluoro-2-methylphenyl.

5. The compound of claim 2, or a pharmaceutically acceptable salt thereof, wherein $R^3$ is pyridin-2-yl, pyridin-4-yl, or pyrazin-2-yl, each of which is optionally substituted with one or two substituents independently chosen from alkyl and halo.

6. The compound of claim 5, or a pharmaceutically acceptable salt thereof, wherein $R^3$ is 5-fluoropyridin-2-yl, pyrazin-2-yl, or 3-methylpyridin-4-yl.

7. The compound of claim 2, or a pharmaceutically acceptable salt thereof, wherein $R^3$ is cyclopropyl or cyclopentyl, each of which is optionally substituted with one or two substituents independently chosen from alkyl and halo.

8. The compound of claim 7, or a pharmaceutically acceptable salt thereof, wherein $R^3$ is cyclopropyl or cyclopentyl.

9. The compound of claim 2, or a pharmaceutically acceptable salt thereof, wherein $R^3$ is isopropyl.

10. The compound of claim 2, or a pharmaceutically acceptable salt thereof, wherein $R^4$ is hydrogen.

11. The compound of claim 1, or a pharmaceutically acceptable salt thereof, wherein the compound of Formula I is a compound of Formula III:

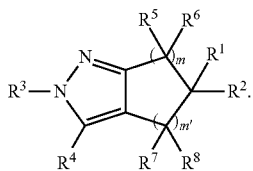

Formula III

12. The compound of claim 11, or a pharmaceutically acceptable salt thereof, wherein $R^3$ is alkyl, haloalkyl, or aralkyl optionally substituted with halo.

13. The compound of claim 12, or a pharmaceutically acceptable salt thereof, wherein $R^3$ is methyl, 2,2,2,-trifluoroethyl, or 4-fluorobenzyl.

14. The compound of claim 11, or a pharmaceutically acceptable salt thereof, wherein $R^3$ is phenyl optionally substituted with one or two substituents independently chosen from alkyl, haloalkyl, alkoxy, haloalkoxy, and halo.

15. The compound of claim 14 or a pharmaceutically acceptable salt thereof, wherein $R^3$ is 2-fluorophenyl, 4-(difluoromethoxy)phenyl, 4-fluoro-2-methylphenyl, or 3-methylphenyl.

16. The compound of claim 11, or a pharmaceutically acceptable salt thereof, wherein $R^3$ is pyridin-2-yl or pyridin-4-yl, each of which is optionally substituted with one or two substituents independently chosen from alkyl and halo.

17. The compound of claim 16, or a pharmaceutically acceptable salt thereof, wherein $R^3$ is 3-methylpyridin-4-yl, 3-chloropyridin-2-yl, or 3-fluoropyridin-2-yl.

18. The compound of claim 11, or a pharmaceutically acceptable salt thereof, wherein $R^4$ is hydrogen, cyclopropyl, or phenyl optionally substituted with halo.

19. The compound of claim 18, or a pharmaceutically acceptable salt thereof, wherein $R^4$ is hydrogen.

20. A compound of Formula I is a compound of Formula IV:

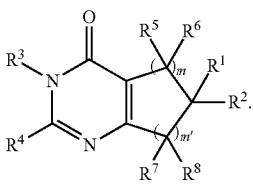

Formula IV or a pharmaceutically acceptable salt thereof, wherein:
$R^1$ is —C(O)NH(OH) or —N(OH)C(O)R$^9$;
$R^2$ is aryl, heteroaryl, or heterocycloalkyl, each of which is optionally substituted with 1 to 3 substituents independently chosen from halo, alkyl, cycloalkyl, haloalkyl, hydroxyl, alkoxy, and nitrile;
$R^3$ and $R^4$ are independently chosen from hydrogen, alkyl, halo, —NHSO$_2$R$^{10}$, C(O)NR$^{11}$R$^{12}$, NR$^{11}$R$^{12}$, nitrile, cycloalkyl, heterocycloalkyl, aryl, heteroaryl, aralkyl, and heteroaralkyl, each of which is optionally substituted with 1 to 3 substituents independently chosen from halo, alkyl, cycloalkyl, haloalkyl, hydroxyl, alkoxy, haloalkoxy, aryl, heteroaryl, and nitrile, wherein alkyl and alkoxy are optionally substituted with amino, (alkyl)amino or di(alkyl)amino;
for each occurrence, $R^5$, $R^6$, $R^7$, and $R^8$ are independently chosen from hydrogen and lower alkyl;
$R^9$ is hydrogen or lower alkyl;
$R^{10}$ is lower alkyl, cycloalkyl, heterocycloalkyl, aryl, or heteroaryl;
$R^{11}$ and $R^{12}$ are independently chosen from hydrogen, lower alkyl, alkoxy, lower haloalkyl and cycloalkyl, wherein alkyl and alkoxy are optionally substituted with amino, (alkyl)amino or di(alkyl)amino, and
m and m' are independently chosen from 0, 1, 2, 3 and 4, provided that 2≤(m+m')≤4.

21. The compound of claim 20, or a pharmaceutically acceptable salt thereof, wherein $R^3$ is hydrogen.

22. The compound of claim 20, or a pharmaceutically acceptable salt thereof, wherein $R^4$ is cyclopropyl.

23. A compound of Formula I is a compound of Formula V:

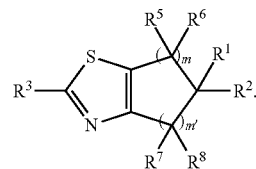

Formula V or a pharmaceutically acceptable salt thereof, wherein:
$R^1$ is —C(O)NH(OH) or —N(OH)C(O)R$^9$;
$R^2$ is aryl, heteroaryl, or heterocycloalkyl, each of which is optionally substituted with 1 to 3 substituents independently chosen from halo, alkyl, cycloalkyl, haloalkyl, hydroxyl, alkoxy, and nitrile;
$R^3$ is hydrogen, alkyl, halo, —NHSO$_2$R$^{10}$, C(O)NR$^{11}$R$^{12}$, NR$^{11}$R$^{12}$, nitrile, cycloalkyl, heterocycloalkyl, aryl, heteroaryl, aralkyl, or heteroaralkyl, each of which is optionally substituted with 1 to 3 substituents independently chosen from halo, alkyl, cycloalkyl, haloalkyl, hydroxyl, alkoxy, haloalkoxy, aryl, heteroaryl, and nitrile, wherein alkyl and alkoxy are optionally substituted with amino, (alkyl)amino or di(alkyl)amino;
for each occurrence, $R^5$, $R^6$, $R^7$, and $R^8$ are independently chosen from hydrogen and lower alkyl;
$R^9$ is hydrogen or lower alkyl;
$R^{10}$ is lower alkyl, cycloalkyl, heterocycloalkyl, aryl, or heteroaryl;
$R^{11}$ and $R^{12}$ are independently chosen from hydrogen, lower alkyl, alkoxy, lower haloalkyl and cycloalkyl, wherein alkyl and alkoxy are optionally substituted with amino, (alkyl)amino or di(alkyl)amino, and
m and m' are independently chosen from 0, 1, 2, 3 and 4, provided that 2≤(m+m')≤4.

24. The compound of claim 23, or a pharmaceutically acceptable salt thereof, wherein R³ is:
hydrogen,
cycloalkyl optionally substituted with one or two groups independently chosen from halo, alkyl, haloalkyl, and alkoxy,
heteroaryl optionally substituted with one or two groups independently chosen from halo, alkyl, haloalkyl, and alkoxy,
phenyl optionally substituted with one or two groups independently chosen from halo, alkyl, haloalkyl, and alkoxy,
benzyl optionally substituted on the aromatic portion with one or two groups independently chosen from halo, alkyl, haloalkyl, and alkoxy, or
—NHS(O)₂R¹⁰, where R¹⁰ is phenyl.

25. The compound of claim 24, or a pharmaceutically acceptable salt thereof, wherein R³ is hydrogen, cyclopropyl, phenyl optionally substituted with one or two groups independently chosen from fluoro and methyl, pyrimidin-5-yl, 1H-pyrazol-5-yl optionally substituted with methyl, 1H-pyrazol-4-yl optionally substituted with methyl, pyridin-2-yl optionally substituted with methoxy, benzyl optionally substituted on the aromatic portion with trifluoromethyl, or —NHS(O)₂R¹⁰, where R¹⁰ is phenyl.

26. The compound of claim 1, or a pharmaceutically acceptable salt thereof, wherein the compound of Formula I is a compound of Formula VI:

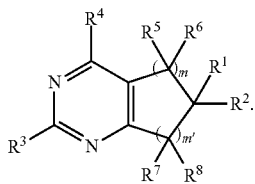

Formula VI

27. The compound of claim 26, or a pharmaceutically acceptable salt thereof, wherein R³ is hydrogen, alkyl, haloalkyl, cycloalkyl, phenyl optionally substituted with halo, or heteroaryl.

28. The compound of claim 27, or a pharmaceutically acceptable salt thereof, wherein R³ is hydrogen, trifluoromethyl, cyclopropyl, phenyl optionally substituted with halo, or pyridin-3-yl.

29. The compound of claim 26, or a pharmaceutically acceptable salt thereof, wherein R⁴ is hydrogen.

30. The compound of claim 1, or a pharmaceutically acceptable salt thereof, wherein the compound of Formula I is a compound of Formula VII:

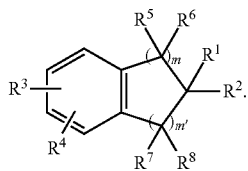

Formula VII

31. The compound of claim 30, or a pharmaceutically acceptable salt thereof, wherein R³ is hydrogen.

32. The compound of claim 30, or a pharmaceutically acceptable salt thereof, wherein R⁴ is hydrogen.

33. A compound of Formula I is a compound of Formula VIII:

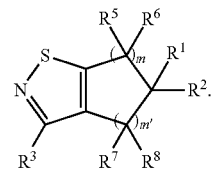

Formula VIII or a pharmaceutically acceptable salt thereof, wherein:
R¹ is —C(O)NH(OH) or —N(OH)C(O)R⁹;
R² is aryl, heteroaryl, or heterocycloalkyl, each of which is optionally substituted with 1 to 3 substituents independently chosen from halo, alkyl, cycloalkyl, haloalkyl, hydroxyl, alkoxy, and nitrile;
R³ is hydrogen, alkyl, halo, —NHSO₂R¹⁰, C(O)NR¹¹R¹², NR¹¹R¹², nitrile, cycloalkyl, heterocycloalkyl, aryl, heteroaryl, aralkyl, or heteroaralkyl, each of which is optionally substituted with 1 to 3 substituents independently chosen from halo, alkyl, cycloalkyl, haloalkyl, hydroxyl, alkoxy, haloalkoxy, aryl, heteroaryl, and nitrile, wherein alkyl and alkoxy are optionally substituted with amino, (alkyl)amino or di(alkyl)amino;
for each occurrence, R⁵, R⁶, R⁷, and R⁸ are independently chosen from hydrogen and lower alkyl;
R⁹ is hydrogen or lower alkyl;
R¹⁰ is lower alkyl, cycloalkyl, heterocycloalkyl, aryl, or heteroaryl;
R¹¹ and R¹² are independently chosen from hydrogen, lower alkyl, alkoxy, lower haloalkyl and cycloalkyl, wherein alkyl and alkoxy are optionally substituted with amino, (alkyl)amino or di(alkyl)amino, and
m and m' are independently chosen from 0, 1, 2, 3 and 4, provided that 2 ≤(m+m')≤4.

34. The compound of claim 33, or a pharmaceutically acceptable salt thereof, wherein R³ is phenyl optionally substituted with 1 to 3 substituents independently chosen from halo, alkyl, cycloalkyl, haloalkyl, hydroxyl, and alkoxy.

35. The compound of claim 34, or a pharmaceutically acceptable salt thereof, wherein R³ is phenyl.

36. The compound of claim 1, or a pharmaceutically acceptable salt thereof, wherein R² is aryl optionally substituted with 1 to 3 substituents independently chosen from halo, alkyl, cycloalkyl, haloalkyl, hydroxyl, alkoxy, and nitrile.

37. The compound of claim 36, or a pharmaceutically acceptable salt thereof, wherein R² is phenyl optionally substituted with 1 to 3 substituents independently chosen from halo, alkyl, cycloalkyl, haloalkyl, hydroxyl, alkoxy, and nitrile.

38. The compound of claim 37, or a pharmaceutically acceptable salt thereof, wherein R² is phenyl optionally substituted with 1 to 3 substituents independently chosen from halo and alkyl.

39. The compound of claim 38, or a pharmaceutically acceptable salt thereof, wherein R² is phenyl and 3-fluoro-2-methylphenyl.

40. The compound of claim 39, or a pharmaceutically acceptable salt thereof, wherein R² is 3-fluoro-2-methylphenyl.

41. The compound of claim 1, or a pharmaceutically acceptable salt thereof, wherein m is 1 and m' is 1.

42. The compound of claim 1, or a pharmaceutically acceptable salt thereof, wherein m is 1 and m' is 2.

43. The compound of claim 1, or a pharmaceutically acceptable salt thereof, wherein m is 0 and m' is 2.

44. The compound of claim 1, or a pharmaceutically acceptable salt thereof, wherein m is 2 and m' is 2.

45. The compound of claim 1, or a pharmaceutically acceptable salt thereof, wherein $R^1$ is —N(OH)C(O)$R^9$.

46. The compound of claim 45, or a pharmaceutically acceptable salt thereof, wherein $R^9$ is lower alkyl.

47. The compound of claim 1, or a pharmaceutically acceptable salt thereof, wherein $R^1$ is —C(O)NH(OH).

48. The compound of claim 1, or a pharmaceutically acceptable salt thereof, wherein, for each occurrence, $R^5$, $R^6$, $R^7$, and $R^8$ are hydrogen.

49. A compound, or a pharmaceutically acceptable salt thereof, selected from:
- (S)-5-(3-Fluoro-2-methylphenyl)-N-hydroxy-1-phenyl-1,4,5,6-tetrahydrocyclopenta[c]pyrazole-5-carboxamide;
- (S)-5-(3-Fluoro-2-methylphenyl)-N-hydroxy-1-(o-tolyl)-1,4,5,6-tetrahydrocyclopenta[c]pyrazole-5-carboxamide;
- (S)-5-(3-Fluoro-2-methylphenyl)-1-(2-fluorophenyl)-N-hydroxy-1,4,5,6-tetrahydrocyclopenta[c]pyrazole-5-carboxamide;
- (S)-1-(3-Chlorophenyl)-5-(3-fluoro-2-methylphenyl)-N-hydroxy-1,4,5,6-tetrahydrocyclopenta[c]pyrazole-5-carboxamide;
- (S)-5-(3-Fluoro-2-methylphenyl)-1-(4-fluorophenyl)-N-hydroxy-1,4,5,6-tetrahydrocyclopenta[c]pyrazole-5-carboxamide;
- (S)-5-(3-Fluoro-2-methylphenyl)-1-(3-fluorophenyl)-N-hydroxy-1,4,5,6-tetrahydrocyclopenta[c]pyrazole-5-carboxamide;
- (S)-1-(2-Chlorophenyl)-5-(3-fluoro-2-methylphenyl)-N-hydroxy-1,4,5,6-tetrahydrocyclopenta[c]pyrazole-5-carboxamide;
- (S)-1-(4-Chlorophenyl)-5-(3-fluoro-2-methylphenyl)-N-hydroxy-1,4,5,6-tetrahydrocyclopenta[c]pyrazole-5-carboxamide;
- (S)-5-(3-Fluoro-2-methylphenyl)-N-hydroxy-1-(p-tolyl)-1,4,5,6-tetrahydrocyclopenta[c]pyrazole-5-carboxamide;
- (S)-1-(3-Chloro-2-fluorophenyl)-5-(3-fluoro-2-methylphenyl)-N-hydroxy-1,4,5,6-tetrahydrocyclopenta[c]pyrazole-5-carboxamide;
- (S)-1-(2,6-Difluorophenyl)-5-(3-fluoro-2-methylphenyl)-N-hydroxy-1,4,5,6-tetrahydrocyclopenta[c]pyrazole-5-carboxamide;
- (S)-1-(2,5-Dimethylphenyl)-5-(3-fluoro-2-methylphenyl)-N-hydroxy-1,4,5,6-tetrahydrocyclopenta[c]pyrazole-5-carboxamide;
- (S)-1-(2,6-Dimethylphenyl)-5-(3-fluoro-2-methylphenyl)-N-hydroxy-1,4,5,6-tetrahydrocyclopenta[c]pyrazole-5-carboxamide;
- (S)-1-(2-Chloro-6-fluorophenyl)-5-(3-fluoro-2-methylphenyl)-N-hydroxy-1,4,5,6-tetrahydrocyclopenta[c]pyrazole-5-carboxamide;
- (S)-5-(3-Fluoro-2-methylphenyl)-1-(2-fluoro-6-methylphenyl)-N-hydroxy-1,4,5,6-tetrahydrocyclopenta[c]pyrazole-5-carboxamide;
- (S)-5-(3-Fluoro-2-methylphenyl)-1-(5-fluoropyridin-2-yl)-N-hydroxy-1,4,5,6-tetrahydrocyclopenta[c]pyrazole-5-carboxamide;
- (S)-1-(2,4-Difluorophenyl)-5-(3-fluoro-2-methylphenyl)-N-hydroxy-1,4,5,6-tetrahydrocyclopenta[c]pyrazole-5-carboxamide;
- (S)-1-Cyclopentyl-5-(3-fluoro-2-methylphenyl)-N-hydroxy-1,4,5,6-tetrahydrocyclopenta[c]pyrazole-5-carboxamide;
- (S)-5-(3-Fluoro-2-methylphenyl)-N-hydroxy-1-(pyrazin-2-yl)-1,4,5,6-tetrahydrocyclopenta[c]pyrazole-5-carboxamide;
- (S)-1-(4-(Difluoromethoxy)phenyl)-5-(3-fluoro-2-methylphenyl)-N-hydroxy-1,4,5,6-tetrahydrocyclopenta[c]pyrazole-5-carboxamide;
- (S)-2-(4-(Difluoromethoxy)phenyl)-5-(3-fluoro-2-methylphenyl)-N-hydroxy-2,4,5,6-tetrahydrocyclopenta[c]pyrazole-5-carboxamide;
- (S)-5-(3-Fluoro-2-methylphenyl)-1-(4-fluoro-2-methylphenyl)-N-hydroxy-1,4,5,6-tetrahydrocyclopenta[c]pyrazole-5-carboxamide;
- (S)-5-(3-Fluoro-2-methylphenyl)-2-(4-fluoro-2-methylphenyl)-N-hydroxy-2,4,5,6-tetrahydrocyclopenta[c]pyrazole-5-carboxamide;
- (S)-5-(3-Fluoro-2-methylphenyl)-N-hydroxy-1-(m-tolyl)-1,4,5,6-tetrahydrocyclopenta[c]pyrazole-5-carboxamide;
- (S)-5-(3-Fluoro-2-methylphenyl)-N-hydroxy-2-(m-tolyl)-2,4,5,6-tetrahydrocyclopenta[c]pyrazole-5-carboxamide;
- (S)-5-(3-Fluoro-2-methylphenyl)-N-hydroxy-1-(3-methylpyridin-4-yl)-1,4,5,6-tetrahydrocyclopenta[c]pyrazole-5-carboxamide;
- (S)-5-(3-Fluoro-2-methylphenyl)-N-hydroxy-2-(3-methylpyridin-4-yl)-2,4,5,6-tetrahydrocyclopenta[c]pyrazole-5-carboxamide;
- (S)-2-(3-Chloropyridin-2-yl)-5-(3-fluoro-2-methylphenyl)-N-hydroxy-2,4,5,6-tetrahydrocyclopenta[c]pyrazole-5-carboxamide;
- (S)-5-(3-Fluoro-2-methylphenyl)-2-(3-fluoropyridin-2-yl)-N-hydroxy-2,4,5,6-tetrahydrocyclopenta[c]pyrazole-5-carboxamide;
- (R)-5-(3-Fluoro-2-methylphenyl)-N-hydroxy-1-phenyl-1,4,5,6-tetrahydrocyclopenta[c]pyrazole-5-carboxamide;
- E1-(abs)-5-(3-Fluoro-2-methylphenyl)-N-hydroxy-1-phenyl-4,5,6,7-tetrahydro-1H-indazole-5-carboxamide;
- E2-(abs)-5-(3-Fluoro-2-methylphenyl)-N-hydroxy-1-phenyl-4,5,6,7-tetrahydro-1H-indazole-5-carboxamide;
- E1-(abs)-5-(3-Fluoro-2-methylphenyl)-2-(2-fluorophenyl)-N-hydroxy-4,5,6,7-tetrahydro-2H-indazole-5-carboxamide;
- E2-(abs)-5-(3-Fluoro-2-methylphenyl)-2-(2-fluorophenyl)-N-hydroxy-4,5,6,7-tetrahydro-2H-indazole-5-carboxamide;
- 5-(3-Fluoro-2-methylphenyl)-N-hydroxy-1-(2,2,2-trifluoroethyl)-4,5,6,7-tetrahydro-1H-indazole-5-carboxamide; and 5-(3-fluoro-2-methylphenyl)-N-hydroxy-2-(2,2,2-trifluoroethyl)-4,5,6,7-tetrahydro-2H-indazole-5-carboxamide;
- 5-(3-Fluoro-2-methylphenyl)-1-(4-fluorobenzyl)-N-hydroxy-4,5,6,7-tetrahydro-1H-indazole-5-carboxamide and 5-(3-fluoro-2-methylphenyl)-2-(4-fluorobenzyl)-N-hydroxy-4,5,6,7-tetrahydro-2H-indazole-5-carboxamide;
- E1-(abs)-5-(3-Fluoro-2-methylphenyl)-N-hydroxy-1-(o-tolyl)-4,5,6,7-tetrahydro-1H-indazole-5-carboxamide;
- E2-(abs)-5-(3-Fluoro-2-methylphenyl)-N-hydroxy-1-(o-tolyl)-4,5,6,7-tetrahydro-1H-indazole-5-carboxamide;

3-Cyclopropyl-5-(3-fluoro-2-methylphenyl)-N-hydroxy-2-(2,2,2-trifluoroethyl)-4,5,6,7-tetrahydro-2H-indazole-5-carboxamide;

2-Cyclopropyl-6-(3-fluoro-2-methylphenyl)-N-hydroxy-4-oxo-3,4,5,6,7,8-hexahydroquinazoline-6-carboxamide;

6-(3-Fluoro-2-methylphenyl)-N-hydroxy-2-(phenylsulfonamido)-4,5,6,7-tetrahydrobenzo[d]thiazole-6-carboxamide;

2-Cyclopropyl-6-(3-fluoro-2-methylphenyl)-N-hydroxy-4,5,6,7-tetrahydrobenzo[d]thiazole-6-carboxamide;

6-(3-Fluoro-2-methylphenyl)-N-hydroxy-2-(pyrimidin-5-yl)-4,5,6,7-tetrahydrobenzo[d]thiazole-6-carboxamide;

6-(3-Fluoro-2-methylphenyl)-N-hydroxy-4,5,6,7-tetrahydrobenzo[d]thiazole-6-carboxamide;

6-(3-Fluoro-2-methylphenyl)-N-hydroxy-5,6,7,8-tetrahydroquinazoline-6-carboxamide;

2-Cyclopropyl-6-(3-fluoro-2-methylphenyl)-N-hydroxy-5,6,7,8-tetrahydroquinazoline-6-carboxamide;

6-(3-Fluoro-2-methylphenyl)-N-hydroxy-2-phenyl-5,6,7,8-tetrahydroquinazoline-6-carboxamide;

(S)-2-(2-Chlorophenyl)-6-(3-fluoro-2-methylphenyl)-N-hydroxy-6,7-dihydro-5H-cyclopenta[d]pyrimidine-6-carboxamide;

(R)-2-(2-Chlorophenyl)-5-(3-fluoro-2-methylphenyl)-N-hydroxy-6,7-dihydro-5H-cyclopenta[d]pyrimidine-5-carboxamide;

(R)-2-Cyclopropyl-6-(3-fluoro-2-methylphenyl)-N-hydroxy-6,7-dihydro-5H-cyclopenta[d]pyrimidine-6-carboxamide;

(S)-2-Cyclopropyl-5-(3-fluoro-2-methylphenyl)-N-hydroxy-6,7-dihydro-5H-cyclopenta[d]pyrimidine-5-carboxamide;

(S)-5-(3-Fluoro-2-methylphenyl)-N-hydroxy-1-isopropyl-1,4,5,6-tetrahydrocyclopenta[c]pyrazole-5-carboxamide;

(R)-4-(3-fluoro-2-methylphenyl)-N-hydroxy-1-phenyl-1,4,5,6-tetrahydrocyclopenta[c]pyrazole-4-carboxamide;

(S)-6-(3-fluoro-2-methylphenyl)-2-(4-fluorophenyl)-N-hydroxy-6,7-dihydro-5H-cyclopenta[d]pyrimidine-6-carboxamide;

(S)-6-(3-Fluoro-2-methylphenyl)-N-hydroxy-2-(trifluoromethyl)-6,7-dihydro-5H-cyclopenta[d]pyrimidine-6-carboxamide;

(R)-2-Cyclopropyl-5-(3-fluoro-2-methylphenyl)-N-hydroxy-6,7-dihydro-5H-cyclopenta[d]pyrimidine-5-carboxamide;

(S)-2-Cyclopropyl-6-(3-fluoro-2-methylphenyl)-N-hydroxy-6,7-dihydro-5H-cyclopenta[d]pyrimidine-6-carboxamide;

(S)-1-Cyclopropyl-5-(3-fluoro-2-methylphenyl)-N-hydroxy-1,4,5,6-tetrahydrocyclopenta[c]pyrazole-5-carboxamide;

(R)-1-Cyclopropyl-4-(3-fluoro-2-methylphenyl)-N-hydroxy-1,4,5,6-tetrahydrocyclopenta[c]pyrazole-4-carboxamide;

(S)-6-(3-fluoro-2-methylphenyl)-N-hydroxy-2-(pyridin-3-yl)-6,7-dihydro-5H-cyclopenta[d]pyrimidine-6-carboxamide;

E1-(abs)-5-(3-Fluoro-2-methylphenyl)-2-(2-fluorophenyl)-N-hydroxy-5,6-dihydro-4H-cyclopenta[d]thiazole-5-carboxamide;

E2-(abs)-5-(3-Fluoro-2-methylphenyl)-2-(2-fluorophenyl)-N-hydroxy-5,6-dihydro-4H-cyclopenta[d]thiazole-5-carboxamide;

5-(3-Fluoro-2-methylphenyl)-N-hydroxy-2-(3-(trifluoromethyl)benzyl)-5,6-dihydro-4H-cyclopenta[d]thiazole-5-carboxamide;

E1-(abs)-5-(3-Fluoro-2-methylphenyl)-2-(3-fluorophenyl)-N-hydroxy-5,6-dihydro-4H-cyclopenta[d]thiazole-5-carboxamide;

E2-(abs)-5-(3-Fluoro-2-methylphenyl)-2-(3-fluorophenyl)-N-hydroxy-5,6-dihydro-4H-cyclopenta[d]thiazole-5-carboxamide;

(R)-5-(3-Fluoro-2-methylphenyl)-2-(4-fluorophenyl)-N-hydroxy-5,6-dihydro-4H-cyclopenta[d]thiazole-5-carboxamide;

(S)-5-(3-Fluoro-2-methylphenyl)-2-(4-fluorophenyl)-N-hydroxy-5,6-dihydro-4H-cyclopenta[d]thiazole-5-carboxamide;

(S)-5-(3-Fluoro-2-methylphenyl)-N-hydroxy-2-(1-methyl-1H-pyrazol-5-yl)-5,6-dihydro-4H-cyclopenta[d]thiazole-5-carboxamide;

(R)-5-(3-Fluoro-2-methylphenyl)-N-hydroxy-2-(1-methyl-1H-pyrazol-5-yl)-5,6-dihydro-4H-cyclopenta[d]thiazole-5-carboxamide;

(R)-2-(1,3-Dimethyl-1H-pyrazol-5-yl)-5-(3-fluoro-2-methylphenyl)-N-hydroxy-5,6-dihydro-4H-cyclopenta[d]thiazole-5-carboxamide;

(R)-5-(3-Fluoro-2-methylphenyl)-N-hydroxy-2-(5-methoxypyridin-2-yl)-5,6-dihydro-4H-cyclopenta[d]thiazole-5-carboxamide;

(S)-2-Cyclopropyl-6-(3-fluoro-2-methylphenyl)-N-hydroxy-5,6-dihydro-4H-cyclopenta[d]thiazole-6-carboxamide;

(S)-6-(3-Fluoro-2-methylphenyl)-N-hydroxy-2-(o-tolyl)-5,6-dihydro-4H-cyclopenta[d]thiazole-6-carboxamide;

E1-(abs)-5-(3-Fluoro-2-methylphenyl)-2-(4-fluoro-2-methylphenyl)-N-hydroxy-5,6-dihydro-4H-cyclopenta[d]thiazole-5-carboxamide;

E2-(abs)-5-(3-Fluoro-2-methylphenyl)-2-(4-fluoro-2-methylphenyl)-N-hydroxy-5,6-dihydro-4H-cyclopenta[d]thiazole-5-carboxamide;

E1-(abs)-2-(1,5-Dimethyl-1H-pyrazol-4-yl)-5-(3-fluoro-2-methylphenyl)-N-hydroxy-5,6-dihydro-4H-cyclopenta[d]thiazole-5-carboxamide;

E2-(abs)-2-(1,5-dimethyl-1H-pyrazol-4-yl)-5-(3-fluoro-2-methylphenyl)-N-hydroxy-5,6-dihydro-4H-cyclopenta[d]thiazole-5-carboxamide;

(S)-6-(3-Fluoro-2-methylphenyl)-2-(4-fluorophenyl)-N-hydroxy-5,6-dihydro-4H-cyclopenta[d]thiazole-6-carboxamide;

(R)-5-(3-Fluoro-2-methylphenyl)-3-(4-fluorophenyl)-N-hydroxy-2-methyl-2,4,5,6-tetrahydrocyclopenta[c]pyrazole-5-carboxamide;

E1-(abs)-5-(3-fluoro-2-methylphenyl)-N-hydroxy-3-phenyl-5,6-dihydro-4H-cyclopenta[d]isothiazole-5-carboxamide;

E2-(abs)-5-(3-fluoro-2-methylphenyl)-N-hydroxy-3-phenyl-5,6-dihydro-4H-cyclopenta[d]isothiazole-5-carboxamide;

2-(3-Fluoro-2-methylphenyl)-N-hydroxy-2,3-dihydro-1H-indene-2-carboxamide;

2-Cyclopropyl-7-(3-fluoro-2-methylphenyl)-N-hydroxy-6,7,8,9-tetrahydro-5H-cyclohepta[d]pyrimidine-7-carboxamide;

E1-(abs)-6-(3-Fluoro-2-methylphenyl)-N-hydroxy-2-(2,2,2-trifluoroethyl)-2,4,5,6,7,8-hexahydrocyclohepta[c]pyrazole-6-carboxamide;

E2-(abs)-6-(3-Fluoro-2-methylphenyl)-N-hydroxy-2-(2,2,2-trifluoroethyl)-2,4,5,6,7,8-hexahydrocyclohepta[c]pyrazole-6-carboxamide; and N-Hydroxy-6-phenyl-2-(2,2,2-trifluoroethyl)-2,4,5,6,7,8-hexahydrocyclohepta[c]pyrazole-6-carboxamide;
E1-(abs)-N-Hydroxy-1-phenyl-2,3-dihydro-1H-indene-1-carboxamide;
E2-(abs)-N-hydroxy-1-phenyl-2,3-dihydro-1H-indene-1-carboxamide;
N-Hydroxy-2-phenyl-2,3-dihydro-1H-indene-2-carboxamide;
(S)-1-(2-Chloro-4-fluorophenyl)-5-(3-fluoro-2-methylphenyl)-N-hydroxy-1,4,5,6-tetrahydrocyclopenta[c]pyrazole-5-carboxamide;
(S)-2-(4,6-Dimethylpyrimidin-2-yl)-5-(3-fluoro-2-methylphenyl)-N-hydroxy-2,4,5,6-tetrahydrocyclopenta[c]pyrazole-5-carboxamide;
(S)-1-Benzyl-5-(3-fluoro-2-methylphenyl)-N-hydroxy-1,4,5,6-tetrahydrocyclopenta[c]pyrazole-5-carboxamide;
(R)-1-Benzyl-4-(3-fluoro-2-methylphenyl)-N-hydroxy-1,4,5,6-tetrahydrocyclopenta[c]pyrazole-4-carboxamide;
(R)-2-Benzyl-4-(3-fluoro-2-methylphenyl)-N-hydroxy-2,4,5,6-tetrahydrocyclopenta[c]pyrazole-4-carboxamide;
(R)-4-(3-fluoro-2-methylphenyl)-2-(2-fluorobenzyl)-N-hydroxy-2,4,5,6-tetrahydrocyclopenta[c]pyrazole-4-carboxamide; and
(R)-5-(3-Fluoro-2-methylphenyl)-N-hydroxy-2-(5-fluoropyridin-2-yl)-5,6-dihydro-4H-cyclopenta[d]thiazole-5-carboxamide.

50. A pharmaceutical composition comprising a compound according to claim 1 or a pharmaceutically acceptable salt thereof and a pharmaceutically acceptable carrier.

51. A process for preparing a pharmaceutical composition comprising admixing a compound according to claim 1 or a pharmaceutically acceptable salt thereof and a pharmaceutically acceptable carrier.

* * * * *